US012673949B2

(12) United States Patent
Irisa et al.

(10) Patent No.: US 12,673,949 B2
(45) Date of Patent: Jul. 7, 2026

(54) HETEROCYCLIC COMPOUND, ORGANIC LIGHT-EMITTING DEVICE INCLUDING THE SAME, AND ELECTRONIC APPARATUS INCLUDING THE ORGANIC LIGHT-EMITTING DEVICE

(71) Applicant: Samsung Electronics Co., Ltd., Suwon-si (KR)

(72) Inventors: Shiro Irisa, Kanagawa (JP); Wataru Sotoyama, Kanagawa (JP); Eigo Miyazaki, Kanagawa (JP); Atsushi Imamura, Kanagawa (JP); Masaru Kinoshita, Kanagawa (JP); Mitsunori Ito, Kanagawa (JP)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 983 days.

(21) Appl. No.: 17/897,297

(22) Filed: Aug. 29, 2022

(65) Prior Publication Data

US 2023/0126543 A1 Apr. 27, 2023

(30) Foreign Application Priority Data

Sep. 17, 2021 (JP) ................................ 2021-152022
Nov. 10, 2021 (KR) ........................ 10-2021-0154292
(Continued)

(51) Int. Cl.
*C07D 471/06* (2006.01)
*C07D 519/00* (2006.01)
(Continued)

(52) U.S. Cl.
CPC ......... *C07D 471/06* (2013.01); *C07D 519/00* (2013.01); *C07F 5/027* (2013.01);
(Continued)

(58) Field of Classification Search
CPC .. C07D 471/06; C07D 519/00; C07D 401/14; C07D 403/14; C07D 405/14;
(Continued)

(56) References Cited

U.S. PATENT DOCUMENTS 10,249,832 B1 * 4/2019 Takahashi .......... H10K 85/6574
2004/0150327 A1 * 8/2004 Kawai ................ H10K 85/6576
313/504
(Continued)

FOREIGN PATENT DOCUMENTS

JP 2013147481 A 8/2013
JP 2021134172 A 9/2021
(Continued)

OTHER PUBLICATIONS

English translation of KR 20210119032 A obtained from Google Patents. (Year: 2021).*
(Continued)

*Primary Examiner* — Braelyn R Watson
(74) *Attorney, Agent, or Firm* — CANTOR COLBURN LLP

(57) ABSTRACT

Provided are a heterocyclic compound represented by Formula 1, an organic light-emitting device including the same, and an electronic apparatus including the organic light-emitting device:
(Continued)

Formula 1

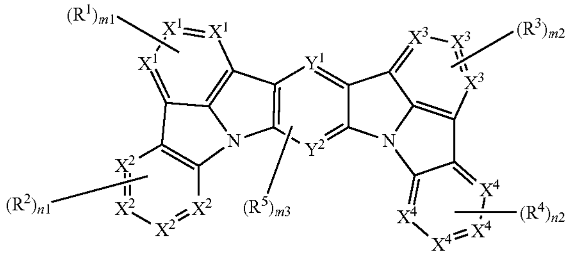

The substituents in Formula 1 are the same as described in the detailed description.

20 Claims, 3 Drawing Sheets

(30) Foreign Application Priority Data

Dec. 23, 2021 (JP) ................................. 2021-209340
May 10, 2022 (KR) ........................ 10-2022-0057393

(51) Int. Cl.

| | |
|---|---|
| ***C07F 5/02*** | (2006.01) |
| ***H10K 50/11*** | (2023.01) |
| ***H10K 85/30*** | (2023.01) |
| ***H10K 85/60*** | (2023.01) |
| *H10K 101/10* | (2023.01) |
| *H10K 101/40* | (2023.01) |

(52) U.S. Cl.
CPC ........... *H10K 50/11* (2023.02); *H10K 85/322* (2023.02); *H10K 85/654* (2023.02); *H10K 85/657* (2023.02); *H10K 85/6572* (2023.02); *H10K 2101/10* (2023.02); *H10K 2101/40* (2023.02)

(58) Field of Classification Search
CPC .. C07D 471/04; C07D 487/04; C07D 471/00; C07D 471/02; C07D 471/12; C07D 471/22; C07D 487/00; C07D 487/02; C07D 487/12; C07D 487/22; C07D 498/00; C07D 498/02; C07D 498/12; C07D 498/22; C07F 5/027; H10K 50/11; H10K 85/322; H10K 85/654; H10K 85/657; H10K 85/6572; H10K 2101/10; H10K 2101/40; H10K 85/342; H01L 51/0072; H01L 51/0071
See application file for complete search history.

(56) References Cited

U.S. PATENT DOCUMENTS

2006/0273714 A1* 12/2006 Forrest .................. H10K 50/11 313/506
2020/0006666 A1* 1/2020 Duan .................. C07D 209/86
2021/0359221 A1 11/2021 Takahashi et al.
2021/0391552 A1* 12/2021 Liu ...................... H10K 50/121
2023/0080626 A1 3/2023 Korai et al.

FOREIGN PATENT DOCUMENTS

JP 2022102050 A 7/2022
KR 20210119032 A * 10/2021 ............ C09K 11/06

OTHER PUBLICATIONS

Wei, Jinbei, et al. "Indolo [3, 2, 1-jk] carbazole embedded multiple-resonance fluorophors for narrowband deep-blue electroluminescence with EQE≈34.7% and CIEy≈0.085." Angewandte Chemie 133.22 (2021): 12377-12381. (Year: 2021).*
Kader, Thomas, et al. "Azaindolo [3, 2, 1-jk] carbazoles: New Building Blocks for Functional Organic Materials." Chemistry—A European Journal 25.17 (2019): 4412-4425. (Year: 2019).*
English Translation of Office Action dated Feb. 12, 2025, issued in corresponding JP Patent Application No. 2021-209340, 4 pp.
Office Action dated Feb. 12, 2025, issued in corresponding JP Patent Application No. 2021-209340, 3 pp.
Claude Niebel et al, "Dibenzo[2,3:5,6]pyrrolizino[1,7-bc]indolo[1,2,3-lm]carbazole: . . . " New Journal of Chemistry (2010), 34(7), 1243-1246.
Ganesha Rai et al, "Ionic liquid mediated efficient reduction of nitroarenes . . . " Tetrahedron Letters, 2005, 46, 3987-3990.
Ha Lim Lee et al, "Narrowband and Pure Violet Organic Emitter with a . . . ", Small (2020), 16(14), 1907569, 5 pp.
Mohamed Abboud et al, "Double N-arylation reaction of polyhalogenated . . . " Beilstein J. Org. Chem. Aug. 2012, 253-258.
Taisei Taniguchi et al, "Construction of Nitrogen-Containing Polycyclic Aromatic Compounds by . . . " Chemistry Letters (2019), 48(9), 1160-1163.
Soo-Ghang Ihn et al, "An Alternative Host Material for Long-Lifespan Blue Organic Light-Emitting Diodes Using Thermally Activated Delayed Fluorescence", Advanced Science, 4(8), 1600502. (2017), 7 pp.

* cited by examiner

HETEROCYCLIC COMPOUND, ORGANIC LIGHT-EMITTING DEVICE INCLUDING THE SAME, AND ELECTRONIC APPARATUS INCLUDING THE ORGANIC LIGHT-EMITTING DEVICE

CROSS-REFERENCE TO RELATED APPLICATION

This application claims priority under 35 U.S.C. § 119 to Korean Patent Application No. 10-2021-0154292, filed on Nov. 10, 2021, and No. 10-2022-0057393, filed on May 10, 2022, in the Korean Intellectual Property Office, and to Japanese Patent Application No. 2021-152022, filed on Sep. 17, 2021, and No. 2021-209340, filed on Dec. 23, 2021, in the Japanese Patent Office, the contents of which are incorporated by reference herein in their entirety.

BACKGROUND

1. Field

The present disclosure relates to a heterocyclic compound, an organic light-emitting device including the same, and an electronic apparatus including the organic light-emitting device.

2. Description of the Related Art

Organic light-emitting devices (OLEDs) are self-emissive devices that, as compared with devices of the related art, have wide viewing angles, high contrast ratios, short response times, and excellent characteristics in terms of luminance, driving voltage, and response speed, and produce full-color images.

OLEDs may include an anode, a cathode, and an organic layer that is located between the anode and the cathode and includes an emission layer. A hole transport region may be located between the anode and the emission layer, and an electron transport region may be located between the emission layer and the cathode. Holes provided from the anode may move toward the emission layer through the hole transport region, and electrons provided from the cathode may move toward the emission layer through the electron transport region. The holes and the electrons recombine in the emission layer to produce excitons. These excitons transition from an excited state to a ground state, thereby generating light.

SUMMARY

Provided are a heterocyclic compound, an organic light-emitting device including the same, and an electronic apparatus including the organic light-emitting device. In detail, provided is a heterocyclic compound having a maximum emission wavelength of about 440 nm to about 480 nm, having improved color purity, and being capable of improving luminescence efficiency of an organic light-emitting device.

Additional aspects will be set forth in part in the description which follows and, in part, will be apparent from the description, or may be learned by practice of the presented embodiments of the disclosure.

According to an aspect of an embodiment, provided is a heterocyclic compound represented by Formula 1:

Formula 1

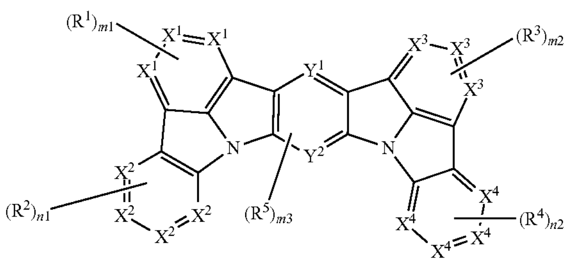

wherein, in Formula 1, $X^1$, $X^2$, $X^3$, and $X^4$ are each independently C or N, and at least one of three $X^1$(s), four $X^2$(s), three $X^3$(s), and four $X^4$(s) is N, $Y_1$ and $Y_2$ are each independently C or N, $R^1$, $R^2$, $R^3$, and $R^4$ are each independently a hydrogen atom, a deuterium atom, a halogen atom, a substituted or unsubstituted aryl group having 6 to 14 ring-forming atoms, a substituted or unsubstituted heteroaryl group having 5 to 14 ring-forming atoms, a substituted or unsubstituted amino group, a substituted or unsubstituted arylamino group having 6 to 14 ring-forming atoms, a substituted or unsubstituted heteroarylamino group having 5 to 14 ring-forming atoms, or a substituted or unsubstituted arylboranyl group having 6 to 14 ring-forming atoms, $R^5$ is a hydrogen atom, a deuterium atom, a halogen atom, a substituted or unsubstituted aryl group having 6 to 14 ring-forming atoms, a substituted or unsubstituted heteroaryl group having 5 to 14 ring-forming atoms, a substituted or unsubstituted amino group, a substituted or unsubstituted arylamino group having 6 to 14 ring-forming atoms, a substituted or unsubstituted heteroarylamino group having 5 to 14 ring-forming atoms, a substituted or unsubstituted indolo[3,2,1-jk]carbazolyl group, or $—R^{51}—R^{52}$, $R^{51}$ is a substituted or unsubstituted arylene group having 6 to 14 ring-forming atoms or a substituted or unsubstituted heteroarylene group having 5 to 14 ring-forming atoms, $R^{52}$ is a substituted or unsubstituted amino group, a substituted or unsubstituted arylamino group having 6 to 14 ring-forming atoms, a substituted or unsubstituted hetero arylamino group having 5 to 14 ring-forming atoms, or a substituted or unsubstituted heteroaryl group having 5 to 14 ring-forming atoms, n1 and n2 are each independently 1, 2, or 3, m1 and m2 are each independently 1 or 2, and m3 is 0, 1, or 2.

According to an aspect of another embodiment, an organic light-emitting device includes: a first electrode; a second electrode; an organic layer including an emission layer between the first electrode and the second electrode; and the heterocyclic compound.

According to an aspect of another embodiment, an electronic apparatus includes the organic light-emitting device.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
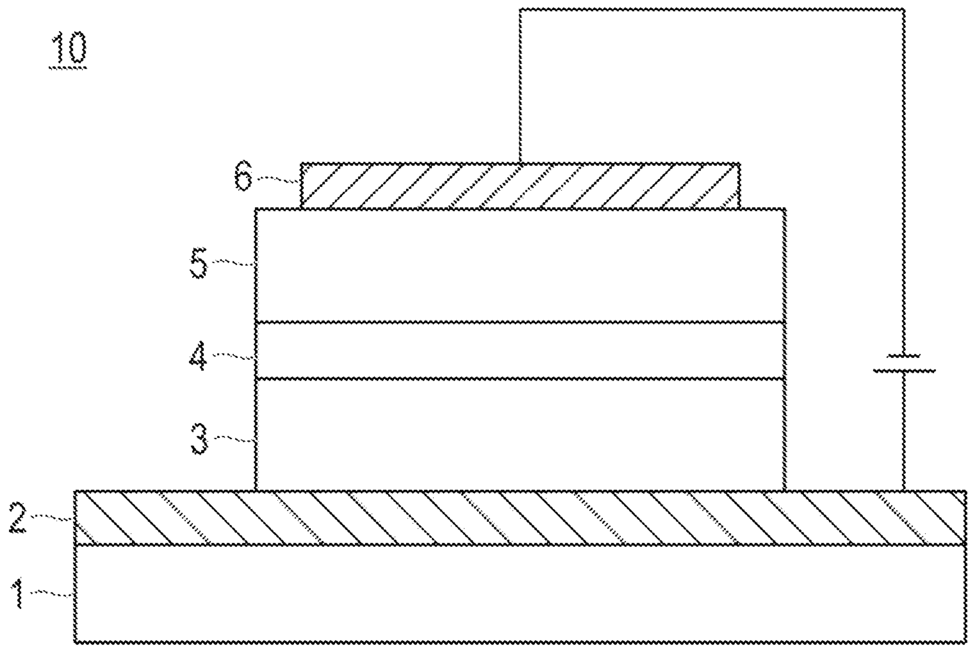
FIG. 1 is a schematic cross-sectional view of an organic light-emitting device according to an exemplary embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Unless otherwise specified, measurements of operation and physical properties are performed at room temperature (20° C. or more and 25° C. or less) and at relative humidity of 40% RH or more and 50% RH or less.

It will be understood that when an element is referred to as being "on" another element, it can be directly on the other element or intervening elements may be present therebetween In contrast, when an element is referred to as being "directly on" another element, there are no intervening elements present It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise.

"Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded Thus, the regions illustrated in the figures are schematic in nature and their shapes are not intended to illustrate the precise shape of a region and are not intended to limit the scope of the present claims.

In the present specification, the term "X and Y may each independently be" may be understood that X and Y may be identical to or different from each other.

In the present specification, the term "group derived from a ring" refers to a group obtained by removing a hydrogen atom bound to a ring-forming atom in a ring structure.

In the present specification, the term "number of ring-forming atoms" refers to the number of atoms constituting the ring itself of a compound (for example, a monocyclic compound, a condensed cyclic compound, a cross-linked compound, a carbocyclic compound, and a heterocyclic compound) having a structure (for example, a monocyclic ring, a condensed ring, and a ring assembly) in which atoms are bonded in a ring-like manner. The number of ring-forming atoms excludes the number of atoms that do not constitute the ring (for example, a hydrogen atom that terminates a bond of atoms constituting the ring), and the number of atoms included in a substituent when the ring is substituted with the substituent. Unless otherwise specified, the same definition of the number of ring-forming atoms applies to descriptions provided below.

For example, a benzene ring has 6 ring-forming atoms, a naphthalene ring has 10 ring-forming atoms, a pyridine ring has 6 ring-forming atoms, and a furan ring has 5 ring-forming atoms.

When a benzene ring is substituted with, for example, an alkyl group as a substituent, the number of carbon atoms in the alkyl group is not included in the number of ring-forming atoms of the benzene ring. Accordingly, a benzene ring substituted with an alkyl group has 6 ring-forming atoms. In addition, when a naphthalene ring is substituted with, for example, an alkyl group as a substituent, the number of atoms in the alkyl group is not included in the number of ring-forming atoms of the naphthalene ring. Accordingly, a naphthalene ring substituted with an alkyl group has 10 ring-forming atoms. For example, the number of hydrogen atoms bonded to a pyridine ring or the number of atoms constituting a substituent thereof is not included in the number of ring-forming atoms of the pyridine ring. Accordingly, a pyridine ring to which hydrogen atoms or a substituent is bonded has 6 ring-forming atoms.

Examples of the halogen atom as a substituent may include a fluorine atom (F), a chlorine atom (Cl), a bromine atom (Br), and an iodine atom (I).

The aryl group may be, but is not particularly limited to, a monovalent group derived from a hydrocarbon ring including one or more aromatic rings. In addition, the hydrocarbon ring constituting the aryl group may be a condensed ring. In addition, when the aryl group includes two or more aromatic rings, the two or more aromatic rings may be bonded to each other via a single bond (in the form of a ring assembly of aromatic hydrocarbon rings).

Examples of the aryl group having 6 to 14 ring-forming atoms may include a phenyl group, a naphthyl group, a phenanthryl group, a biphenylenyl group, an anthryl group, a fluorenyl group, an azulenyl group, an acenaphthyl group, and the like.

The heteroaryl group may be, but is not particularly limited to, a monovalent group derived from a ring including one or more aromatic hetero rings having one or more heteroatoms (for example, nitrogen atoms (N), oxygen atoms (O), phosphorus atoms (P), sulfur atoms (S), and silicon atoms (Si)) as ring-forming atoms, wherein the remaining ring-forming atoms are carbon atoms (C). When the heteroaryl group includes two or more heteroatoms, the two or more heteroatoms may be identical to or different from each other. In addition, a ring constituting the heteroaryl group may be a condensed ring. In addition, when the heteroaryl group includes two or more aromatic hetero rings, the two or more aromatic hetero rings may be bonded to each other via a single bond. As such, the heteroaryl group may be a monocyclic heteroaryl group or a polycyclic heteroaryl group.

Examples of the heteroaryl group having 5 to 14 ring-forming atoms may include a thienyl group, a furanyl group, a pyrrolyl group, an imidazole group, a thiazolyl group, an oxazolyl group, an oxadiazolyl group, a triazolyl group, a pyridyl group, a bipyridyl group, a pyrimidyl group, a triazinyl group, a triazolyl group, an acridinyl group, a pyridazinyl group, a pyridinyl group, a quinolinyl group, a quinazolinyl group, a quinoxalinyl group, a phenoxazinyl group, a phthalazinyl group, a pyridopyrimidinyl group, a pyridopyrazinyl group, a pyrazinopyrazinyl group, an isoquinolinyl group, an indolyl group, a benzoxazolyl group, a benzimidazolyl group, a benzothiazolyl group, a benzothiophenyl group, a dibenzothiophenyl group, a thienothienyl group, a benzofuranyl group, a phenanthrolinyl group, an isoxazolyl group, an oxadiazolyl group, a thiadiazolyl group, a phenothiazolyl group, a phenothiazinyl group, and a dibenzofuranyl group.

The arylamino group may be a monoarylamino group or a diarylamino group. The aryl group having 6 to 14 ring-forming atoms that constitutes the arylamino group is the same as described above. Examples of the arylamino group having 6 to 14 ring-forming atoms may include an N-phenylamino group, an N-biphenylamino group, an N-terphenylamino group, an N,N-diphenylamino group, an N-biphenyl-N-phenyl amino group, and the like.

The heteroarylamino group may be a monoheteroarylamino group or a diheteroarylamino group. The heteroaryl group having 5 to 14 ring-forming atoms that constitutes the heteroarylamino group is the same as described above. Examples of the heteroarylamino group having 5 to 14 ring-forming atoms may include an N-thienylamino group, an N-furanylamino group, an N-pyrrolylamino group, an N,N-dithienylamino group, and the like.

The arylboranyl group may be a monoarylboranyl group or a diarylboranyl group. The aryl group having 6 to 14 ring-forming atoms that constitutes the arylboranyl group is the same as described above. In addition, when the arylboranyl group is a diarylboranyl group, two aryl groups constituting the arylboranyl group may be bonded to each other via —O—, —S—, —NR—, —CR'R"— or a single bond to form a ring, wherein R, R', and R" may each independently be a substituted or unsubstituted alkyl group, a substituted or unsubstituted aryl group, or a substituted or unsubstituted heteroaryl group. Examples of the alkyl group will be described in detail below. Examples of the aryl group and the heteroaryl group are respectively the same as those described above in connection with the aryl group having 6 to 14 ring-forming atoms and the heteroaryl group having 5 to 14 ring-forming atoms.

Examples of the arylboranyl group may include a diphenylboranyl group and a monovalent group represented by Formula B1:

B1

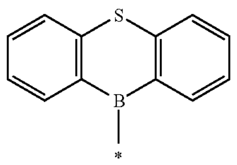

wherein, in Formula B1, * indicates a binding site to a neighboring atom.

The arylene group may be, but is not particularly limited to, a divalent group derived from a hydrocarbon ring including one or more aromatic rings. In addition, the hydrocarbon ring constituting the arylene group may be a condensed ring. In addition, when the arylene group includes two or more aromatic rings, the two or more aromatic rings may be bonded to each other via a single bond (in the form of a ring assembly of aromatic hydrocarbon rings).

Examples of the arylene group having 6 to 14 ring-forming atoms may include a phenylene group, a naphthylene group, a phenanthrenylene group, a biphenylenylene group, an anthracenylene group, a fluorenylene group, an azulenylene group, an acenaphthenylene group, and the like.

The heteroarylene group may be, but is not particularly limited to, a divalent group derived from a ring including one or more aromatic hetero rings having one or more heteroatoms (for example, nitrogen atoms (N), oxygen atoms (O), phosphorus atoms (P), sulfur atoms (S), and silicon atoms (Si)) as ring-forming atoms, wherein the remaining ring-forming atoms are carbon atoms (C)). When the heteroarylene group includes two or more heteroatoms, the two or more heteroatoms may be identical to or different from each other. In addition, a ring constituting the heteroarylene group may be a condensed ring. In addition, when the heteroarylene group includes two or more aromatic hetero rings, the two or more aromatic hetero rings may be bonded to each other via a single bond. As such, the heteroarylene group may be a monocyclic heteroarylene group or a polycyclic heteroarylene group.

Examples of the heteroarylene group having 5 to 14 ring-forming atoms may include a thienylene group, a furanylene group, a pyrrolylene group, an imidazolylene group, a thiazolylene group, an oxazolylene group, an oxadiazolylene group, a triazolylene group, a pyridylene group, a bipyridylene group, a pyrimidylene group, a triazinylene group, an acridinylene group, a pyridazinylene group, a quinolinylene group, a quinazolinylene group, a quinoxalinylene group, a phenoxazinylene group, a phthalazinylene group, a pyridopyrimidinylene group, a pyridopyrazinylene group, a pyrazinopyridazinylene group, an isoquinolinylene group, an indolylene group, a carbazolylene group, a benzoxazolylene group, a benzimidazolylene group, a benzothiazolylene group, a benzothiophenylene group, a dibenzothiophenylene group, a thienothiophenylene group, a benzofuranylene group, a phenanthrolinylene group, an isoxazolylene group, an oxadiazolylene group, a thiadiazolylene group, a phenothiazinylene group, a dibenzosilolylene group, a dibenzofuranylene group, and the like.

At least one hydrogen atom of the aryl group, the heteroaryl group, the amino group, the arylamino group, the heteroarylamino group, the arylboranyl group, the indolo[3,2,1-jk]carbazolyl group, the arylene group, the heteroarylene group, and the carbazolyl group may be substituted. In this case, the type of a substituent is not particularly limited, and the substituent may be a deuterium atom, a halogen atom, a substituted or unsubstituted alkyl group, a substituted or unsubstituted aryl group, a substituted or unsubstituted heteroaryl group, a substituted or unsubstituted alkoxy group, a substituted or unsubstituted aryloxy group, a substituted or unsubstituted heteroaryloxy group, a substituted or unsubstituted diarylamino group, a substituted or unsubstituted diheteroarylamino group, or a substituted or unsubstituted arylheteroarylamino group. When two or more hydrogen atoms are substituted, the types of substituents may be identical to or different from each other.

When the substituent is further substituted, the type of a substituent thereof is not particularly limited. When the substituent is further substituted, the substituent thereof may be, for example, a deuterium atom, a halogen atom, an unsubstituted alkyl group, an unsubstituted aryl group, an unsubstituted heteroaryl group, an unsubstituted alkoxy group, an unsubstituted aryloxy group, an unsubstituted heteroaryloxy group, an unsubstituted arylamino group, or an unsubstituted heteroarylamino group. When the substituent is further substituted, and two or more substituents thereof are present, the types of the substituents may be identical to or different from each other. In addition, the substituent does not substitute a group of the same type. For example, a substituent substituting an alkyl group does not include an alkyl group.

Examples of the halogen atom, the aryl group, the heteroaryl group, the arylamino group, and the heteroarylamino group as a substituent are the same as those described above, and thus, descriptions thereof are omitted here.

The alkyl group as a substituent may have any one of a linear shape, a branched shape, and a cyclic shape. The number of carbon atoms in the alkyl group may be, but is not particularly limited to, 1 or more and 30 or less, and may be 1 or more and 20 or less. In addition, the number of carbons in the alkyl group may be 1 or more and 10 or less, and may be 1 or more and 6 or less. Examples of the alkyl group may include, but are not particularly limited to, a methyl group, an ethyl group, an n-propyl group, an isopropyl group, an n-butyl group, a sec-butyl group, a tert-butyl group, an isobutyl group, a 2-ethylbutyl group, a 3,3-dimethylbutyl group, an n-pentyl group, an isopentyl group, a neopentyl group, a tert-pentyl group (a t-pentyl group), a pentyl group, a 1-methylpentyl group, a 3-methylpentyl group, a 2-ethylpentyl group, a 4-methyl-2-pentyl group, an n-hexyl group, a 1-methylhexyl group, a 2-ethylhexyl group, a 2-butylhexyl group, a cyclohexyl group, a 4-methylcyclo hexyl group, a 4-tert-butylcyclohexyl group (a 4-t-butylcyclohexyl group), an n-heptyl group, a 1-methylheptyl group, a 2,2-dimethylheptyl group, a 2-ethylheptyl group, a 2-butylheptyl group, an n-octyl group, a tert-octyl group (a t-octyl group), a 2-ethyloctyl group, a 2-butyloctyl group, a 2-hexyloctyl group, a 3,7-dimethyloctyl group, a cyclooctyl group, an n-nonyl group, an n-decyl group, an adamantyl group, a 2-ethyldecyl group, a 2-butyldecyl group, a 2-hexyldecyl group, a 2-octyldecyl group, an n-undecyl group, an n-dodecyl group, a 2-ethyldodecyl group, a 2-butyldodecyl group, a 2-hexyldecyl group, a 2-octyldecyl group, an n-tridecyl group, an n-tetradecyl group, an n-pentadecyl group, an n-hexadecyl group, a 2-ethylhexadecyl group, a 2-butylhexadecyl group, a 2-hexylhexadecyl group, a 2-octylhexadecyl group, an n-heptadecyl group, an n-octadecyl group, an n-nonadecyl group, an n-eicosyl group, a 2-ethyleicosyl group, a 2-butyleicosyl group, a 2-hexyleicosyl group, a 2-octyleicosyl group, an n-heneicosyl group, an n-docosyl group, an n-tricosyl group, an n-tetracosyl group, an n-pentacosyl group, an n-hexacosyl group, an n-heptacosyl group, an n-octacosyl group, an n-nonacosyl group, and an n-triacontyl group.

The alkoxy group as a substituent may have any one of a linear shape, a branched shape, and a cyclic shape. The alkyl group constituting the alkoxy group is not particularly limited, and examples thereof may the same as those mentioned in the above description of the alkyl group as a substituent. The number of carbon atoms in the alkoxy group may be, but is not particularly limited to, 1 or more. In addition, the number of carbon atoms in the alkoxy group may be 20 or less, 10 or less, and 4 or less. Examples of the alkoxy group may include, but are not particularly limited to, a methoxy group, an ethoxy group, an n-propyloxy group, an isopropyloxy group, an n-butyloxy group, a sec-butyloxy group, a tert-butyloxy group, an isobutyloxy group, a 2-ethylbutyloxy group, a 3,3-dimethylbutyloxy group, an n-pentyloxy group, an isopentyloxy group, a neopentyloxy group, a tert-pentyloxy group, a cyclopentyloxy group, a 1-methylpentyloxy group, a 3-methylpentyloxy group, a 2-ethylpentyloxy group, a 4-methyl-2-pentyloxy group, an n-hexyloxy group, a 1-methylhexyloxy group, a 2-ethylhexyloxy group, a 2-butylhexyloxy group, a hexyloxy group, a 4-methylcyclohexyloxy group, a 4-tert-butylcyclohexyloxy group, an n-heptyloxy group, a 1-methyl heptyloxy group, a 2,2-dimethylheptyloxy group, a 2-ethylheptyloxy group, a 2-butylheptyloxy group, an n-octyloxy group, a tert-octyloxy group, a 2-ethyloctyloxy group, a 2-butyloctyloxy group, a 2-hexyloctyloxy group, a 3,7-dimethyloctyloxy group, a cyclooctyloxy group, an n-nonyloxy group, an n-decyloxy group, and an adamantyloxy group.

The aryloxy group as a substituent is not particularly limited. The number of carbon atoms in the aryloxy group may be, but is not particularly limited to, 6 or more and 30 or less. The number of carbon atoms in the aryloxy group may be 6 or more and 12 or less, and may be 6. Examples of the aryloxy group may include, but are not particularly limited to, a phenyloxy group, a biphenyloxy group, a terphenyloxy group, a naphthyloxy group, a fluorenyloxy group, an anthracenyloxy group, a quaterphenyloxy group, a pentaphenyloxy group, a triphenylenyloxy group, a pyrenyloxy group, a benzofluorenyloxy group, a chrysenyloxy group, and a combination thereof.

The heteroaryloxy group as a substituent is not particularly limited. A heteroaryl group constituting the heteroaryloxy group is not particularly limited, and examples thereof may be the same as those mentioned in the above description of the heteroaryl group. The number of ring-forming atoms in the heteroaryloxy group may be, but is not particularly limited to, 5 or more and 30 or less. In addition, the number of ring-forming atoms in the heteroaryloxy group may be 5 or more and 14 or less, and may be 5 or more and 13 or less. The number of heteroatoms as ring-forming atoms in the heteroaryloxy group may be, but is not particularly limited to, 1 or more and 3 or less. In addition, the number of heteroatoms as ring-forming atoms in the heteroaryloxy group may be 1 or more and 2 or less, and may be 1. Examples of the heteroaryloxy group may include, but are not particularly limited to, a thiophenyloxy group, a furanyloxy group, a pyrrolyloxy group, an imidazolyloxy group, a thiazolyloxy group, an oxazolyloxy group, an oxadiazolyloxy group, a triazolyloxy group, a pyridyloxy group, a bipyridyloxy group, a pyrimidyloxy group, a triazinyloxy group, a triazolyloxy group, an acridinyloxy group, a pyridazinyloxy group, a quinolinyloxy group, a quinazolinyloxy group, a quinoxalinyloxy group, a phenoxazinyloxy group, a phthalazinyloxy group, a pyridopyrimidinyloxy group, a pyridopyrazinyloxy group, a pyrazinopyridazinyloxy group, an isoquinolinyloxy group, an indolyloxy group, a carbazolyloxy group, a benzoxazolyloxy group, a benzimidazolyloxy group, a benzothiazolyloxy group, a benzocarbazolyloxy group, a benzothiophenyloxy group, a dibenzothiophenoxy group, a thienothiophenylethyloxy group, a benzofuranyloxy group, a phenanthrolinyloxy group, a thiazolyloxy group, an isoxazolyloxy group, an oxadiazolyloxy group, a thiadiazolyloxy group, a phenothiazinyloxy group, a dibenzosilolyloxy group, a dibenzofuranyloxy group, a xanthonyloxy group, and a combination thereof.

Heterocyclic Compound

A heterocyclic compound according to an embodiment of the disclosure may be represented by Formula 1:

Formula 1

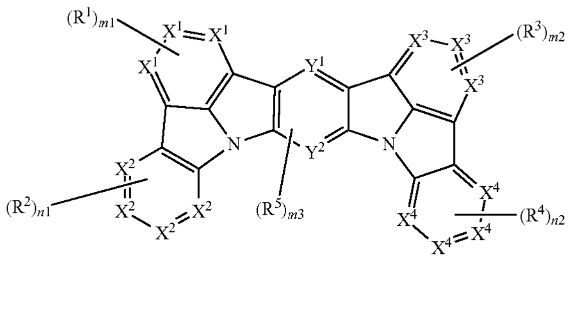

wherein, in Formula 1, $X^1$, $X^2$, $X^3$, and $X^4$ may each independently be C or N, and at least one of three $X^1$(s), four $X^2$(s), three $X^3$(s), and four $X^4$(s) may be N, $Y_1$ and $Y_2$ may each independently be C or N, $R^1$, $R^2$, $R^3$, and $R^4$ may each independently be a hydrogen atom, a deuterium atom, a halogen atom, a substituted or unsubstituted aryl group having 6 to 14 ring-forming atoms, a substituted or unsubstituted heteroaryl group having 5 to 14 ring-forming atoms, a substituted or unsubstituted amino group, a substituted or unsubstituted arylamino group having 6 to 14 ring-forming atoms, a substituted or unsubstituted heteroarylamino group having 5 to 14 ring-forming atoms, or a substituted or unsubstituted arylboranyl group having 6 to 14 ring-forming atoms, $R^5$ may be a hydrogen atom, a deuterium atom, a halogen atom, a substituted or unsubstituted aryl group having 6 to 14 ring-forming atoms, a substituted or unsubstituted heteroaryl group having 5 to 14 ring-forming atoms, a substituted or unsubstituted amino group, a substituted or unsubstituted arylamino group having 6 to 14 ring-forming atoms, a substituted or unsubstituted heteroarylamino group having 5 to 14 ring-forming atoms, a substituted or unsubstituted indolo[3,2,1-jk]carbazolyl group, or $—R^{51}—R^{52}$, $R^{51}$ may be a substituted or unsubstituted arylene group having 6 to 14 ring-forming atoms or a substituted or unsubstituted heteroarylene group having 5 to 14 ring-forming atoms, $R^{52}$ may be a substituted or unsubstituted amino group, a substituted or unsubstituted arylamino group having 6 to 14 ring-forming atoms, a substituted or unsubstituted hetero arylamino group having 5 to 14 ring-forming atoms, or a substituted or unsubstituted heteroaryl group having 5 to 14 ring-forming atoms, n1 and n2 may each independently be 1, 2, or 3, m1 and m2 may each independently be 1 or 2, and m3 may be 0, 1, or 2.

For example, in Formula 1, $Y^1$ and $Y^2$ may each be C; $Y^1$ may be N, and $Y^2$ may be C; $Y^1$ may be C, and $Y^2$ may be N; or $Y^1$ and $Y^2$ may each be N.

For example, $R^1$, $R^2$, $R^3$, and $R^4$ in Formula 1 may each independently be a hydrogen atom, a substituted or unsubstituted phenyl group, a substituted or unsubstituted pyridyl group, a substituted or unsubstituted biphenylboranyl group, or a monovalent group represented by Formula B1. When these substituents are substituted, a substituent may be an alkyl group having 1 or more and 6 or less carbon atoms, and for example, may be a tert-butyl group:

B1

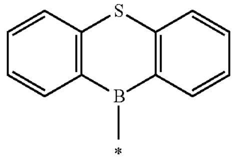

wherein, in Formula B1, * indicates a binding site to a neighboring atom.

When $R^1$, $R^2$, $R^3$, and $R^4$ in Formula 1 are not each a hydrogen atom, $R^1$, $R^2$, $R^3$ and $R^4$ may be the same group as each other.

For example, in Formula 1, at least one of $X^1$(s) may be N, at least one of $X^2$(s) may be N, at least one of $X^3$(s) may be N, and at least one of $X^4$(s) may be N.

In an embodiment, in Formula 1, at least one of $X^2$(s) may be N, at least one of $X^3$(s) may be N, and at least one of $X^4$(s) may be N; at least one of $X^1$(s) may be N, at least one of $X^2$(s) may be N, and at least one of $X^3$(s) may be N; at least one of $X^1$(s) may be N, and at least one of $X^3$(s) may be N; at least one of $X^2$(s) may be N, and at least one of $X^4$(s) may be N; at least one of $X^2$(s) may be N, and at least one of $X^3$(s) may be N; at least one of $X^1$(s) may be N, and at least one of $X^2$(s) may be N; at least one of $X^4$(s) may be N; or at least one of $X^3$(s) may be N.

In an embodiment, in Formula 1, one of $X^1$(s) may be N, one of $X^2$(s) may be N, one of $X^3$(s) may be N, and one of $X^4$(s) may be N.

In particular, in Formula 1, one of $X^2$(s) may be N, one of $X^3$(s) may be N, and one of $X^4$(s) may be N; one of $X^1$(s) may be N, one of $X^2$(s) may be N, and one of $X^3$(s) may be N; one of $X^1$(s) may be N, and one of $X^3$(s) may be N; one of $X^2$(s) may be N, and one of $X^4$(s) may be N; one of $X^2$(s) may be N, and one of $X^3$(s) may be N; one of $X^1$(s) may be N, and one of $X^2$(s) may be N; one of $X^4$(s) may be N; or one of $X^3$(s) may be N.

For example, in Formula 1, n1 and n2 may each be 3, and m1 and m2 may each be 2.

In an embodiment, in Formula 1, when two of $X^1$(s) and two of $X^3$(s) are each C, and m1 and m2 are each 2, one of $R^1$(s) and one of $R^3$(s) may each be a hydrogen atom, and another one of $R^1$(s) and another one of $R^3$(s) may each be a substituted or unsubstituted phenyl group, a substituted or unsubstituted pyridyl group, a substituted or unsubstituted biphenylboranyl group, or a monovalent group represented by Formula B1.

In one or more embodiments, in Formula 1, when three of $X^2$(s) and three of $X^4$(s) are each C, and n1 and n2 are each 3, two of $R^2$(s) and two of $R^4$(s) may each be a hydrogen atom, and another one of $R^2$(s) and another one of $R^4$(s) may each be a substituted or unsubstituted phenyl group, a substituted or unsubstituted pyridyl group, a substituted or unsubstituted biphenylboranyl group, or a monovalent group represented by Formula B1.

For example, m3 in Formula 1 may be 1 or 2.

For example, in Formula 1, $R^5$ may be a hydrogen atom, a substituted or unsubstituted phenyl group, a substituted or unsubstituted carbazolyl group, a substituted or unsubstituted indolo[3,2,1-jk]carbazolyl group, a substituted or unsubstituted N,N-diphenylamino group, a substituted or unsubstituted phenoxazinyl group, or $—R^{51}—R^{52}$. When $R^5$ is $—R^{51}—R^{52}$, $R^{51}$ may be a phenylene group, and $R^{52}$ may be a substituted or unsubstituted N,N-diphenylamino group or a substituted or unsubstituted phenoxazinyl group. When these groups are substituted, a substituent may be a halogen atom, or for example, a fluorine atom.

In an embodiment, the heterocyclic compound may be represented by one of Formulae 1-1 to 1-324. In Formulae 1-1 to 1-324, when $R^1$ to $R^5$ are essentially hydrogen atoms (that is, $X^1—R^1$, $X^2—R^2$, $X^3—R^3$, $X^4—R^4$, $Y^1—R^5$, and $Y^2—R^5$ are essentially CH), descriptions of $R^1$ to $R^5$ are omitted:

(1-1)

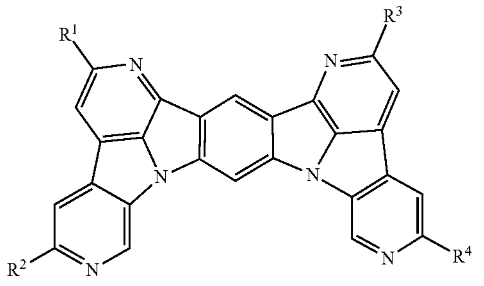

(1-2)

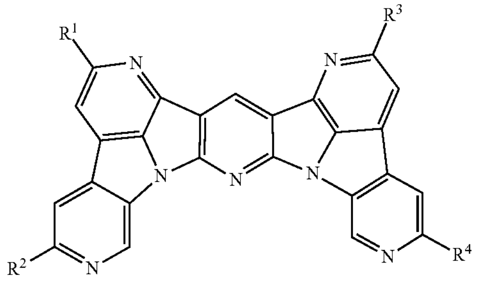

(1-3)

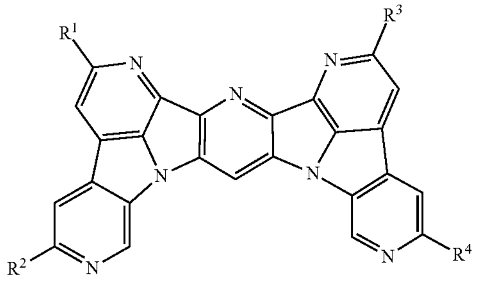

(1-4)

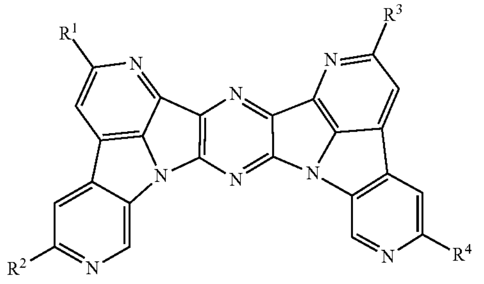

(1-5)

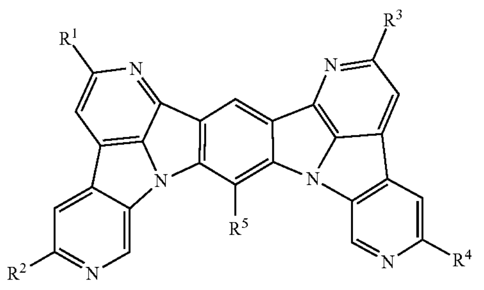

-continued
(1-6)
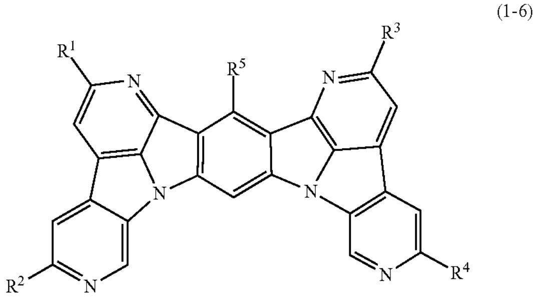
(1-7)
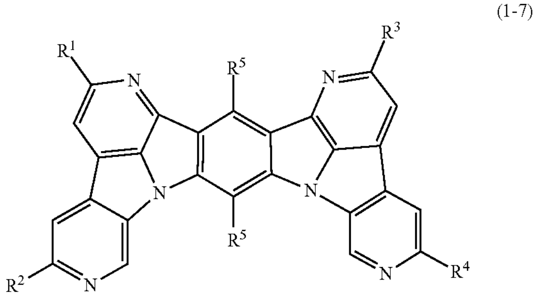
(1-8)
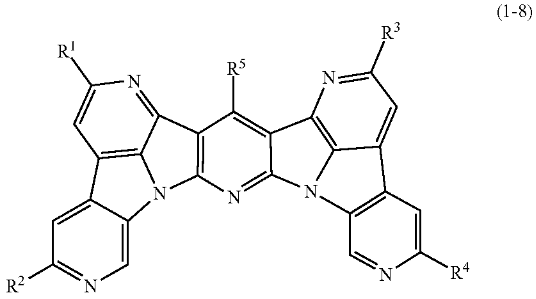
(1-9)
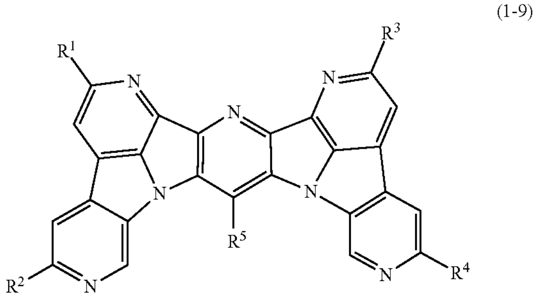
(1-10)
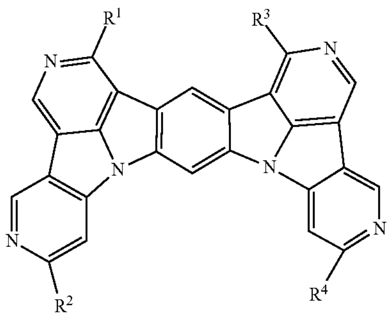
-continued
(1-11)
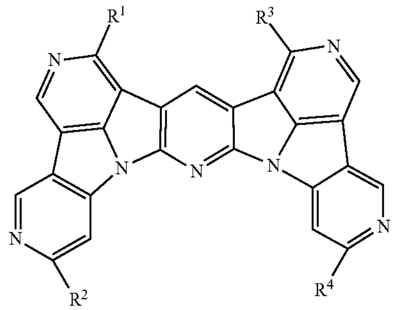
(1-12)
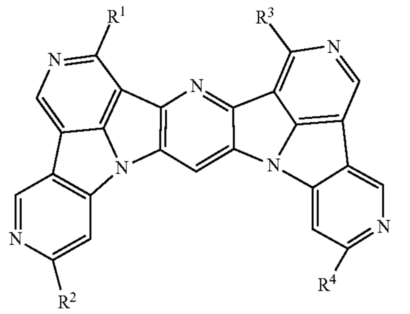
(1-13)
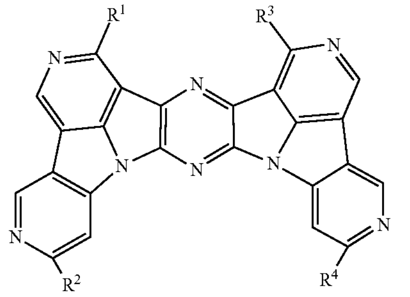
(1-14)
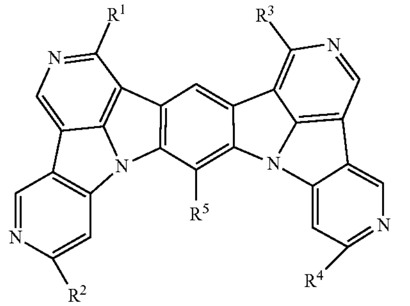
(1-15)
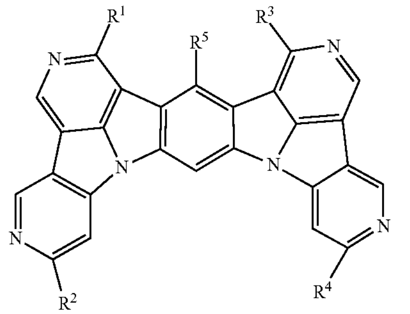

(1-16)
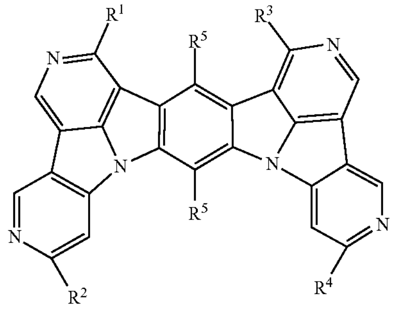
(1-17)
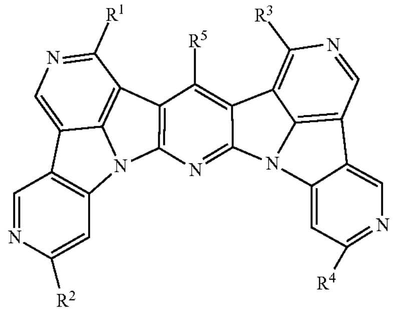
(1-18)
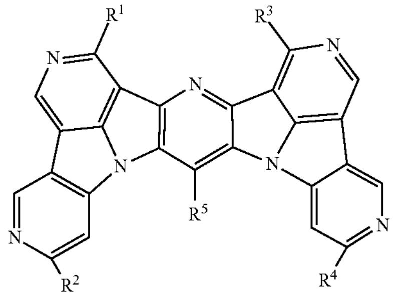
(1-19)
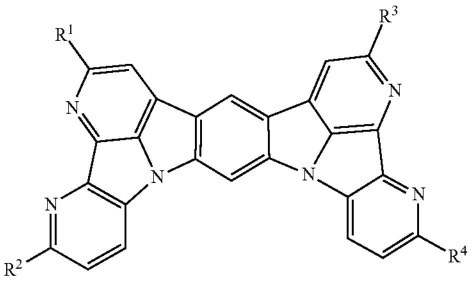
(1-20)
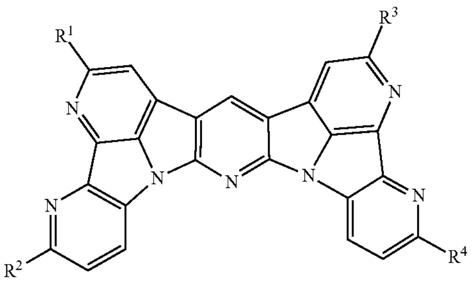
(1-21)
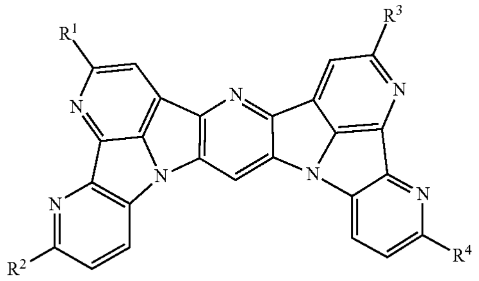
(1-22)
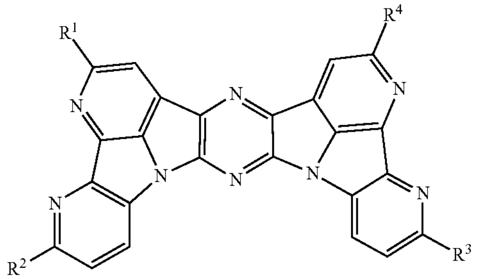
(1-23)
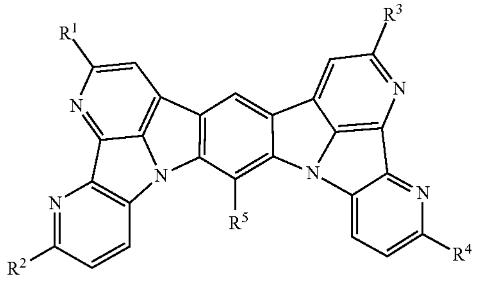
(1-24)
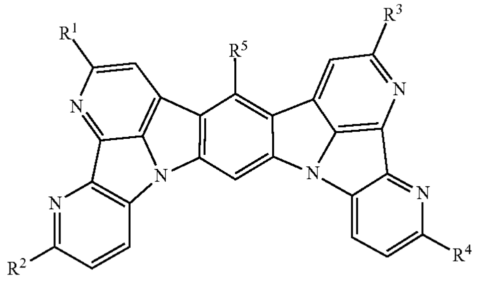
(1-25)
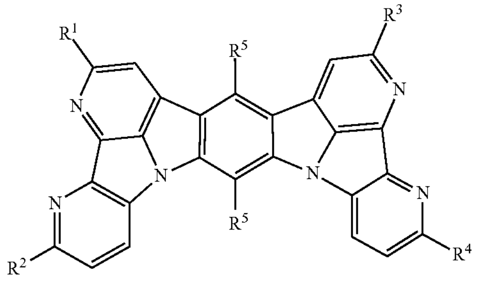

-continued
(1-26)
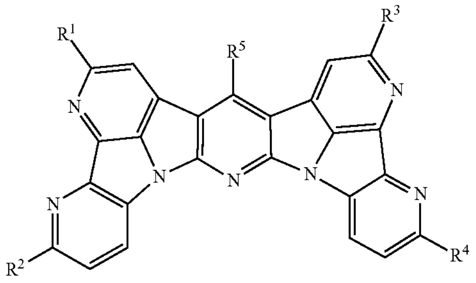
(1-27)
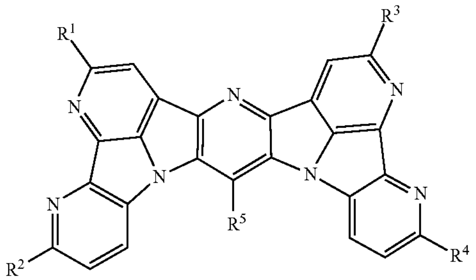
(1-28)
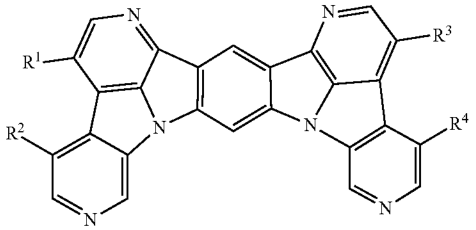
(1-29)
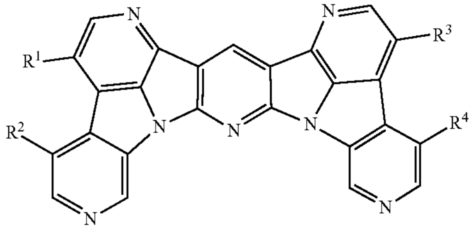
(1-30)
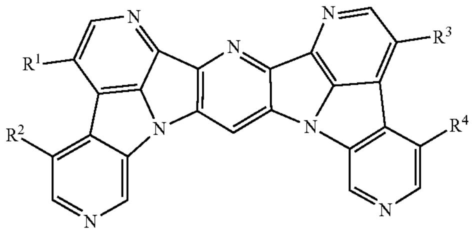
(1-31)
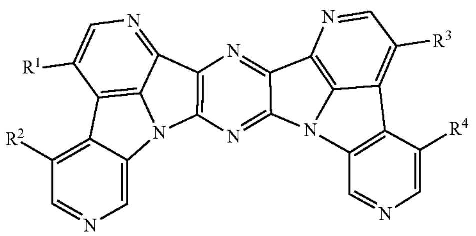
-continued
(1-32)
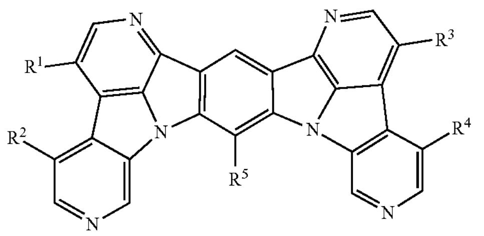
(1-33)
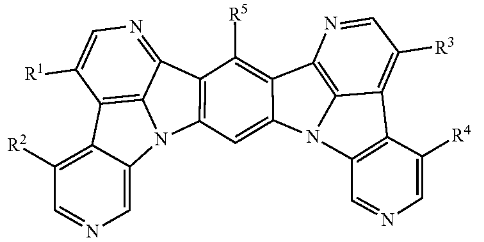
(1-34)
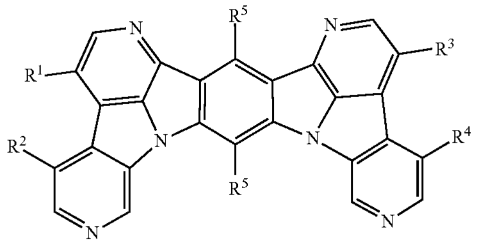
(1-35)
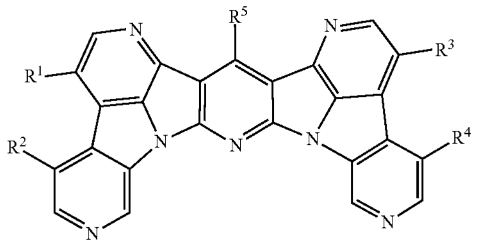
(1-36)
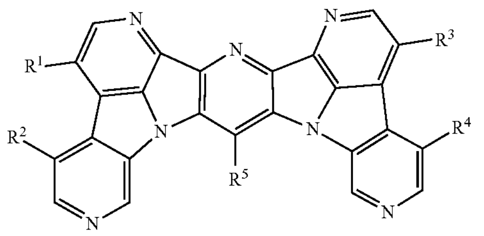
(1-37)
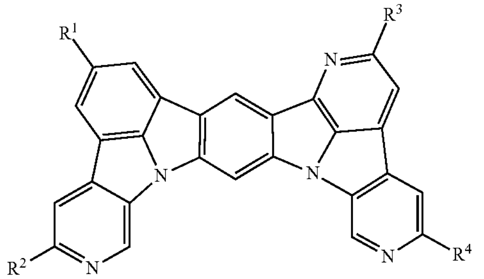

-continued
(1-38)
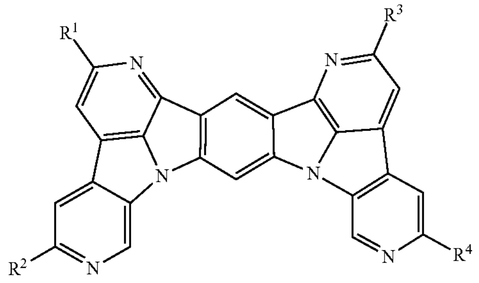
(1-39)
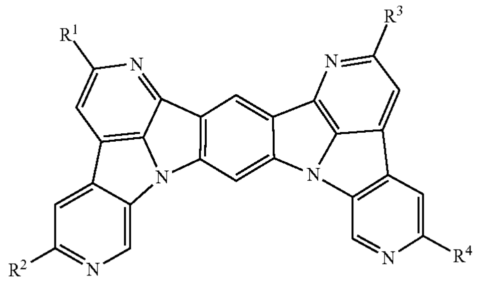
(1-40)
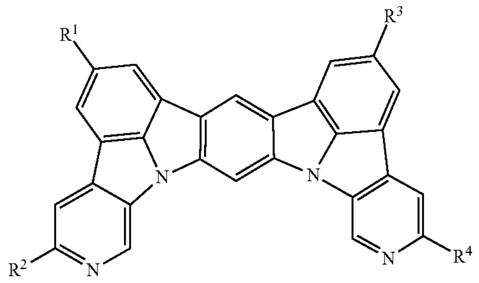
(1-41)
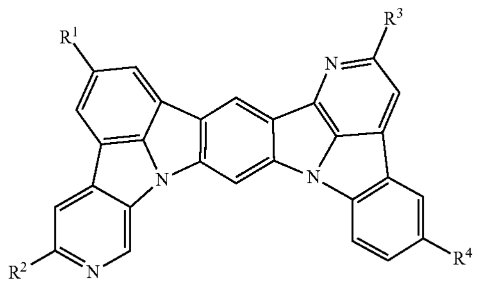
(1-42)
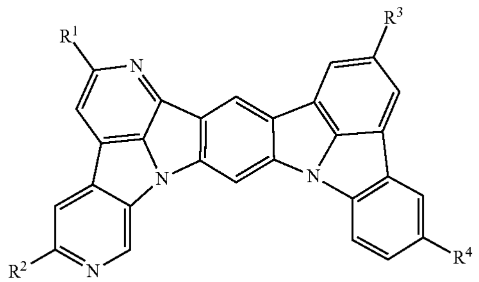
-continued
(1-43)
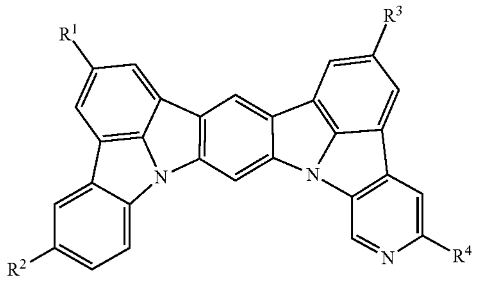
(1-44)
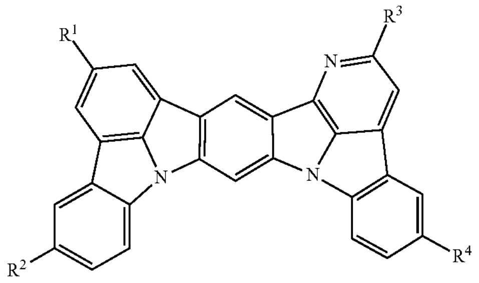
(1-45)
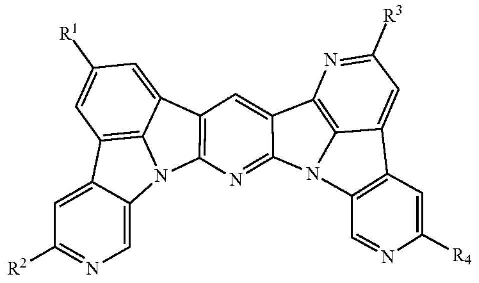
(1-46)
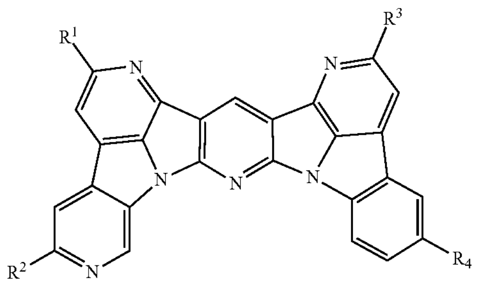
(1-47)
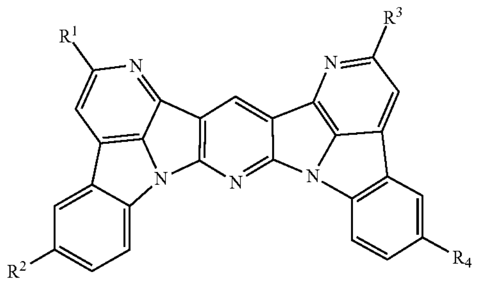

-continued
(1-48)
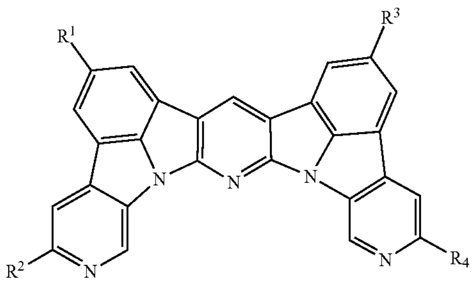
(1-49)
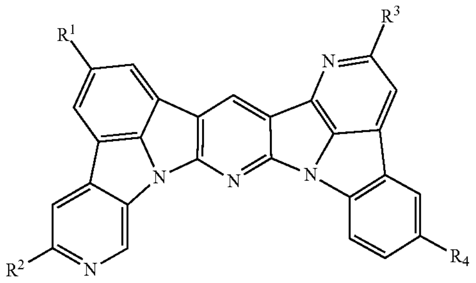
(1-50)
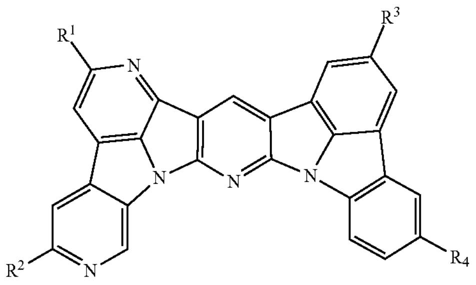
(1-51)
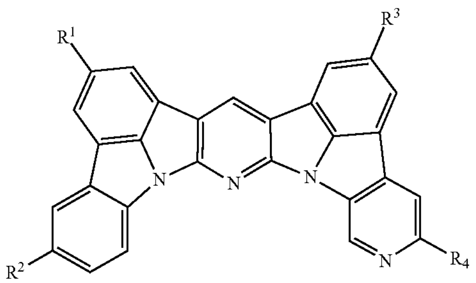
(1-52)
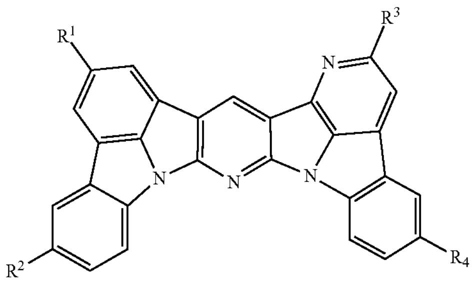
-continued
(1-53)
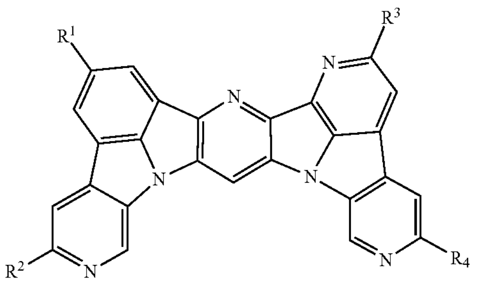
(1-54)
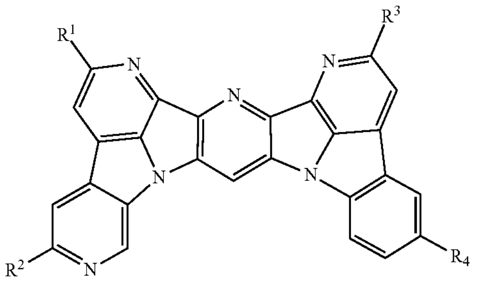
(1-55)
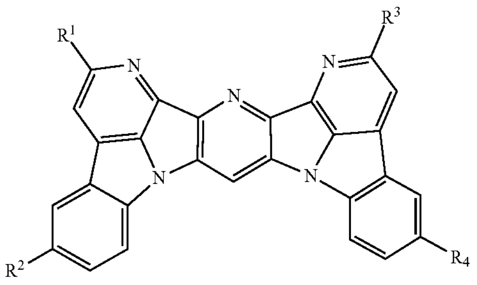
(1-56)
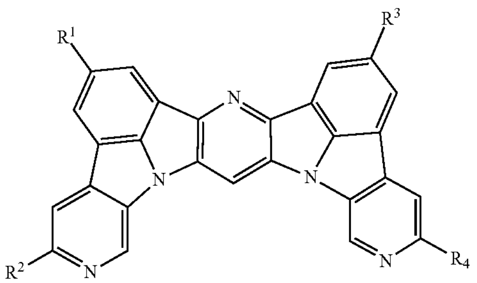
(1-57)
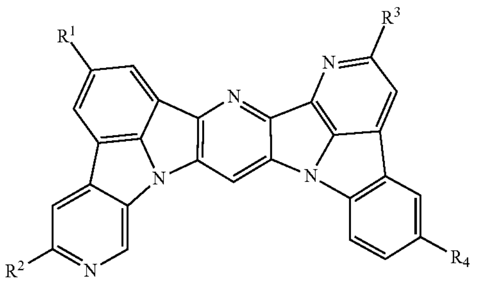

-continued
(1-58)
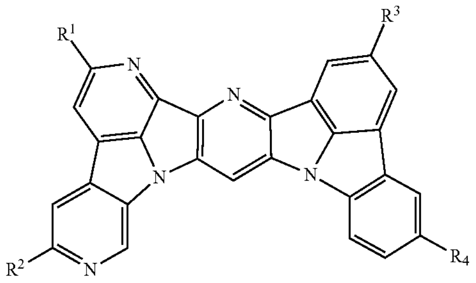
(1-59)
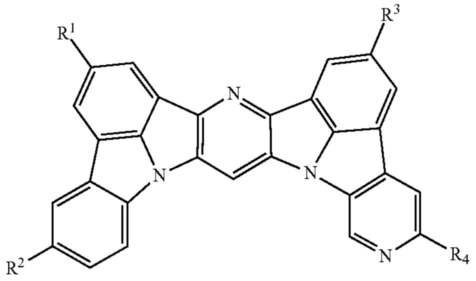
(1-60)
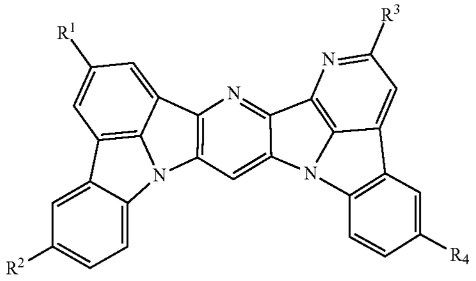
(1-61)
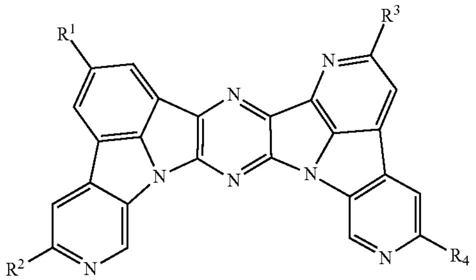
(1-62)
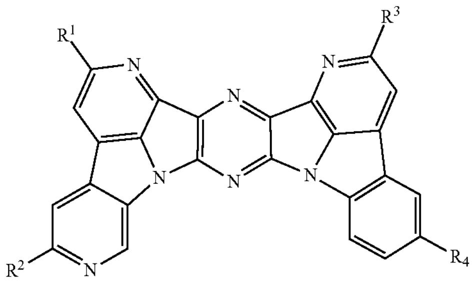
-continued
(1-63)
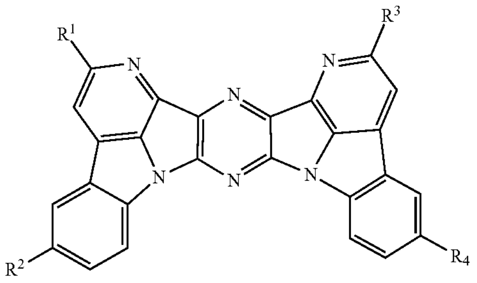
(1-64)
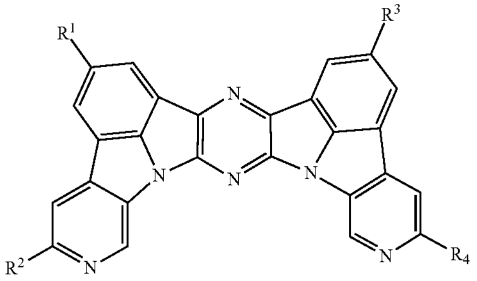
(1-65)
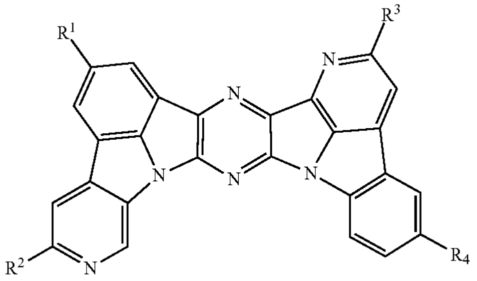
(1-66)
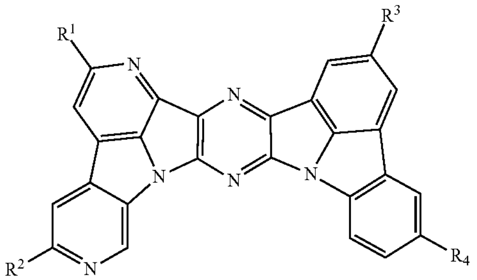
(1-67)
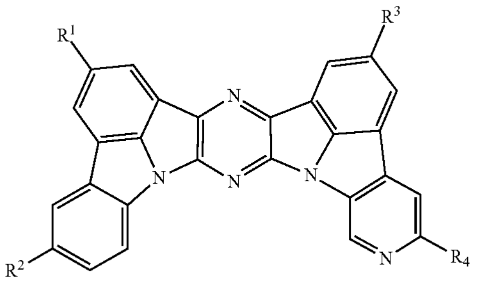

-continued
(1-68)
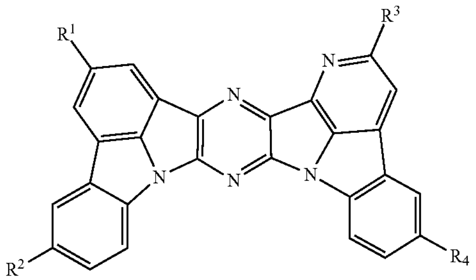
(1-69)
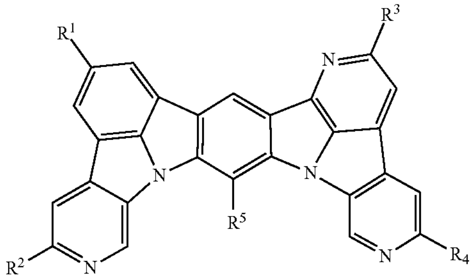
(1-70)
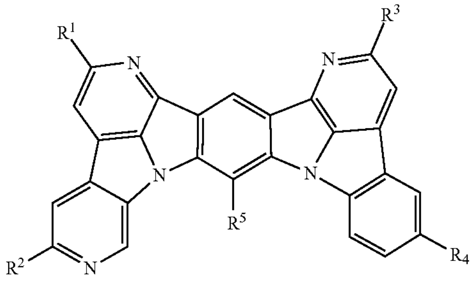
(1-71)
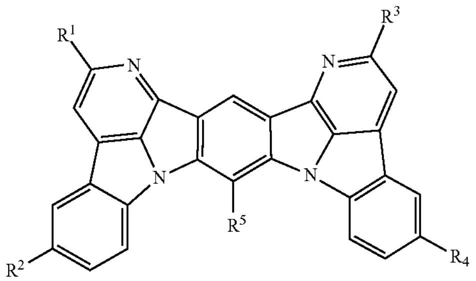
(1-72)
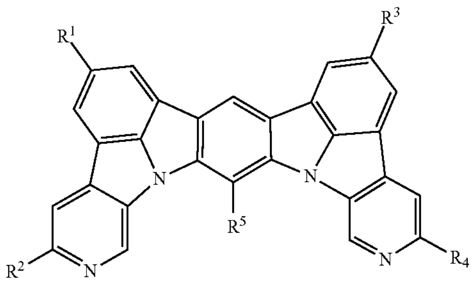
-continued
(1-73)
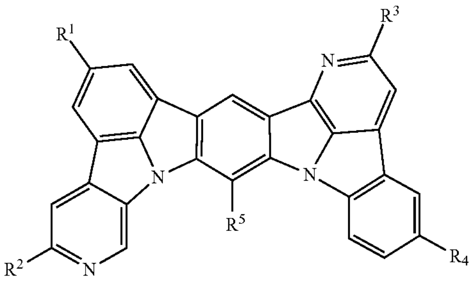
(1-74)
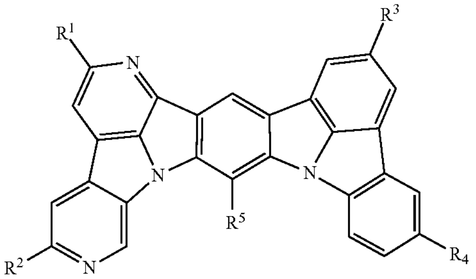
(1-75)
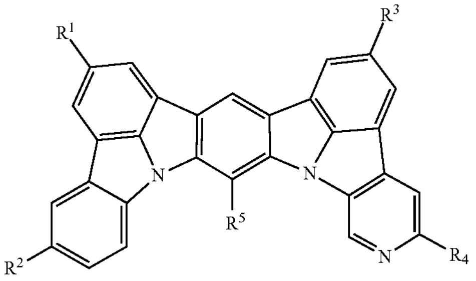
(1-76)
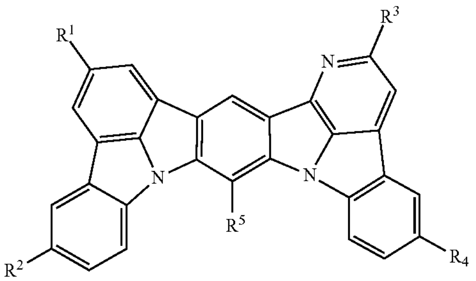
(1-77)
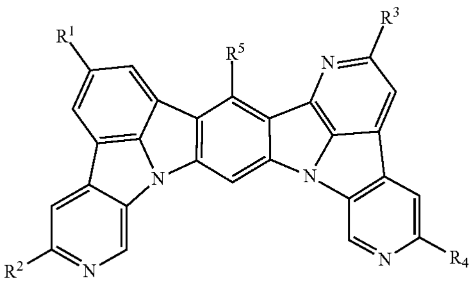

-continued
(1-78)
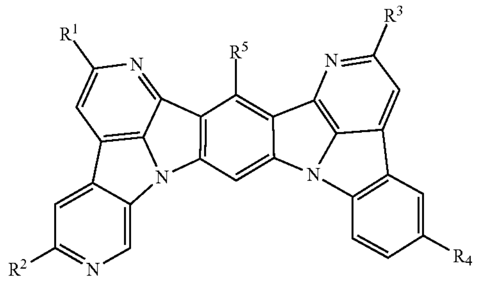
(1-79)
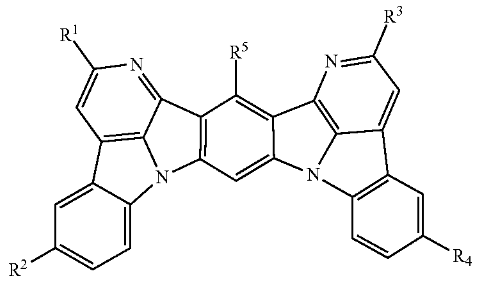
(1-80)
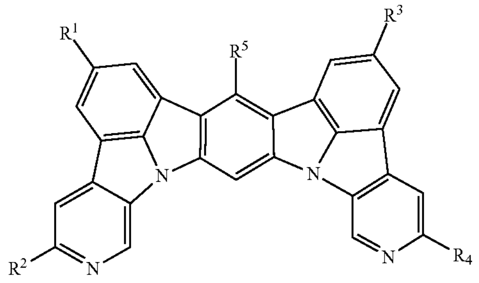
(1-81)
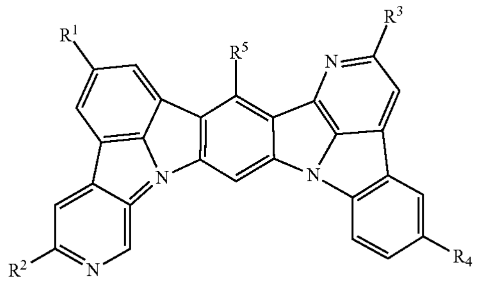
(1-82)
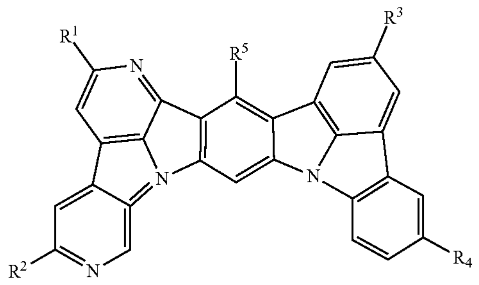
-continued
(1-83)
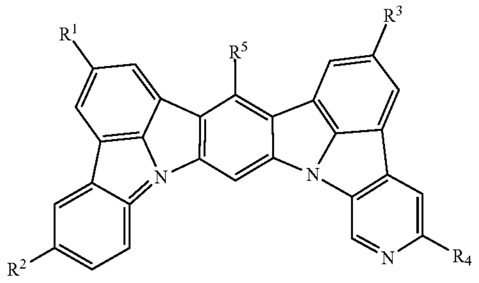
(1-84)
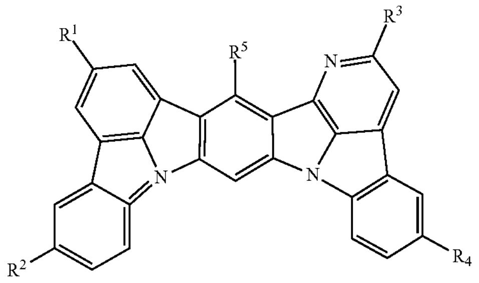
(1-85)
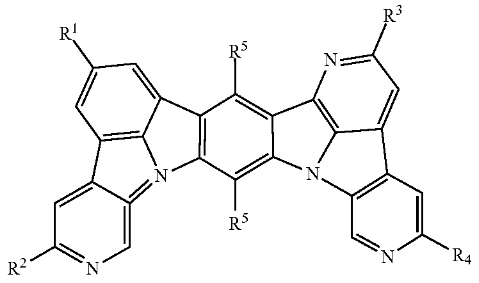
(1-86)
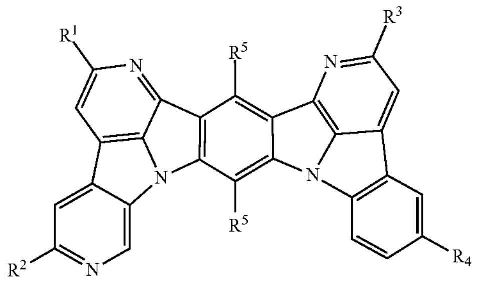
(1-87)
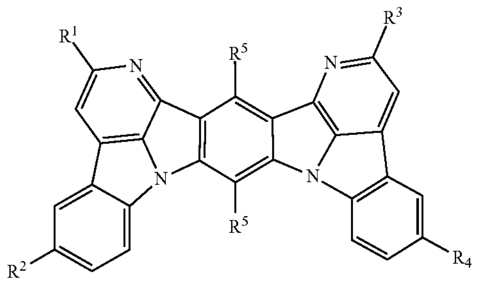

-continued
(1-88)
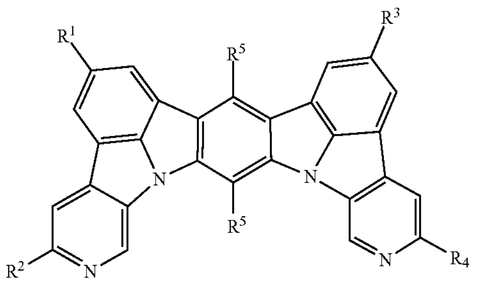
(1-89)
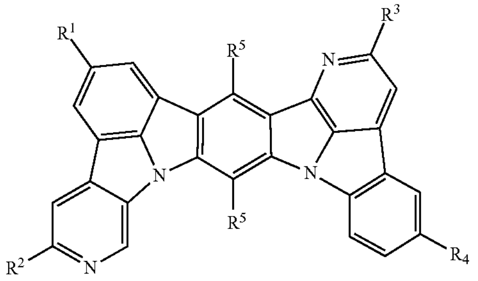
(1-90)
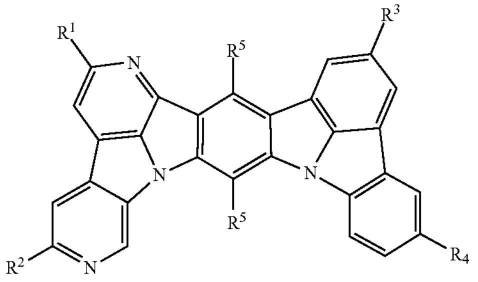
(1-91)
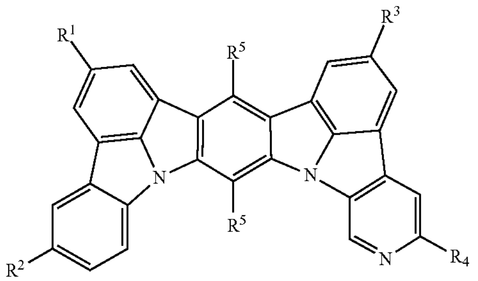
(1-92)
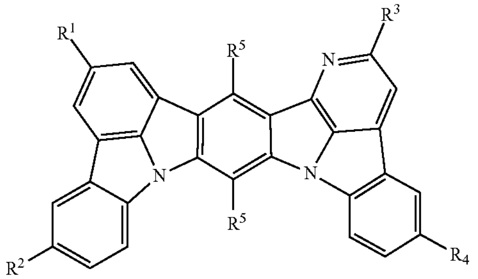
-continued
(1-93)
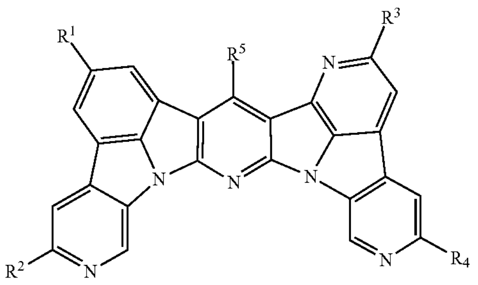
(1-94)
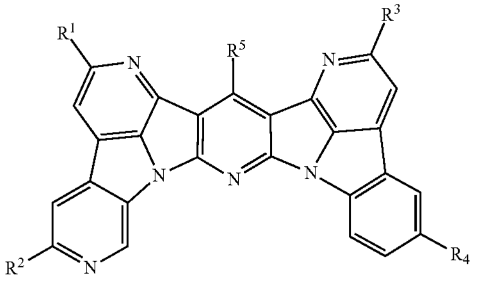
(1-95)
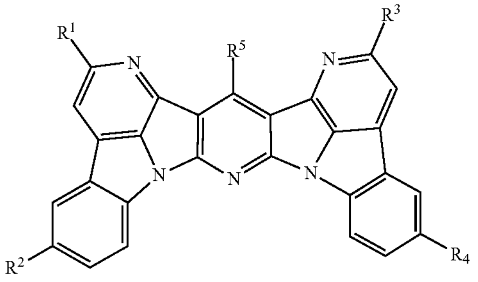
(1-96)
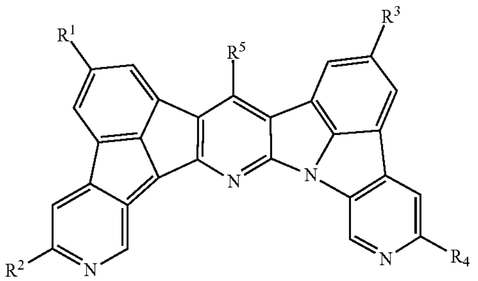
(1-97)
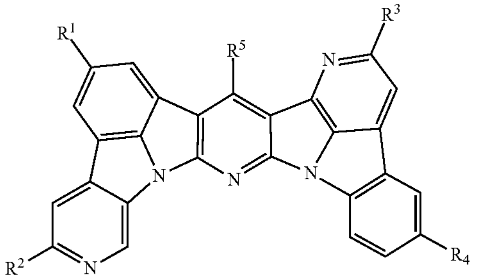

-continued
(1-98)
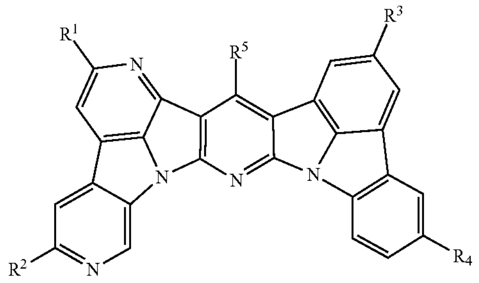
(1-99)
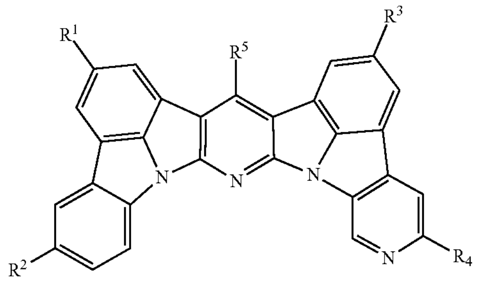
(1-100)
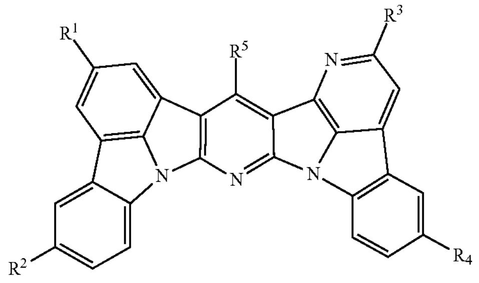
(1-101)
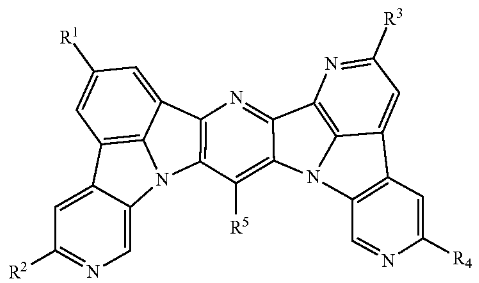
(1-102)
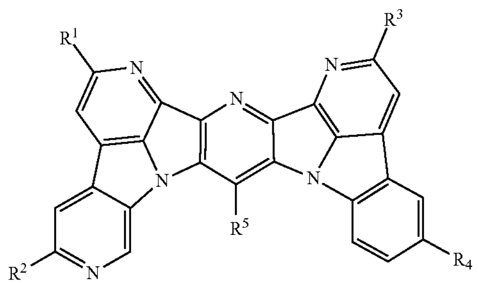
-continued
(1-103)
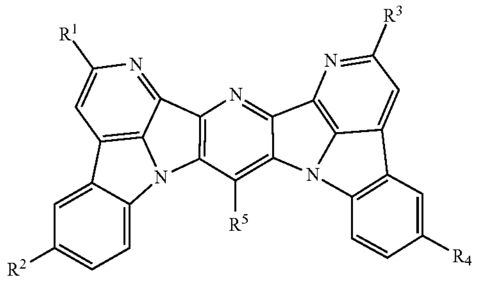
(1-104)
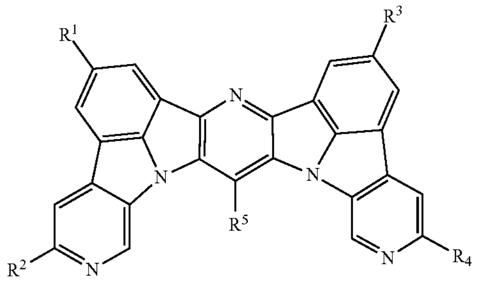
(1-105)
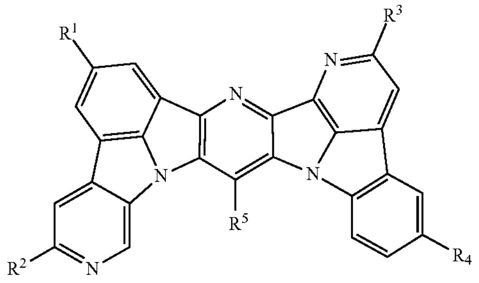
(1-106)
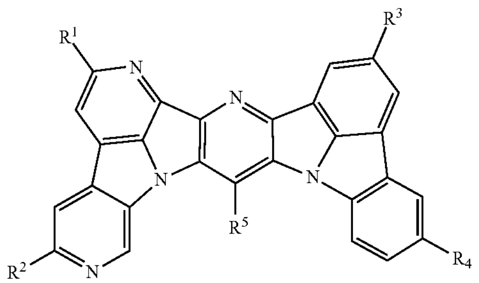
(1-107)
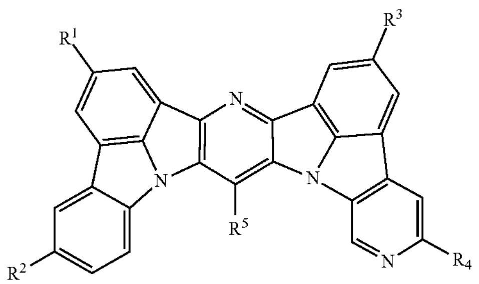

-continued
(1-108)
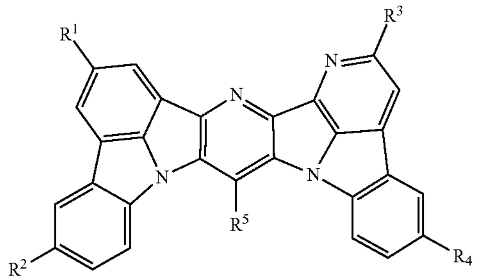
(1-109)
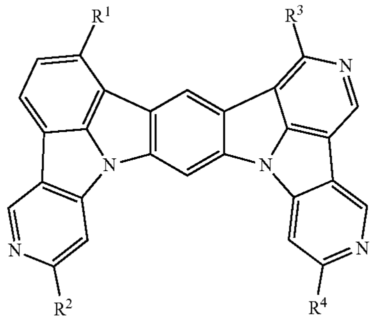
(1-110)
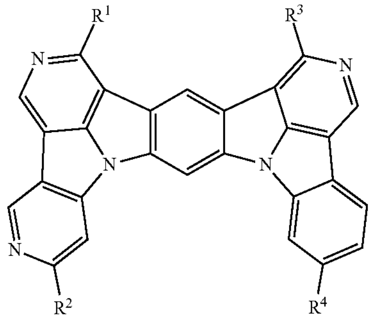
(1-111)
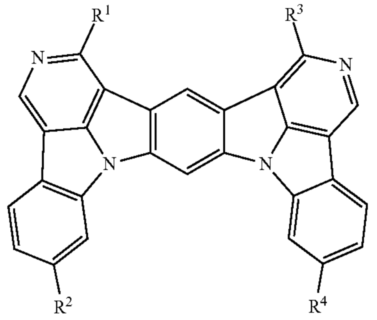
-continued
(1-112)
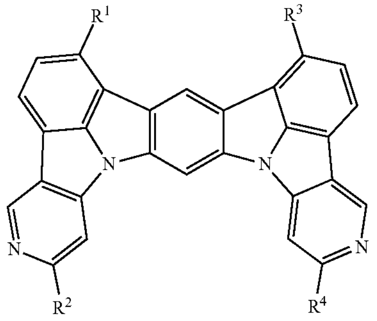
(1-113)
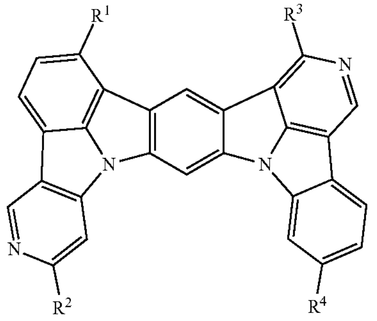
(1-114)
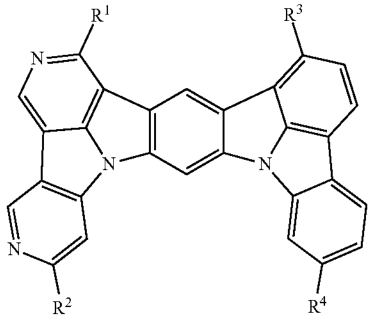
(1-115)
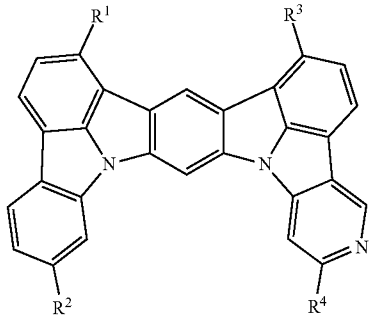
(1-116)
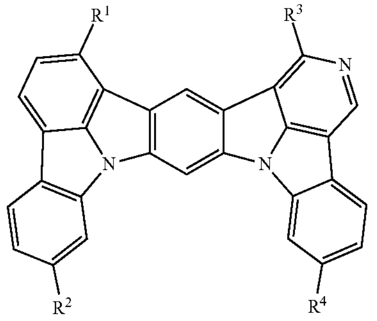

-continued
(1-117)
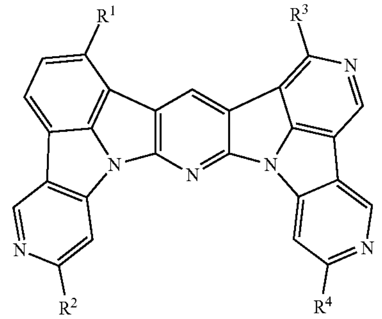
(1-118)
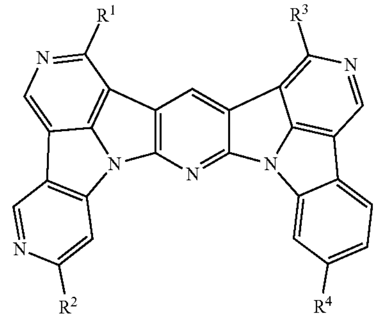
(1-119)
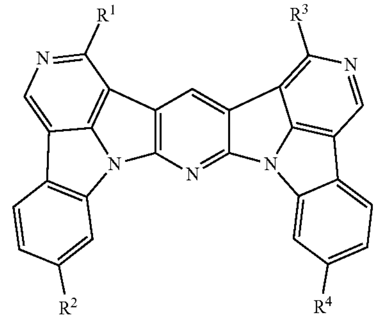
(1-120)
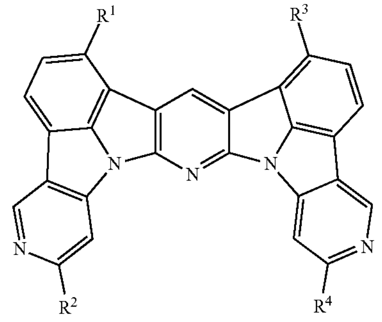
(1-121)
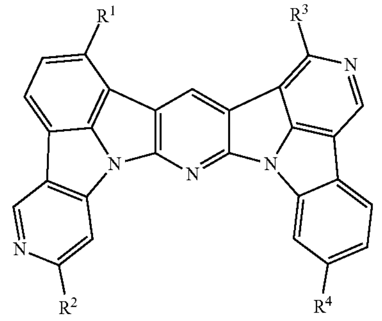
-continued
(1-122)
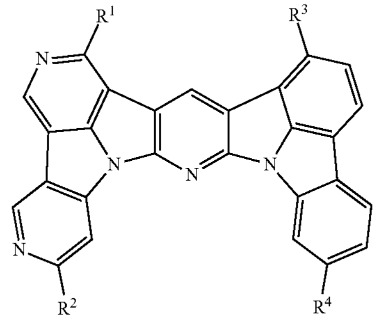
(1-123)
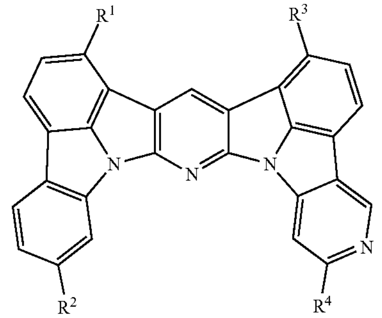
(1-124)
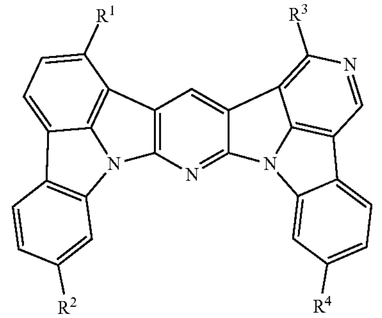
(1-125)
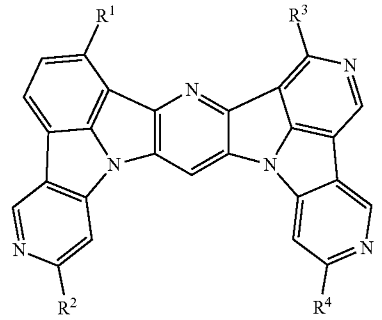
(1-126)
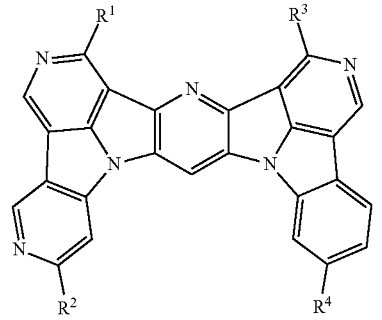

-continued
(1-127)
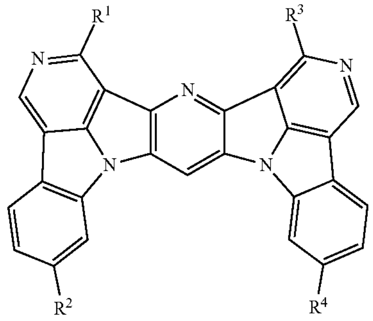
(1-128)
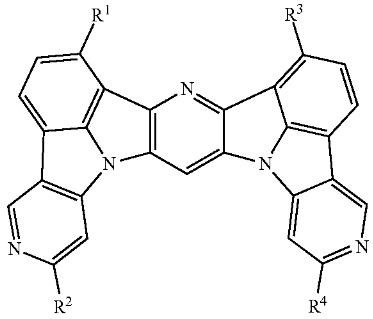
(1-129)
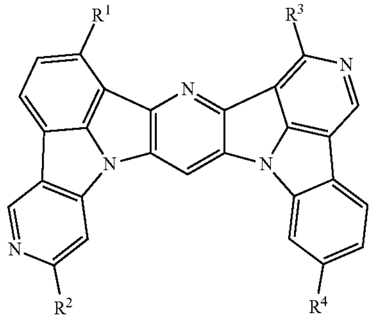
(1-130)
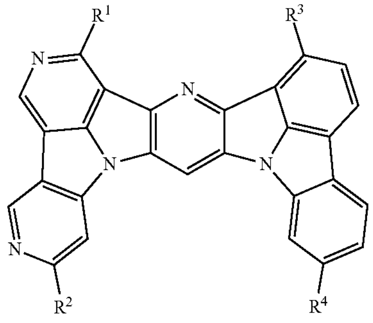
(1-131)
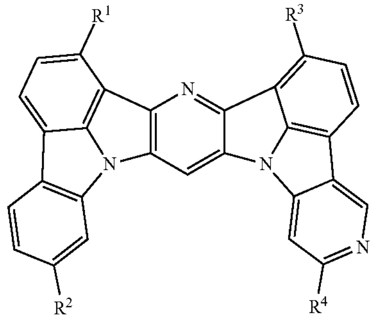
-continued
(1-132)
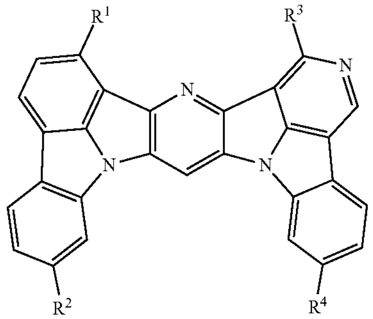
(1-133)
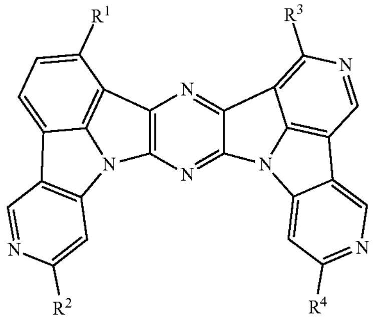
(1-134)
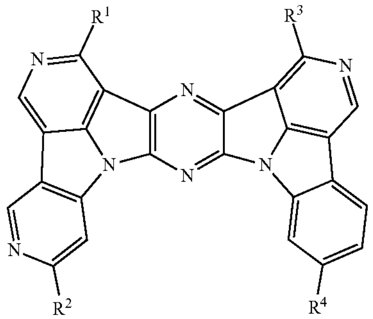
(1-135)
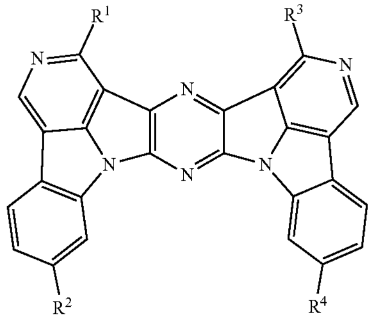
(1-136)
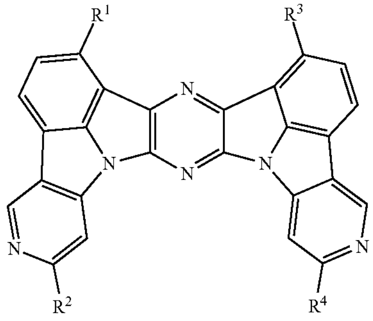

-continued
(1-137)
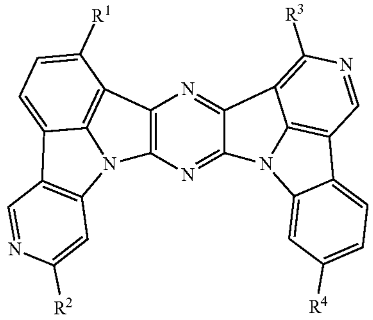
(1-138)
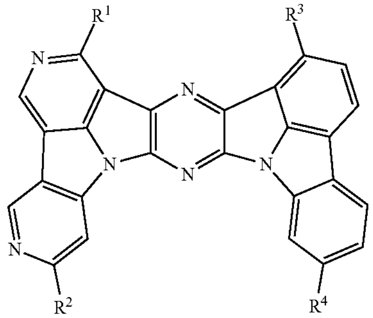
(1-139)
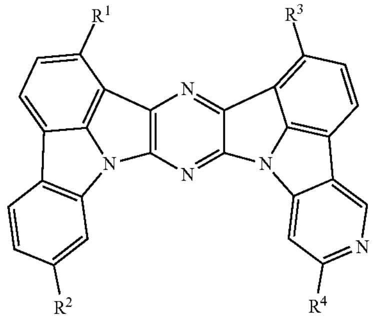
(1-140)
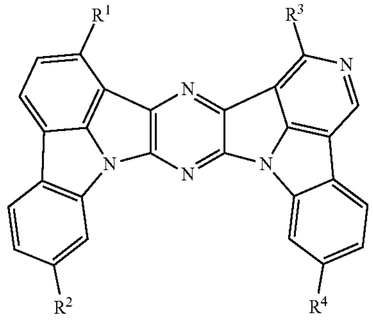
(1-141)
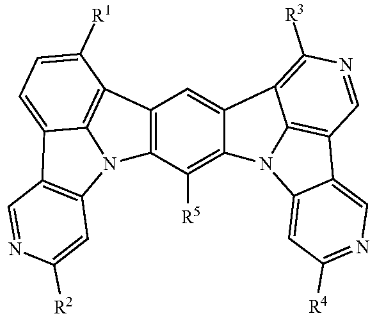
-continued
(1-142)
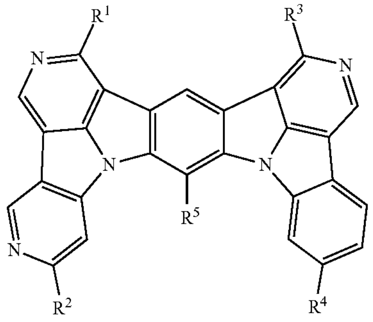
(1-143)
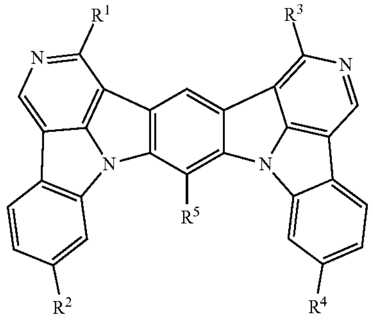
(1-144)
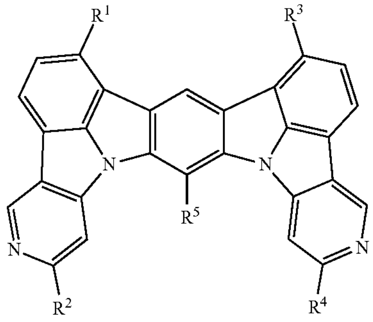
(1-145)
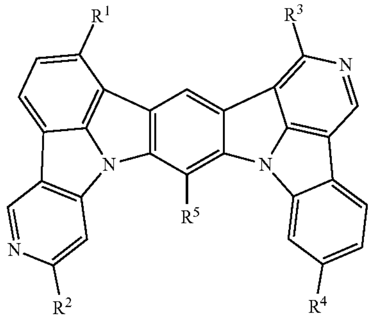
(1-146)
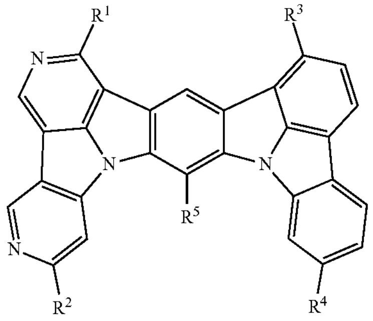

(1-147)
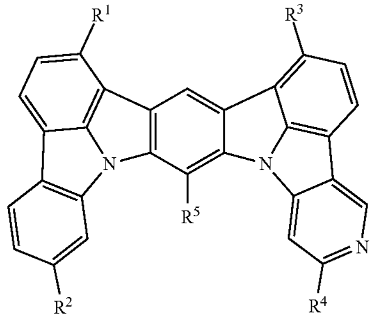
(1-148)
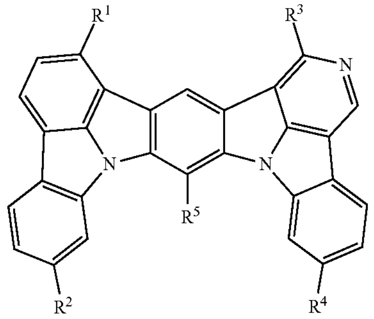
(1-149)
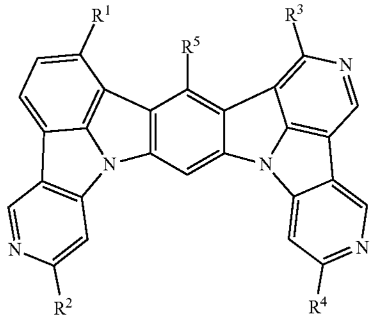
(1-150)
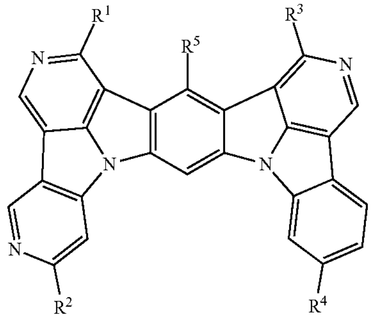
(1-151)
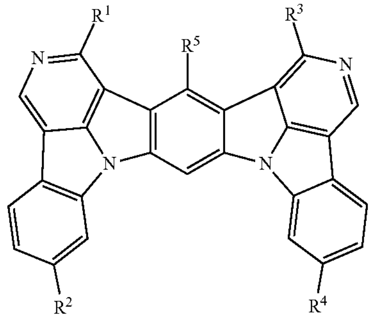
(1-152)
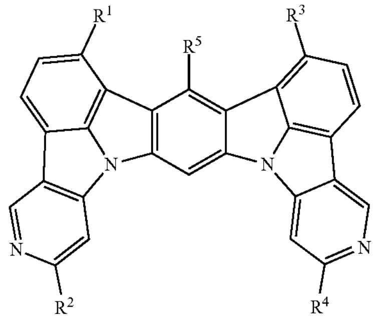
(1-153)
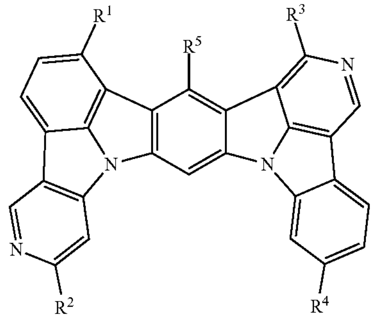
(1-154)
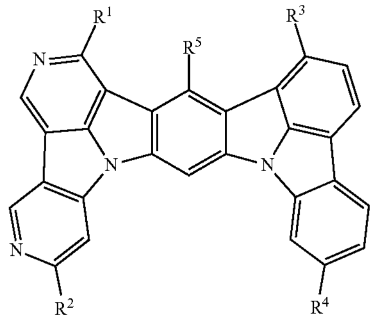
(1-155)
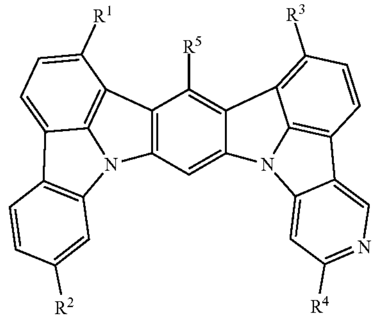
(1-156)
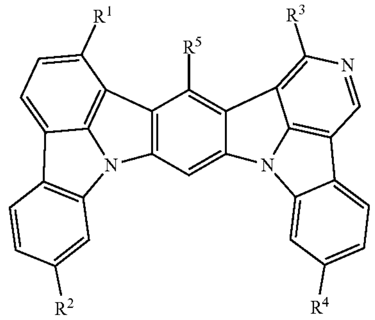

-continued
(1-157)
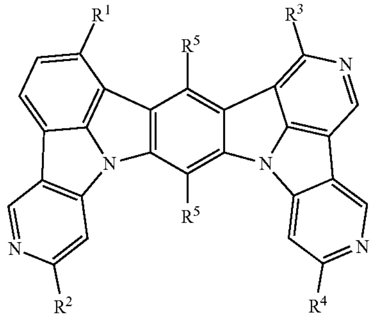
(1-158)
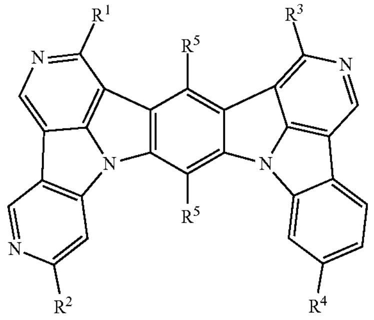
(1-159)
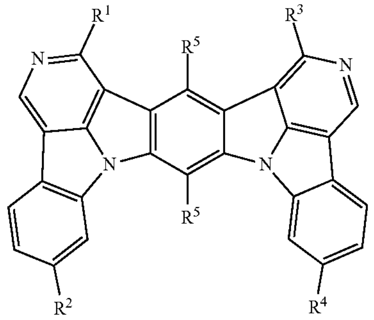
(1-160)
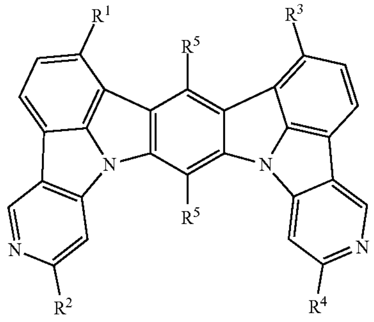
(1-161)
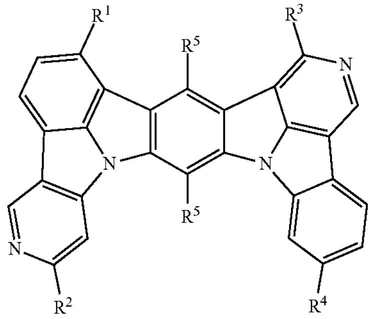
-continued
(1-162)
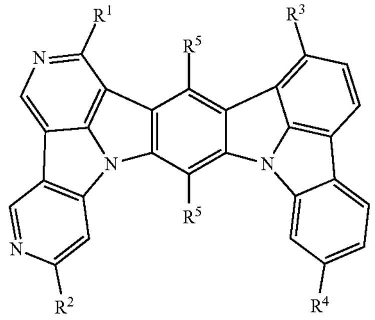
(1-163)
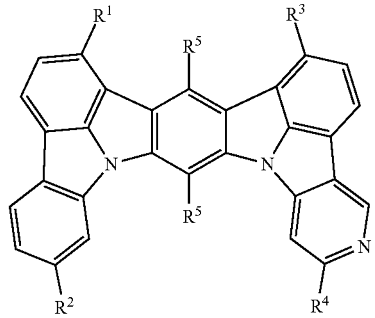
(1-164)
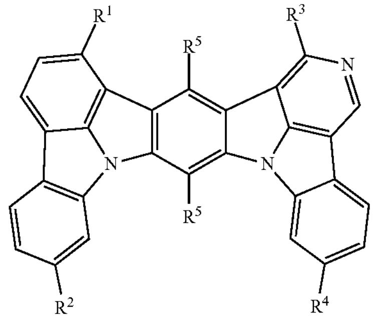
(1-165)
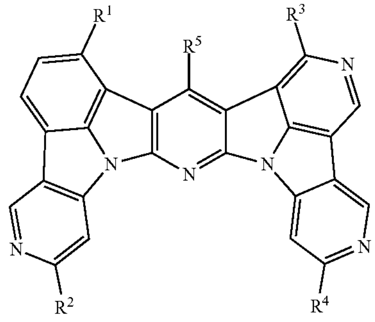
(1-166)
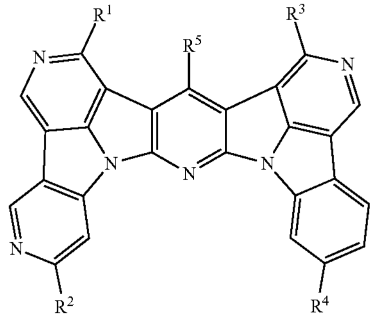

-continued
(1-167)
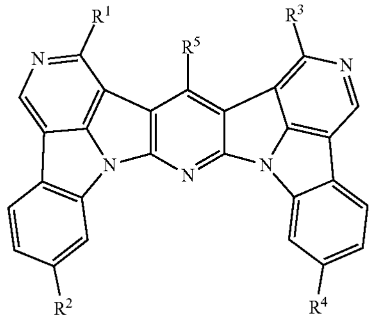
(1-168)
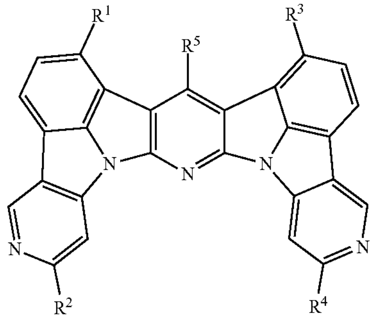
(1-169)
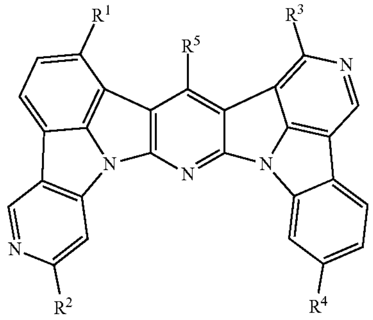
(1-170)
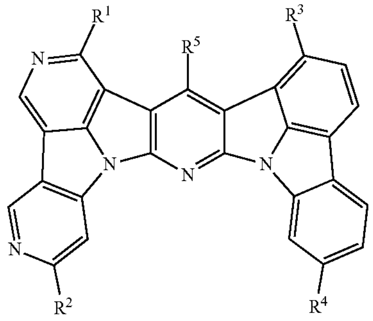
(1-171)
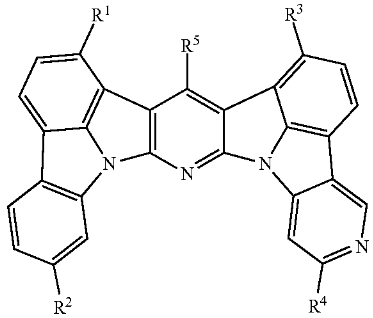
-continued
(1-172)
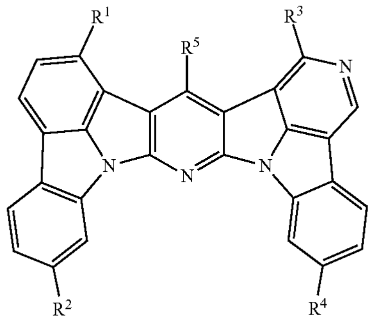
(1-173)
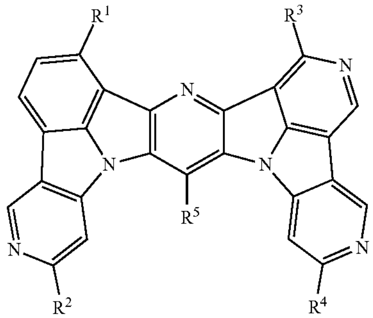
(1-174)
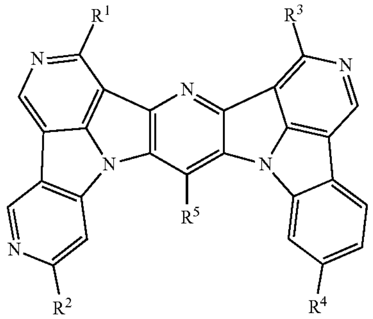
(1-175)
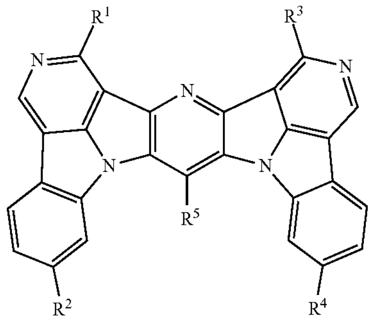
(1-176)
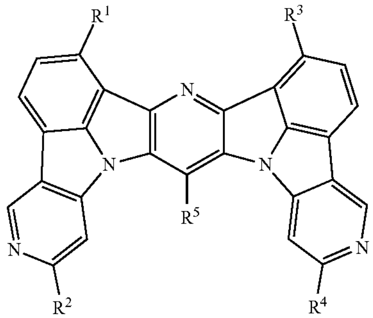

-continued
(1-177)
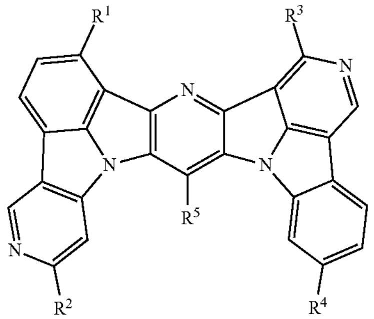
(1-178)
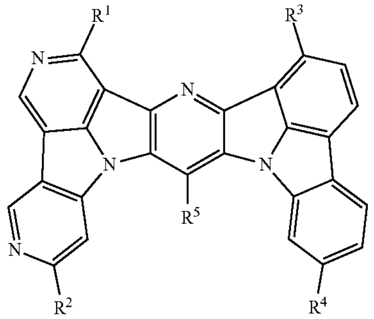
(1-179)
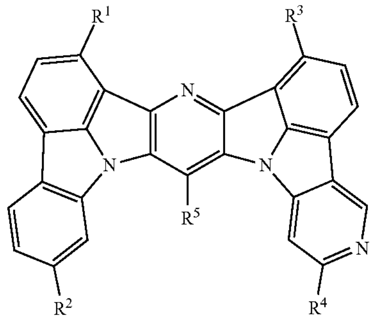
(1-180)
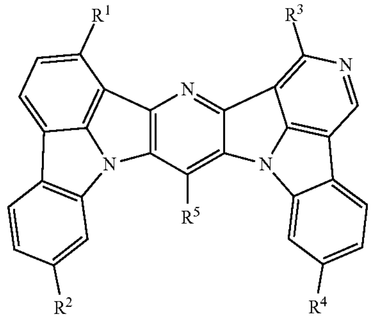
(1-181)
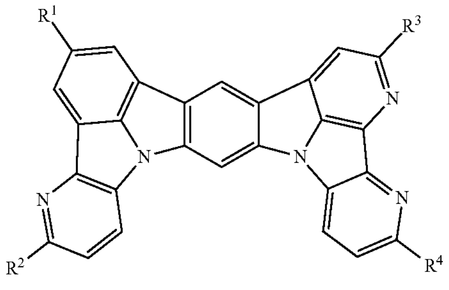
-continued
(1-182)
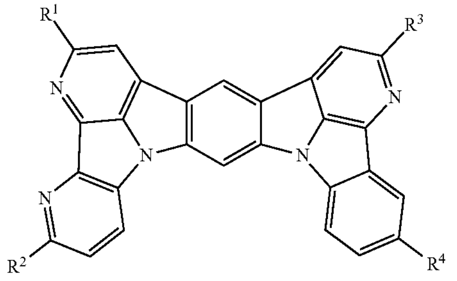
(1-183)
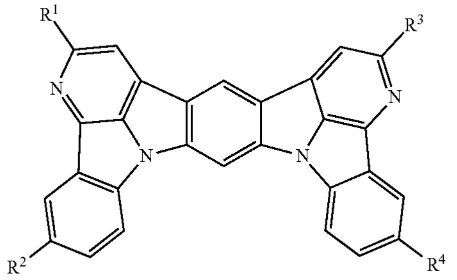
(1-184)
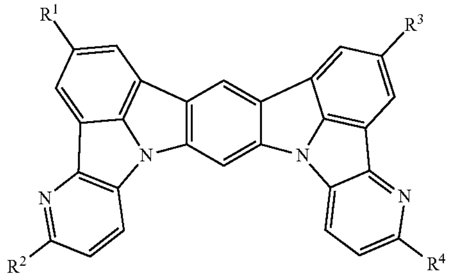
(1-185)
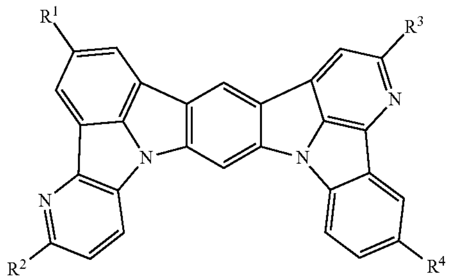
(1-186)
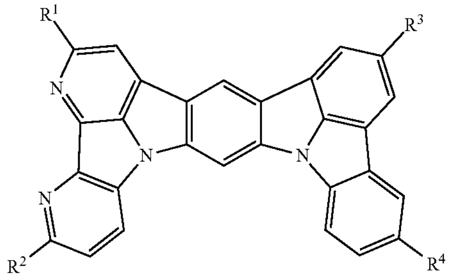

-continued
(1-187)
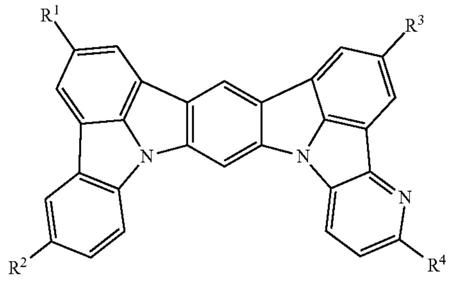
(1-188)
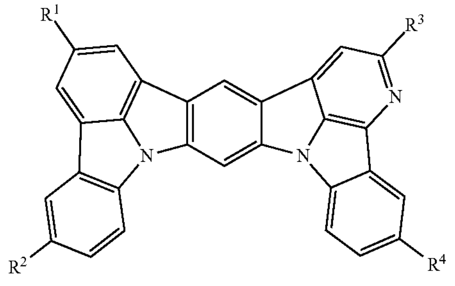
(1-189)
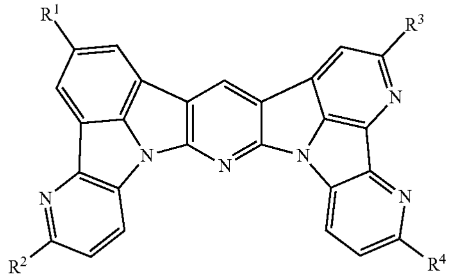
(1-190)
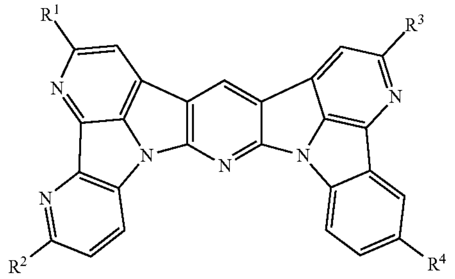
(1-191)
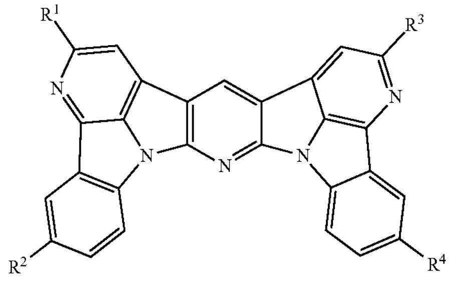
-continued
(1-192)
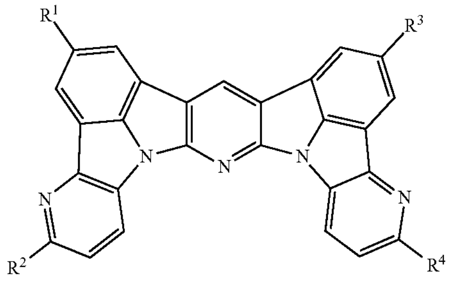
(1-193)
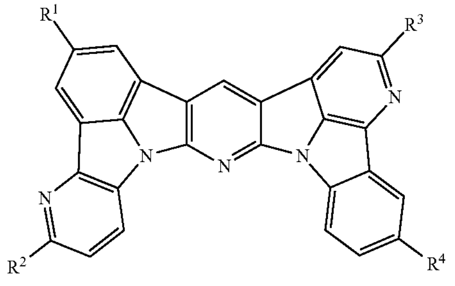
(1-194)
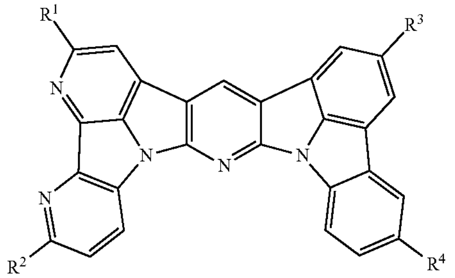
(1-195)
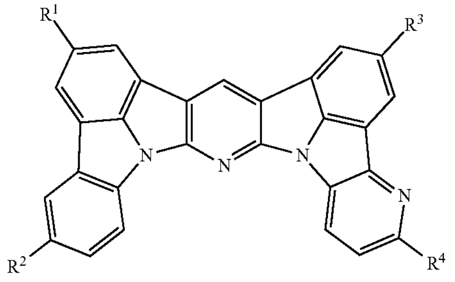
(1-196)
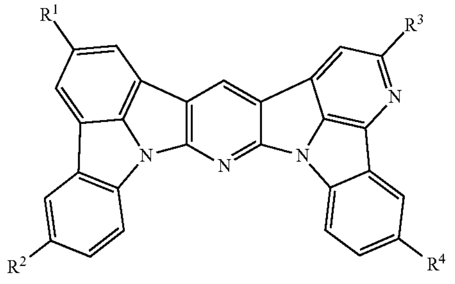

-continued
(1-197)
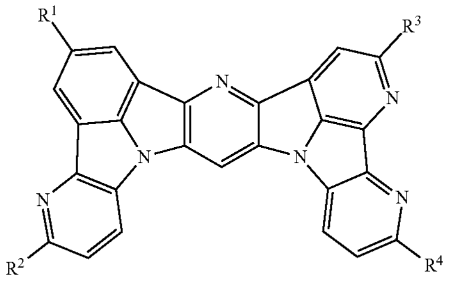
(1-198)
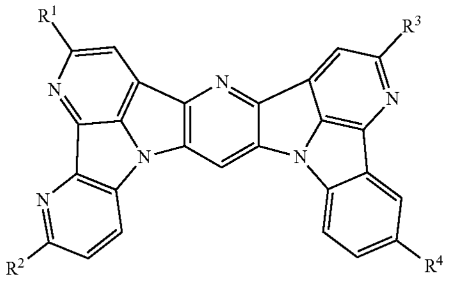
(1-199)
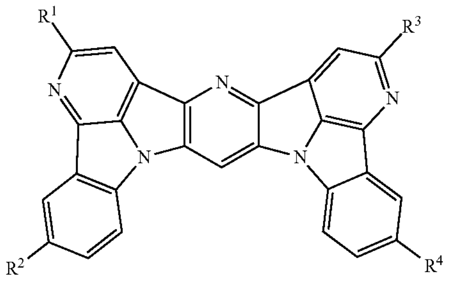
(1-200)
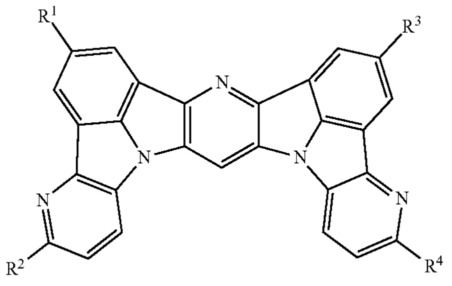
(1-201)
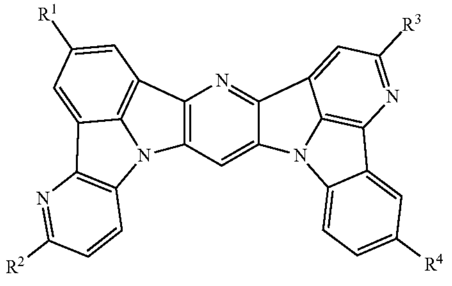
-continued
(1-202)
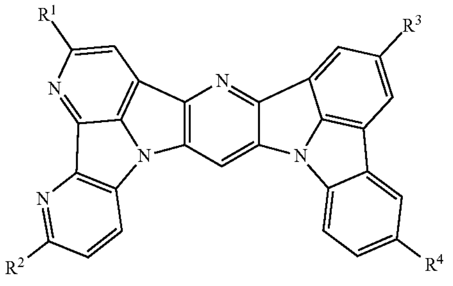
(1-203)
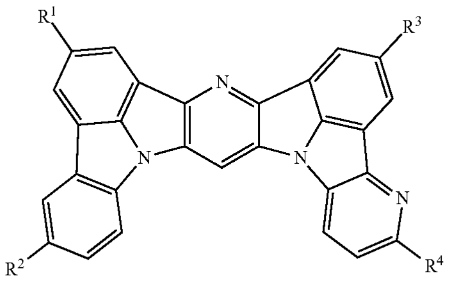
(1-204)
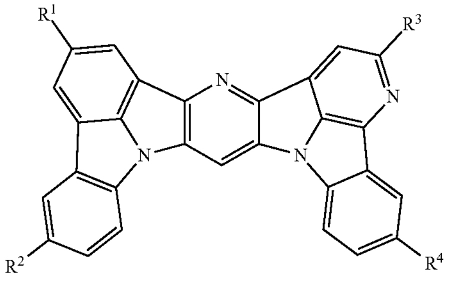
(1-205)
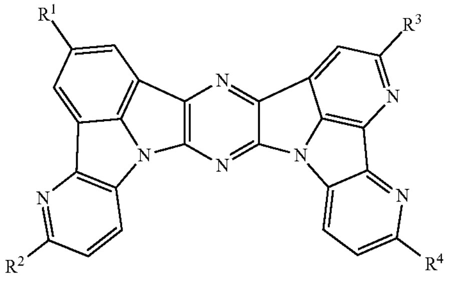
(1-206)
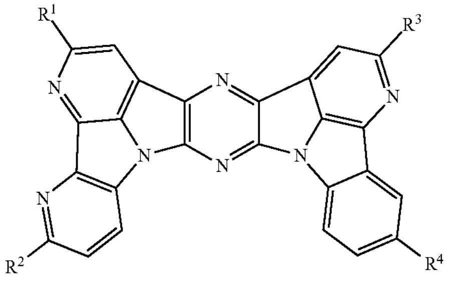

-continued
(1-207)
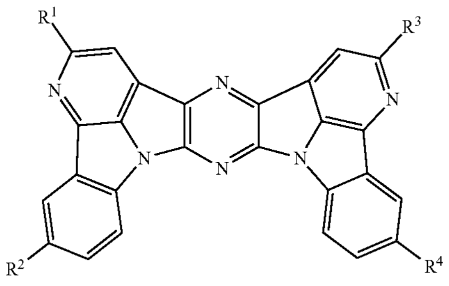
(1-208)
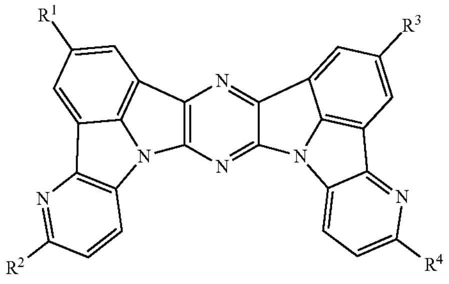
(1-209)
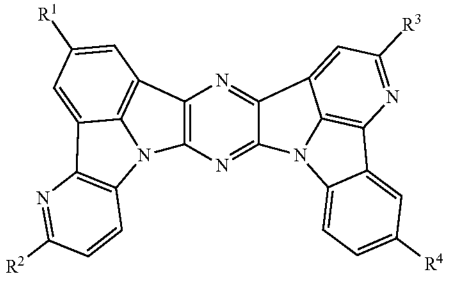
(1-210)
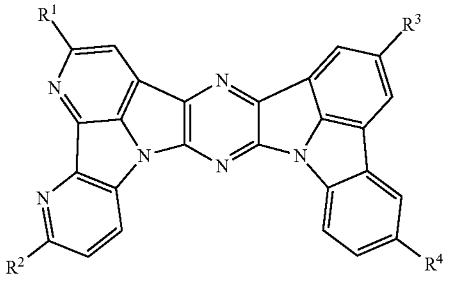
(1-211)
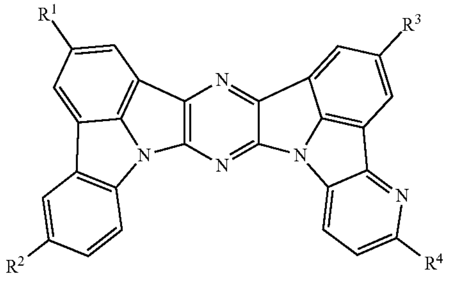
-continued
(1-212)
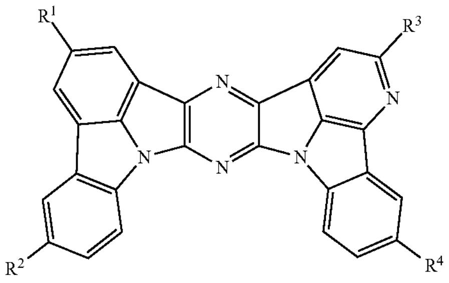
(1-213)
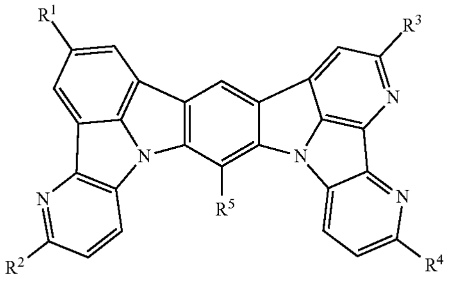
(1-214)
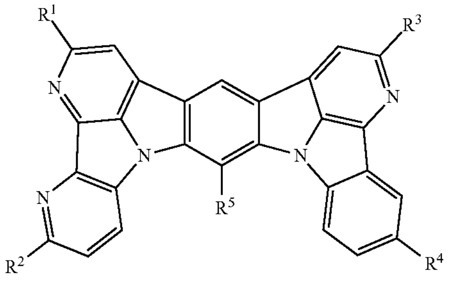
(1-215)
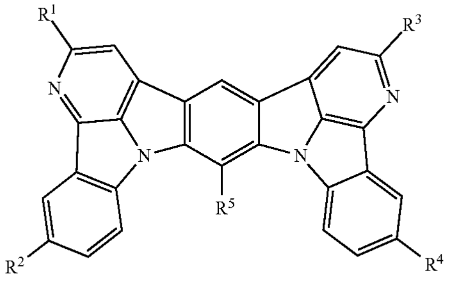
(1-216)
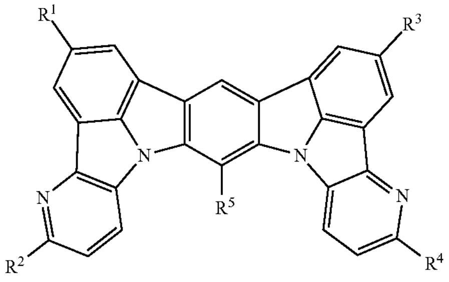

-continued
(1-217)
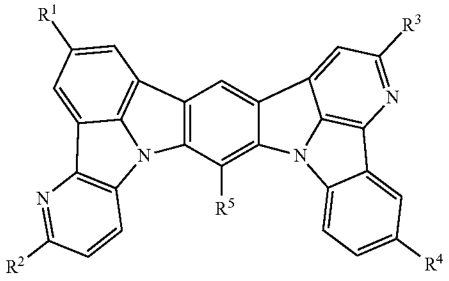
(1-218)
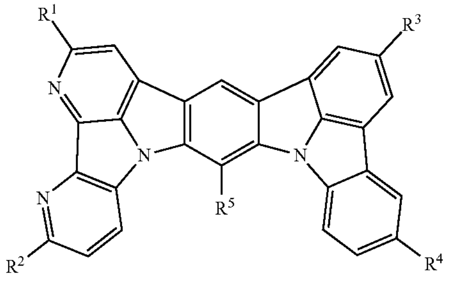
(1-219)
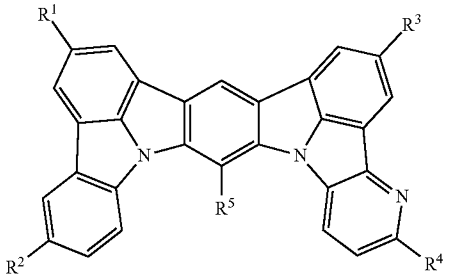
(1-220)
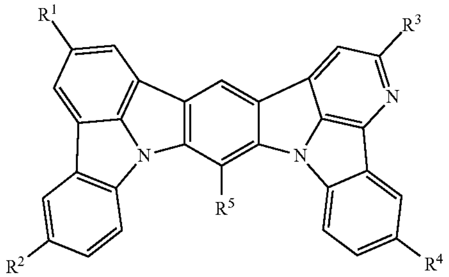
(1-221)
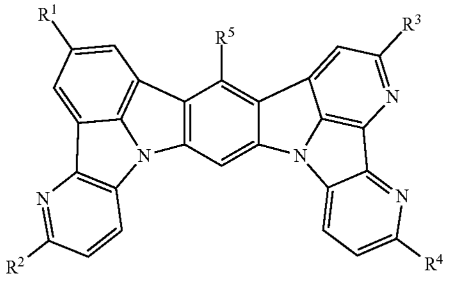
-continued
(1-222)
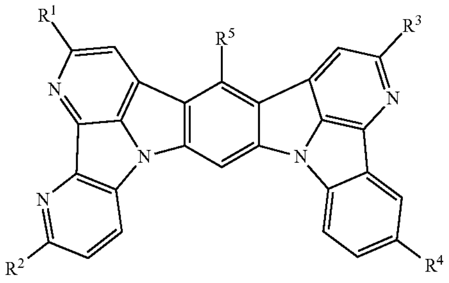
(1-223)
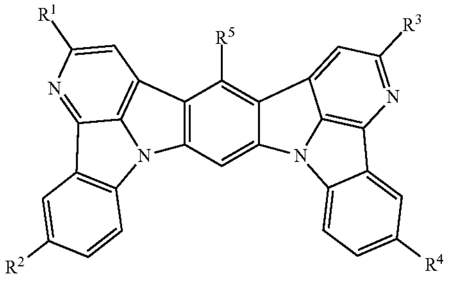
(1-224)
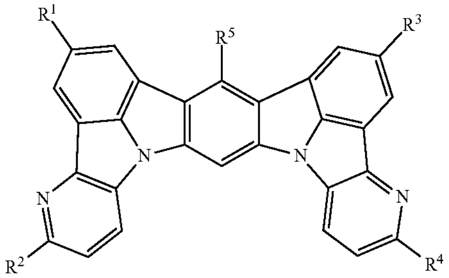
(1-225)
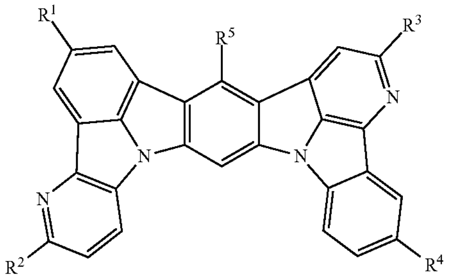
(1-226)
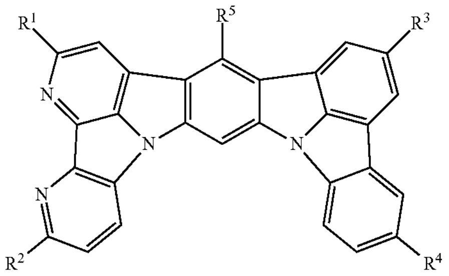

-continued
(1-227)
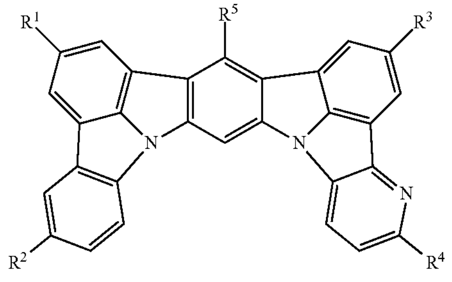
(1-228)
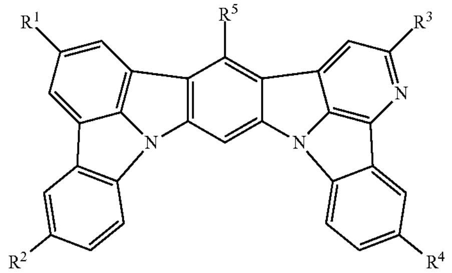
(1-229)
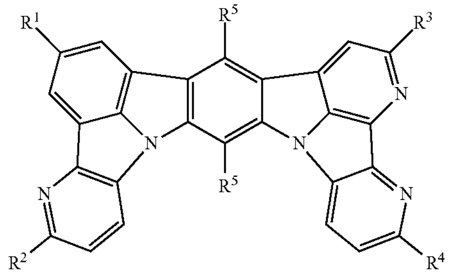
(1-230)
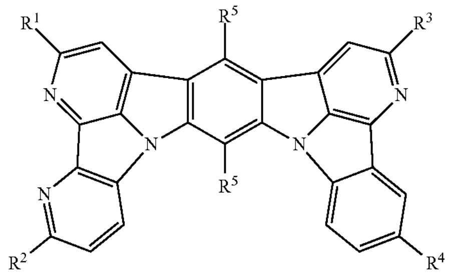
(1-231)
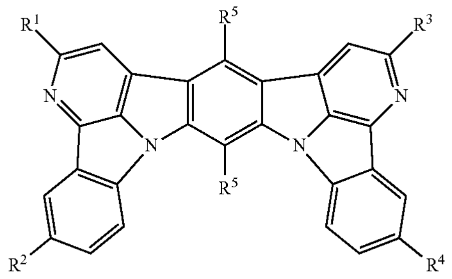
-continued
(1-232)
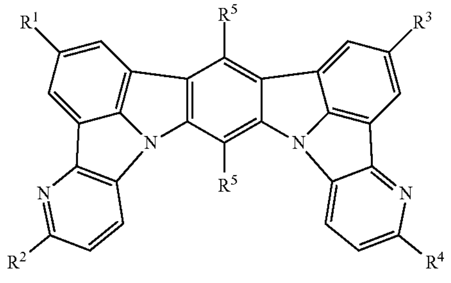
(1-233)
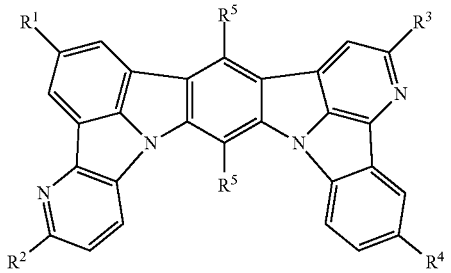
(1-234)
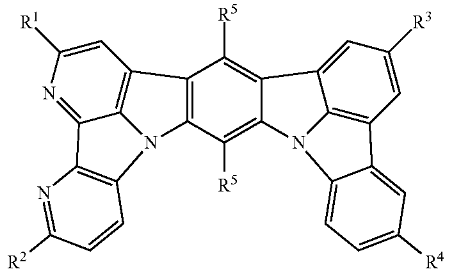
(1-235)
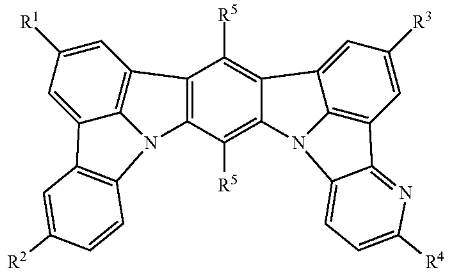
(1-236)
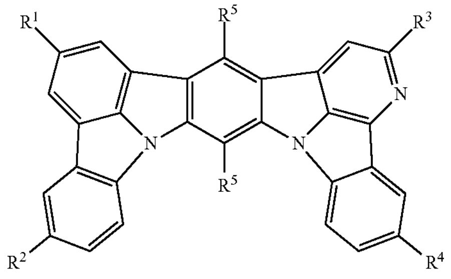

-continued
(1-237)
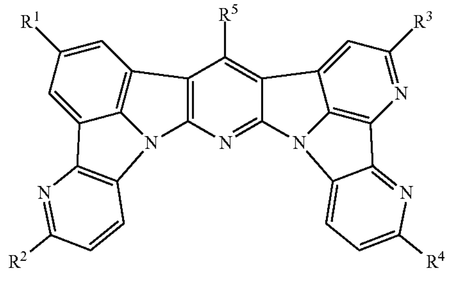
(1-238)
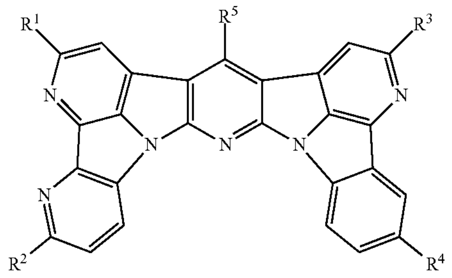
(1-239)
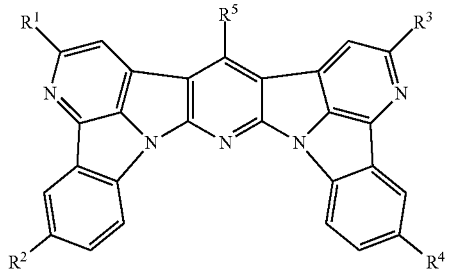
(1-240)
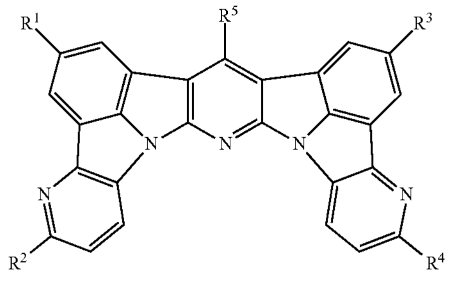
(1-241)
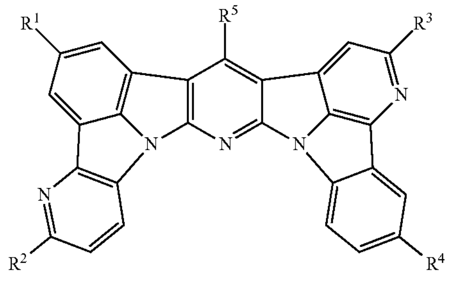
-continued
(1-242)
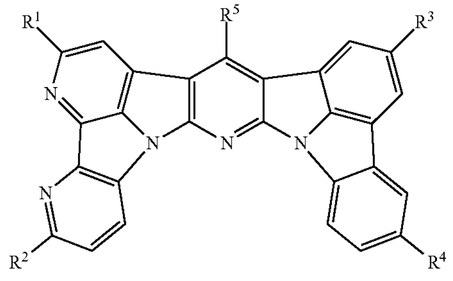
(1-243)
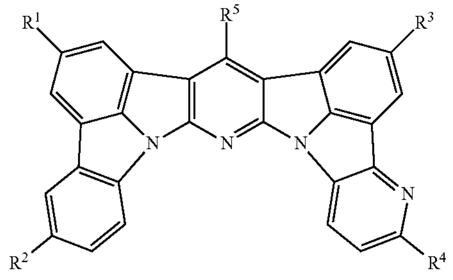
(1-244)
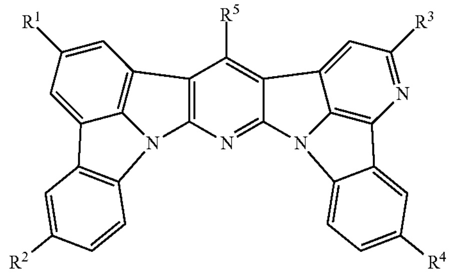
(1-245)
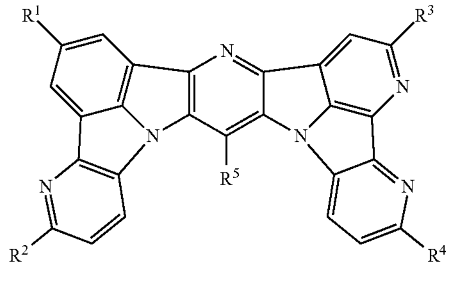
(1-246)
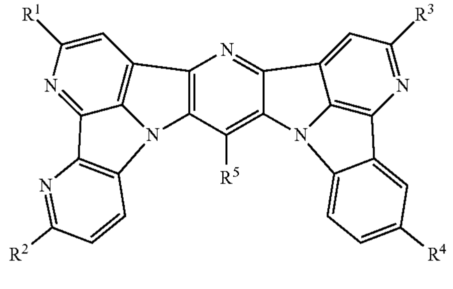

-continued
(1-247)
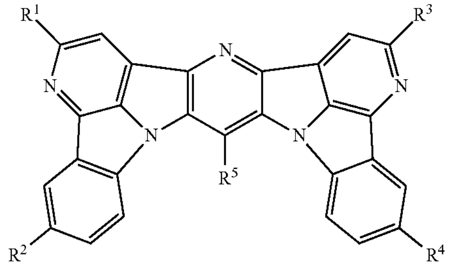
(1-248)
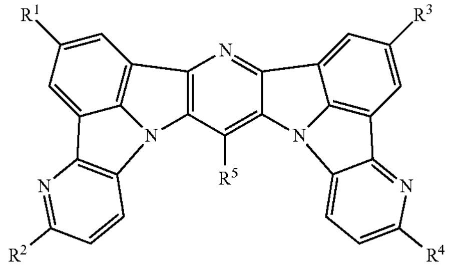
(1-249)
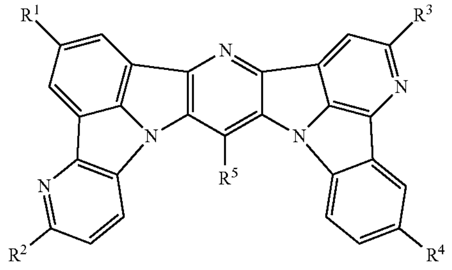
(1-250)
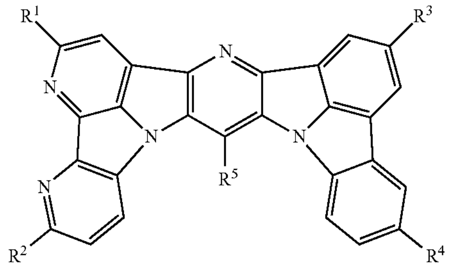
(1-251)
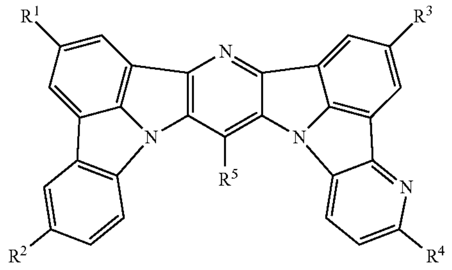
(1-252)
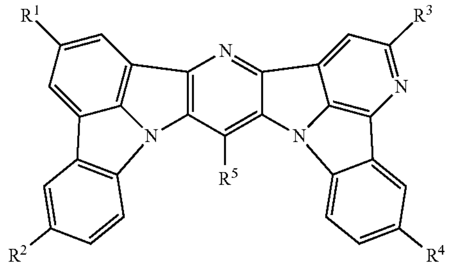
-continued
(1-253)
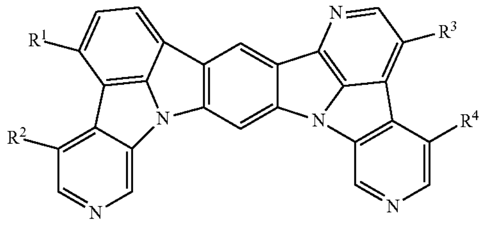
(1-254)
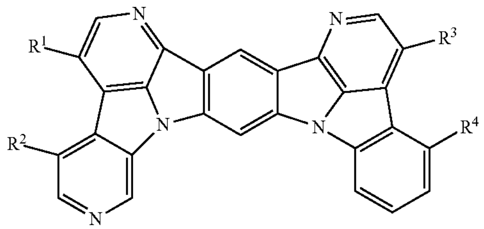
(1-255)
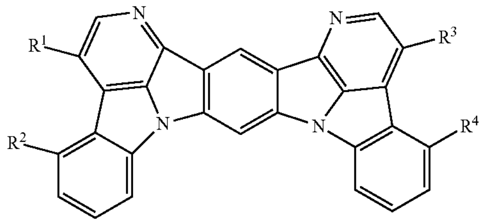
(1-256)
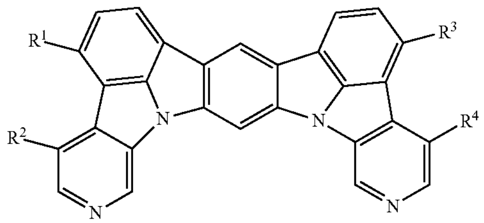
(1-257)
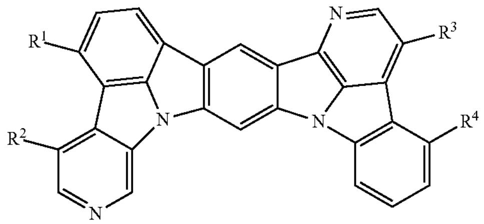
(1-258)
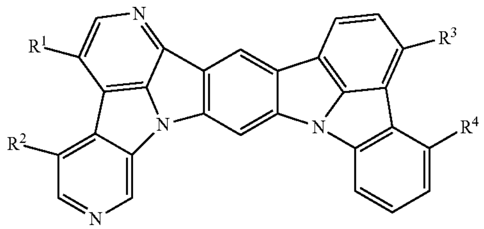

-continued
(1-259)
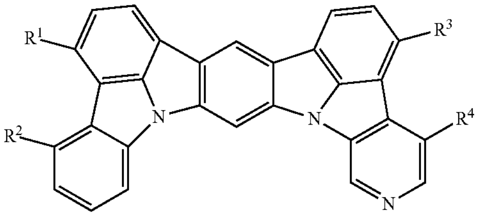
(1-260)
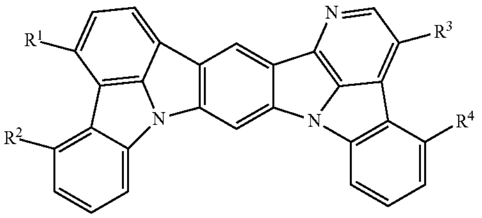
(1-261)
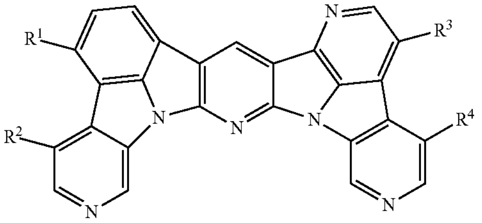
(1-262)
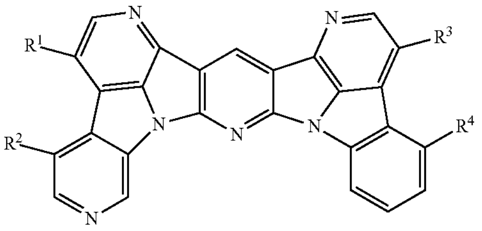
(1-263)
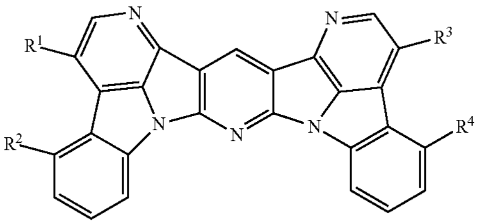
(1-264)
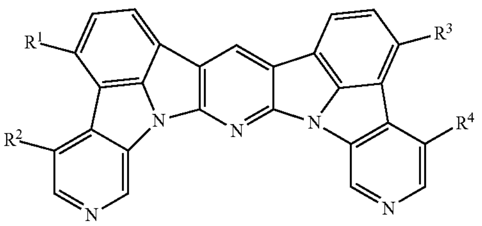
-continued
(1-265)
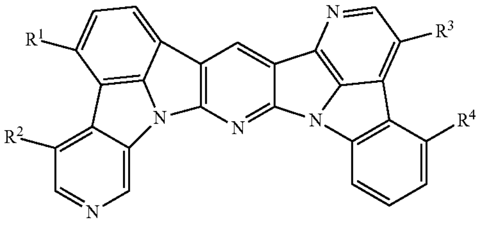
(1-266)
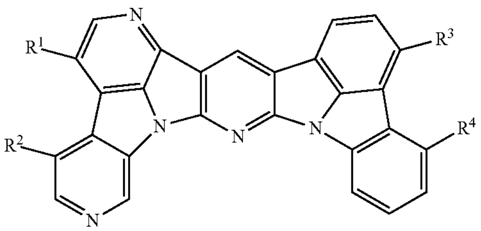
(1-267)
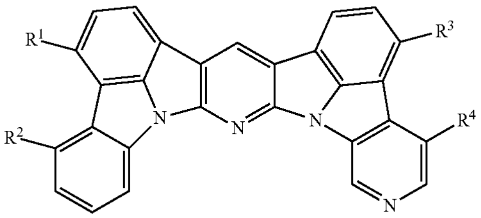
(1-268)
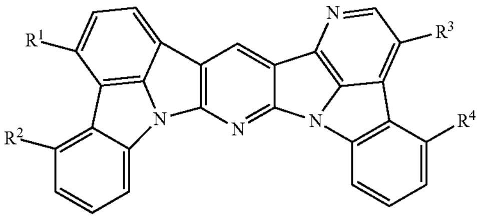
(1-269)
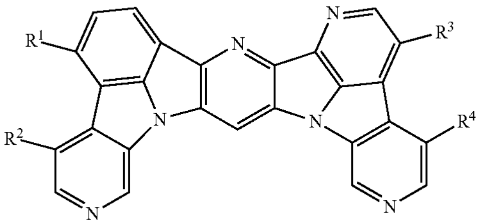
(1-270)
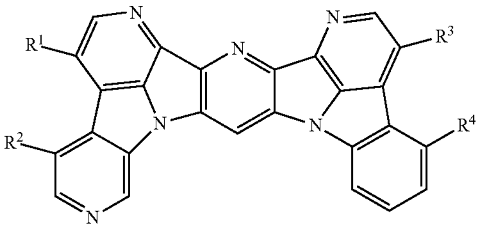

(1-271)
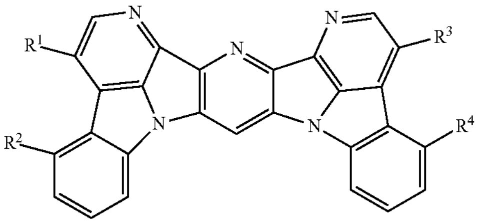
(1-272)
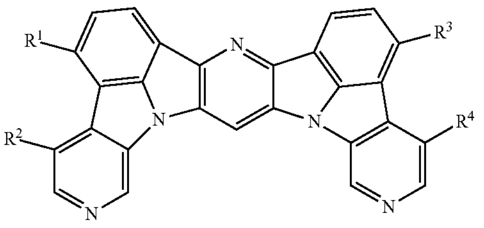
(1-273)
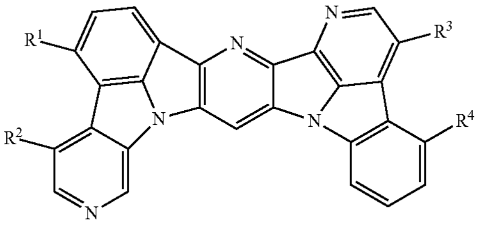
(1-274)
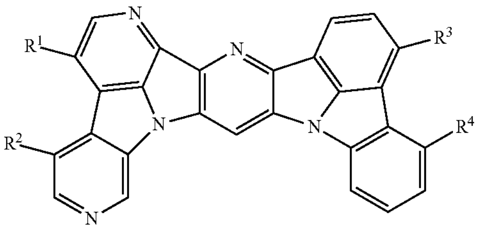
(1-275)
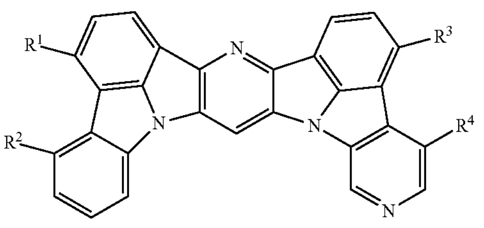
(1-276)
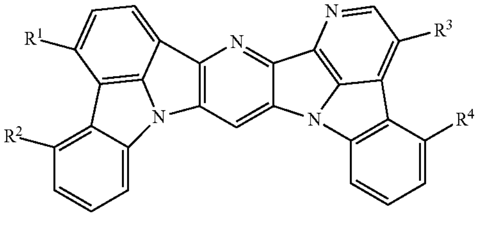
(1-277)
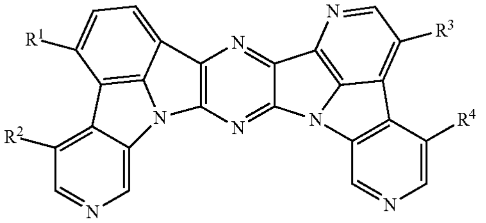
(1-278)
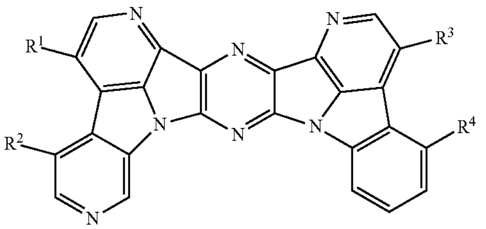
(1-279)
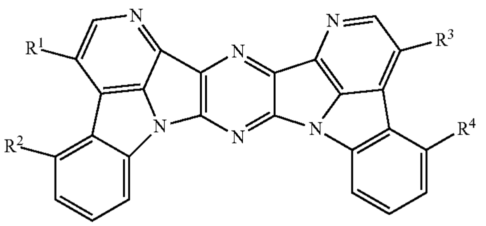
(1-280)
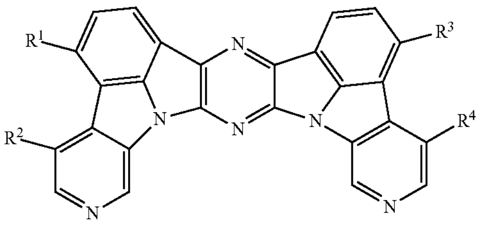
(1-281)
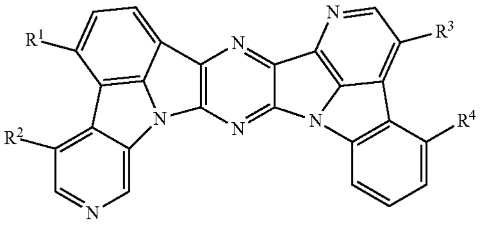
(1-282)
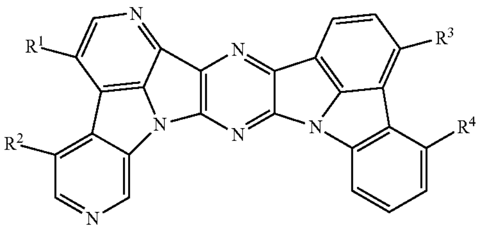

-continued
(1-283)
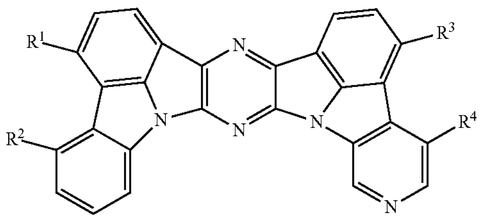
(1-284)
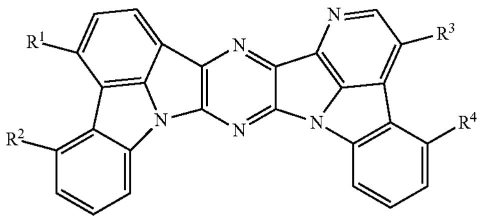
(1-285)
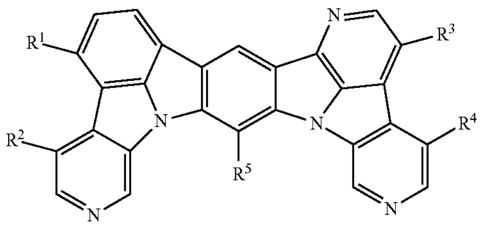
(1-286)
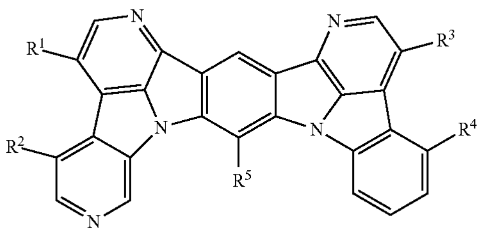
(1-287)
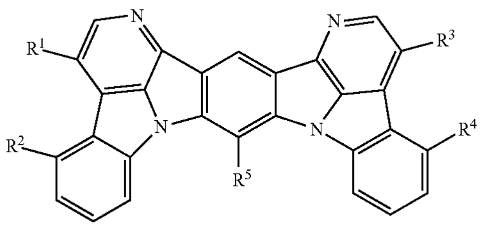
(1-288)
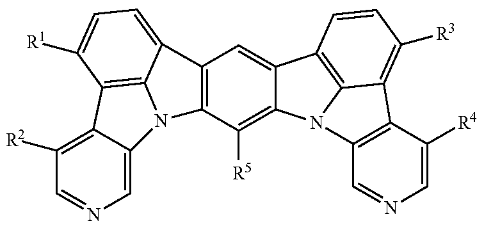
-continued
(1-289)
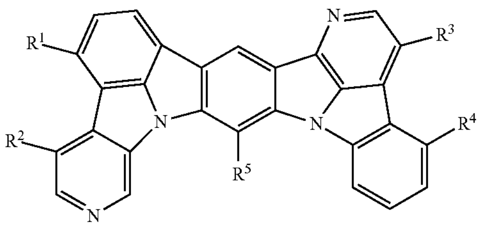
(1-290)
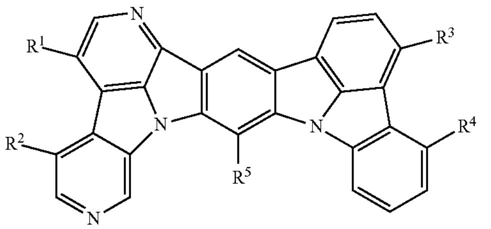
(1-291)
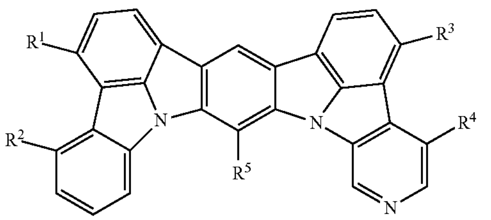
(1-292)
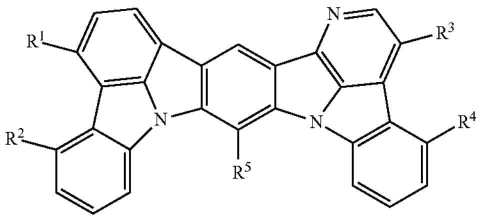
(1-293)
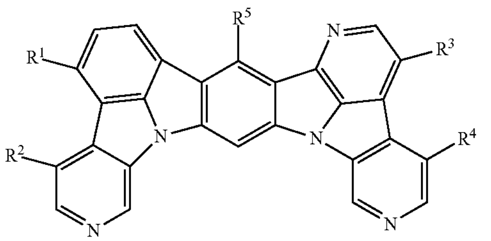
(1-294)
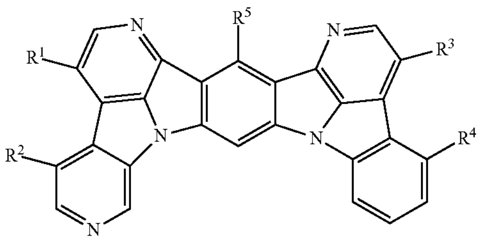

-continued
(1-295)
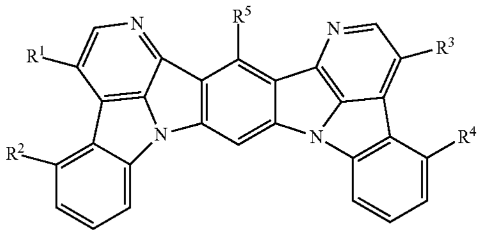
(1-296)
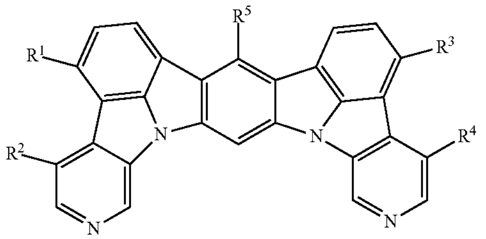
(1-297)
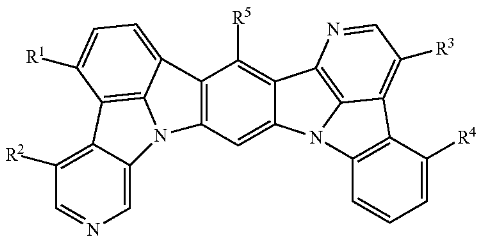
(1-298)
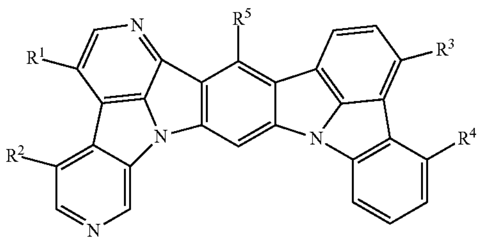
(1-299)
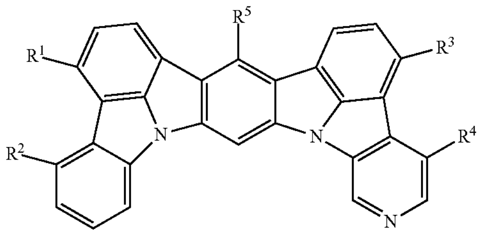
(1-300)
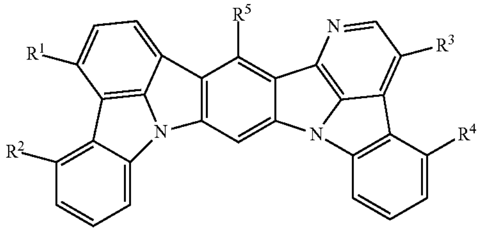
-continued
(1-301)
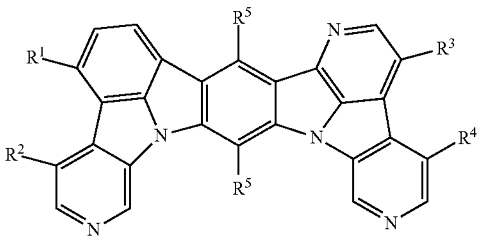
(1-302)
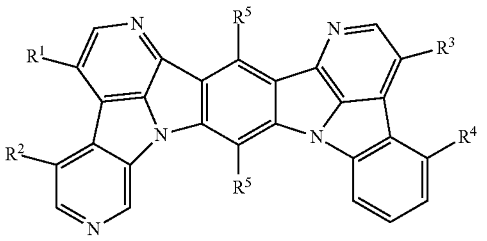
(1-303)
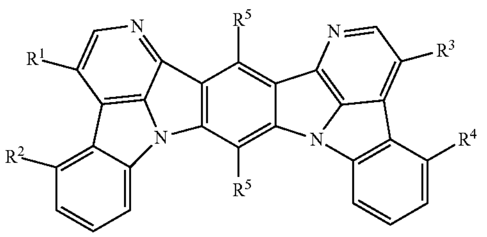
(1-304)
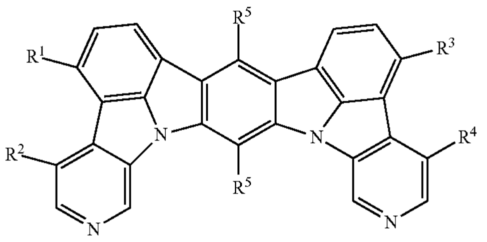
(1-305)
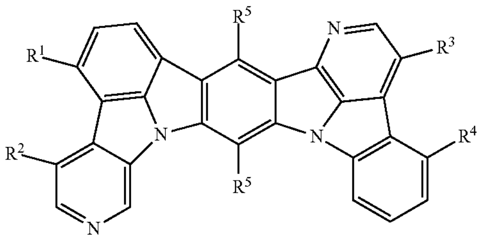
(1-306)
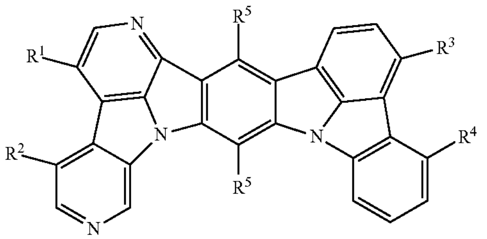

-continued
(1-307)
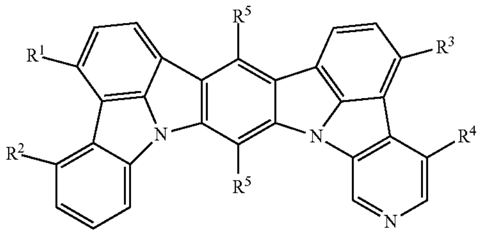
(1-308)
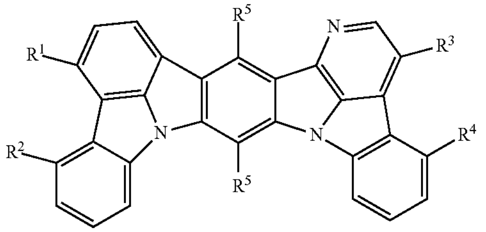
(1-309)
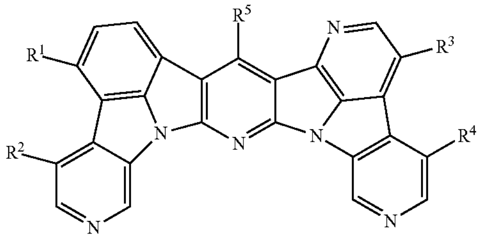
(1-310)
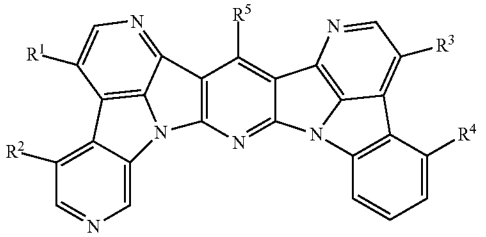
(1-311)
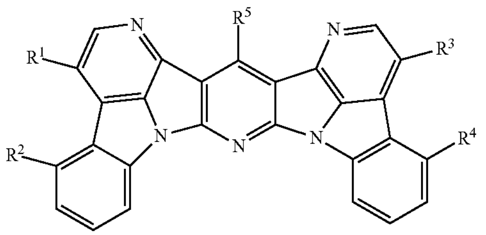
(1-312)
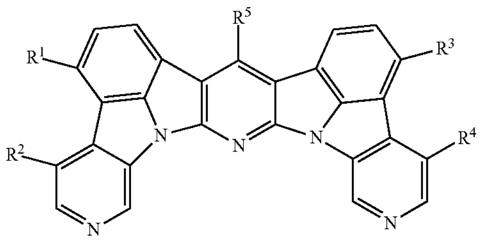
-continued
(1-313)
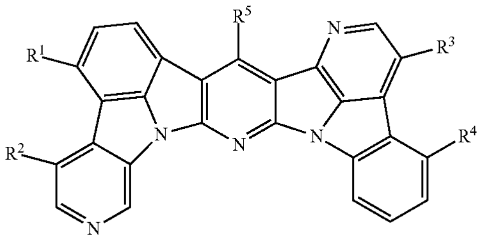
(1-314)
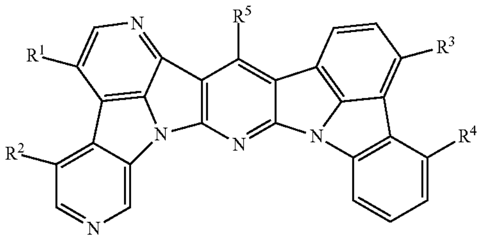
(1-315)
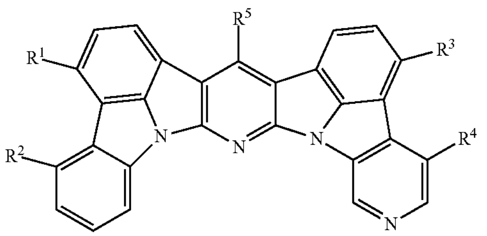
(1-316)
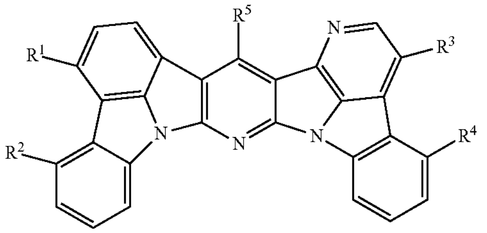
(1-317)
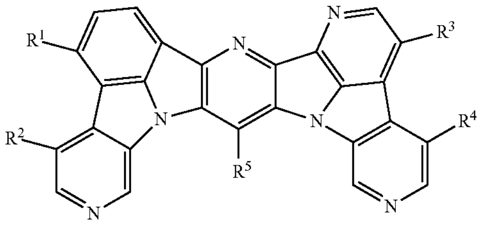
(1-318)
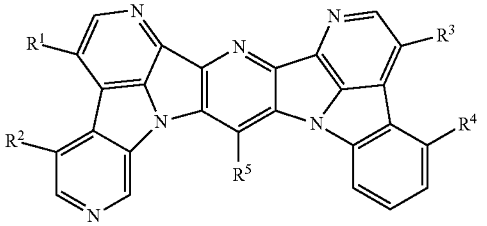

-continued
(1-319)
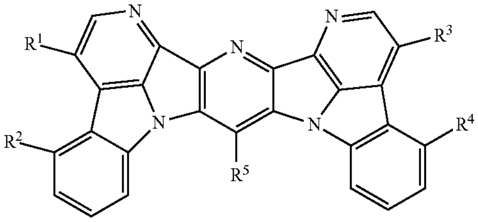
(1-320)
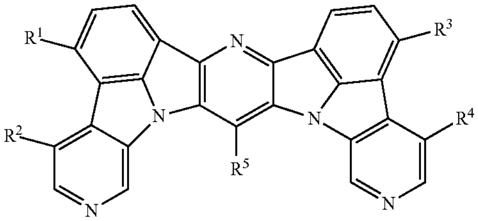
(1-321)
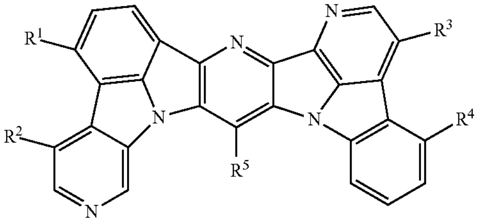
-continued
(1-322)
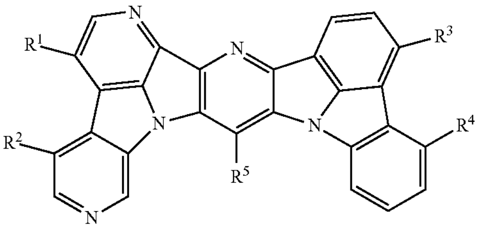
(1-323)
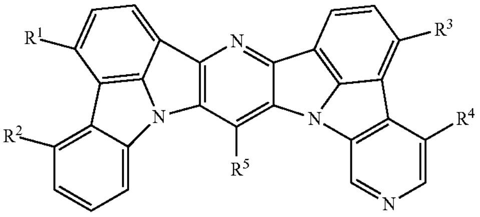
(1-324)
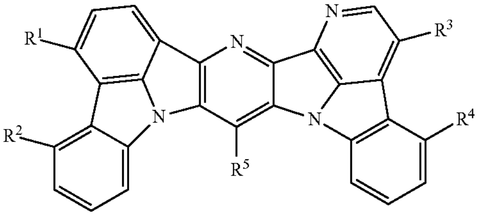
wherein, in Formulae 1-1 to 1-324, $R^1$ to $R^5$ are the same as described above.
In one or more embodiments, the heterocyclic compound may be selected from compounds of Group I:
Group I
1
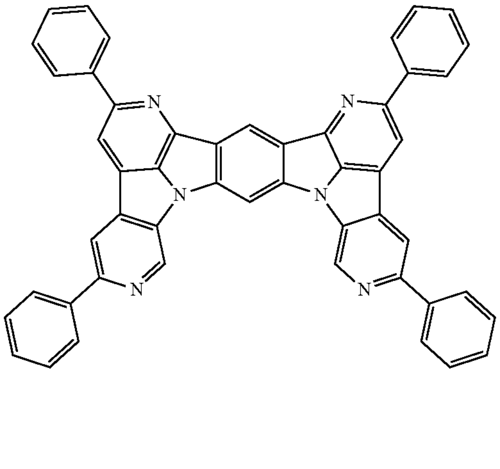
2
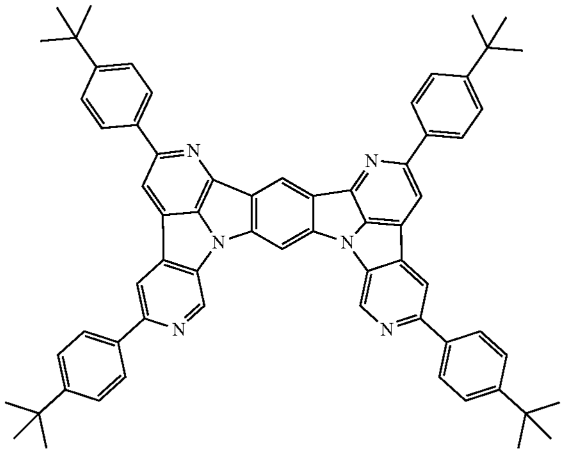

-continued
3
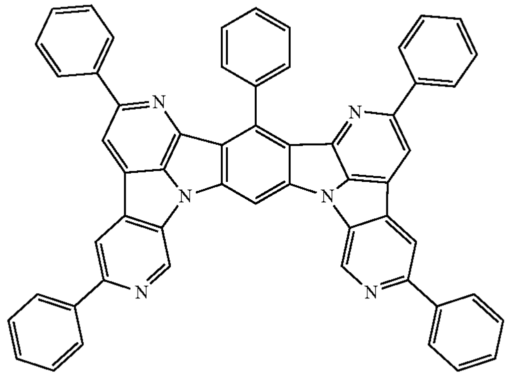
4
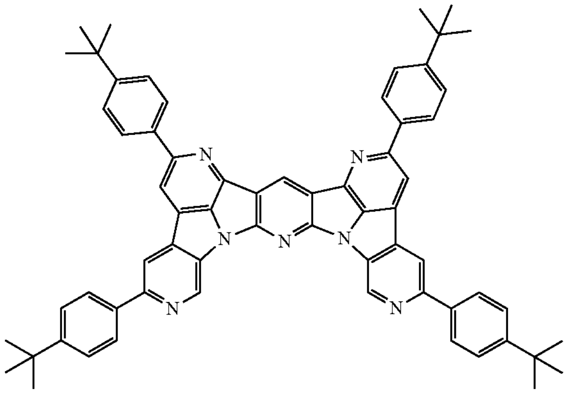
5
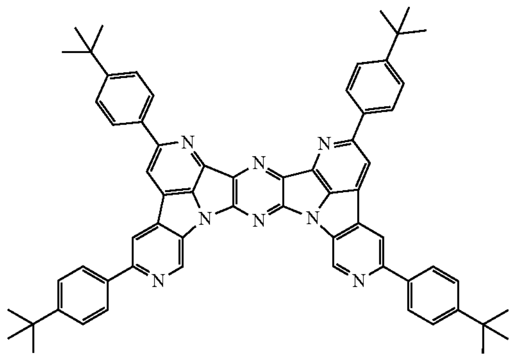
6
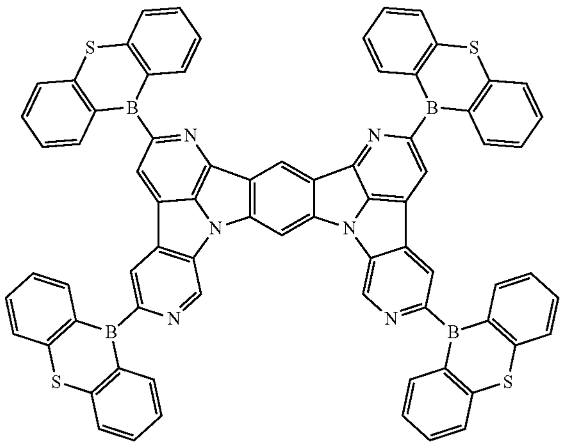
7
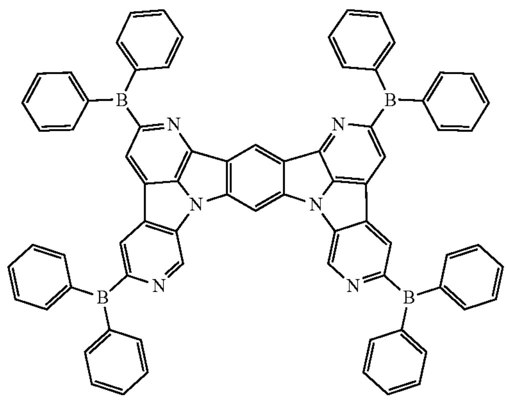
8
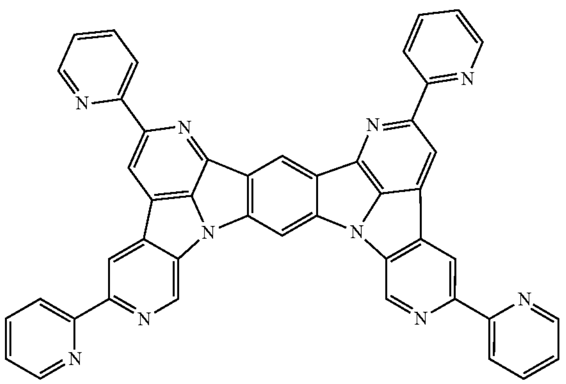

-continued
9
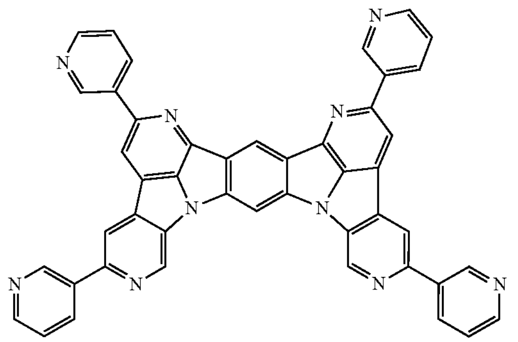
10
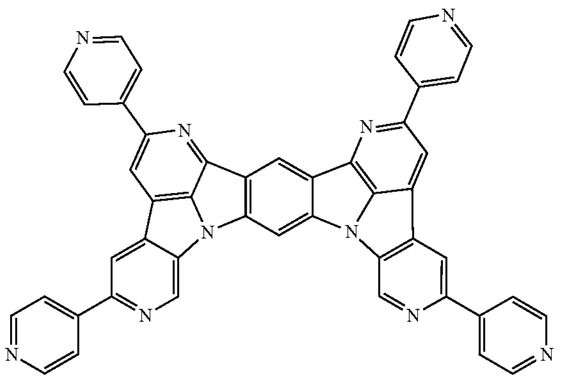
11
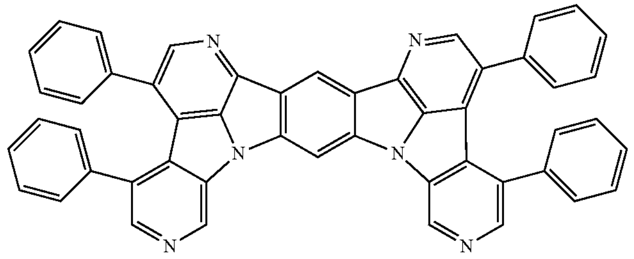
12
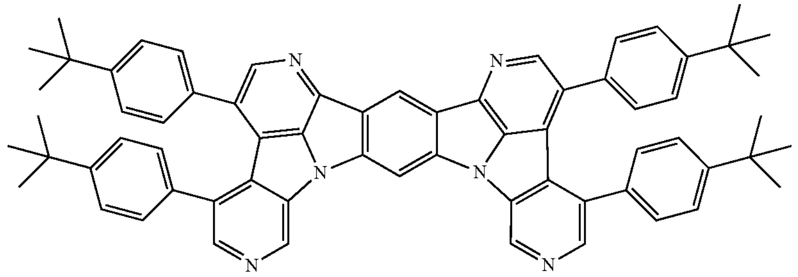
13
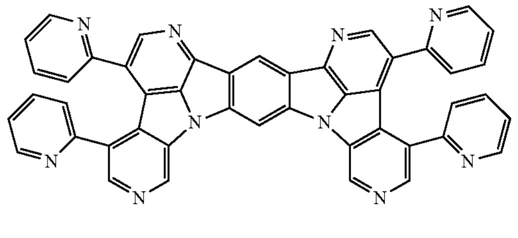
14
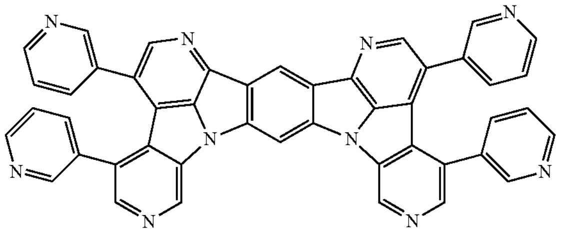
15
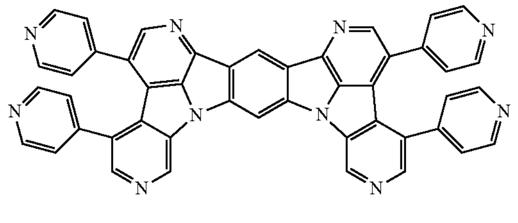
16
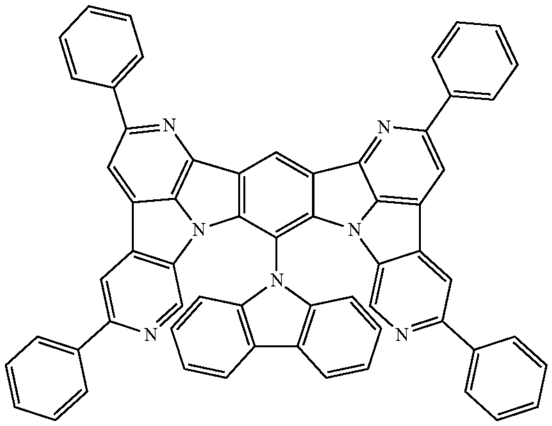

-continued
17
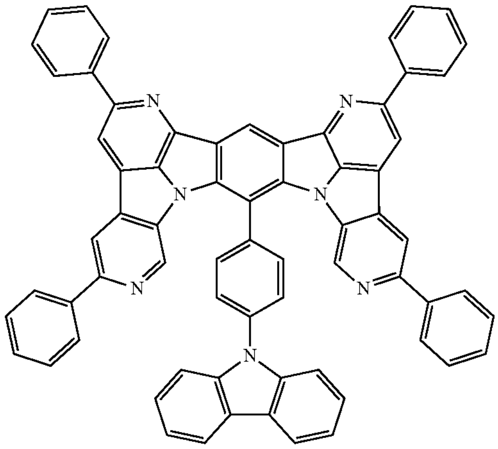
18
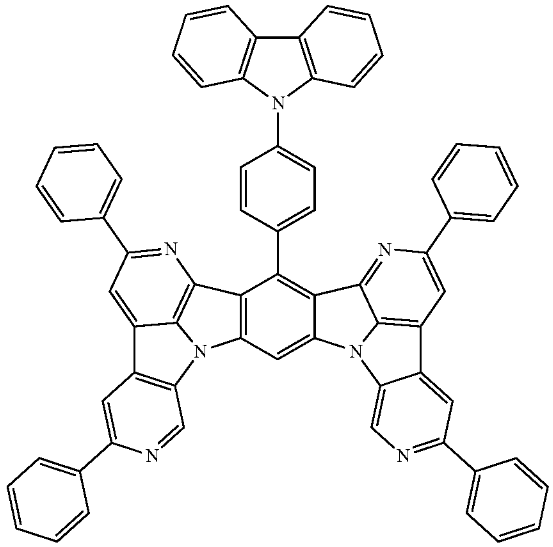
19
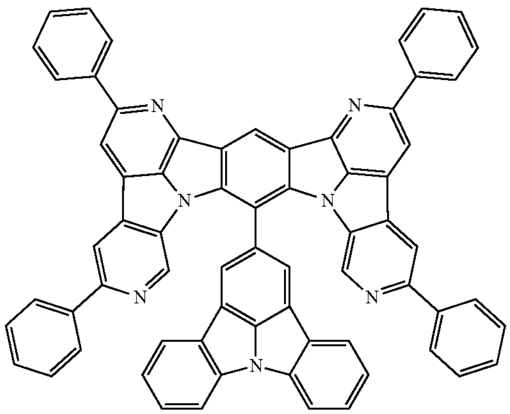
20
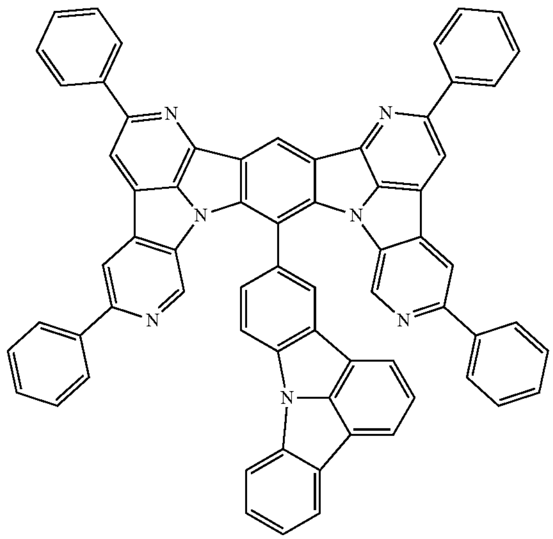
21
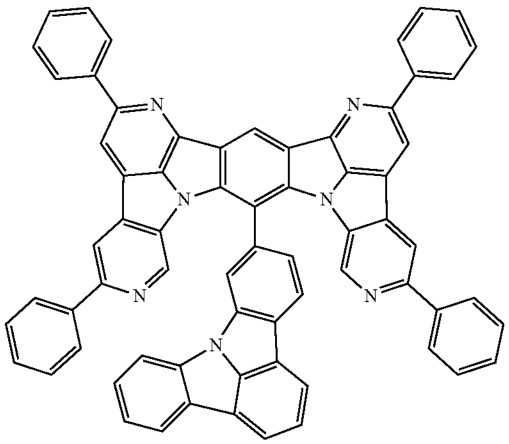
22
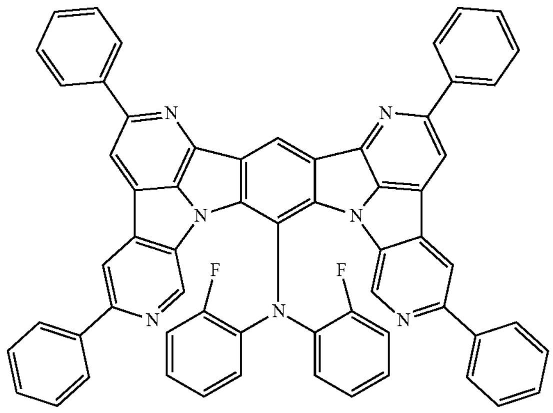

-continued
23
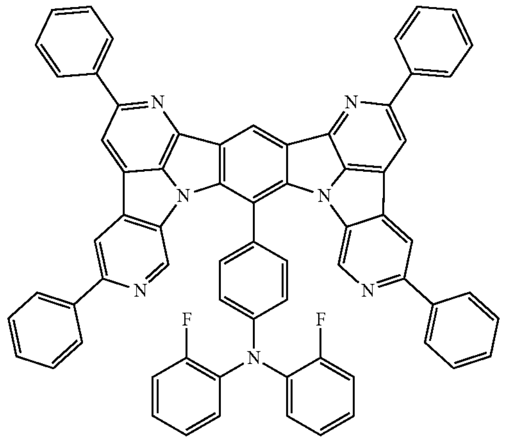
24
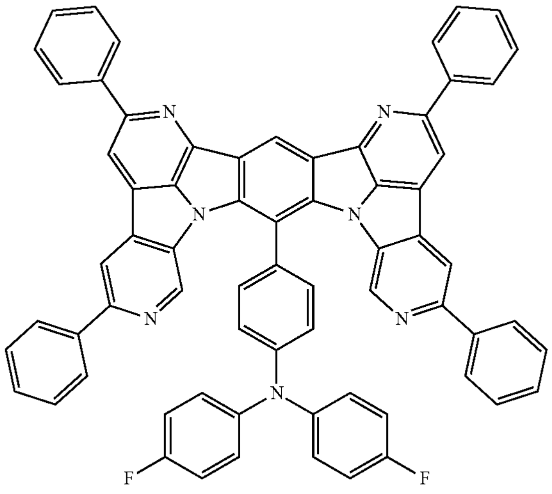
25
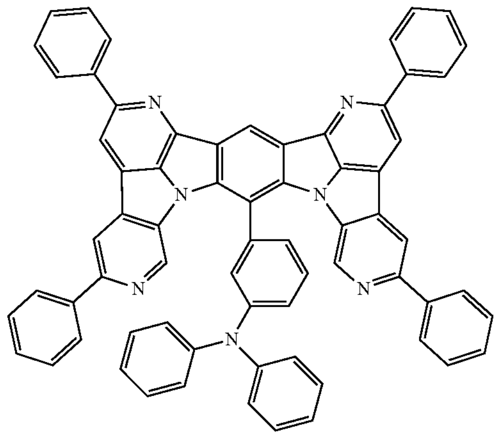
26
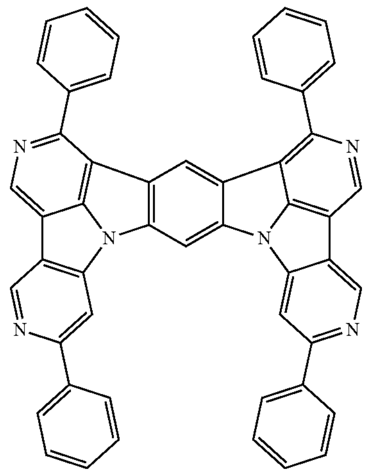
27
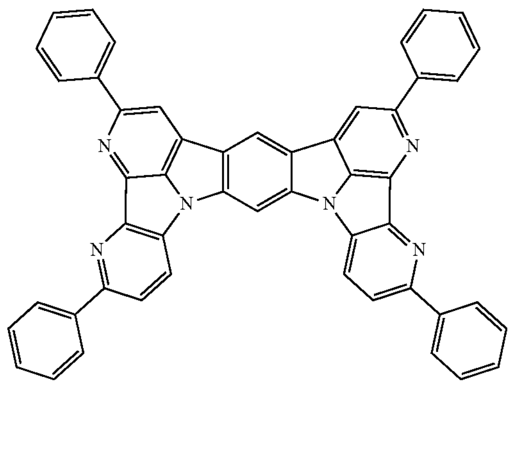
28
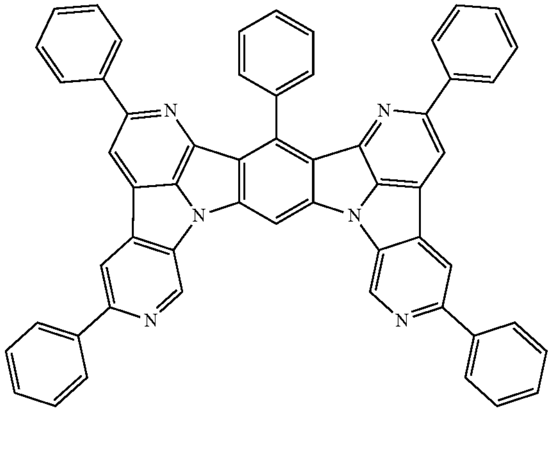

-continued
29
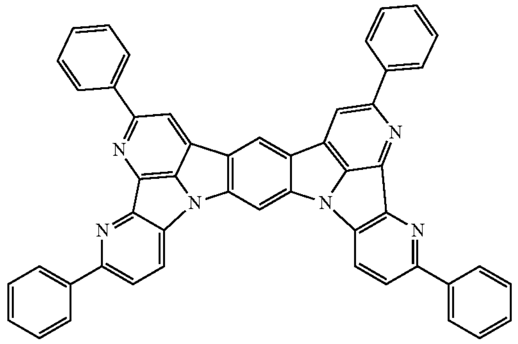
30
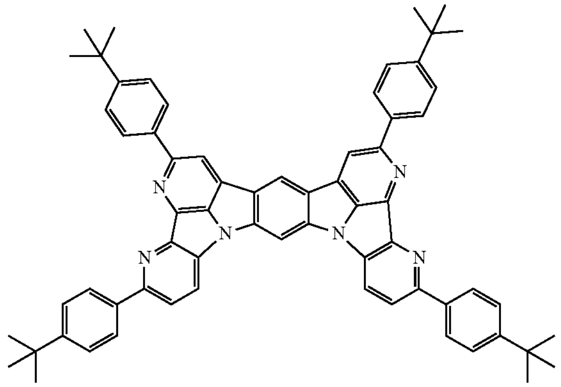
31
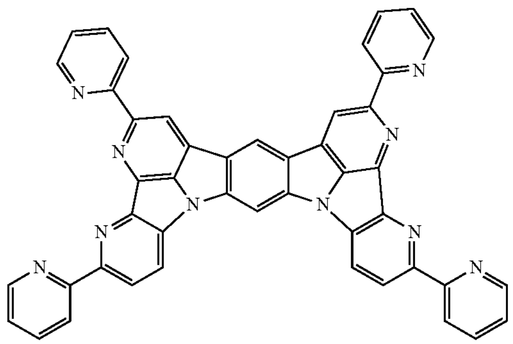
32
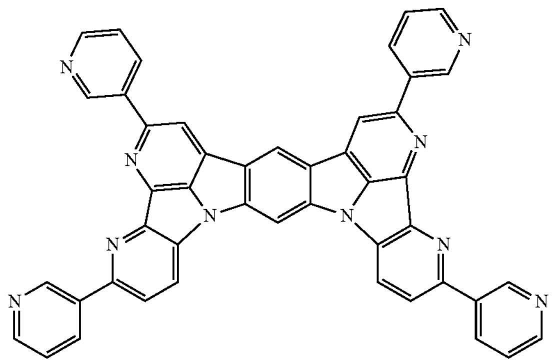
33
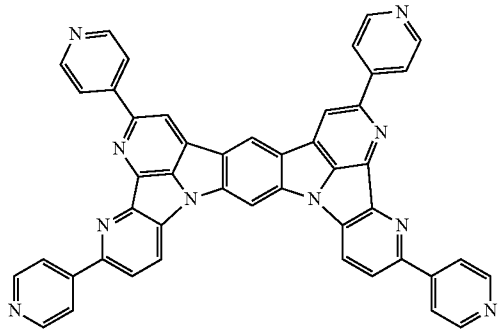
34
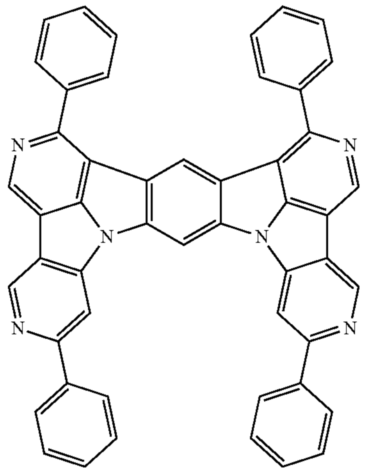

-continued
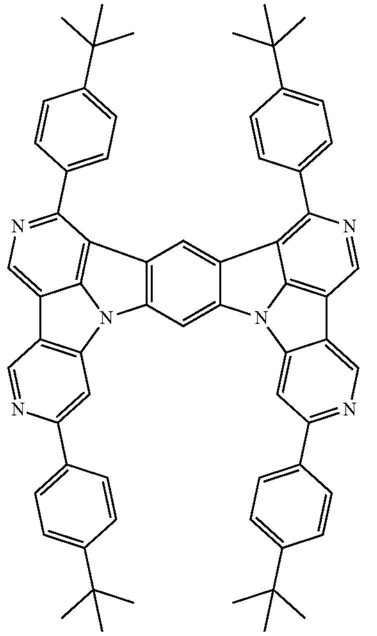
35
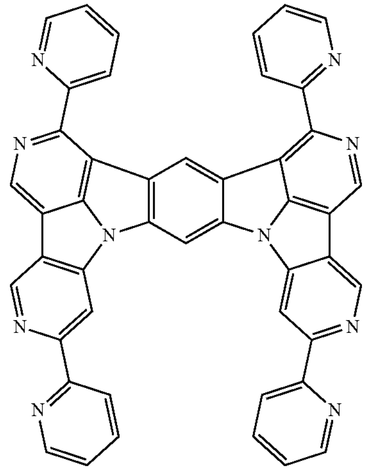
36
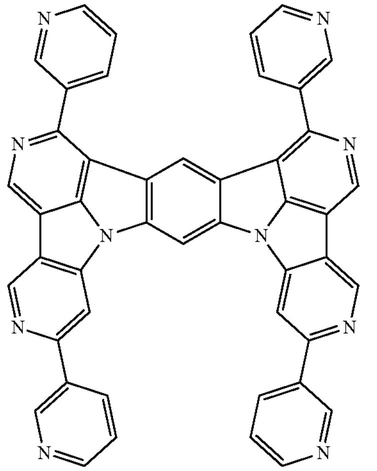
37
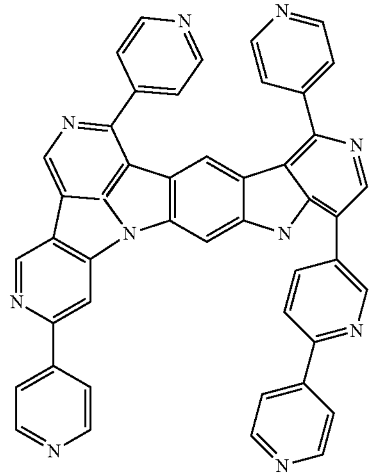
38
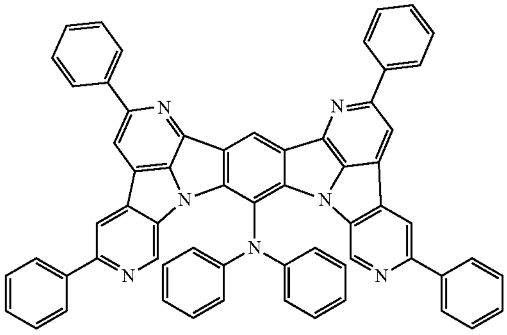
39
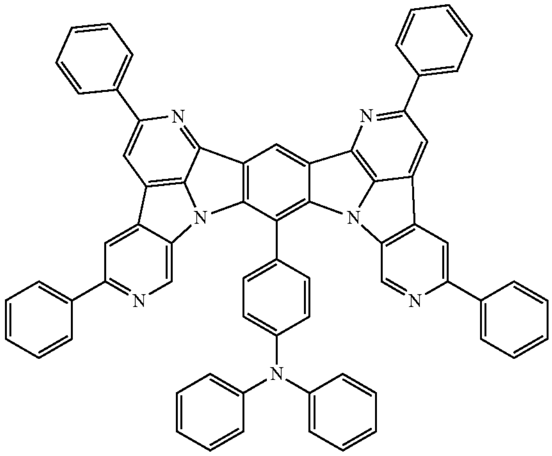
40

-continued
41
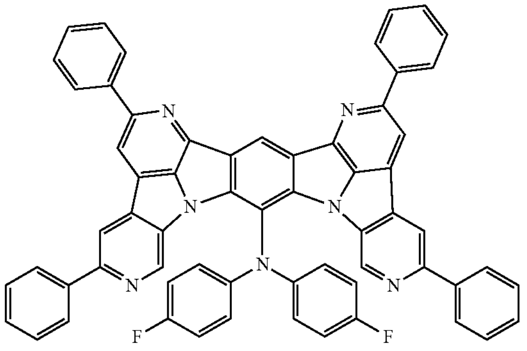
42
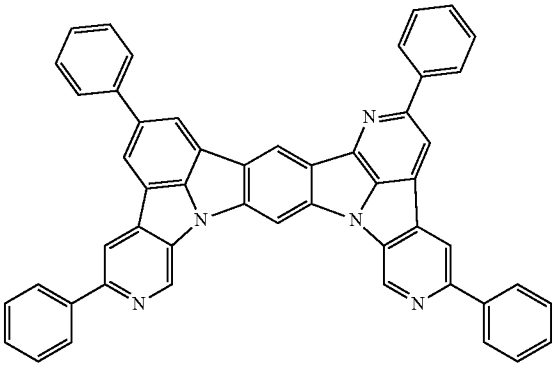
43
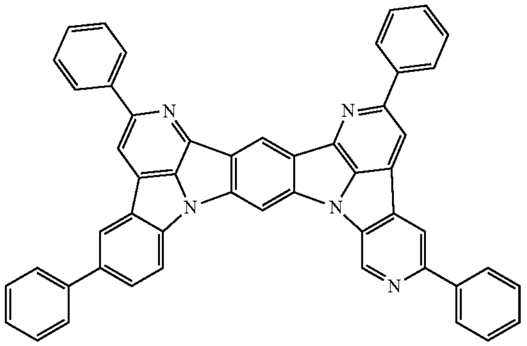
44
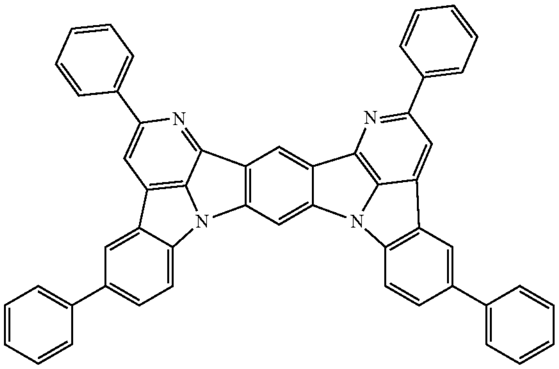
45
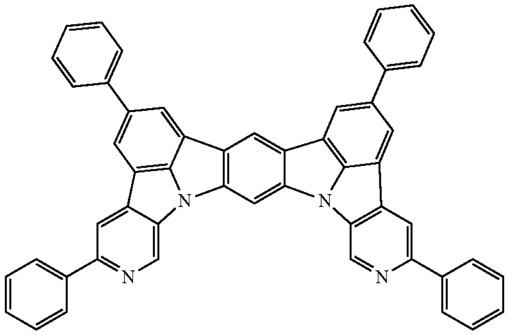
46
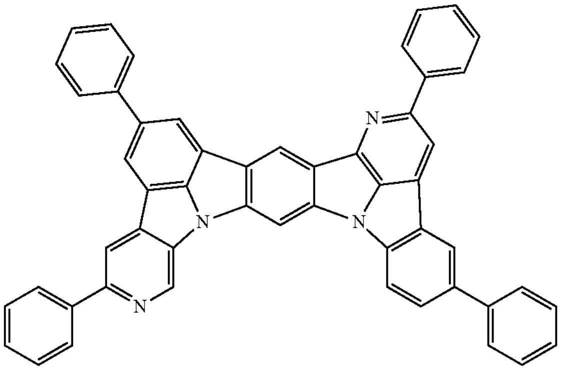
47
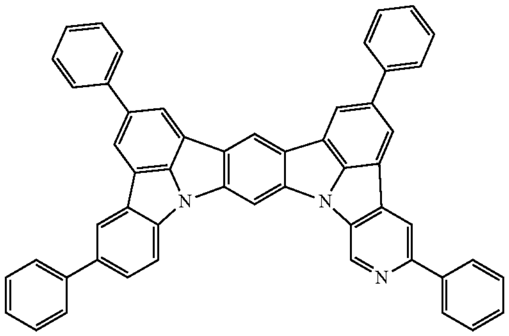
48
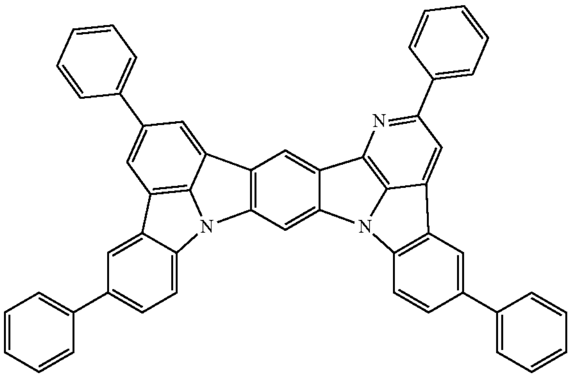

-continued
49
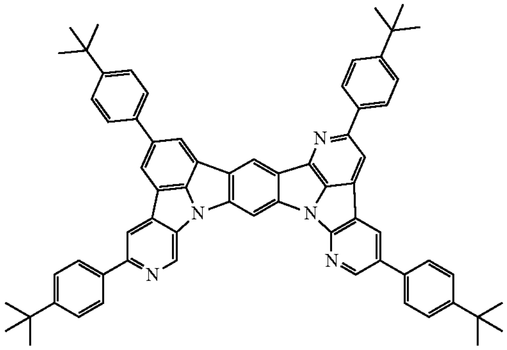
50
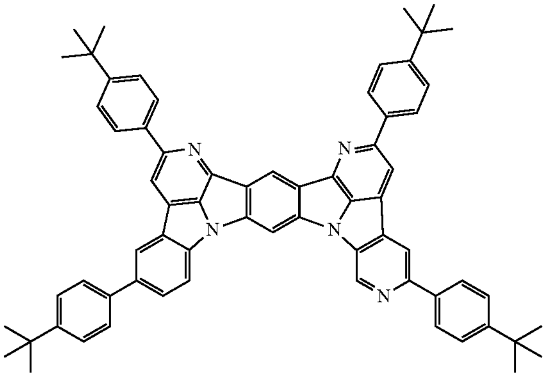
51
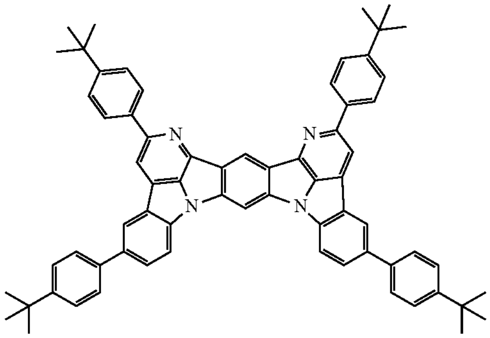
52
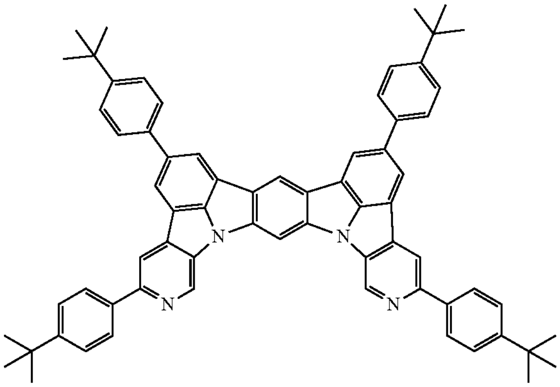
53
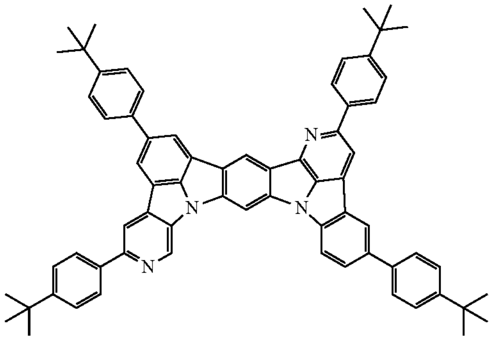
54
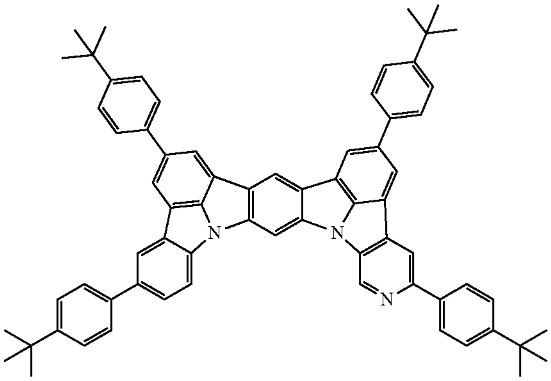

-continued
55
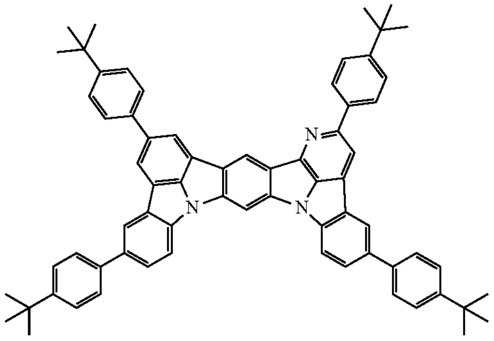
56
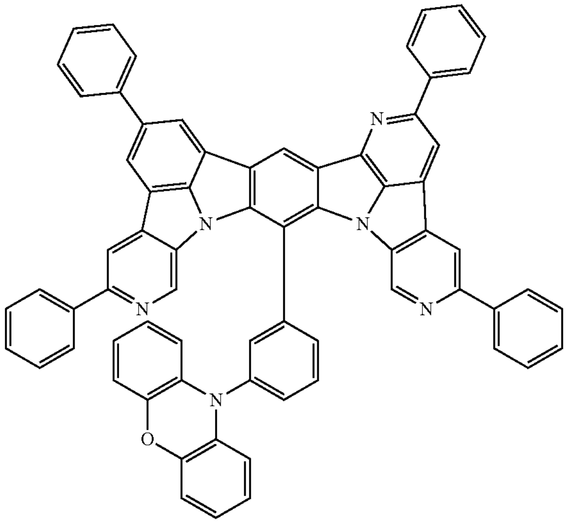
57
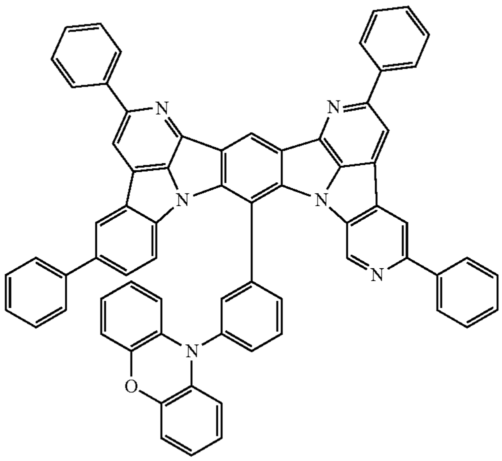
58
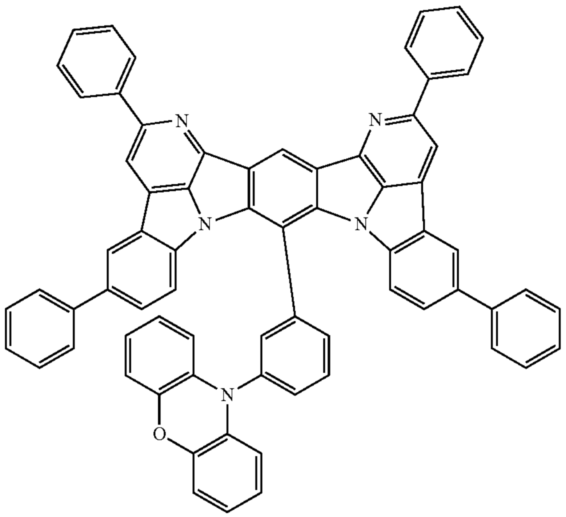
59
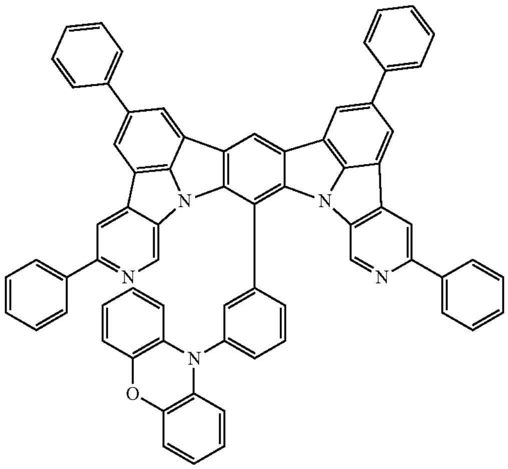
60
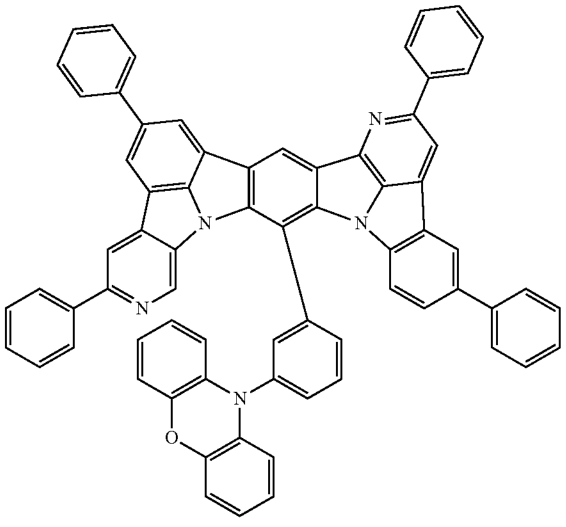

-continued
61
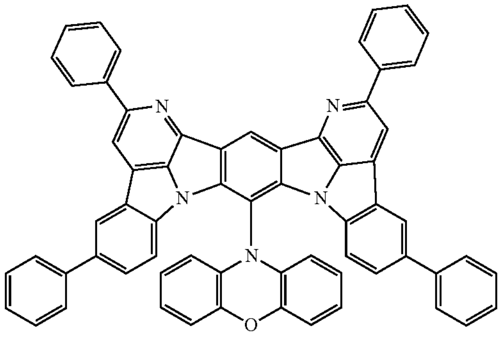
62
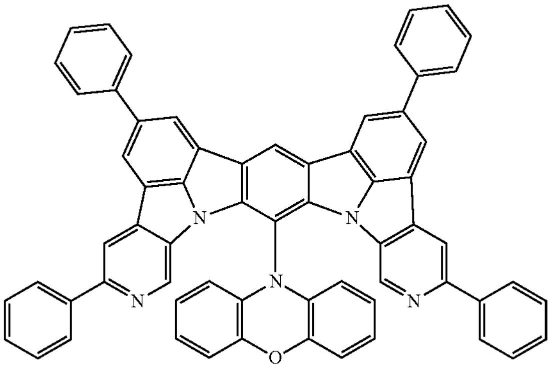
63
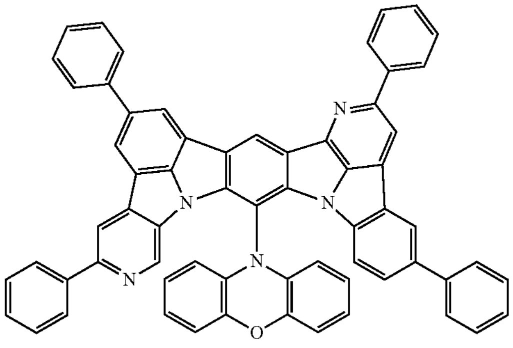
64
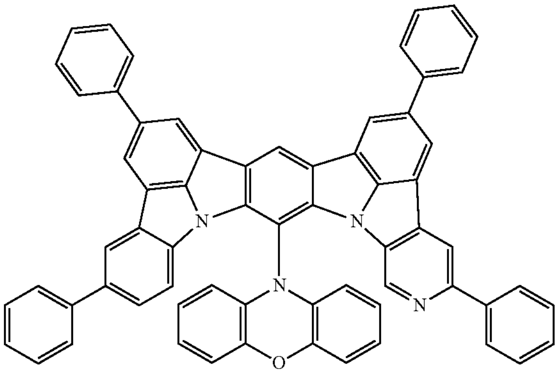
65
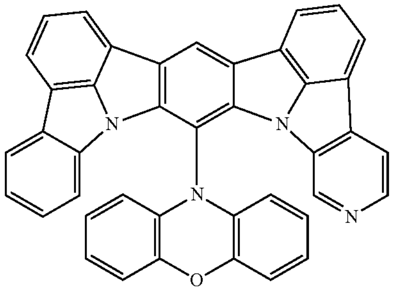
66
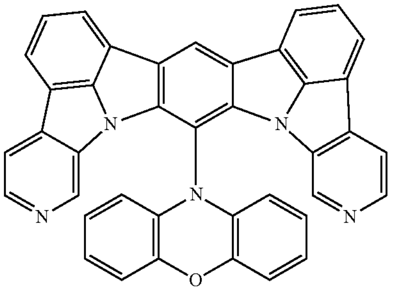
67
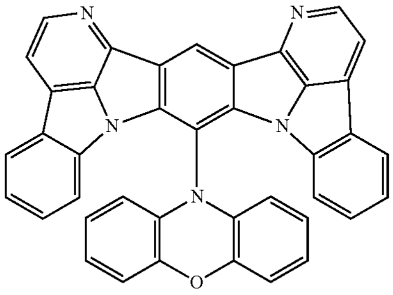
68
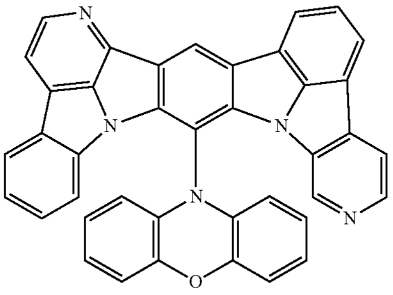

-continued
69
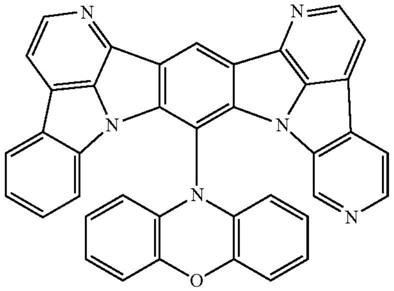
70
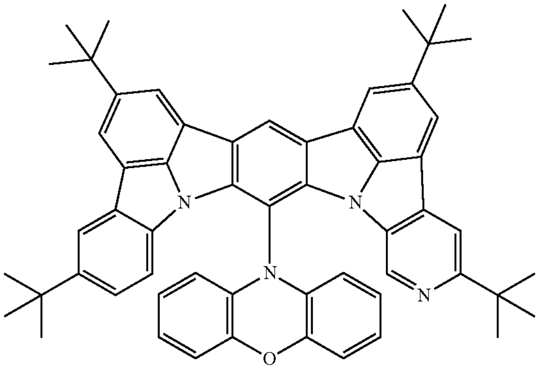
71
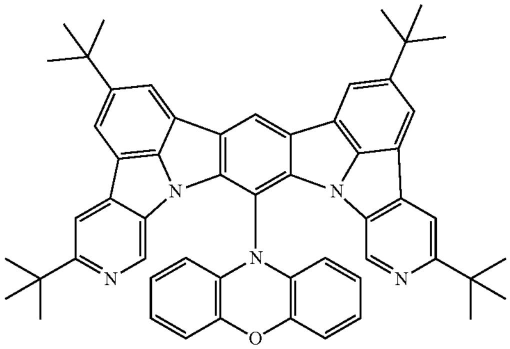
72
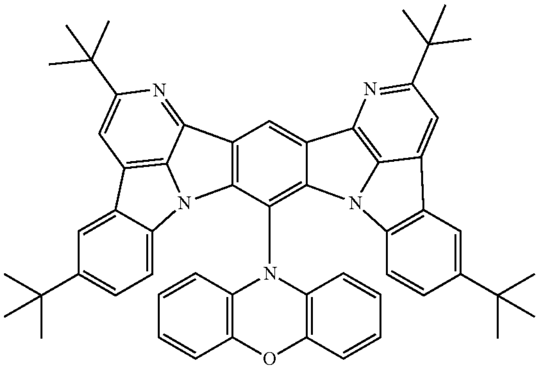
73
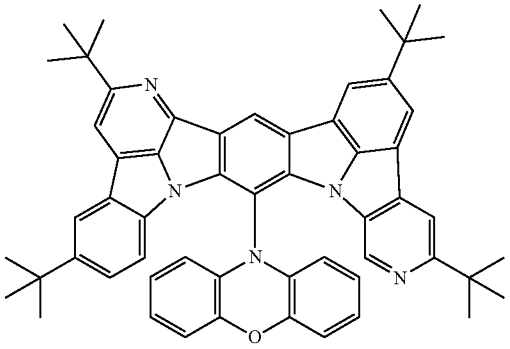
74
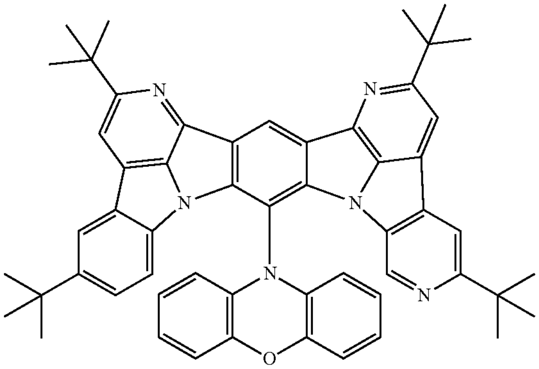

-continued
75
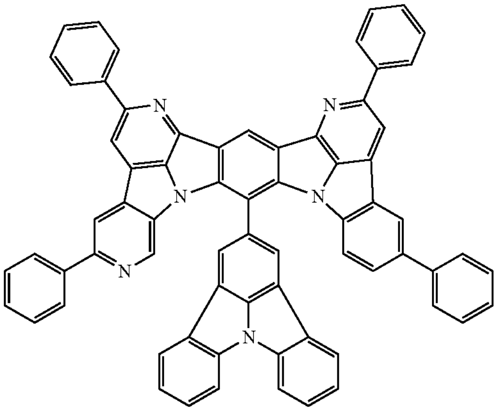
76
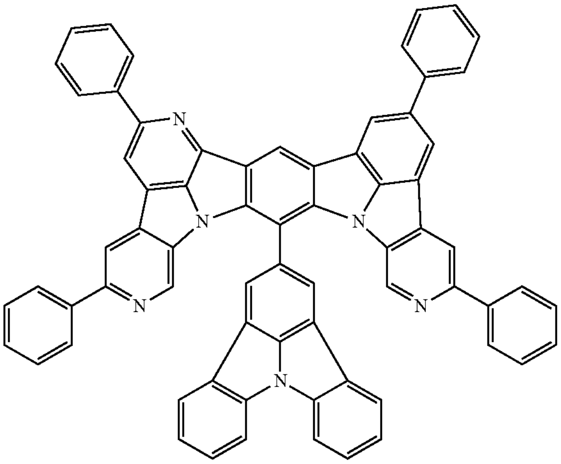
77
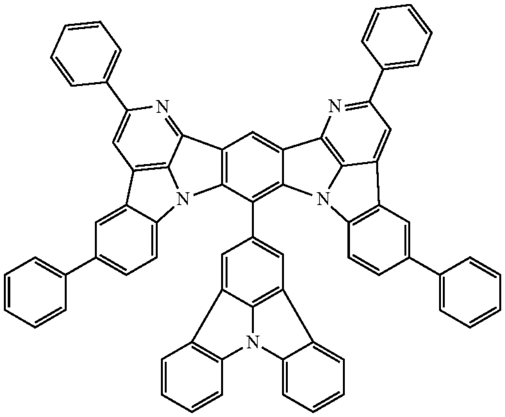
78
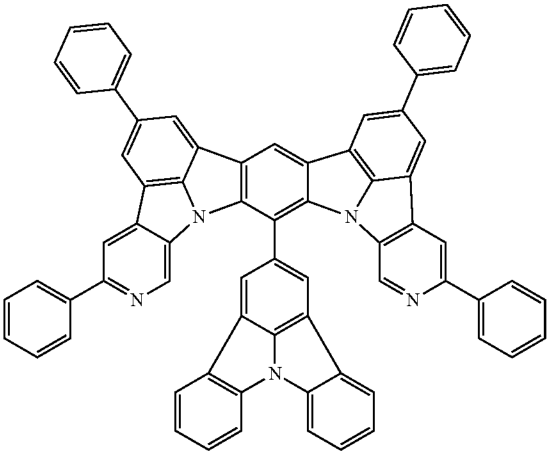
79
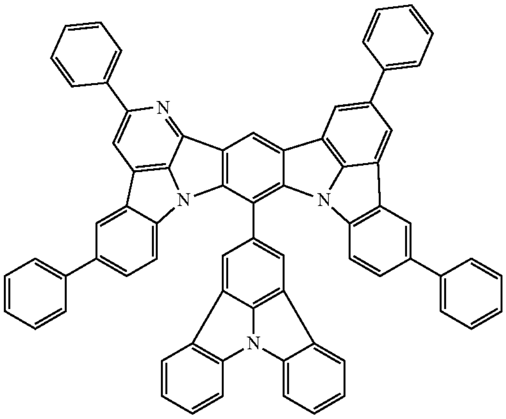
80
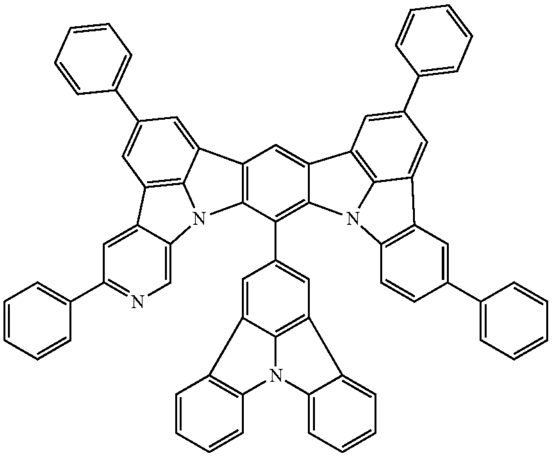

-continued
81
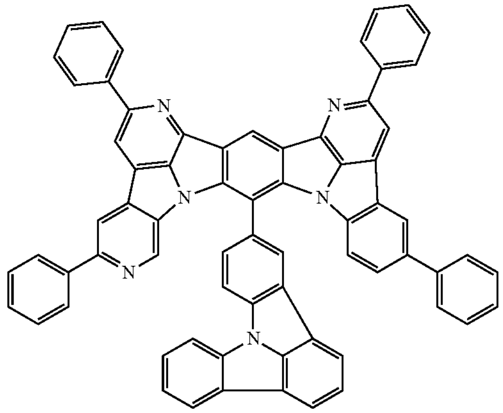
82
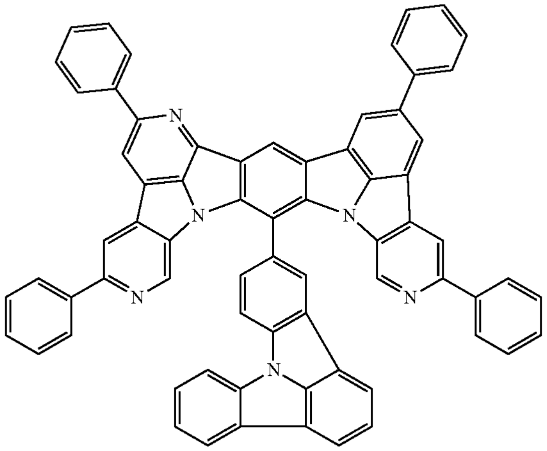
83
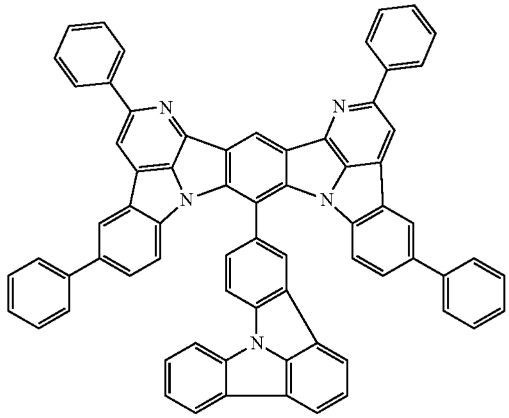
84
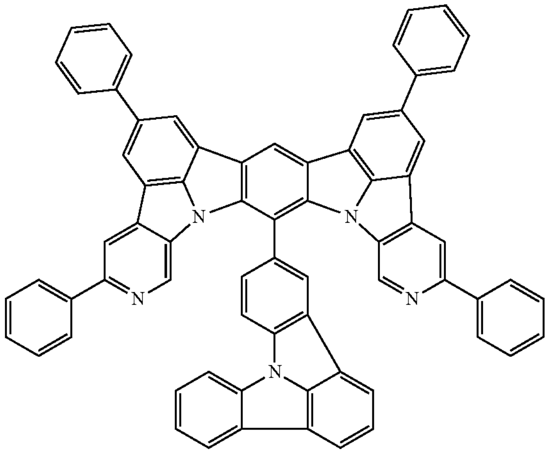
85
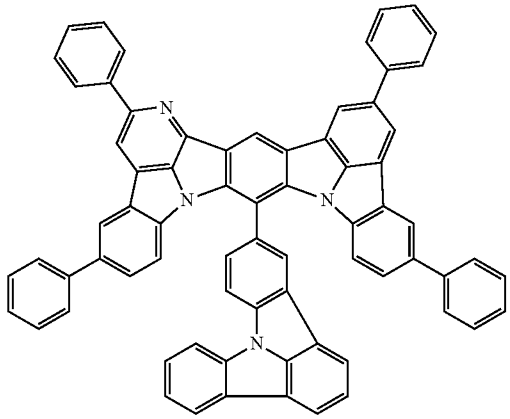
86
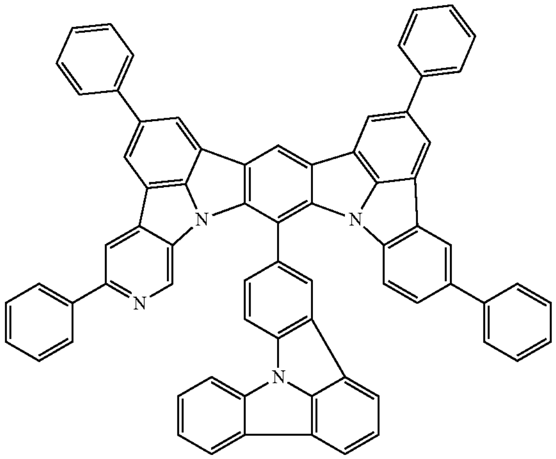

-continued
87
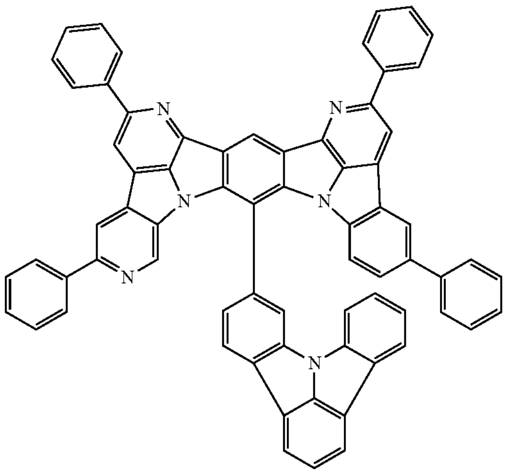
88
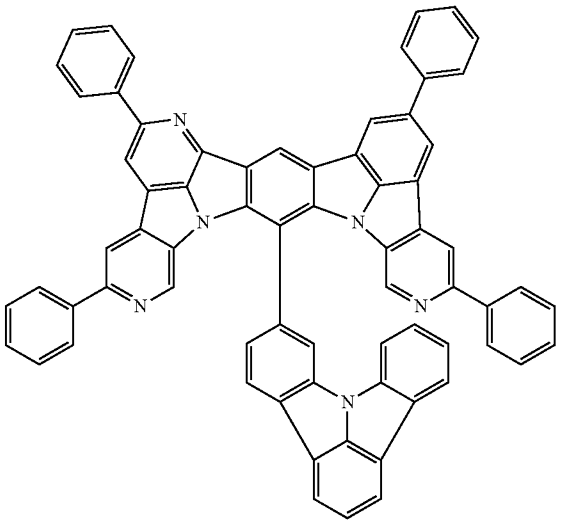
89
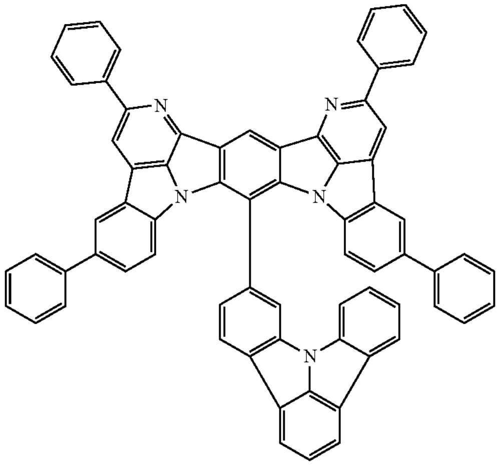
90
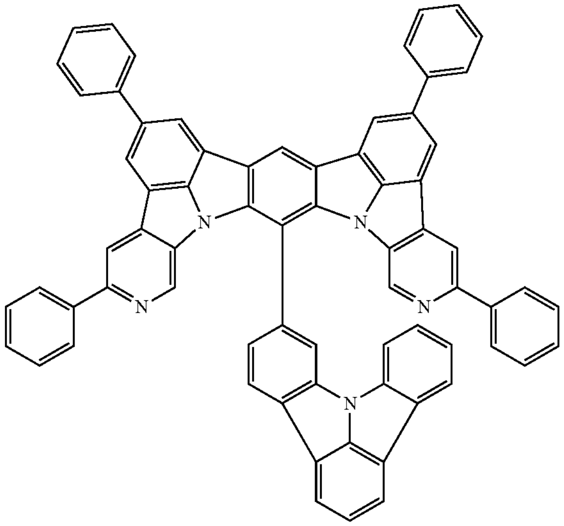
91
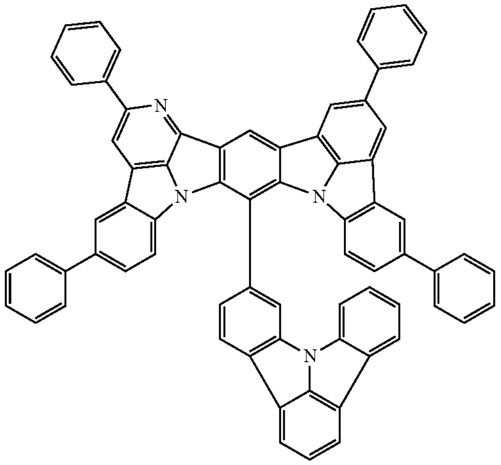
92
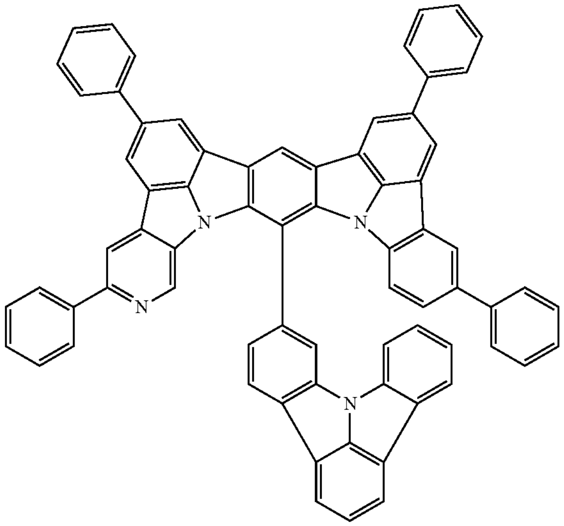
.

In an embodiment, the heterocyclic compound may be Compound 1, 2, or 25.

In an organic light-emitting device, a luminescent material having high color purity for each of red, green, and blue is preferred to cover a wide color region. However, it is difficult to realize light emission of high color purity for a blue luminescent material, and a blue luminescent material in the related art may not have sufficient luminescence efficiency and may have a relatively short emission wavelength.

By introducing at least one nitrogen N into $X^1$ to $X^4$, the heterocyclic compound may have a deeper lowest unoccupied molecular orbital (LUMO), a longer emission wavelength, and a narrower $\Delta E_{ST}$.

In addition, since the heterocyclic compound has a rigid structure, structural relaxation in an excited state may be suppressed. As a result, the heterocyclic compound may have a narrow width of blue emission spectrum and improved color purity. In this regard, a spectrum width of fluorescence in photoluminescence (PL) (a full width at half maximum (FWHM) of the fluorescence spectrum peak) may be used as an index of color purity. The narrower the FWHM of the heterocyclic compound, the higher the color purity.

In an embodiment, the FWHM of the heterocyclic compound may be less than about 20 nm, or less than or equal to about 15 nm, and may be greater than 0 nm. When the above range is satisfied, light emission with improved color purity may be obtained.

In addition, without wishing to be bound by theory, the atomic orbital of the imine nitrogen of the heterocyclic compound is a nitrogen atom in which one 2s orbital and two 2p orbitals are mixed, and thus has a greater electronegativity than a carbon atom, and thus, the electron deficiency may be relatively high, and the LUMO may be relatively deep. Accordingly, since the heterocyclic compound has the imine nitrogen, $\Delta E_{S0-S1}$ (eV) may become smaller, and thus, the emission wavelength may become longer. In addition, since the lowest excited triplet energy (T1) level does not change as much as the lowest excited singlet energy (S1) level, $\Delta E_{ST}$ may become narrower.

In an embodiment, $\Delta E_{ST}$ of the heterocyclic compound may be about 0.300 eV or less. In an embodiment, $\Delta E_{ST}$ of the heterocyclic compound may be about 0.280 eV or less, or about 0.260 eV or less. When the above range is satisfied, the width of the emission spectrum of the heterocyclic compound may be large, and light emission with high efficiency may be obtained.

The highest occupied molecular orbital (HOMO) level of the heterocyclic compound according to an embodiment may be, but is not particularly limited to, about −6.50 eV or more, for example, about −6.40 eV or more, or about −6.30 eV or more. In addition, the HOMO level of the heterocyclic compound according to an embodiment may be about −4.6 eV or less, −4.8 eV or less, or −5.0 eV or less, from the viewpoint of consistency with an energy diagram of other general materials forming the emission layer and the stability in the atmosphere. Within these ranges, the organic light-emitting device may have a low driving voltage.

The LUMO level of the heterocyclic compound according to an embodiment may be, but is not particularly limited to, about −2.60 eV or less, or for example, about −3.00 eV or less. In addition, the LUMO level of the heterocyclic compound according to an embodiment may be about −4.0 eV or more from the viewpoint of consistency with an energy diagram of other general materials forming the emission layer. Within these ranges, the organic light-emitting device may have a low driving voltage.

The peak wavelength in PL of the heterocyclic compound may be, but is not particularly limited to, about 440 nm or more and about 480 nm or less. When the above range is satisfied, the heterocyclic compound may be more suitable for blue light emission. The peak wavelength is obtained by converting the adiabatic first excited singlet state (S1) energy (hereinafter, also referred to as "adiabatic S1 excitation energy") level (eV) into a light wavelength (nm).

The peak wavelength in PL and the FWHM in PL may each be measured and/or calculated using a spectrofluorophotometer F-7000 manufactured by Hitachi High-Tech Science Co., Ltd. In addition, the measurement and/or calculation methods are described in the Examples.

The HOMO, LUMO, peak wavelength, and $\Delta E_{ST}$ were calculated using Gaussian 16 (Gaussian Inc.) by a density functional theory (DFT). The detailed calculation method is the same as described in the Examples.

However, it is known that $\Delta E_{ST}$ is calculated to be large in the calculation method described in the Examples. Accordingly, a calculated value of $\Delta E_{ST}$ of the heterocyclic compound may be about 0.450 eV or less.

In addition, as shown in the Examples below, the peak wavelength may be different from a calculated value in the calculation method described in the Examples, and thus, correction may be necessary. A calculated value of the peak wavelength of the heterocyclic compound may be 416 nm or more and 480 nm or less.

The synthesis method of the heterocyclic compound according to one or more embodiments is not particularly limited, and the heterocyclic compound may be synthesized according to a known synthesis method. In particular, the heterocyclic compound may be synthesized according to or in view of the method described in the Examples. For example, in the method described in the Examples, the heterocyclic compound according to one or more embodiments may be synthesized through modifications such as changing raw materials and reaction conditions, adding or excluding some processes, or appropriately combining with other known synthesis methods.

The method of identifying a structure of the heterocyclic compound according to one or more embodiments is not particularly limited. The heterocyclic compound according to one or more embodiments may be identified by a known method, for example, NMR or LC-MS.

Material for Organic Light-Emitting Device

Another embodiment of the present disclosure relates to a material for an organic light-emitting device including the heterocyclic compound. The material for the organic light-emitting device may include the heterocyclic compound and other materials used in an organic light-emitting device.

The other materials used in an organic light-emitting device may be, but are not limited to, materials known in the art. For example, as the other materials used in an organic light-emitting device, materials constituting each layer described in the below description of the organic light-emitting device may be used. Among the materials constituting each layer, a dopant material or a host material described in the below description of an emission layer of the organic light-emitting device may be used. In addition, a TADF material, a phosphorescent material, or a host material described in the below description of the emission layer of the organic light-emitting device may be used. In this regard, the phosphorescent material may be a platinum complex to be described below.

Accordingly, an embodiment of the present disclosure may provide, in addition to the heterocyclic compound, a material for an organic light-emitting device that further includes a TADF material or a phosphorescent material to be described below. In particular, a material for an emission layer may include a TADF material or a phosphorescent material in addition to the heterocyclic compound, thereby significantly improving the luminescence efficiency and/or device lifespan of the organic light-emitting device.

The material for an organic light-emitting device may be a liquid material further including a solvent. The solvent may be, but is not particularly limited to, a solvent having a boiling point of 100° C. or more and 350° C. or less at atmospheric pressure (101.3 kPa, 1 atm). In an embodiment, the boiling point of the solvent at atmospheric pressure may be 150° C. or more and 320° C. or less, or 180° C. or more and 300° C. or less. When the above range is satisfied, the processability or film-forming capability of a wet film forming method may be improved, especially in an inkjet method.

The solvent having a boiling point of 100° C. or more and 350° C. or less at atmospheric pressure is not particularly limited, and a known solvent may be appropriately used. Hereinafter, the solvent having a boiling point of 100° C. or more and 350° C. or less at atmospheric pressure will be described in detail, but embodiments of the present disclosure are not limited thereto.

Examples of a hydrocarbon-based solvent may include octane, nonane, decane, undecane, dodecane, and the like. Examples of an aromatic hydrocarbon-based solvent may include toluene, xylene, ethylbenzene, n-propyl benzene, iso-propyl benzene, mesitylene, n-butyl benzene, sec-butyl benzene, 1-phenyl pentane, 2-phenyl pentane, 3-phenyl pentane, phenyl cyclopentane, phenyl cyclohexane, 2-ethyl biphenyl, 3-ethyl biphenyl, and the like. Examples of an ether-based solvent may include 1,4-dioxane, 1,2-diethoxyethane, diethyleneglycol dimethyl ether, diethyleneglycol diethyl ether, anisole, ethoxybenzene, 3-methylanisole, m-dimethoxy benzene, and the like. Examples of a ketone-based solvent may include 2-hexanone, 3-hexanone, cyclohexanone, 2-heptanone, 3-heptanone, 4-heptanone, cycloheptanone, and the like. Examples of an ester-based solvent may include butyl acetate, butyl propionate, heptyl butyrate, propylene carbonate, methyl benzoate, ethyl benzoate, 1-propyl benzoate, 1-butyl benzoate, and the like. Examples of a nitrile-based solvent may include benzonitrile, 3-methyl benzonitrile, and the like. Examples of an amide-based solvent may include dimethyl formamide, dimethyl acetamide, N-methyl pyrrolidone, and the like. Such solvent may be used alone or in combination of two or more.

The material for an organic light-emitting device according to an embodiment may be a material for an emission layer.

The material for an organic light-emitting device according to an embodiment may not be a liquid composition. That is, the material for an organic light-emitting device may be substantially free of a solvent. In this regard, the term "material substantially free of a solvent" indicates that the amount of the solvent is less than 1 wt % based on the total weight of the composition. When the material for an organic light-emitting device is not a liquid composition, the organic light-emitting device may be substantially free of a solvent, and may not include a solvent (wherein the amount of the solvent is 0 wt % based on the total weight of the composition). As used herein "substantially free of a solvent" means less than about 5 wt %, less than about 1 wt %, or less than about 1000 ppm, based on the total weight of the composition.

An amount of the heterocyclic compound based on the total weight (in the case of a liquid composition, the total weight excluding the solvent) of the material for an organic light-emitting device (in particular, the material for an emission layer) is the same as an amount of the heterocyclic compound based on the total weight of the emission layer of the organic light-emitting device to be described below.

In addition, an amount of the TADF material or the phosphorescent material (specifically, the phosphorescent material) based on the total weight (in the case of a liquid composition, the total weight excluding the solvent) of the material for an organic light-emitting device (in particular, the material for an emission layer) is the same as an amount of the TADF material or the phosphorescent material (specifically, the phosphorescent material) based on the total weight of the emission layer of the organic light-emitting device to be described below, In addition, the amount of the TADF material or the phosphorescent material based on the total weight of the material for an organic light-emitting device is the same as an amount (parts by weight) of the TADF material or the phosphorescent material (specifically, the phosphorescent material) based on 100 parts by weight of the heterocyclic compound in the material for an organic light-emitting device (in particular, the material for an emission layer).

In addition, an amount of the host material based on the total weight (in the case of a liquid composition, the total weight excluding the solvent) of the material for an organic light-emitting device (in particular, the material for an emission layer) is the same as an amount of the host material based on the total weight of the emission layer of the organic light-emitting device to be described below.

In addition, an amount (parts by weight) of the host material based on 100 parts by weight of the heterocyclic compound in the material for an organic light-emitting device (in particular, the material for an emission layer) is the same as an amount (parts by weight) of the host material based on 100 parts by weight of the heterocyclic compound in the emission layer of the organic light-emitting device to be described below.

When the amounts of the heterocyclic compound, the TADF material or the phosphorescent material, and the host material in the material for an organic light-emitting device are within the above ranges, respectively, an organic light-emitting device having improved luminescence efficiency and/or lifespan may be obtained according to the emission color purity.

Organic Light-Emitting Device

Another embodiment of the present disclosure relates to an organic light-emitting device having an organic layer including the heterocyclic compound. The organic light emitting device may have a narrow emission spectrum, and may realize luminescence with high color purity. In addition, the organic light-emitting device may realize improved luminescence efficiency.

Figure 2:
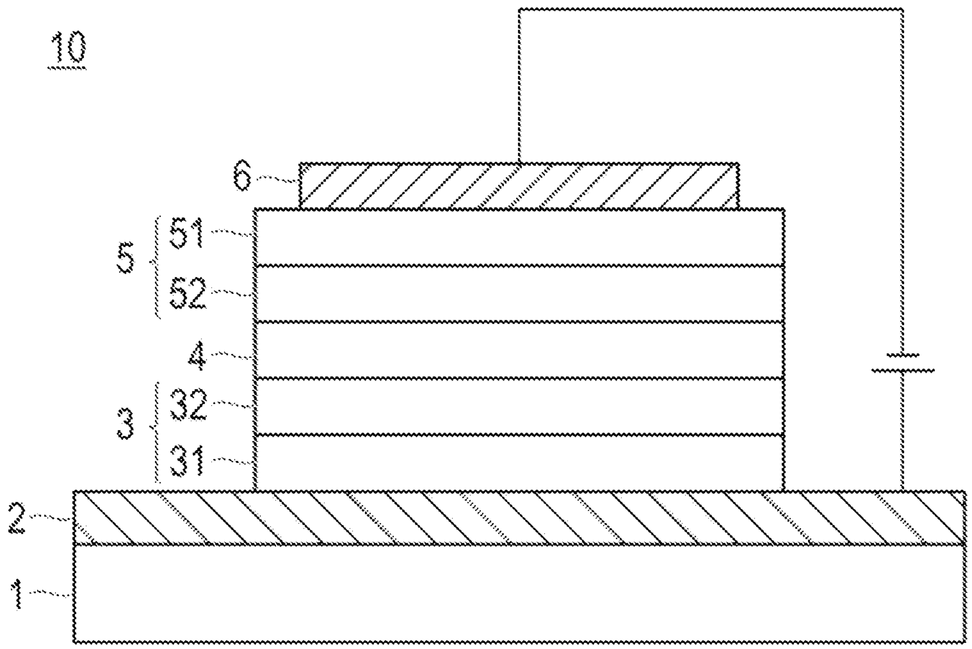
FIG. 2 is a schematic cross-sectional view of an organic light-emitting device according to an exemplary embodiment.
Figure 3:
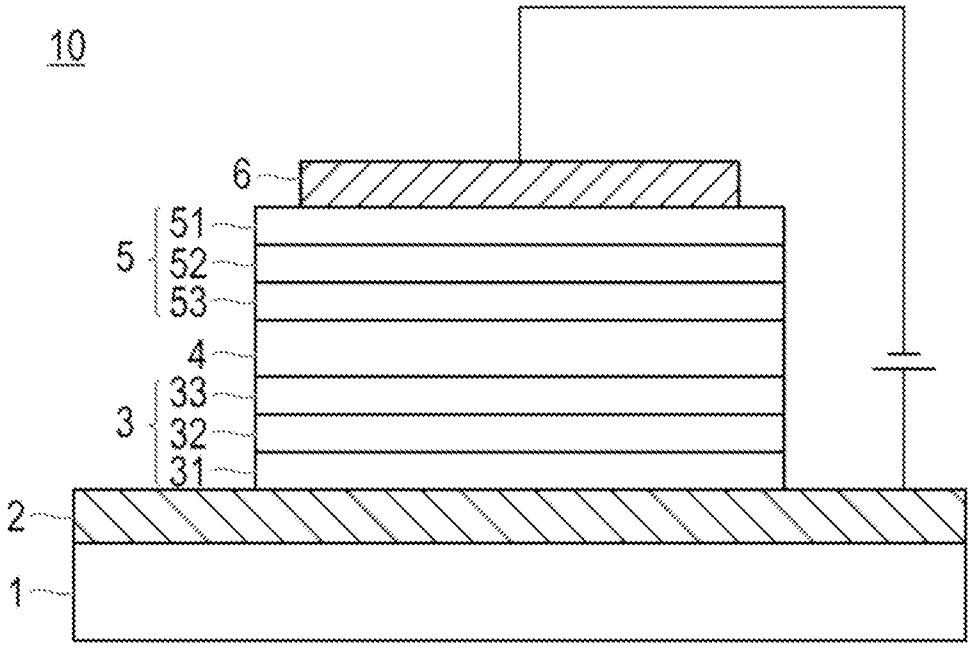
FIG. 3 is a schematic cross-sectional view of an organic light-emitting device according to an exemplary embodiment.

Description of FIGS. 1 to 3

Hereinafter, an organic light-emitting device 10 according to an embodiment will be described in detail with reference to FIGS. 1 to 3.

FIG. 1 is a schematic cross-sectional view of the organic light-emitting device 10 according to an exemplary embodiment. The organic light-emitting device 10 according to an embodiment may include a substrate 1, a first electrode 2, a hole transport region 3, an emission layer 4, an electron transport region 5, and a second electrode 6, which are sequentially stacked in this stated order.

FIG. 2 is a schematic cross-sectional view of the organic light-emitting device 10 according to another exemplary embodiment. The organic light-emitting device 10 according to an embodiment may include the substrate 1, the first electrode 2, the hole transport region 3, the emission layer 4, the electron transport region 5, and the second electrode 6. As shown in FIG. 2, the hole transport region 3 may include a hole injection layer 31 and a hole transport layer 32, which are sequentially stacked in this stated order. In addition, as shown in FIG. 2, the electron transport region 5 may include an electron transport layer 52 and an electron injection layer 51, which are sequentially stacked in this stated order.

FIG. 3 is a schematic cross-sectional view of the organic light-emitting device 10 according to another exemplary embodiment. The organic light-emitting device 10 according to an embodiment may include the substrate 1, the first electrode 2, the hole transport region 3, the emission layer 4, the electron transport region 5, and the second electrode 6. As shown in FIG. 3, the hole transport region 3 may include the hole injection layer 31, the hole transport layer 32, and an electron blocking layer 33, which are sequentially layered in the stated order. In addition, as shown in FIG. 3, the electron transport region 5 may include a hole blocking layer 53, the electron transport layer 52, and the electron injection layer 51, which are sequentially layered in the stated order.

An embodiment may include, for example, an organic electroluminescence device including a first electrode, a second electrode, and a single or a plurality of emission layers. The second electrode may be arranged on the first electrode.

In the present specification, "on" may not apply only to a case of "just on" another part and may also include a case where another part may be present therebetween. Similarly, when a part such as a layer, a membrane, a regions, a plate, or the like is described as being "below" or "under" another part, a case of "just under" another part and also a case where another part present therebetween may be included.

In the present specification, "arrangement" may include a case where a portion is arranged not only on an upper part but also on a lower part.

The organic light-emitting device 10 may include the heterocyclic compound according to an embodiment. For example, the heterocyclic compound according to an embodiment may be included in an organic layer arranged between the first electrode 2 and the second electrode 6. In an embodiment, the heterocyclic compound may be included in the emission layer 4.

Hereinafter, an embodiment in which the emission layer includes the heterocyclic compound according to an embodiment will be described.

Emission Layer 4

The emission layer 4 may emit light by fluorescence or phosphorescence.

The emission layer 4 may be a single layer consisting of a single material or a single layer consisting of a plurality of different materials. In addition, the emission layer 4 may have a multi-layered structure having multiple layers including a plurality of different materials.

In the emission layer 4, the heterocyclic compound may be used alone or two or more thereof may be combined.

The amount of the heterocyclic compound may be, but is not particularly limited to, 0.05 wt % or more based on the total weight of the emission layer. In an embodiment, the amount of the heterocyclic compound may be 0.1 wt % or more, 0.2 wt % or more, 50 wt % or less, 30 wt % or less, or 25 wt % or less, based on the total weight of the emission layer. Within these ranges, an organic light-emitting device having improved color purity, luminescence efficiency and/or lifespan may be obtained.

In an embodiment, the emission layer 4 may further include a host, the host and the heterocyclic compound may be different from each other, and the emission layer 4 may consist of the host and the heterocyclic compound. In this regard, the host may not emit light, and the heterocyclic compound may emit light. That is, the heterocyclic compound may be a dopant.

In one or more embodiments, the emission layer 4 may further include a host and a dopant, the host, the dopant, and the heterocyclic compound may be different from one another, and the emission layer 4 may consist of the host, the dopant, and the heterocyclic compound. In this regard, the host and the heterocyclic compound may not each emit light, and the dopant may emit light.

In the Examples, the host and the dopant will be described in more detail.

The emission layer 4 may include a known host material and a known dopant material.

For example, the emission layer may include, in addition to the heterocyclic compound, an anthracene derivative, a pyrene derivative, a fluoranthene derivative, a chrysene derivative, a dihydrobenzoanthracene derivative, or a triphenylene derivative.

For example, the emission layer may include, as the host material, at least one of bis[2-(diphenylphosphino)phenyl] etheroxide (DPEPO), 4,4'-bis(carbazol-9-yl)biphenyl (CBP), 3,3'-bis(carbazol-9-yl)biphenyl (mCBP), 1,3-bis (carbazol-9-yl)benzene (mCP), 2,8-bis(diphenylphosphoryl) dibenzo[b,d]furan (PPF), 4,4',4"-tris(carbazol-9-yl)triphenylamine (TcTa), 1,3,5-tris(N-phenylbenzimidazole-2-yl) benzene (TPBi), or any combination thereof. However, the host material is not limited thereto, and the emission layer may include, for example, tris(8-hydroxyquinolino)aluminum (Alq3), 4,4'-bis(N-carbazolyl)-1,1'-biphenyl (CBP), poly(n-vinylcarbazole) (PVK), 9,10-di(naphthalene-2-yl) anthracene (ADN), 4,4',4"-tris(carbazol-9-yl)-triphenylamine (TCTA), 1,3,5-tris(N-phenylbenzimidazol-2-yl)benzene (TPBi), 3-tert-butyl-9,10-di(naphth-2-yl)anthracene (TBADN), distyrylarylene (DSA), 4,4'-bis(9-carbazolyl)-2,2'-dimethylbiphenyl (CDBP), 2-methyl-9,10-bis(naphthalene-2-yl)anthracene (MADN), bis[2-(diphenylphosphino) phenyl]etheroxide (DPEPO), hexaphenylcyclotriphosphazene (CP1), 1,4-bis(triphenylsilyl)benzene (IGH2), hexaphenylcyclotrisiloxane ($DPSiO_3$), octaphenylcyclotetrasiloxane (DPSiO4), or 2,8-bis(diphenylphosphoryl)dibenzofuran (PPF).

In addition, the emission layer may include, as the host material, a material having a HOMO level of about −5.2 eV or less. In addition, the emission layer may include, as the host material, a material having a LUMO level of about −1.4 eV or less. By using a host material having a low HOMO level and low LUMO level and high electron transport properties, the driving durability in an organic light-emitting device, particularly in a blue organic light-emitting device, may be improved. Such a material is not particularly limited, and an example thereof may include Compound A represented by the formula below, which is disclosed in "An Alternative Host Material for Long-Lifespan Blue Organic Light-Emitting Diodes Using Thermally Activated Delayed Fluorescence", Soo-Ghang Ihn, Namheon Lee, Soon Ok Jeon, Myungsun Sim, Hosuk Kang, Yongsik Jung, Dal Ho Huh, Young Mok Son, Sae Youn Lee, Masaki Numata, Hiroshi Miyazaki, Rafael Gomez-Bombarelli, Jorge Aguilera-Iparraguirre, Timothy Hirzel, Alan Aspuru-Guzik, Sunghan Kim, and Sangyoon Lee, Advanced Science News 2017, 4, 1600502. When the emission layer is formed in combination with such a host material, a blue luminescent material in the related art may become a deep hole trap, thereby causing undesirable effects such as an increase in driving voltage. The heterocyclic compound has weak hole trapping properties, and thus is expected to suppress the increase in the driving voltage.

Compound A

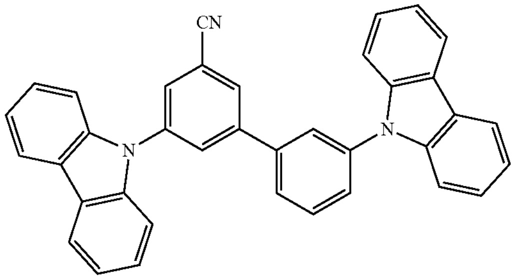

In addition, the emission layer may include the compounds below as the host material.

H-H1

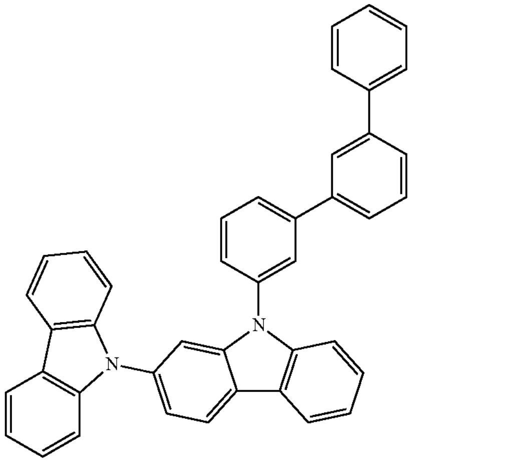

H-E1

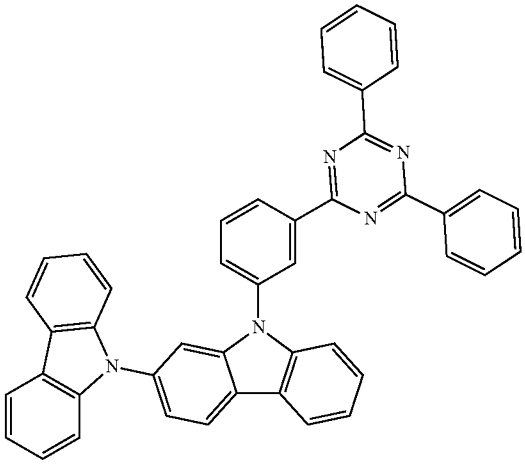

-continued

H-H2

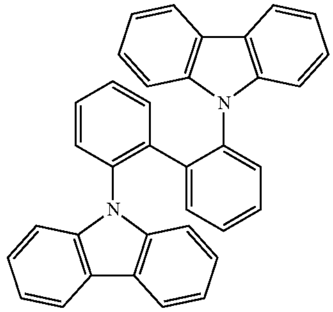

H-E2

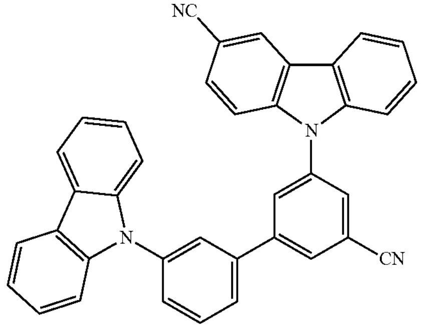

Among these compounds, the emission layer may include, as the host material, Compound H-H1 and/or Compound H-E1, and in particular, may include Compound H-H1 and Compound H-E1. In one or more embodiments, the emission layer may include, as the host material, Compound H-H2 and/or Compound H-E2, and in particular, may include Compound H-H2 and Compound H-E2.

The amount of the host material based on the total weight of the emission layer may be, but is not particularly limited to, about 5 wt % or more. In an embodiment, the amount may be about 10 wt % or more, or about 20 wt % or more. In addition, the amount of the host material based on the total weight of the emission layer may be about 99 wt % or less. In an embodiment, the amount may be about 95 wt % or less, or about 90 wt % or less. Within these ranges, an organic light-emitting device having improved luminescence efficiency and/or lifespan may be obtained.

When the emission layer includes a host material, the amount thereof may be, but is not particularly limited to, about 1,000 parts by weight or more, or about 200,000 parts by weight or less, based on 100 parts by weight of the heterocyclic compound. In an embodiment, the amount may be about 2,000 parts by weight or more, about 3,000 parts by weight or more, about 150,000 parts by weight or less, or about 100,000 parts by weight or less, based on 100 parts by weight of the heterocyclic compound. Within these ranges, an organic light-emitting device having improved luminescence efficiency and/or lifespan may be obtained.

The emission layer is not particularly limited, and may include, for example, a known dopant material. For example, the emission layer may include a styryl derivative (for example, 1,4-bis[2-(3-N-ethylcarbazolyl)vinyl]benzene (BCzVB), 4-(Di-p-tolylamino)-4'-[(di-p-tolylamino)styryl]stilbene (DPAVB), or N-(4-((E)-2-(6-((E)-4-(diphenylamino)styryl)naphthalene-2-yl)vinyl)phenyl)-N-phenylbenzeneamine (N-BDAVBi)), perylene or a derivative thereof (for example, 2,5,8,11-tetra-tert-butylperylene (TBP)), or pyrene or a derivative thereof (for example, 1,1-dipyrene, 1,4-dipyrenylbenzene, or 1,4-bis(N,N-diphenylamino)pyrene).

In addition, the emission layer may further include a known TADF compound or phosphorescent material in addition to the heterocyclic compound. The term "thermally activated delayed fluorescence" refers to a phenomenon in which reverse intersystem crossing occurs between triplet excitons and singlet excitons in a compound with a small energy difference ($\Delta E_{ST}$) between the singlet level and the triplet level, and the term "TADF material" refers to a material in which such a phenomenon occurs.

As is known in the related art, in the emission layer of an organic light-emitting device, singlet excitons and triplet excitons are generated at a ratio of 1:3 by recombination of holes and electrons. In a device including only a fluorescent material as a luminescent material, only singlet excitons are involved in light emission, whereas in a device including a TADF material or a phosphorescent material as a luminescent material, both singlet excitons and triplet excitons may be used for light emission. Accordingly, the luminescence efficiency of the device including the TADF material or the phosphorescent material as a luminescent material may be significantly improved. Excitons generated on the TADF material or the phosphorescent material generally have a long lifespan of 1 μs or more. The excitons are in an unstable state with high energy, and thus, material degradation may occur while the excitons are present, leading to a reduction in device lifespan. When the TADF material or the phosphorescent material is present in the emission layer, in addition to the heterocyclic compound, excitons are generated with high efficiency on the TADF material or the phosphorescent material, and energy is transferred to the heterocyclic compound through a Förster resonance energy transfer (FRET) mechanism. As a result, highly efficient fluorescence may be obtained from the heterocyclic compound, and the time for which excitons are present on the TADF material or the phosphorescent material may be shortened. Thus, the possibility of material deterioration may be significantly reduced, and the device lifespan may be significantly improved.

The amount of the TADF material or the phosphorescent material (in particular, the phosphorescent material) based on the total mass of the emission layer may be, but is not particularly limited to, about 0.1 wt % or more. In an embodiment, the amount may be about 0.5 wt % or more, about 1 wt % or more, about 3 wt % or more, or about 5 wt % or more. In addition, the amount of the TADF material or the phosphorescent material (in particular, the phosphorescent material) based on the total mass of the emission layer may be 50 wt % or less. In an embodiment, the amount may be about 40 wt % or less, or about 30 wt % or less. In addition, when the emission layer includes both the TADF material and the phosphorescent material, the total amount thereof may be within the above ranges. Within these ranges, an organic light-emitting device having improved luminescence efficiency and/or lifespan may be obtained.

When the emission layer includes the TADF material or the phosphorescent material (in particular, the phosphorescent material), the amount thereof may be, but is not particularly limited to, about 100 parts by mass or more based on 100 parts by mass of the heterocyclic compound. In an embodiment, the amount may be about 150 parts by mass or more, or about 200 parts by mass or more, based on 100 parts by mass of the heterocyclic compound. In addition, the amount of the TADF material or the phosphorescent material (in particular, the phosphorescent material) may be about 10,000 parts by mass or less based on 100 parts by mass of the heterocyclic compound. In an embodiment, the amount may be about 7,500 parts by mass or less, or about 5,000 parts by mass or less, based on 100 parts by mass of the heterocyclic compound. In addition, when the emission layer includes both the TADF material and the phosphorescent material, the total amount thereof may be within the above ranges. Within these ranges, an organic light-emitting device having improved luminescence efficiency and/or lifespan may be obtained.

Examples of the TADF material may include the following compounds.

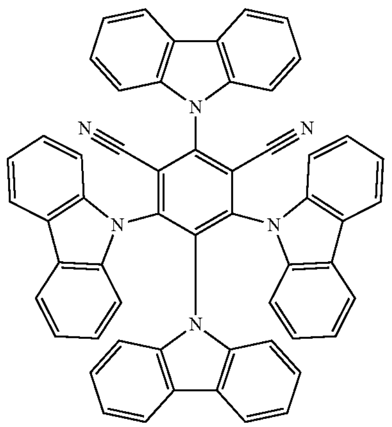

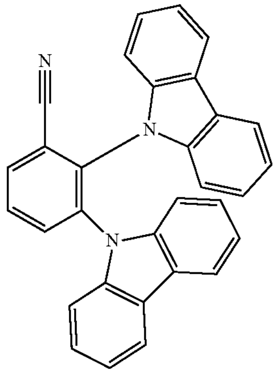

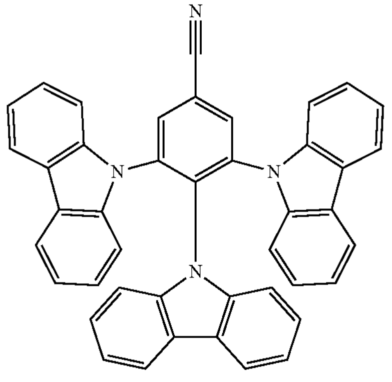

-continued
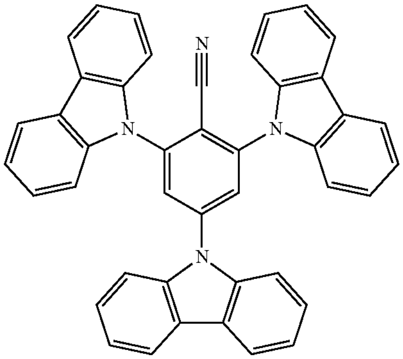
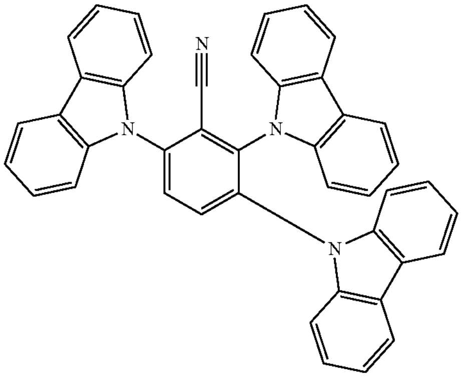
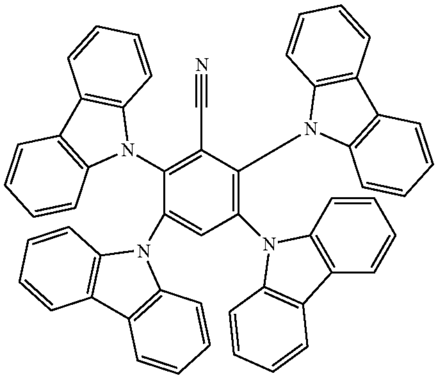
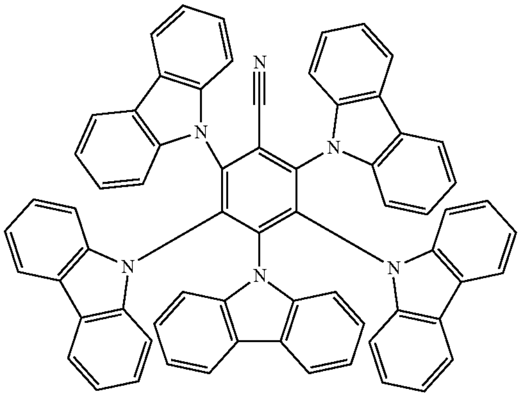
-continued
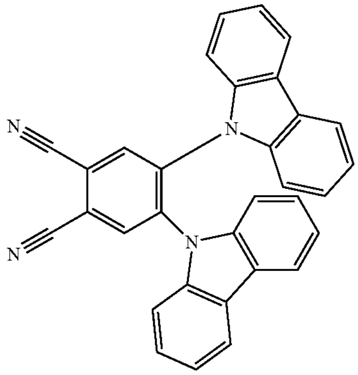
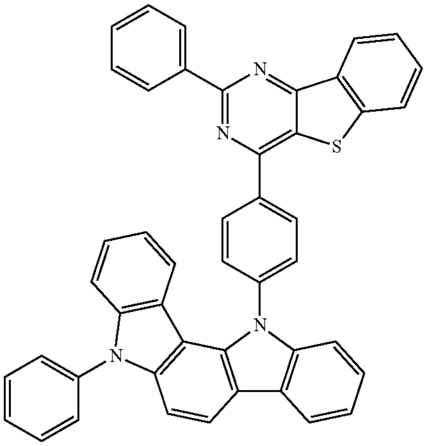
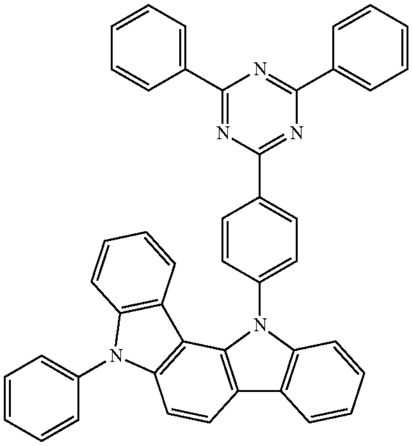

-continued
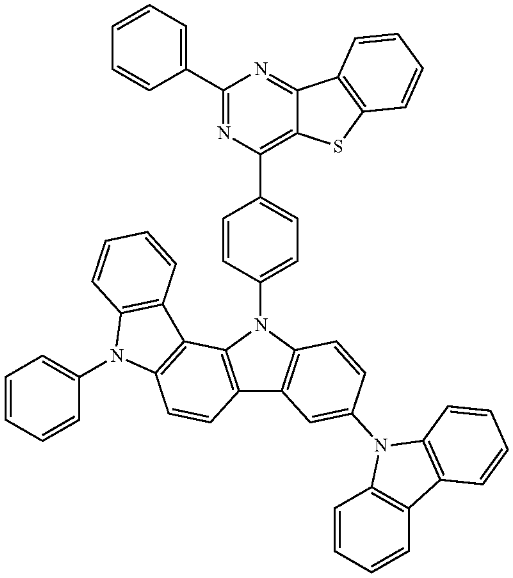
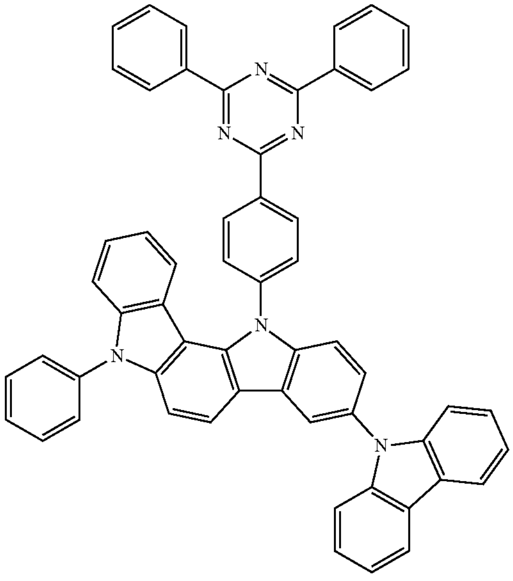
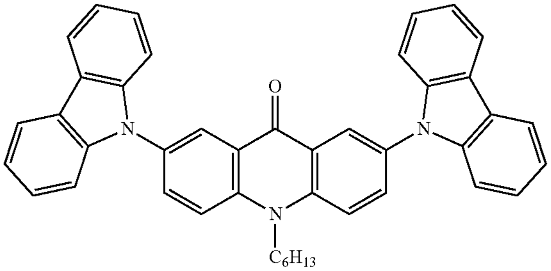
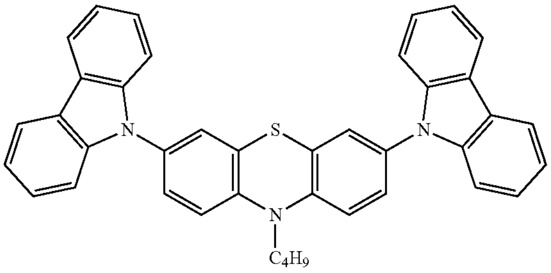
-continued
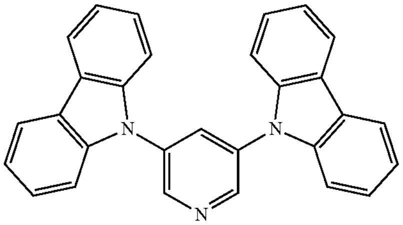
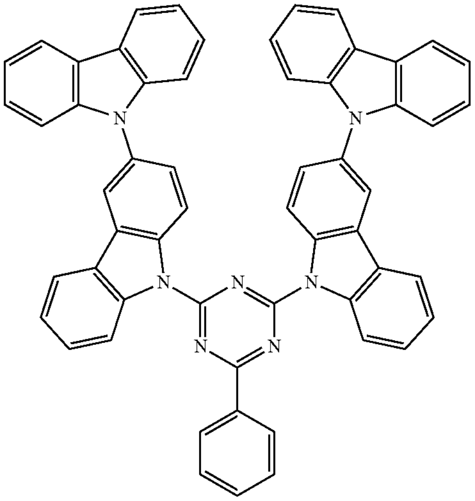
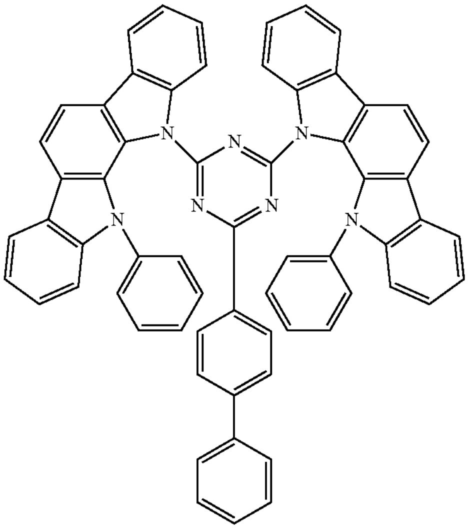
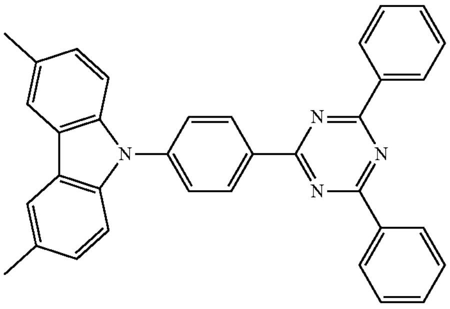

-continued

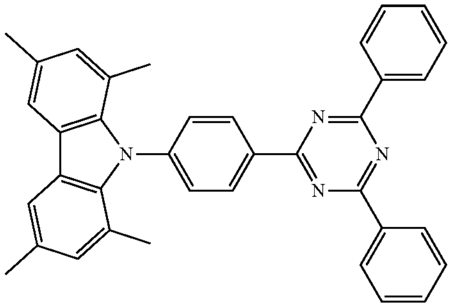

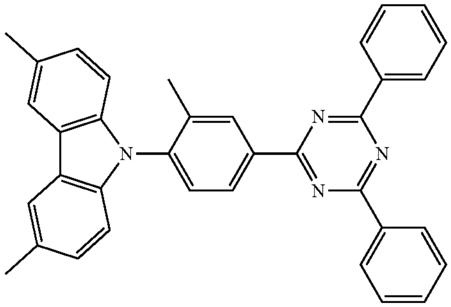

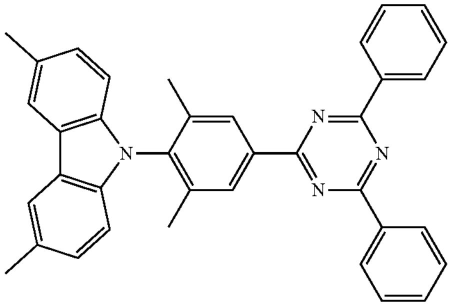

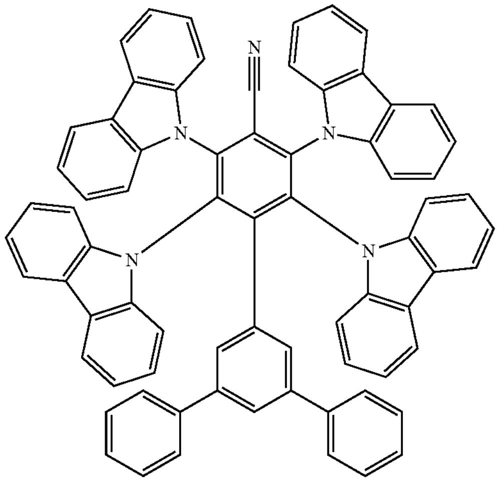

-continued

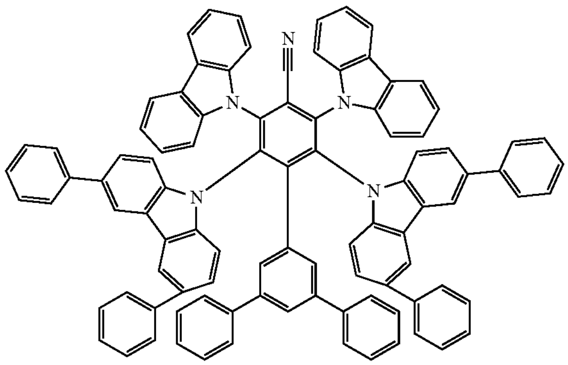

The TADF material may be used alone or in combination of two or more.

In addition, the emission layer may include a phosphorescent material (phosphorescent compound) in addition to the heterocyclic compound. The phosphorescent material (phosphorescent compound) is not particularly limited, and a known phosphorescent compound may be used. Among known phosphorescent compounds, a phosphorescent complex may be used, and in particular, a platinum complex may be used.

Examples of the phosphorescent material (phosphorescent compound) may include the following compounds.

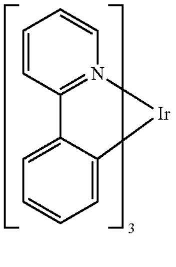

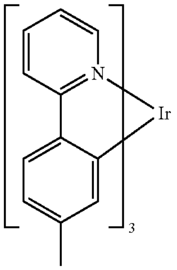

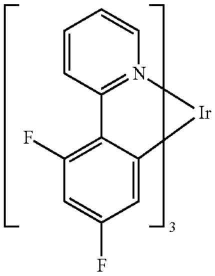

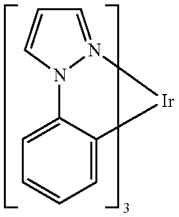

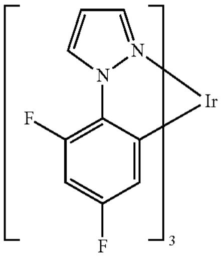

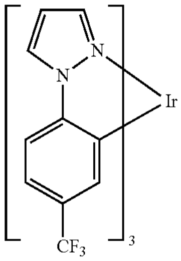

-continued
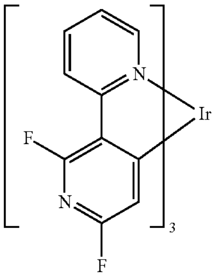
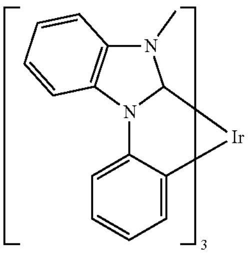
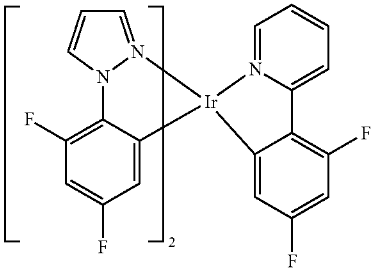
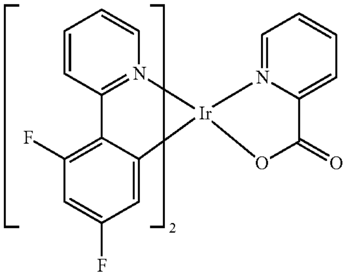
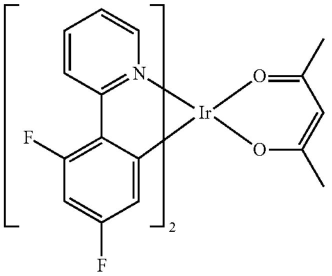
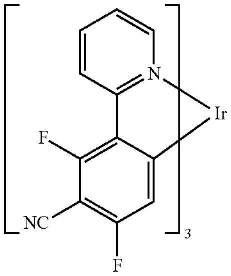
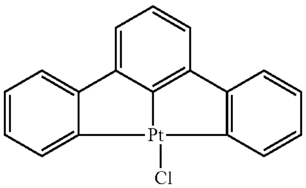
-continued
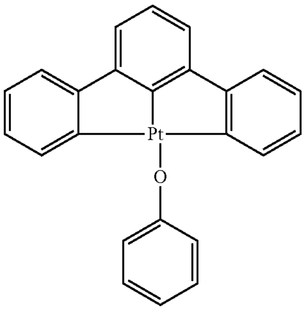
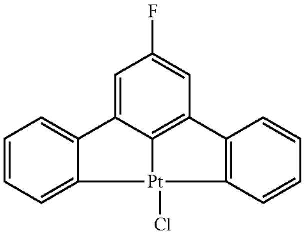
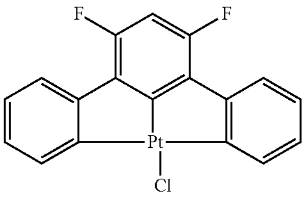
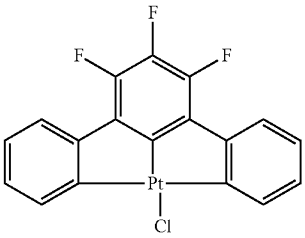
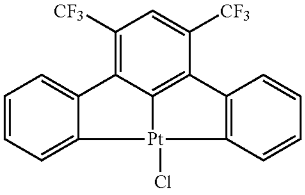
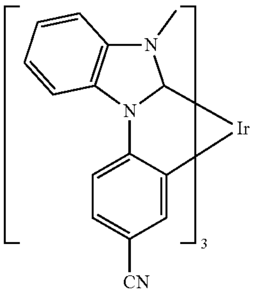

-continued
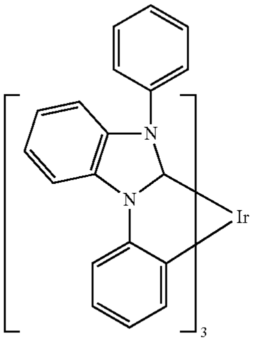
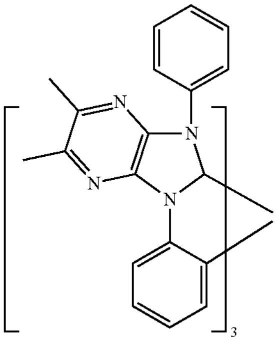
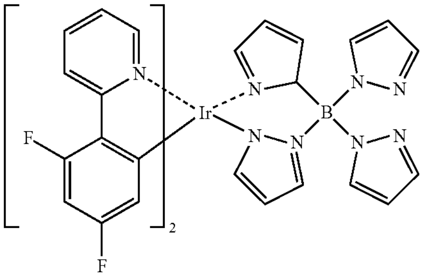
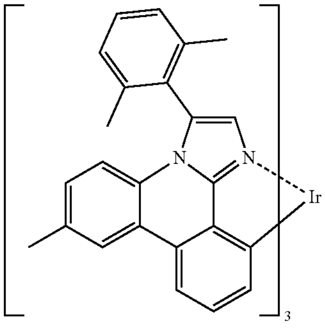
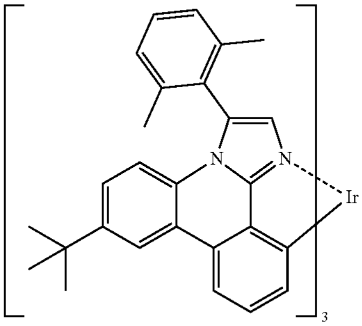
-continued
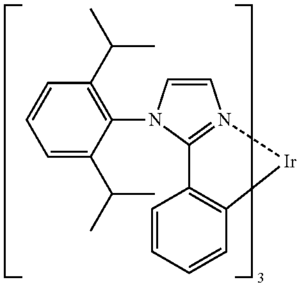
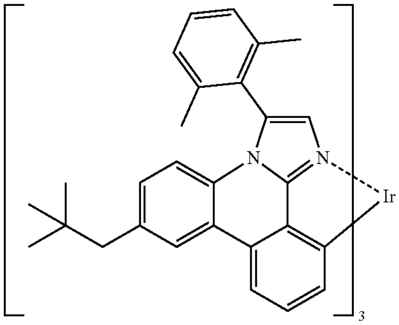
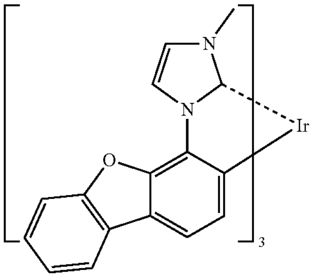
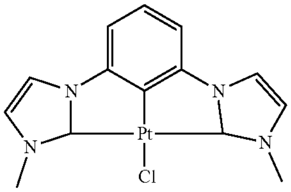
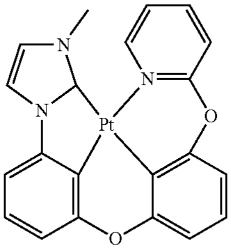
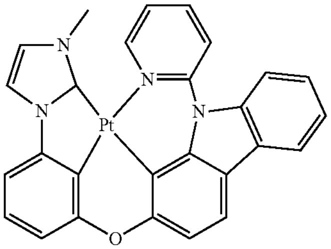

-continued
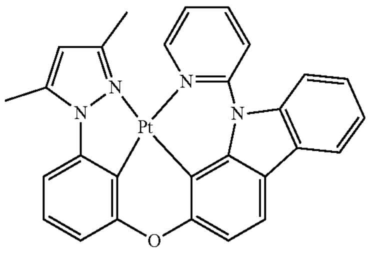
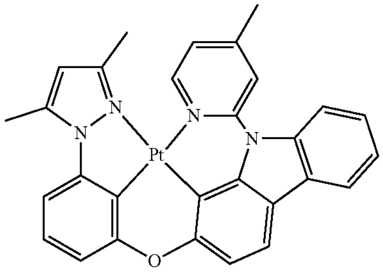
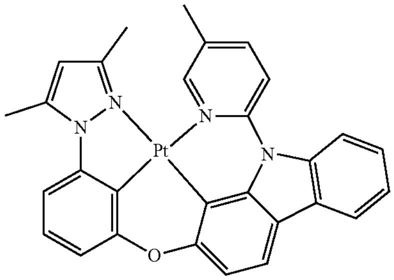
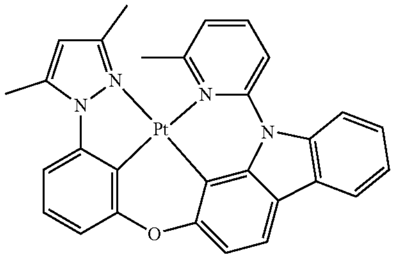
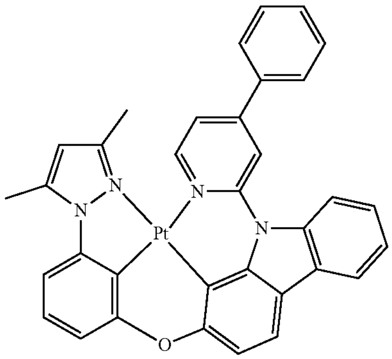
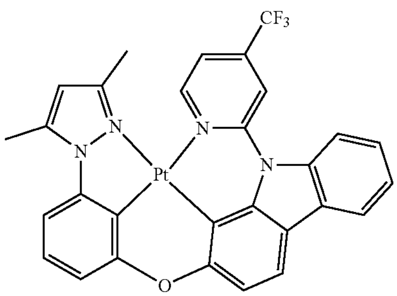
-continued
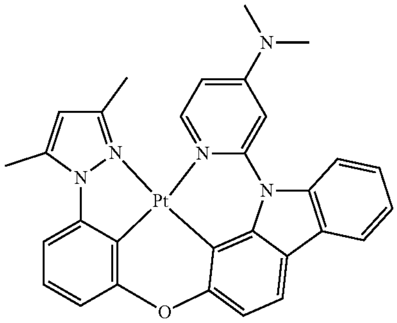
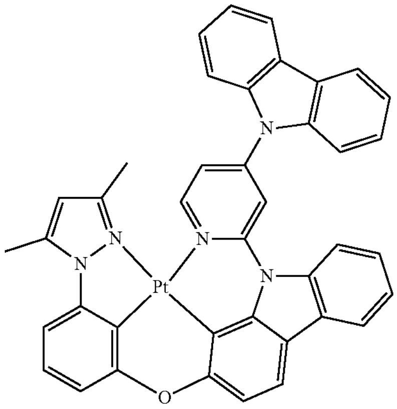
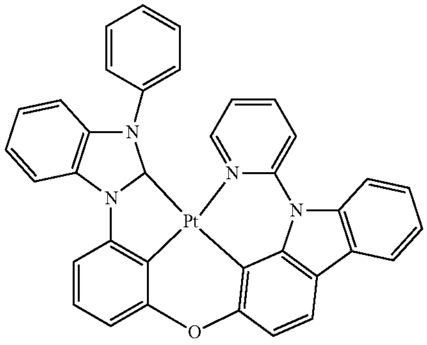
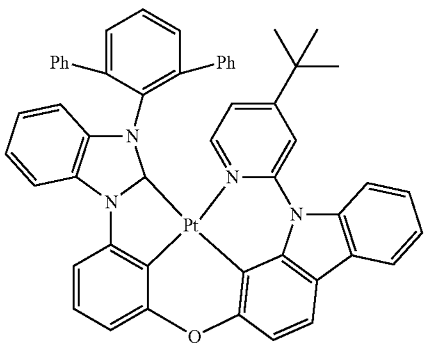

-continued
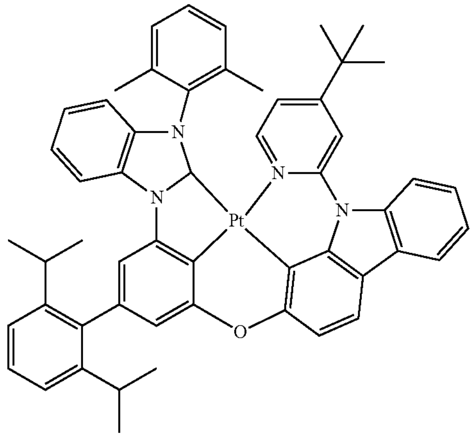
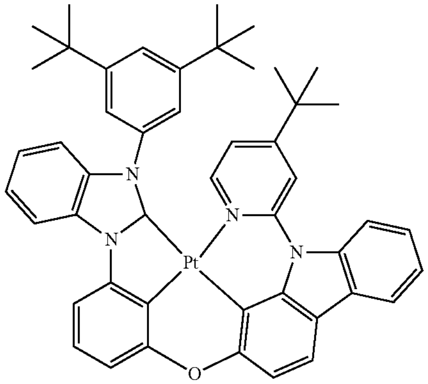
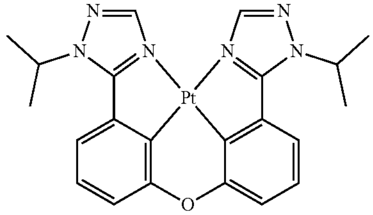
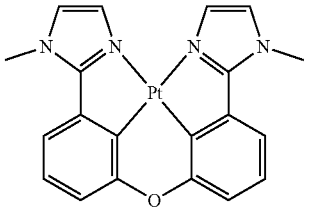
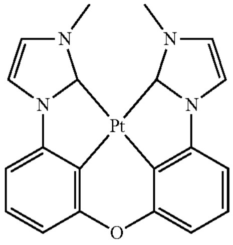
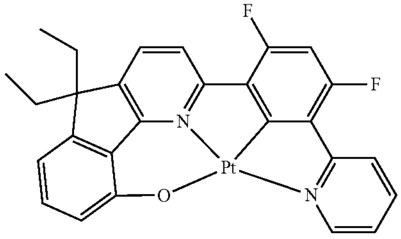
-continued
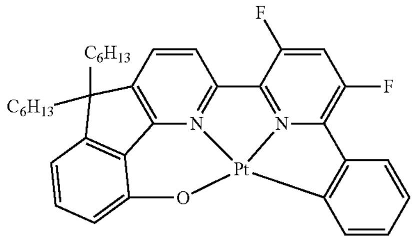
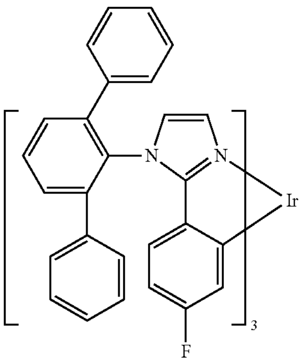
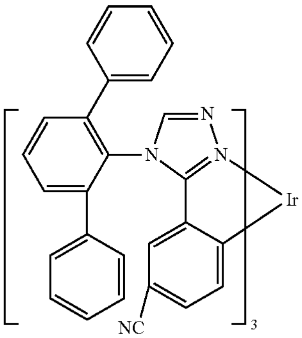
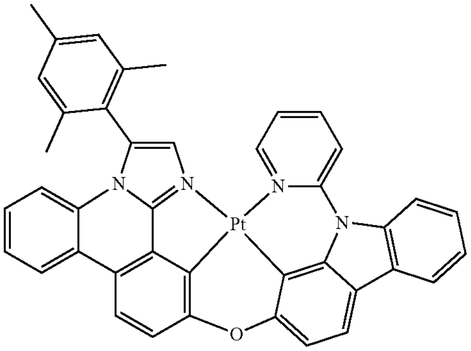
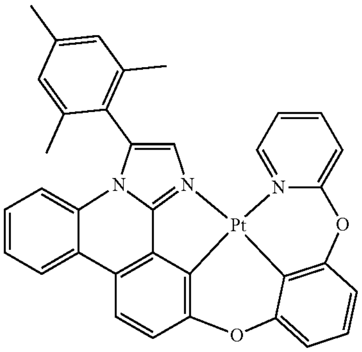

-continued
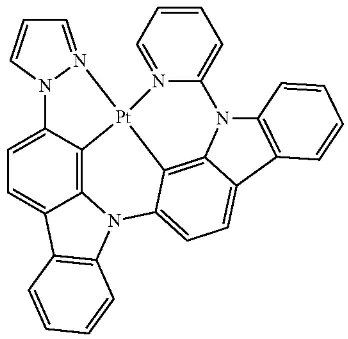
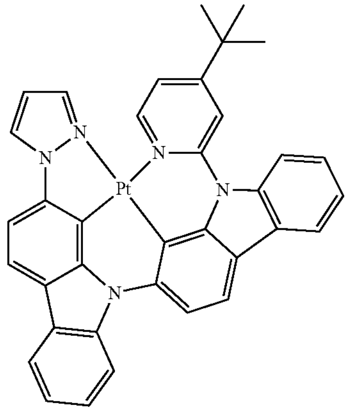
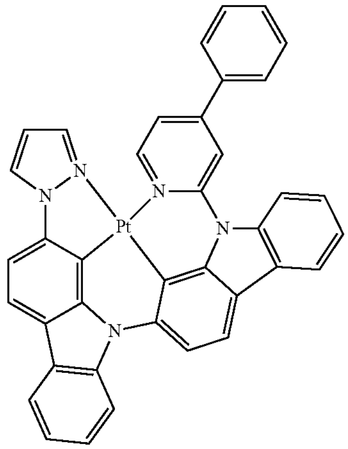
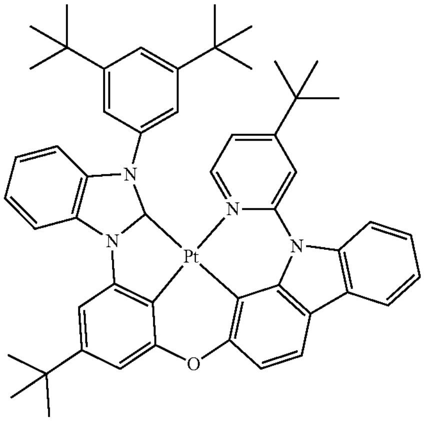
-continued
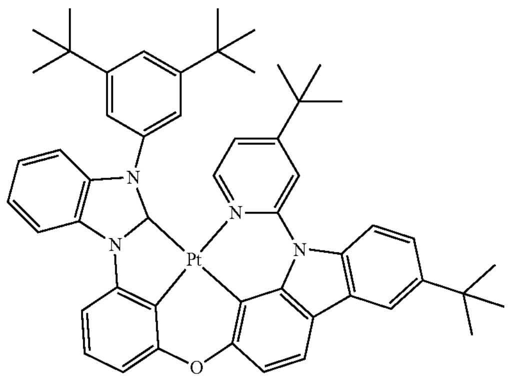
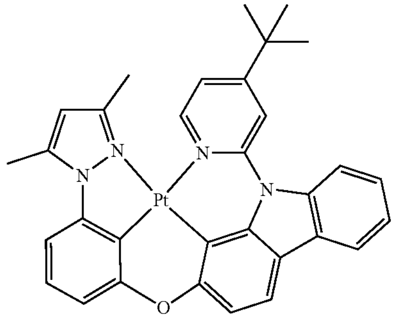
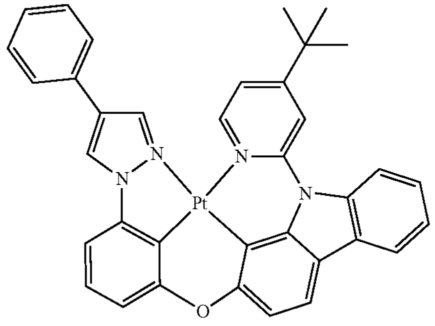
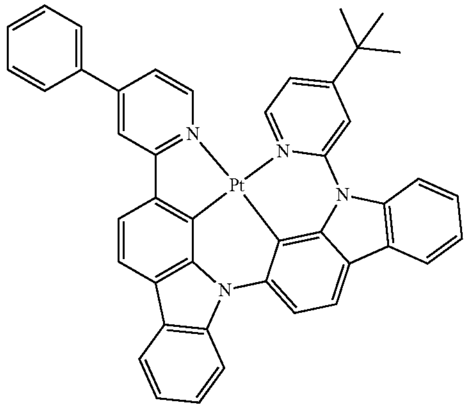

-continued
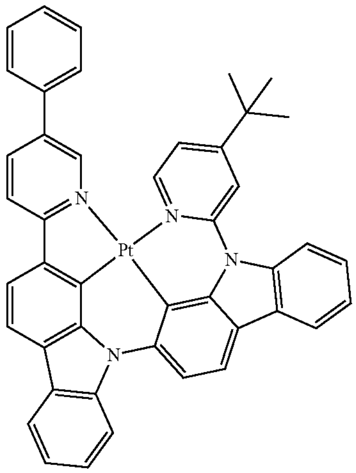
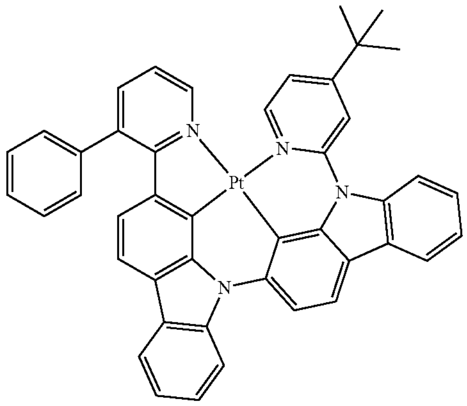
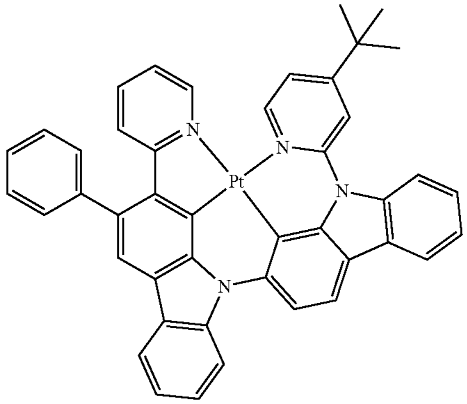
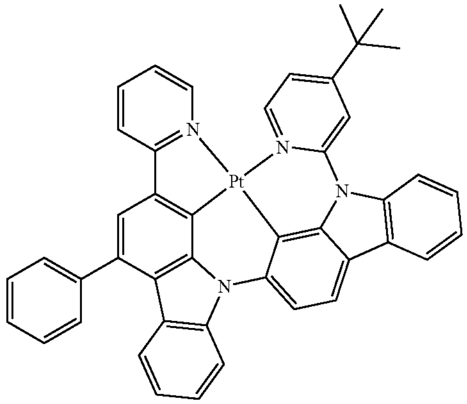
-continued
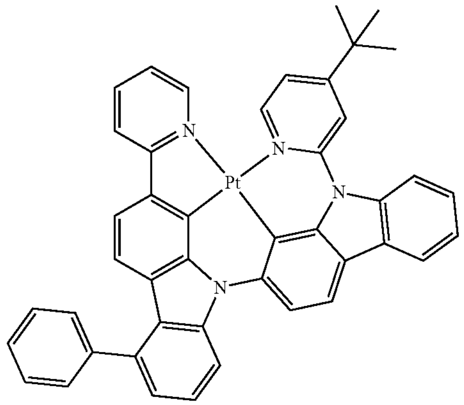
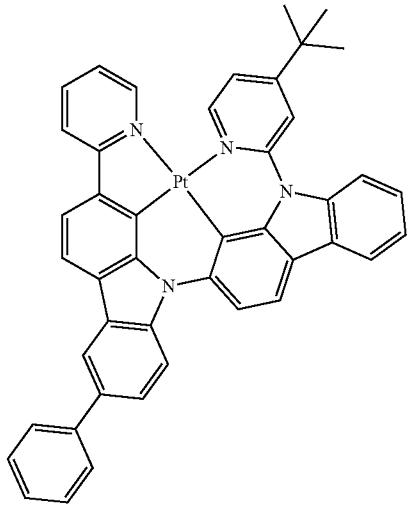
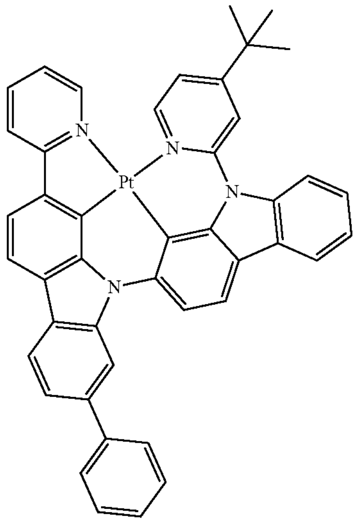

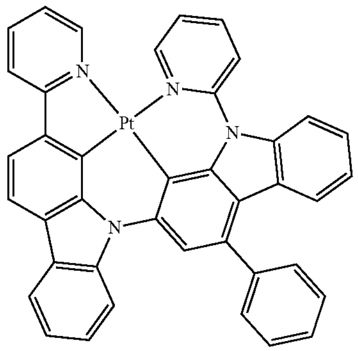
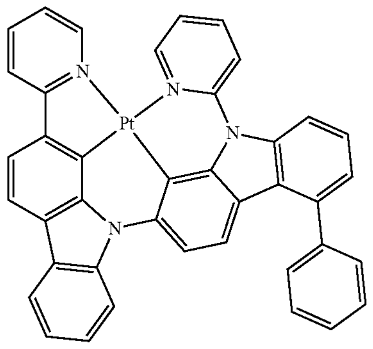
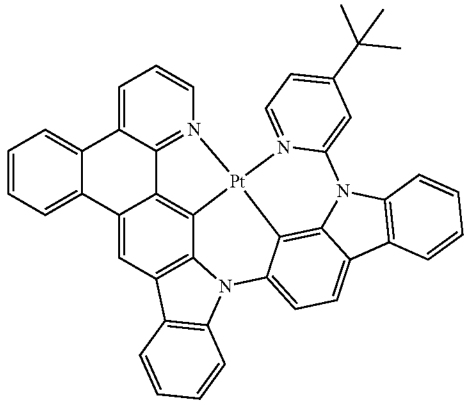
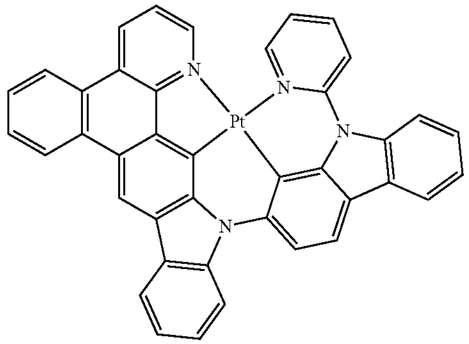
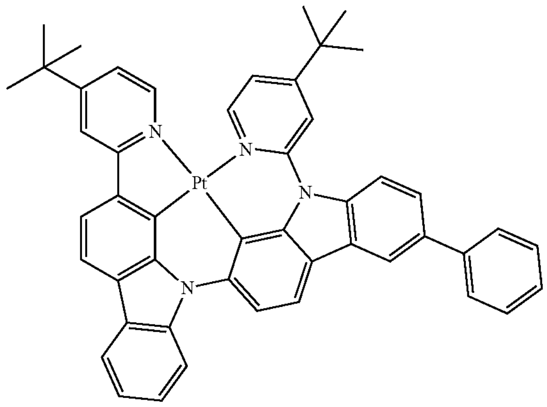
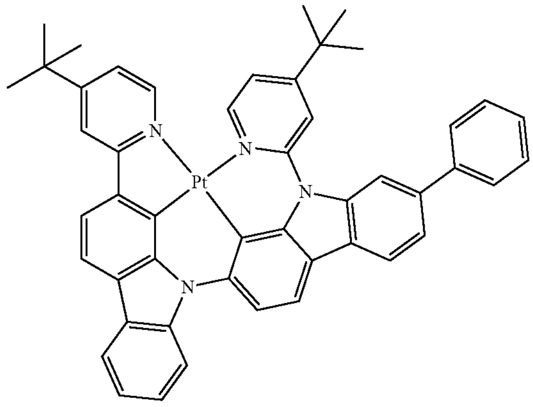
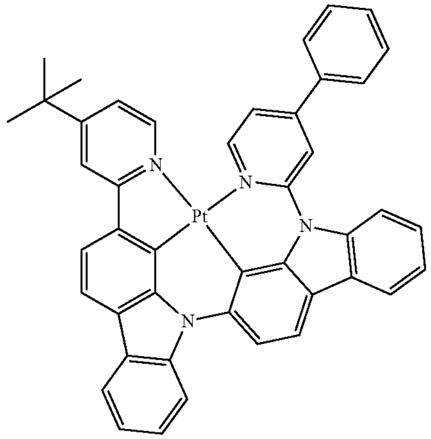
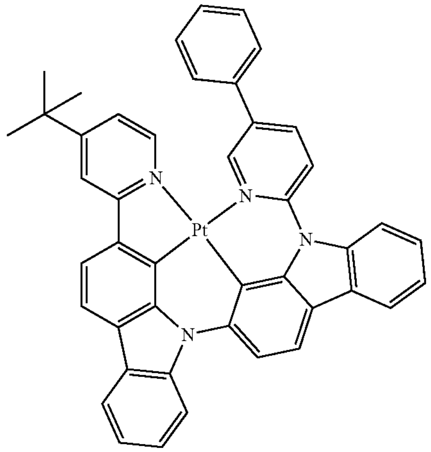

-continued
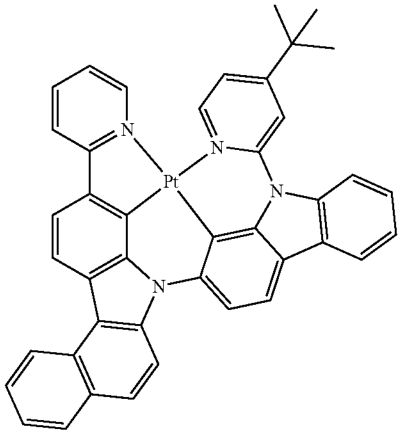
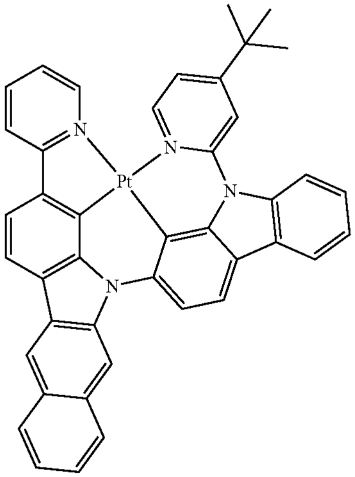
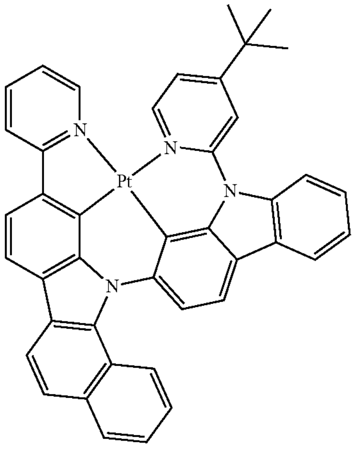
-continued
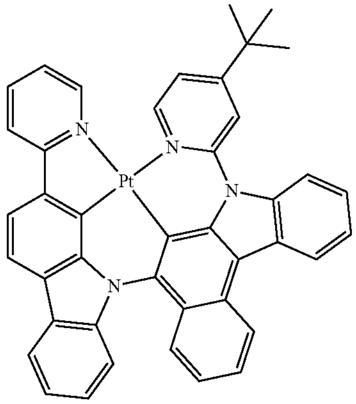
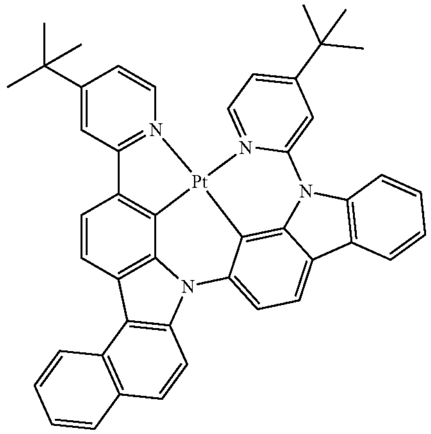
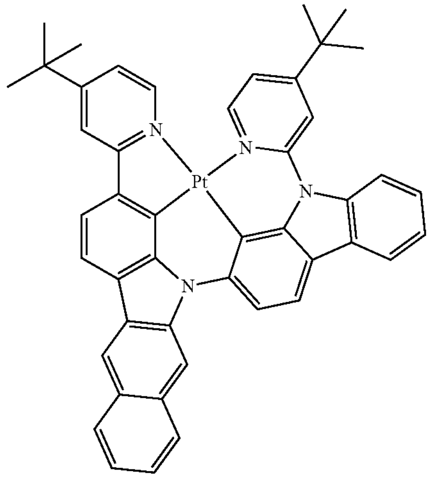

-continued

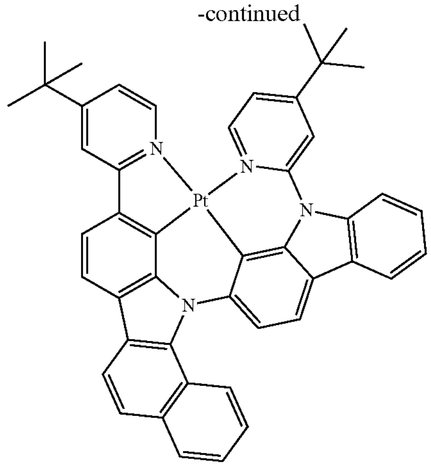

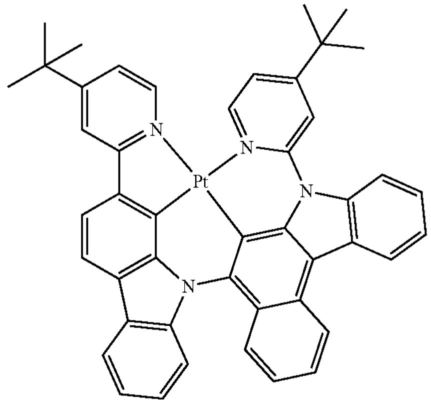

The phosphorescent material (phosphorescent compound) may be used alone or in a combination of two or more phosphorescent materials (phosphorescent compounds).

A thickness of the emission layer is not particularly limited and may be in a range about 1 nm to about 100 nm, or for example, about 10 nm to about 30 nm.

The emission wavelength of the organic light-emitting device is not particularly limited. However, the organic light-emitting device may emit light having a peak in a wavelength range of about 360 nm or more to about 515 nm or less, about 380 nm or more to about 505 nm or less, about 400 nm or more to about 500 nm or less, about 420 nm or more to about 490 nm or less, or about 430 nm or more to about 480 nm or less.

In addition, the FWHM of an emission spectrum of the organic light-emitting device may be about 30 nm or less, about 25 nm or less, about 20 nm or less, or about 0 nm or more.

Hereinafter, each region and each layer other than the emission layer 4 will be described in detail.

Substrate 1

The organic light-emitting device 10 may include the substrate 1. The substrate 1 may be any suitable substrate generally used in organic light-emitting devices. For example, the substrate 1 may be a glass substrate, a silicon substrate, or a transparent plastic substrate having excellent mechanical strength, thermal stability, transparency, surface smoothness, ease of handling, and water repellency, but embodiments are not limited thereto.

First Electrode 2

The first electrode 2 may be formed on the substrate 1. The first electrode 2 may be an anode and be formed from a material with a relatively high work function such as a metal, an alloy, a conductive compound, or a combination thereof, for facilitating hole injection. The first electrode 2 may be a pixel electrode. The first electrode 2 may be a reflective electrode, a semi-transmissive electrode, or a transmissive electrode.

The materials for forming the first electrode 2 are not particularly limited and may include, for example, indium tin oxide (ITO), indium zinc oxide (IZO), tin oxide ($SnO_2$), zinc oxide (ZnO), indium tin zinc oxide (ITZO), or the like, having excellent transparency and conductivity, when the first electrode 2 is a transparent electrode. When the first electrode 2 is a semi-transmissive or reflective electrode, Ag, Mg, Cu, Al, Pt, Pd, Au, Ni, Nd, Ir, Cr, Li, Ca, In, LiF/Ca, LiF/Al, Mo, Ti, or a mixture thereof (for example, a mixture of Ag and Mg or a mixture of Mg and In) may be included.

The first electrode 2 may be a single layer consisting of a single material or a single layer consisting of a plurality of different materials. In one or more embodiments, the first electrode 2 may have a multi-layer structure including a plurality of layers including various different materials.

A thickness of the first electrode 2 may be, but is not particularly limited to, about 10 nm or more and about 1,000 nm or less, or about 100 nm or more and about 300 nm or less.

Hole Transport Region 3

The hole transport region 3 may be arranged on the first electrode 2.

The hole transport region 3 may include at least one of a hole injection layer 31, a hole transport layer 32, an electron blocking layer 33, a hole buffer layer (not shown), or a combination thereof.

The hole transport region 3 may be a single layer consisting of a single material or a single layer consisting of a plurality of different materials. In one or more embodiments, the hole transport region 3 may have a multi-layer structure including a plurality of layers including various different materials.

The hole transport region 3 may include the hole injection layer 31 only or the hole transport layer 32 only. In one or more embodiments, the hole transport region 3 may be a single layer including a hole injection material and a hole transport material. The hole transport region 3 may have a hole injection layer/hole transport layer structure, a hole injection layer/hole buffer layer structure, a hole injection layer/hole transport layer/hole buffer layer structure, or a hole injection layer/hole transport layer/electron blocking layer structure, wherein, for each structure, respective layers are sequentially stacked in this stated order from the first electrode 2.

Layers forming the hole injection layer 31 and other layers included in the hole transport region 3 are not particularly limited, and a known hole injection material and/or a hole transport material may be included.

Examples of the hole injection material may include a phthalocyanin compound such as copper phthalocyanin, N,N'-diphenyl-N,N'-bis-[4-phenyl-m-tril-amino)-phenyl]-biphenyl-4,4'-diamine (DNTPD), (4,4',4"-tris(3-methylphenylphenylamino)triphenylamine) (m-MTDATA), 4,4',4"-tris (N,N-diphenylamino)triphenylamine (TDATA), 4,4',4"-tris{N,-(2-naphthyl)-N-phenyl amino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPB), polyetherketone including triphenylamine (TPAPEK), 4-isopropyl-4'-methyldiphenyliodonium tetrakis(pentafluorophenyl)borate, dipyrazino[2,3-f:2',3'-h]quinoxaline-2,3,6,7,10,11-hexacarbonitrile (HAT-CN), 1,3,4,5,7,8-hexafluorotetracyano-2,6-naphthoquinodimethane (F6-TCNNQ), and the like.

Examples of the hole transport material may include N-phenylcarbazole, a carbazole-based derivative such as polyvinyl carbazole, a fluorene-based derivative, N,N'-bis(3-methylphenyl)-N,N'-diphenyl-[1,1-biphenyl]-4,4'-diamine (TPD), a triphenylamine-based derivative such as 4,4',4"-tris(N-carbazolyl)triphenylamine (TCTA), N,N'-di(naphthalene-1-yl)-N,N'-diphenylbenzidine (NPB), 4,4'-cyclohexylidenbis[N,N-bis(4-methylphenyl)benzenamine] (TAPC), 4,4'-bis[N,N'-(3-tril)amino]-3,3'-dimethylbiphenyl (HMTPD), 1,3-bis(N-carbazolyl)benzene (mCP), Compound H1, Compound H2, Compound HT01, and the like.

H1

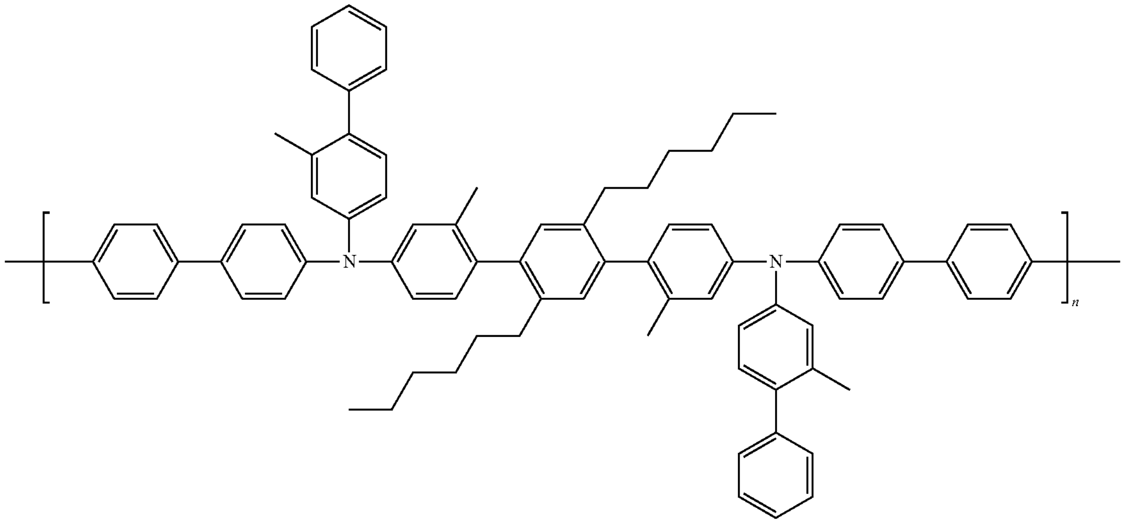

(n is an integer greater than or equal to 1)

H2

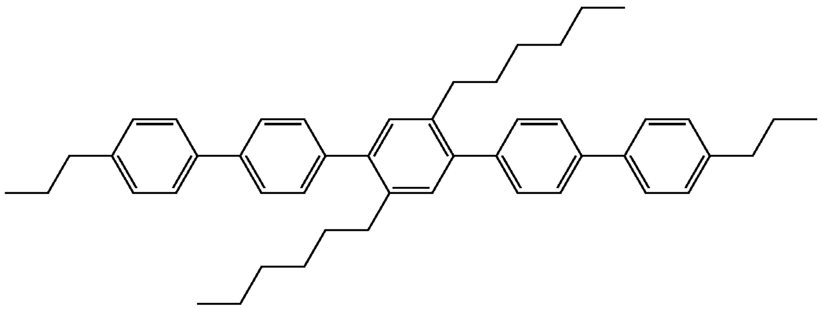

HT01

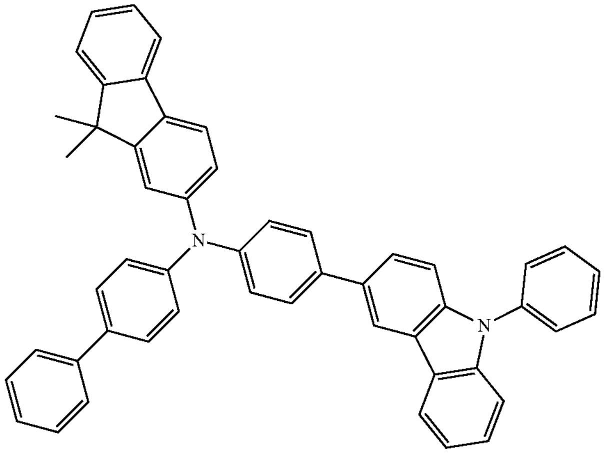

The hole transport region 3 may include, in addition to the materials described above, a charge generating material to improve conductive properties of the hole transport region. The charge generating material may be homogeneously or non-homogeneously dispersed in the hole transport region 3.

The charge generating material is not particularly limited and may be, for example, a p-dopant. Examples of the p-dopant may include: a quinone derivative, such as tetracyanoquinodimethane (TCNQ) or 2,3,5,6-tetrafluoro-tetracyano-1,4-benzoquinonedimethane (F4-TCNQ); a metal oxide, such as a tungsten oxide or a molybdenum oxide; and a compound containing a cyano group, but are not limited thereto.

The hole buffer layer (not shown) may increase the luminescence efficiency by compensating for an optical resonance distance according to the wavelength of light emitted by the emission layer 4. Materials included in the hole buffer layer (not shown) are not particularly limited, and a known hole buffer layer material may be used. For example, the compounds that may be included in the hole transport region 3.

The electron blocking layer 33 may prevent electron injection from the electron transport region 5 to the hole transport region 3. Materials included in the electron blocking layer 33 are not particularly limited, and a known electron blocking layer material may be used. For example, the host materials that may be included in the emission layer and Compound H-H1 as a host material may be included.

A thickness of the hole transport region 3 may be, but is not particularly limited to, about 1 nm or more and about 1,000 nm or less, or for example, about 10 nm or more and about 500 nm or less. In addition, a thickness of the hole injection layer 31 may be, but is not particularly limited to, about 3 nm or more and about 100 nm or less. A thickness of the hole transport layer 32 may be, but is not particularly limited to, about 3 nm or more and about 100 nm or less. A thickness of the electron blocking layer 33 may be, but is not particularly limited to, about 1 nm or more and about 100 nm or less. In addition, a thickness of the hole buffer layer (not shown) is not particularly limited, as long as the hole buffer layer may not adversely effect on functions of an organic light-emitting device. When the thickness of the hole transport region 3, the hole injection layer 31, the hole transport layer 32, or the electron blocking layer 33 is within the above ranges, excellent hole transport characteristics may be obtained without a substantial increase in driving voltage.

Emission Layer 4

The emission layer 4 may be arranged on the hole transport region 3. The emission layer 4 may be understood by referring to the description of the emission layer 4 described above.

Electron Transport Region 5

The electron transport region 5 may be arranged on the emission layer 4. The electron transport region 5 may include at least one of a hole blocking layer 53, the electron transport layer 52, the electron injection layer 51, or any combination thereof.

The electron transport region 5 may be a single layer consisting of a single material or a single layer consisting of a plurality of different materials. In one or more embodiments, the electron transport region 5 may have a multi-layered structure including a plurality of layers including various different materials.

The electron transport region 5 may include the electron transport layer 52 only or the electron injection layer 51 only. In one or more embodiments, the electron transport region 5 may be a single layer including an electron injection material and an electron transport material. The electron transport region 5 may have an electron transport layer/electron injection layer structure or a hole blocking layer/electron transport layer/electron injection layer structure, wherein, for each structure, respective layers are sequentially stacked in this stated order from the emission layer 4.

The electron injection layer 51 is not particularly limited and may include, for example, a known electron injection material. Examples of the electron injection layer material may include Yb, a lithium compound such as (8-hydroxyquinolinato)lithium (Liq) and lithium fluoride (LiF), sodium chloride (NaCl), cesium fluoride (CsF), rubidium fluoride (RbCl), lithium oxide ($Li_2O$), and barium oxide (BaO).

In one or more embodiments, the electron injection layer 51 may include an electron transporting material and an insulating organic metal salt to be described below. The metal salt is not particularly limited and may be, for example, a material having an energy band gap of about 4 eV or more. The organic metal salt may include, for example, an acetate metal salt, a benzoate metal salt, an acetate metal salt, an acetyl acetonate metal salt, or a stearate metal salt.

The electron transport layer 52 is not particularly limited and may include, for example, a known electron transport material. Examples of the electron transport material may include an anthracene-based compound, tris(8-hydroxyquinolinolate)aluminum) (Alq3), 1,3,5-tri[(3-pyridyl)-pen-3-yl]benzene, 2,4,6-tris(3'-pyridine-3-yl)biphenyl-3-yl)-1,3,5-triazine, 2-(4-(N-phenylbenzimidazolyl-1-ylphenyl)-9,10-dinaphthylanthracene, 1,3,5-tri(1-phenyl-1H-benzo[d]imidazole-2-yl)phenyl (TPBi), 2,9-dimethyl-4,7-diphenyl-1,10-phenanthroline (BCP), 4,7-diphenyl-1,10-phenanthroline (Bphen), 3-(4-biphenyl)-4-phenyl-5-tert-butylphenyl-1,2,4-triazole (TAZ), 4-(naphthalene-1-yl)-3,5-diphenyl-4H-1,2,4-triazole (NTAZ), 2-(4-biphenyl)-5-(4-tert-butylphenyl)-1,3,4-oxadiazole (tBu-PBD), bis(2-methyl-8-quinolinolate-N1,O8)-(1,1'-biphenyl-4-orato) aluminum (BAlq), berylliumbis(benzoquinoline-10-orato) (Bebq2), 9,10-di(naphthalene-2-yl)anthracene (ADN), lithium quinolate (LiQ), Compound ET1, and the like.

ET1

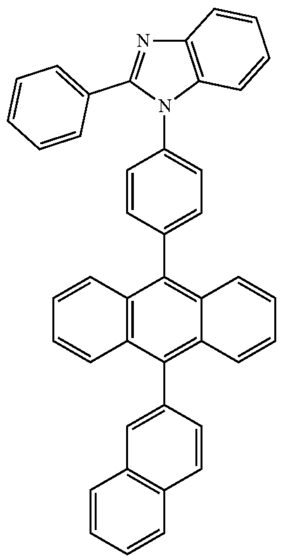

The hole blocking layer 53 may prevent hole injection from the hole transport region 3 to the electron transport region 5. Materials included in the hole blocking layer 53 are not particularly limited, and a known hole blocking material may be used. The hole blocking layer 53 may include, for example, 2,9-dimethyl-4,7-diphenyl-1,10-phenanthroline (BCP), 4,7-diphenyl-1,10-phenanthroline (Bphen), and the like. In addition, examples of the hole blocking material may include the host materials that may be included in the emission layer, and Compound H-E1 as a host material.

A thickness of the electron transport region 5 may be, but is not particularly limited to, about 0.1 nm or more and about 210 nm or less, or for example, about 100 nm or more and about 150 nm or less. A thickness of the electron transport layer 52 may be, but is not particularly limited to, about 10 nm or more and about 100 nm or less, or for example, about 15 nm or more and about 50 nm or less. A thickness of the hole blocking layer 53 may be, but is not particularly limited to, about 10 nm or more and about 100 nm or less, or for example, about 15 nm or more and about 50 nm or less. A thickness of the electron injection layer 51 may be, but is not particularly limited to, about 0.1 nm or more and about 10 nm or less, or for example, about 0.3 nm or more and about 9 nm or less. When the thickness of the electron injection layer 51 is within the above ranges, excellent electron injection characteristics may be obtained without a substantial increase in driving voltage. In addition, when the thickness of the electron transport region 5, the electron injection layer 51, the electron transport layer 52, or the hole blocking layer 53 is within the above ranges, excellent hole transport characteristics may be obtained without a substantial increase in driving voltage.

Second Electrode 6

The second electrode 6 may be arranged on the electron injection layer 51. The second electrode 6 may be a cathode and be formed from a material with a relatively low work function such as a metal, an alloy, or a conductive compound, for facilitating electron injection. The second electrode 6 may be a common electrode. The second electrode 6 may be a reflective electrode, a semi-transmissive electrode, or a transmissive electrode. The second electrode 6 may have a single-layered structure or a multi-layered structure including a plurality of layers. Materials for forming the second electrode 6 are not particularly limited. For example, when the second electrode 6 is a transparent electrode, the second electrode 6 may include a transparent metal oxide, for example, ITO, IZO, ZnO, or ITZO. When the second electrode 6 is a semi-transmissive or reflective electrode, Ag, Mg, Cu, Al, Pt, Pd, Au, Ni, Nd, Ir, Cr, Li, Ca, In, LiF/Ca, LiF/, Mo, Ti, or a mixture thereof (for example, a mixture of Ag and Mg or a mixture of Mg and In) may be included.

The second electrode 6 may be a single layer consisting of a single material or a single layer consisting of a plurality of different materials. In one or more embodiments, the second electrode 6 may have a multi-layered structure including a plurality of layers including various different materials.

A thickness of the second electrode 6 may be, but is not particularly limited to, about 10 nm or more and about 1,000 nm or less.

The second electrode 6 may be further connected to an auxiliary electrode (not shown). When the second electrode 6 is connected to the auxiliary electrode, the resistance of the second electrode 6 may be further reduced.

An encapsulation layer (not shown) may be further arranged on the second electrode 6. The encapsulation layer (not shown) is not particularly limited and may include, for example, α-NPD, NPB, TPD, m-MTDATA, Alq3, CuPc, N4,N4,N4',N4'-tetra(phenyl-4-yl)biphenyl-4,4'-diamine (TPD15), TCTA, N,N'-bis(naphthalene-1-yl), and the like.

In addition, a stacking structure of the organic light-emitting device 10 according to an embodiment is not limited to the above descriptions. The organic light-emitting device 10 according to an embodiment may have a different stacking structure known in the art. For example, the organic light-emitting device 10 may not include at least one of a hole injection layer 31, a hole transport layer 32, an electron transport layer 52, an electron injection layer 51, or any combination thereof, and may further include another layer. In one or more embodiments, each layer of the organic light-emitting device 10 may be formed as a single layer or as multiple layers.

Methods of forming each layer of the organic light-emitting device 10 according to one or more embodiments are not particularly limited. For example, vacuum-deposition, solution coating, a laser printing method, Langmuir-Blodgett (LB) method, or laser induced thermal imaging (LITI), may be used in forming each layer thereof.

The solution coating may include spin coating, casting, micro-gravure coating, gravure coating, bar coating, roll coating, wire bar coating, dip coating, spray coating, screen printing, flexographic printing, offset printing, or ink-jet printing.

The vacuum deposition may be performed at a deposition temperature in a range of about 100° C. to about 500° C., at a vacuum pressure in a range of about $10^{-8}$ torr to about $10^{-3}$ torr, and at a deposition rate in a range of about 0.01 nm per second (nm/sec) to about 10 nm/sec, though the conditions may vary depending on a compound that is used and a structure and thermal properties of a desired layer.

In an embodiment, the first electrode 2 may be an anode, and the second electrode 6 may be a cathode.

For example, the first electrode 2 may be an anode, the second electrode 6 may be a cathode, and an organic layer may include the emission layer 4 between the first electrode 2 and the second electrode 6 and may further include a hole transport region 3 between the first electrode 2 and the emission layer 4 and an electron transport region 5 between the emission layer 4 and the second electrode 6, wherein the hole transport region 3 may include at least one of the hole injection layer 31, the hole transport layer 32, a hole buffer layer, an electron blocking layer, or a combination thereof, and the electron transport region 5 may include at least one of a hole blocking layer, the electron transport layer 52, and the electron injection layer 51.

In one or more embodiments, the first electrode 2 may be a cathode, and the second electrode 6 may be an anode.

In the organic light-emitting device 10 of FIGS. 1 to 3, since a voltage is applied to each of the first electrode 2 and the second electrode 6, holes provided from the first electrode 2 may move toward the emission layer 4 through the hole transport region 3, and electrons provided from the second electrode 6 may move toward the emission layer 4 through the electron transport region 5. The holes and the electrons may recombine in the emission layer 4 to produce excitons, and these excitons may transition from an excited state to a ground state to thereby generate light.

Hereinbefore, the organic light-emitting device 10 has been described with reference to FIGS. 1 to 3, but embodiments are not limited thereto.

Electronic Apparatus

The organic light-emitting device may be included in various electronic apparatuses.

The electronic apparatus may further include a thin-film transistor, in addition to the organic light-emitting device.

The thin-film transistor may include a source electrode, a drain electrode, and an activation layer, wherein one of the source electrode and the drain electrode may be electrically connected to one of the first electrode and the second electrode of the organic light-emitting device.

Hereinafter, an organic light-emitting device, according to an embodiment, will be described in more detail with reference to Synthesis Examples and Examples; however, the present disclosure is not limited thereto. The wording "'B' was used instead of 'A'" as used in describing Synthesis Examples means that an amount of 'A' used was identical to an amount of 'B' used, in terms of a molar equivalent.

EXAMPLES

Example 1

Synthesis Example 1: Synthesis of Compound 1

In an argon atmosphere, 160 ml of tetrahydrofuran (THF) was added to a three-neck flask and cooled to −80° C. 2.0 M lithium diisopropylamide (LDA) (84.4 ml, 1.0 eq, 168.9 mmol) was added dropwise thereto. Then, a solution of 2,5-dibromopyridine (40 g, 168.9 mmol) dissolved in 120 ml of THF was added dropwise thereto. After stirring for 1 hour, anhydrous $CuCl_2$ (54.5 g, 2.4 eq, 405.3 mmol) was added thereto, the temperature was raised to room temperature, and the reaction solution was stirred overnight. The reaction solution was washed with a mixed solution of aqueous ammonia, aqueous ammonia chloride solution, and water, extracted with $CH_2Cl_2$, and passed through silica gel. Then, the solvent was removed therefrom by distillation under reduced pressure, and recrystallization was performed thereon with ethanol/hexane to obtain Intermediate 1 (19.2 g, yield: 48.3%).

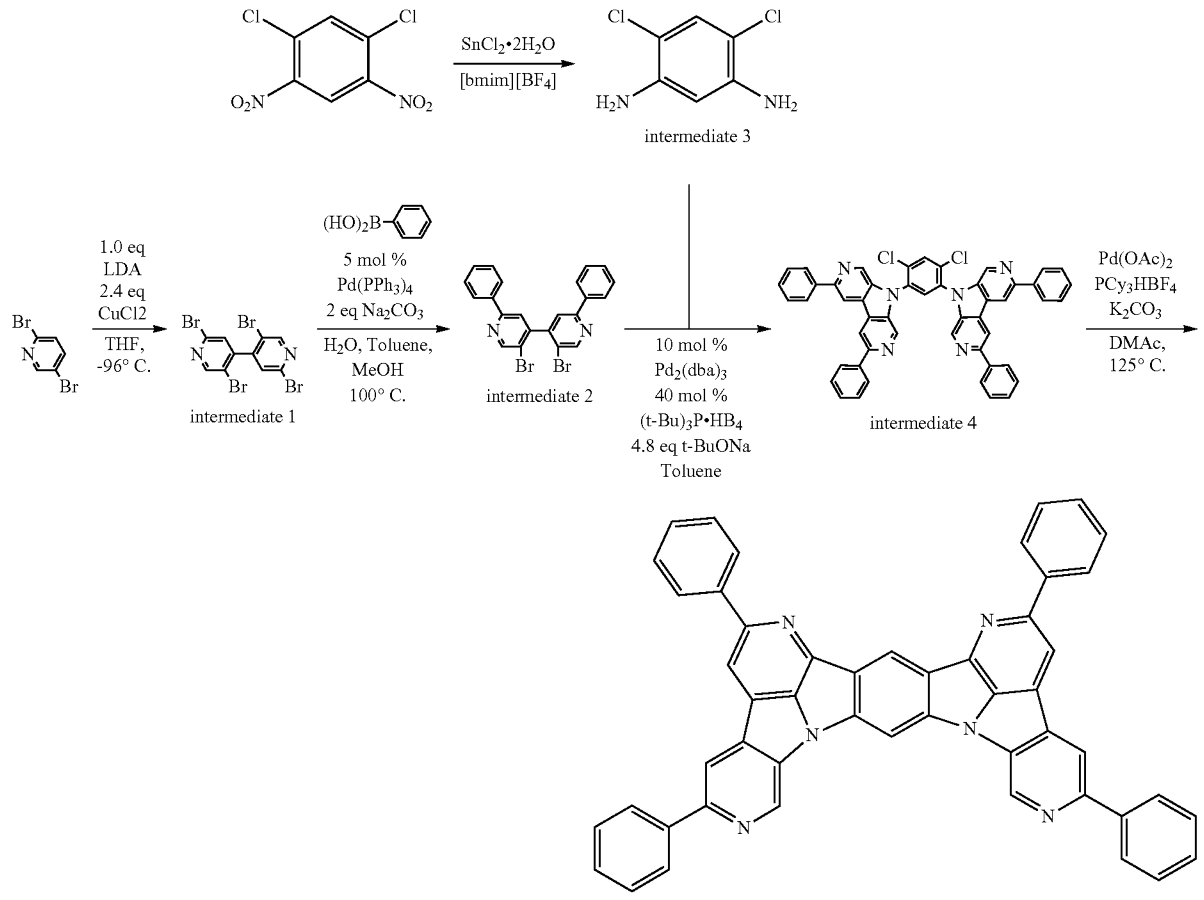

compound 1

Synthesis of Intermediate 1

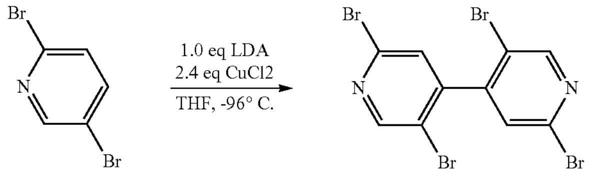

intermediate 1

Synthesis of Intermediate 2

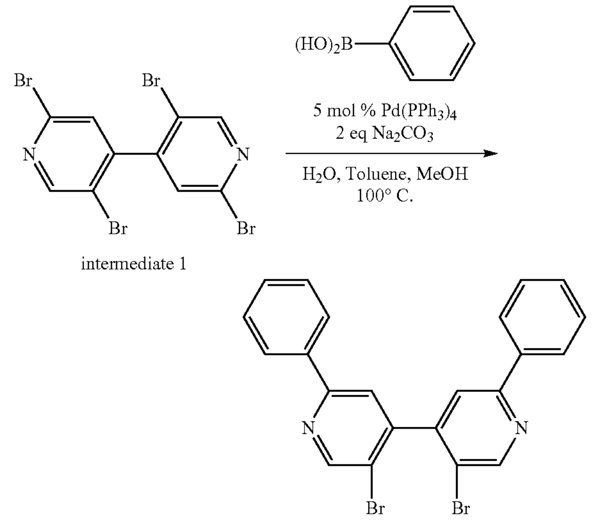

intermediate 1 intermediate 2

In an argon atmosphere, Intermediate 1 (7.28 g, 15.43 mmol), phenylboronic acid (3.76 g, 2.0 eq, 30.86 mmol), tetrakis(triphenylphosphine)palladium (0) (0.3 g, 0.05 eq, 1.16 mmol), $Na_2CO_3$ (3.3 g, 2.0 eq, 30.86 mmol), toluene (58 ml), methanol (29 ml), and $H_2O$ (29 ml) were added to a three-neck flask and stirred under reflux for 12 hours. After cooling to room temperature, toluene was added thereto to wash the resulting organic layer. After the organic layer was dried with $MgSO_4$, the solvent was removed therefrom by distillation under reduced pressure, and purification was performed thereon using column chromatography to obtain Intermediate 2 (5.5 g, yield: 76.5%).

Synthesis of Intermediate 3

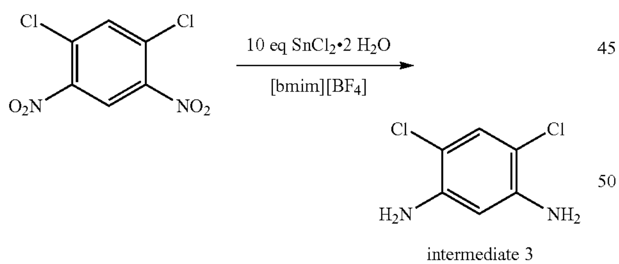

intermediate 3

1,5-dichloro-2,4-dinitrobenzene (2.3 g, 9.49 mmol), tin chloride dihydrate (21.4 g, 10.0 eq, 94.94 mmol), and tetrafluoroboric acid 1-butyl-3-methylimidazolium (20 ml) were added to a three-neck flask and stirred at room temperature for 1 hour. After completion of the reaction, the reaction solution was neutralized with aqueous $NaHCO_3$ solution, and extracted three times with ethyl acetate. The resulting organic layer was dried with $Na_2SO_4$ and then passed through silica gel, and the solvent was removed therefrom by distillation under reduced pressure to obtain Intermediate 3 (1.1 g, yield: 65.0%).

Synthesis of Intermediate 4

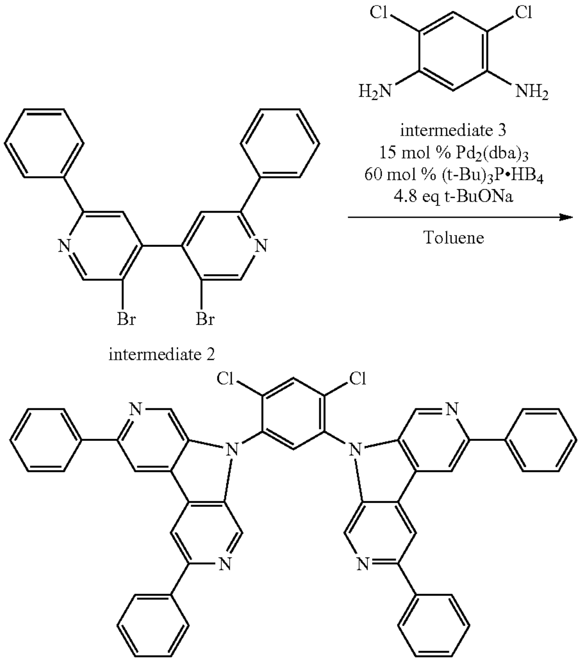

intermediate 3 intermediate 2 intermediate 4

In an argon atmosphere, Intermediate 2 (0.5 g, 2.05 eq, 1.07 mmol), Intermediate 3 (0.093 g, 1.0 eq, 0.52 mmol), $Pd_2(dba)_3$ (0.007 g, 0.15 eq, 0.08 mmol), $(t\text{-}Bu)_3P\cdot HBF_4$ (0.09 g, 0.60 eq, 0.31 mmol), sodium tert-butoxide (0.24 g, 4.80 eq, 2.51 mmol), and toluene (4.6 ml) were added to a three-neck flask, degassed under reduced pressure five times, and heated while stirring at 65° C. for 3 hours. After confirming that Intermediate 3 had disappeared, the reaction solution was heated while stirring under reflux for 5 hours. After completion of the reaction, the reaction solution was passed through a pad of silica gel, and the solvent was removed therefrom by distillation under reduced pressure. Purification was performed thereon using column chromatography to obtain Intermediate 4 (0.2 g, yield: 49.0%).

Synthesis of Compound 1

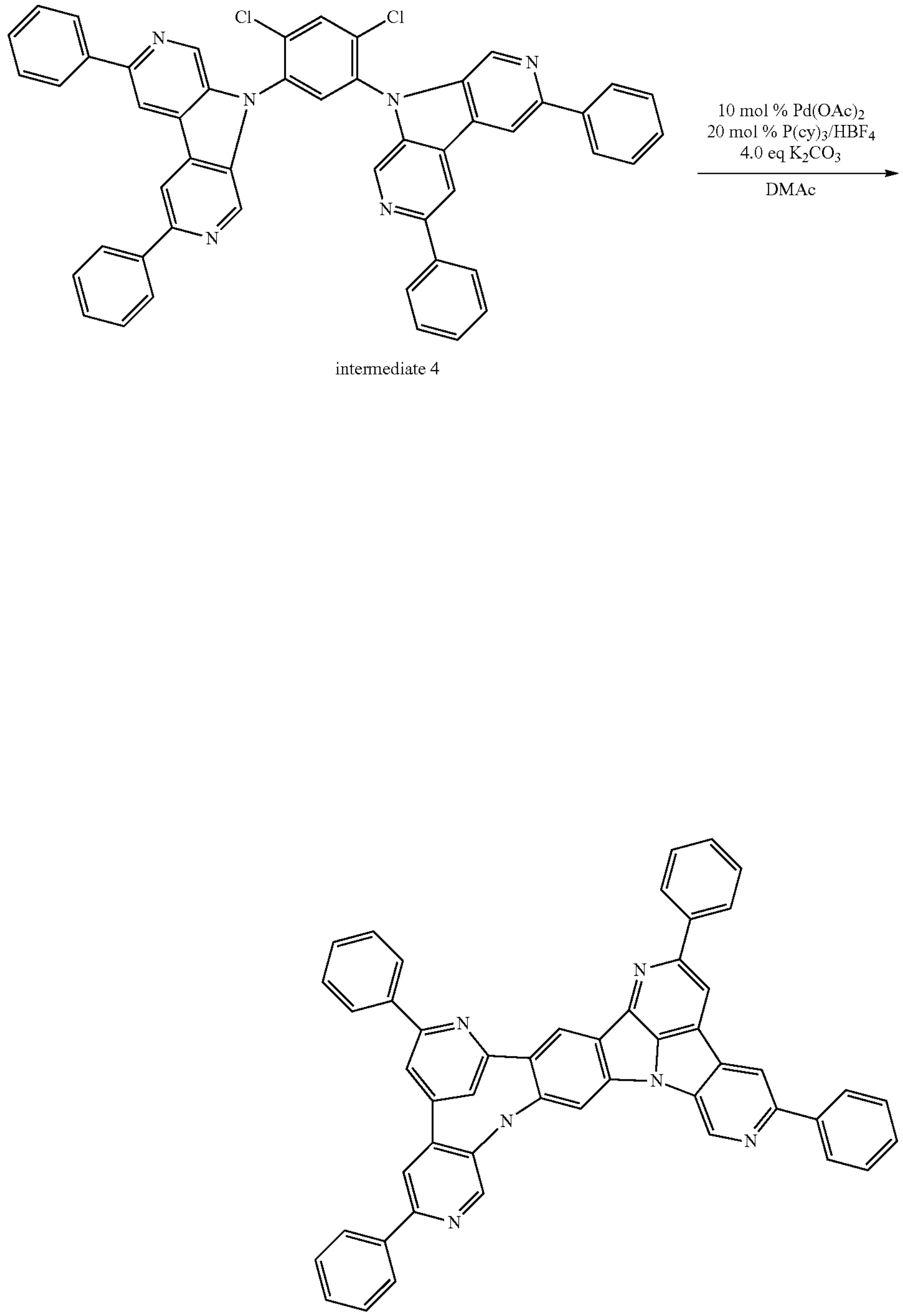

intermediate 4 compound 1

In an argon atmosphere, Intermediate 4 (0.23 g, 0.29 mmol), $K_2CO_3$ (0.16 g, 4.0 eq, 1.17 mmol), and dimethylacetamide (4.6 ml) were added to a three-neck flask and degassed five times under reduced pressure, and palladium acetate (0.013 g, 0.2 eq, 0.06 mmol) and tricyclohexylphosphonium tetrafluoroborate (0.07 g, 0.4 eq, 0.12 mmol) were added thereto, followed by degassing five more times under reduced pressure. The reaction solution was heated while stirring at 125° C. for 10 hours, and the reaction was stopped. After cooling to room temperature, the reaction solution was added to water, and the insoluble materials were filtered off. The resulting solid was washed with acetonitrile. Then, washing was performed thereon three times using a 5% aqueous ethylenediamine solution, 5 ml of dimethylacetamide was added thereto, and heat-cleaning was performed thereon at 125° C. to obtain crystals of Compound 1 (0.11 g, yield: 53.0%).

The structure of Compound 1 obtained was identified by a nuclear magnetic resonance device ($^1$H-NMR).

$^1$H NMR (300 MHz, DMSO-$d_6$) δ 6.15 (s, 2H), 6.63-6.81 (m, 17H), 7.08-7.2 (m, 4H), 7.75-7.90 (m, 3H), 9.5 (s, 2H).

Example 2
Synthesis Example 2: Synthesis of Compound 2
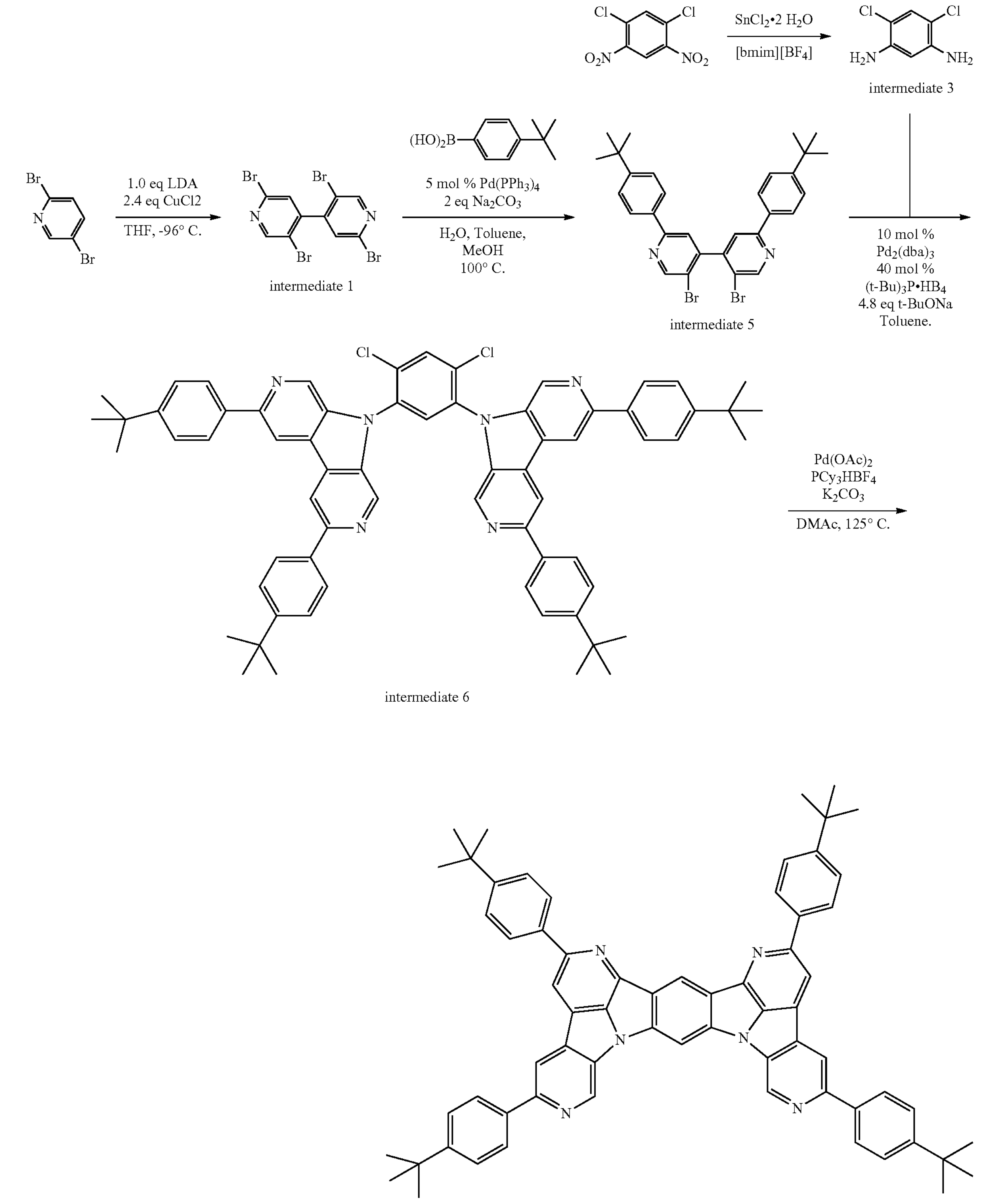
intermediate 3
intermediate 1
intermediate 5
intermediate 6
compound 2

Synthesis of Intermediate 5

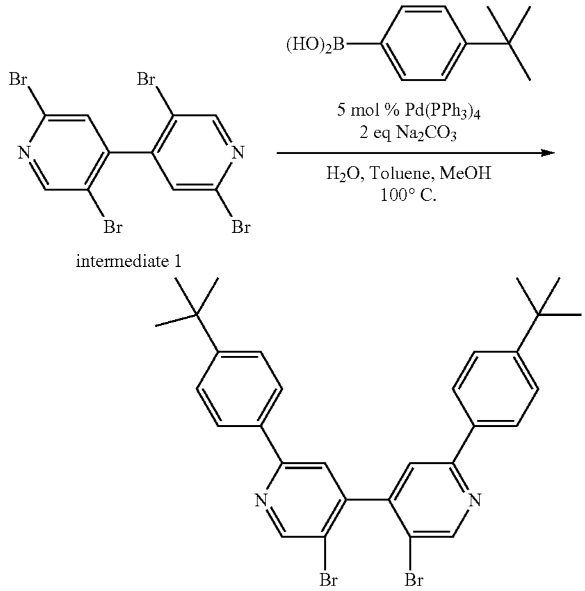

intermediate 1 intermediate 5

In an argon atmosphere, Intermediate 1 (19.1 g, 40.49 mmol), tert-butylphenylboronic acid (14.4 g, 2.0 eq, 80.97 mmol), tetrakis(triphenylphosphine)palladium (0) (2.3 g, 0.05 eq, 2.02 mmol), $Na_2CO_3$ (8.6 g, 2.0 eq, 80.97 mmol), toluene (764 ml), methanol (382 ml), and $H_2O$ (382 ml) were added to a three-neck flask and stirred while heating under reflux for 12 hours. After cooling to room temperature, toluene was added thereto to wash the resulting organic layer. After the organic layer was dried with $MgSO_4$, the solvent was removed therefrom by distillation under reduced pressure, and purification was performed thereon using column chromatography to obtain Intermediate 5 (10.8 g, yield: 46.2%).

Synthesis of Intermediate 6

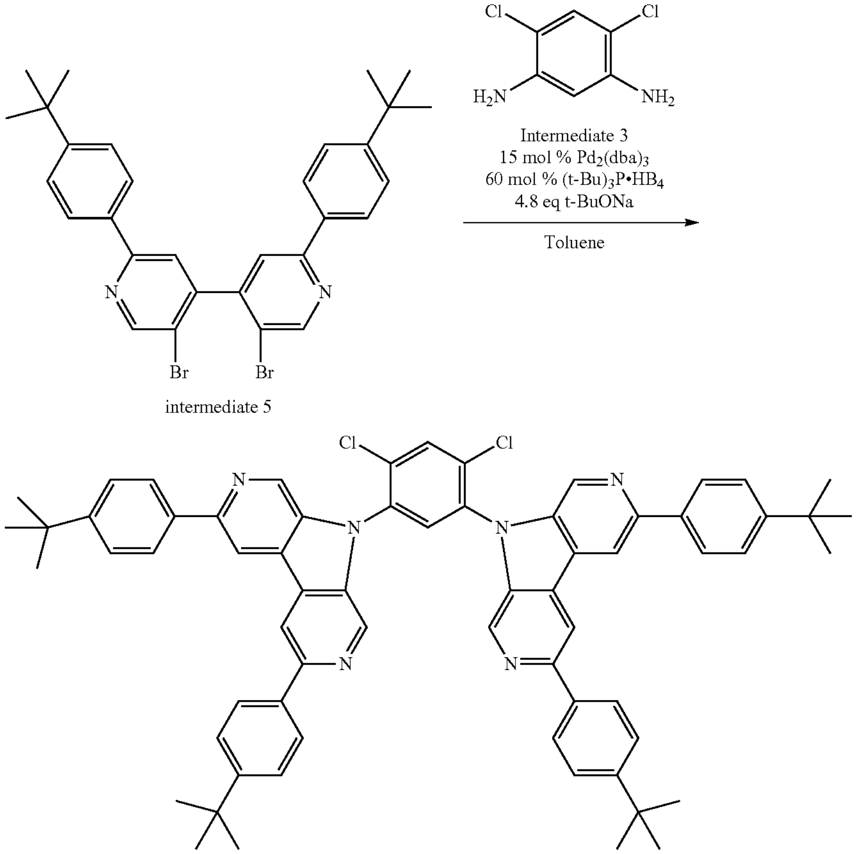

intermediate 5 intermediate 6

In an argon atmosphere, Intermediate 5 (1.3 g, 2.05 eq, 2.25 mmol), Intermediate 3 (0.194 g, 1.0 eq, 1.10 mmol), $Pd_2(dba)_3$ (0.15 g, 0.15 eq, 0.16 mmol), $(t\text{-}Bu)_3P{\cdot}HBF_4$ (0.19 g, 0.60 eq, 0.66 mmol), sodium tert-butoxide (0.51 g, 4.80 eq, 5.26 mmol), and toluene (9.7 ml) were added to a three-neck flask, degassed under reduced pressure five times, and heated while stirring at 65° C. for 3 hours. After confirming that Intermediate 3 had disappeared, the reaction solution was heated while stirring under reflux for 5 hours. After completion of the reaction, the reaction solution was passed through a pad of silica gel, and the solvent was removed therefrom by distillation under reduced pressure. Purification was performed thereon using column chromatography to obtain Intermediate 6 (0.51 g, yield: 46.2%).

Synthesis of Compound 2

In an argon atmosphere, Intermediate 6 (0.46 g, 0.45 mmol), $K_2CO_3$ (0.25 g, 4.0 eq, 1.81 mmol), and dimethylacetamide (18.3 ml) were added to a three-neck flask and degassed under reduced pressure five times, and palladium acetate (0.02 g, 0.2 eq, 0.09 mmol), tricyclohexylphosphonium tetrafluoroborate (0.07 g, 0.4 eq, 0.18 mmol) were added thereto, followed by degassing five more times under reduced pressure. The reaction solution was heated while stirring at 125° C. for 10 hours, and the reaction was stopped. After cooling to room temperature, the reaction solution was added to water, and the insoluble materials were filtered off. The resulting solid was washed with acetonitrile, dissolved in THF while heating under reflux, and passed through a pad of silica gel. The solvent was removed therefrom by distillation under reduced pressure, and washing was performed thereon using ethyl acetate to obtain crystals of Compound 2 (0.18 g, yield: 43.6%).

The structure of Compound 2 obtained was identified by a nuclear magnetic resonance device ($^1$H-NMR).

$^1$H NMR (300 MHz, THF-$d_8$) δ 1.58 (s, 36H), 7.71-7.79 (d, 8H), 8.33-8.45 (m, 8H), 8.50 (s, 2H), 8.75 (s, 2H), 8.79 (s, 1H), 9.23 (s, 1H), 9.82 (s, 2H).

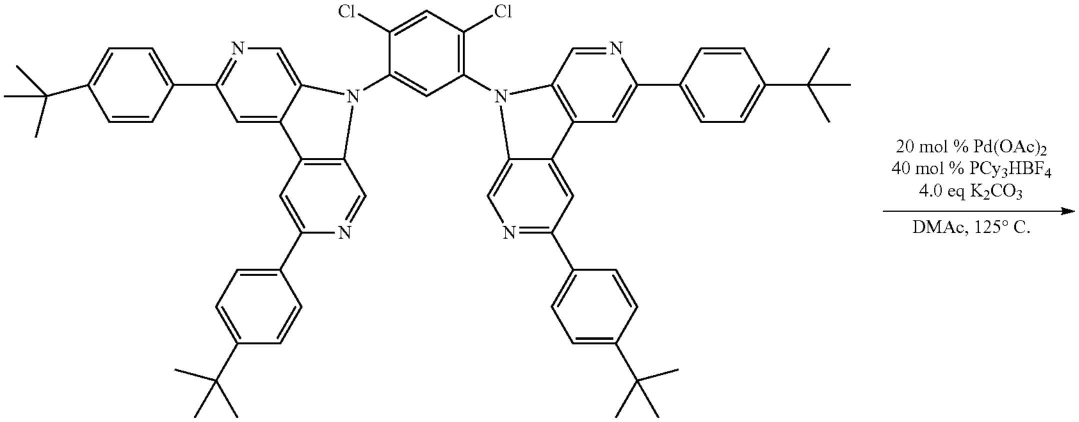

intermediate 6

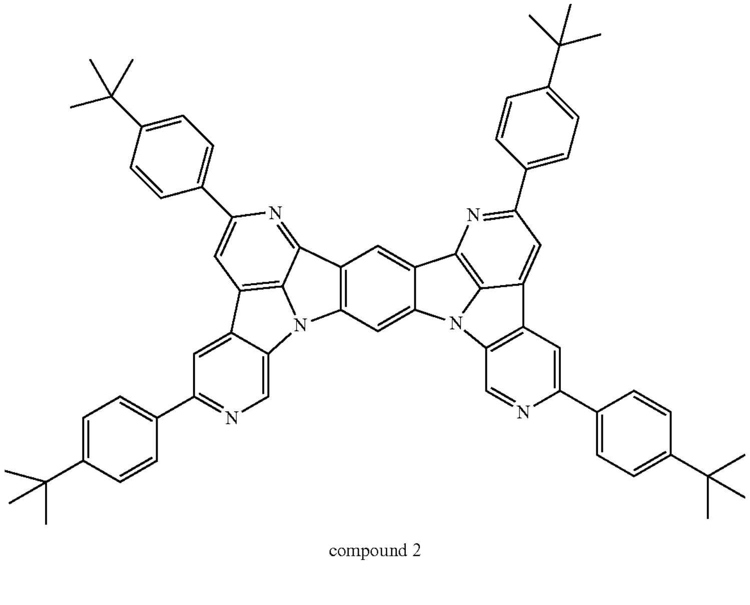

compound 2

Example 3
Synthesis Example 3: Synthesis of Compound
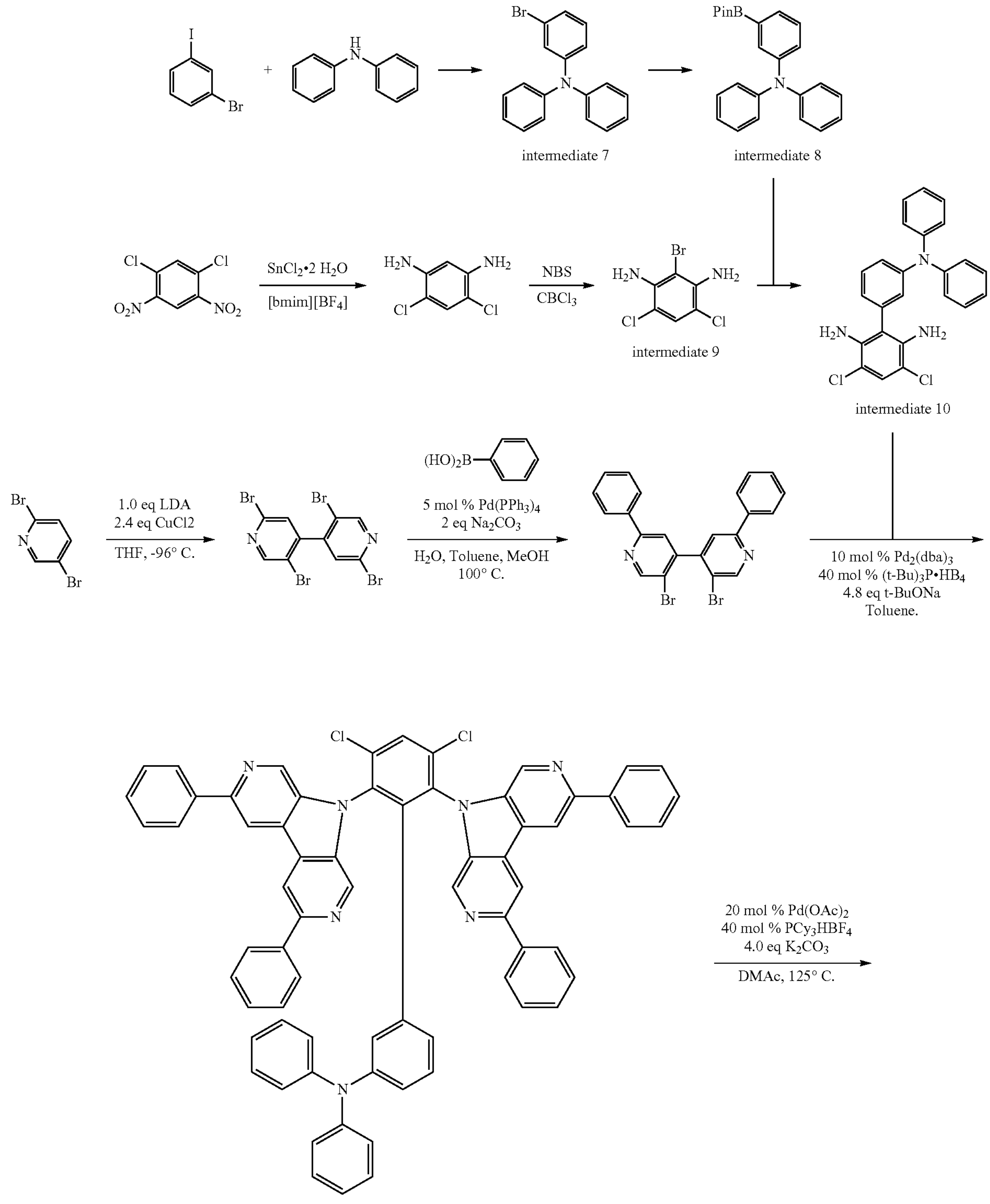
intermediate 7
intermediate 8
intermediate 9
intermediate 10
intermediate 11

-continued

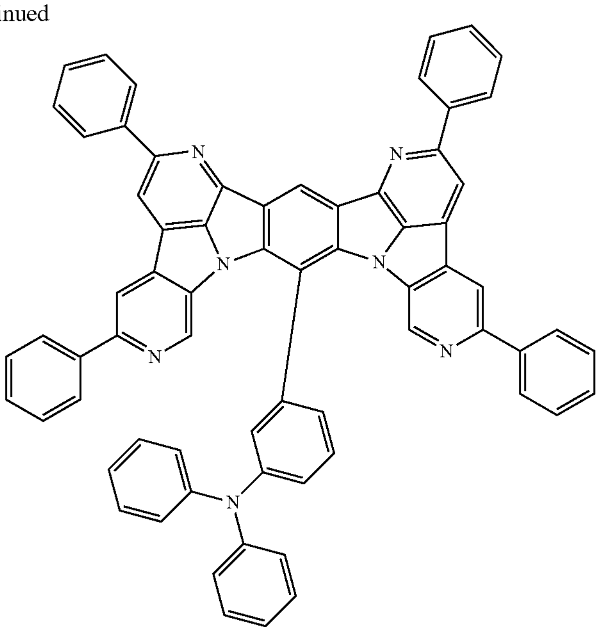

Compound 25

Synthesis of Intermediate 9

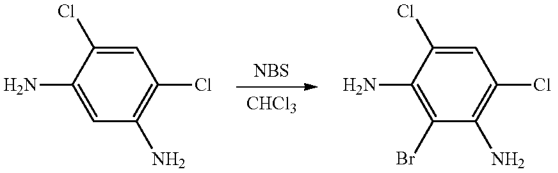

intermediate 3 intermediate 9

Intermediate 3 (5.5 g, 1.0 eq, 31.07 mmol), NBS (6.08 g, 1.1 eq, 34.17 mmol), and $CHCl_3$ (82.5 ml) were added to a three-neck flask and stirred at room temperature for 3 hours. After completion of the reaction, washing was performed thereon using a saturated aqueous $NaHCO_3$ solution, a 10% aqueous sodium thiosulfate solution, and water, in this stated order. Then, the solvent was removed therefrom by distillation under reduced pressure. Purification was performed thereon using column chromatography to obtain Intermediate 9 (6.73 g, yield: 85.1%).

Synthesis of Intermediate 7

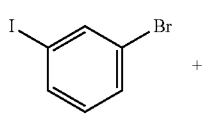

+

-continued

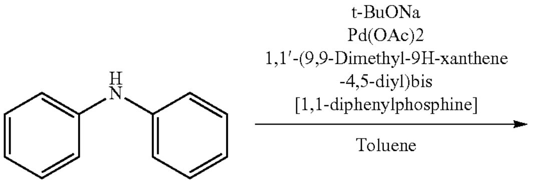

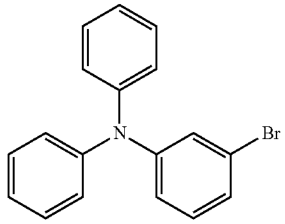

intermediate 7

In an argon atmosphere, m-iodine-bromobenzene (44.0 g, 1.0 eq, 155 mmol), diphenylamine (22.1 g, 0.84 eq, 130.6 mmol), palladium acetate (0.35 g, 0.01 eq, 1.56 mmol), 1,1'-(9,9-dimethyl-9H-xanthene-4,5-diyl)bis[1,1-diphenylphosphine] (0.35 g, 0.01 eq, 1.56 mmol), sodium tert-butoxide (21.97 g, 1.47 eq, 228.6 mmol), and toluene (440 ml) were added to a three-neck flask, degassed under reduced pressure five times, and heated while stirring at 110° C. for 3 hours. After confirming that diphenylamine had disappeared, the reaction solution was passed through a pad of silica gel, and the solvent was removed therefrom by distillation under reduced pressure. Purification was performed thereon using column chromatography to obtain Intermediate 7 (42 g, yield: 83.3%).

Synthesis of Intermediate 8

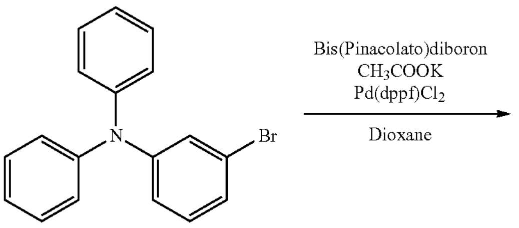

intermediate 7

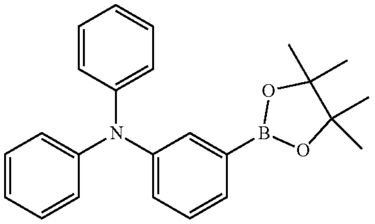

intermediate 8

In an argon atmosphere, Intermediate 7 (1.0 eq, 131 mmol, 42.5 g), bis(pinacolato)diboron (1.25 eq, 163.9 mmol, 41.6 g), Pd(dppf)$Cl_2$ (0.03 eq, 4.33 mmol, 3.17 g), $CH_3COOK$ (3.0 eq, 393.3 mmol, 38.6 g), and dioxane (425 ml) were added to a three-neck flask, and heated while stirring at 100° C. for 5 hours. After confirming that Intermediate 7 had disappeared, the reaction solution was passed through a pad of silica gel, and the solvent was removed therefrom by distillation under reduced pressure. Purification was performed thereon using column chromatography to obtain Intermediate 8 (35 g, yield: 72%).

Synthesis of Intermediate 10

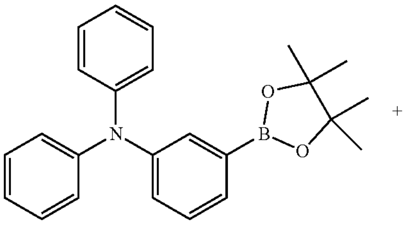

intermediate 8

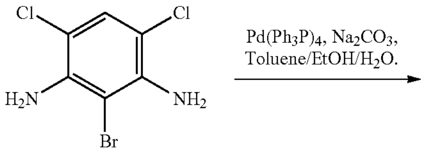

intermediate 9

-continued

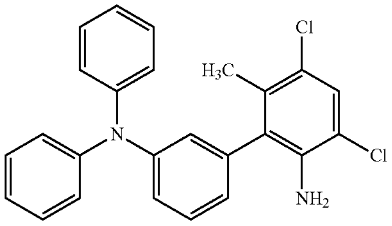

intermediate 10

In an argon atmosphere, Intermediate 8 (9.8 g, 1.0 eq, 26.30 mmol), Intermediate 9 (6.73 g, 1.0 eq, 26.30 mmol), tetrakis(triphenylphosphine)palladium(0) (1.5 g, 0.05 eq, 1.31 mmol), $Na_2CO_3$ (6.9 g, 2.0 eq, 65.74 mmol), toluene (98 ml), ethanol (24 ml), and $H_2O$ (78 ml) were added to a three-neck flask, and heated while stirring under reflux for 12 hours. After cooling to room temperature, the reaction solution was filtered to obtain crystals. After dissolving the crystals by adding THF thereto, the reaction solution was passed through a pad of silica gel, and the solvent was removed therefrom by distillation under reduced pressure to obtain Intermediate 10 (2.8 g, yield: 25.3%).

Synthesis of Intermediate 11

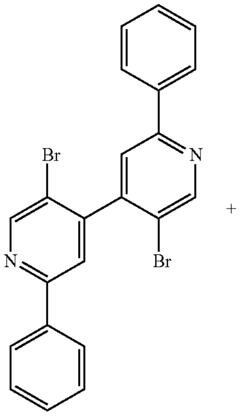

intermediate 2

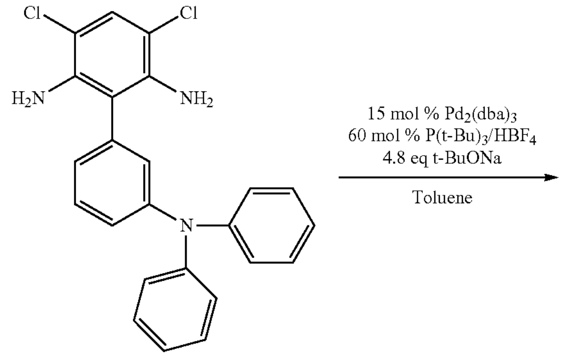

intermediate 10

-continued

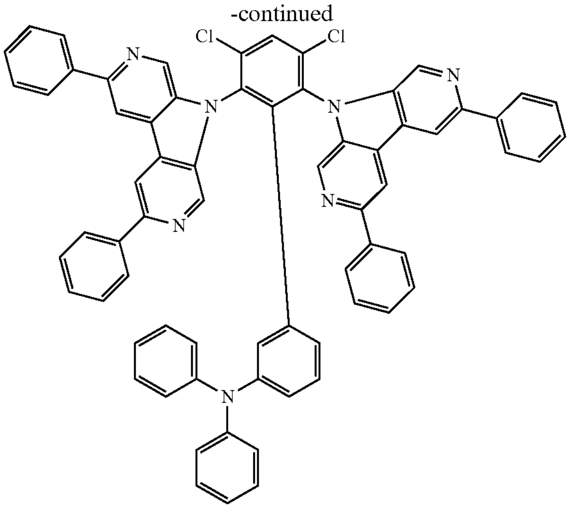

intermediate 11

In an argon atmosphere, Intermediate 10 (0.1 g, 1.0 eq, 0.24 mmol), Intermediate 2 (0.227 g, 2.05 eq, 0.49 mmol), $Pd_2(dba)_3$ (0.033 g, 0.15 eq, 0.04 mmol), $(t\text{-}Bu)_3/HBF_4$ (0.04 g, 0.60 eq, 0.14 mmol), sodium tert-butoxide (0.11 g, 4.80 eq, 1.14 mmol), and toluene (5.0 ml) were added to a three-neck flask, degassed under reduced pressure five times, and heated while stirring at 65° C. for 3 hours. After confirming that Intermediate 10 had disappeared, the reaction solution was heated to reflux, and then heated while stirring for 7 hours. After completion of the reaction, the reaction solution was passed through a pad of silica gel, and the solvent was removed therefrom by distillation under reduced pressure. Then, purification was performed thereon using column chromatography to obtain Intermediate 11 (0.051 g, yield: 26.8%).

Synthesis of Compound 25

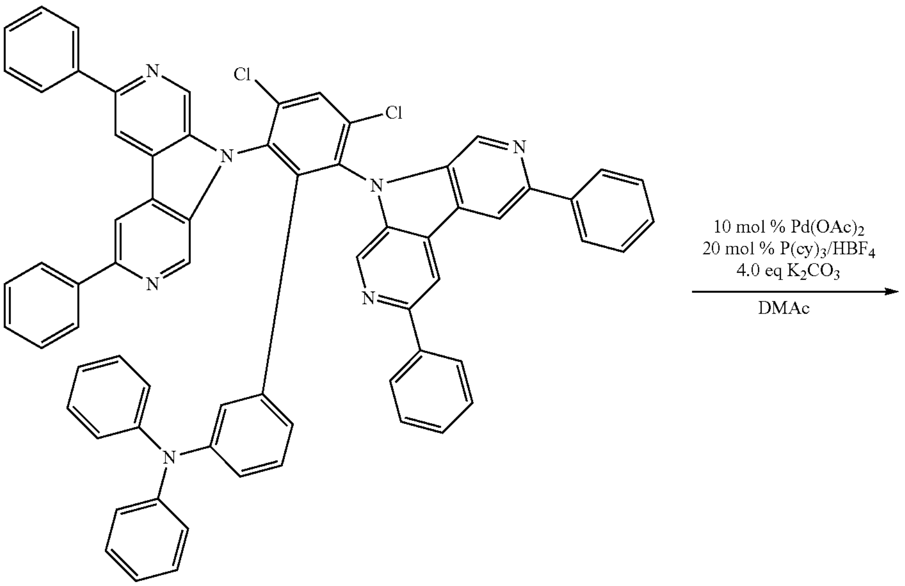

intermediate 11

-continued

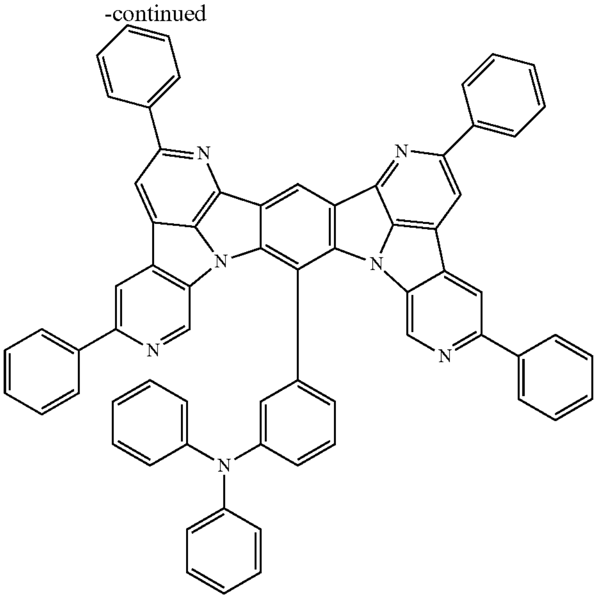

Compound 25

In an argon atmosphere, Intermediate 11 (0.50 g, 0.05 mmol), $K_2CO_3$ (0.03 g, 4.0 eq, 0.21 mmol), and dimethylacetamide (1.0 ml) were added to a three-neck flask and degassed five times under reduced pressure, and palladium acetate (0.003 g, 0.2 eq, 0.01 mmol) and tricyclohexylphosphonium tetrafluoroborate (0.008 g, 0.4 eq, 0.02 mmol) were added thereto, followed by degassing five more times under reduced pressure. The reaction solution was heated while stirring at 125° C. for 24 hours, and the reaction was stopped. After cooling to room temperature, the reaction solution was added to water, and the insoluble materials were filtered off. The resulting solid was washed with acetonitrile, dissolved in THF while heating under reflux, and passed through a pad of silica gel. The solvent was removed therefrom by distillation under reduced pressure, purification was performed thereon using column chromatography, and then, washing was performed thereon using methanol to obtain crystals of Compound 25 (0.001 g, yield: 2.1%).

The structure of Compound 25 obtained was identified by a nuclear magnetic resonance device ($^1H$-NMR).

$^1H$ NMR (300 MHz, THF-$d_8$) δ 6.9 (t, 2H), 7.15 (t, 5H), 7.25 (s, 2H), 7.35-7.48 (m, 8H), 7.48-7.62 (m, 8H), 7.7-7.8 (m, 2H), 7.9 (s, 1H), 8.35 (dd, 8H), 8.62 (s, 2H), 8.78 (s, 2H), 9.27 (s, 1H).

Comparative Example 1: Preparation Comparative Compounds 1 to 3

The following compounds were prepared as Comparative Compounds 1 to 3.

Comparative Compound 1

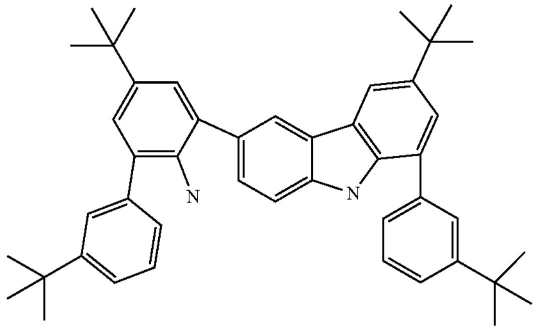

Comparative Compound 2

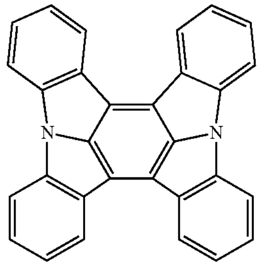

-continued

Comparative Compound 3

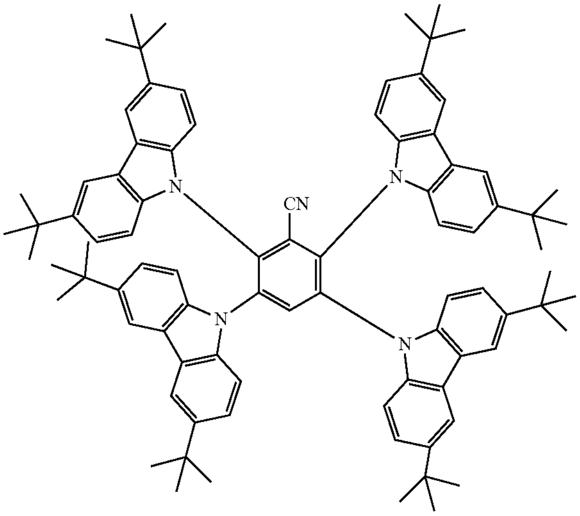

Comparative Compounds 1 and 2 were prepared with reference to the following documents, each of which is incorporated by reference in their entirety:

Comparative Compound 1: Small (2020), 16(14), 1907569

Comparative Compound 2: New Journal of Chemistry (2010), 34 (7), 1243-1246.

Comparative Compound 3 was purchased from Lumtec Inc.

Evaluation Example 1: Measurement of S1 Value, T1 Value, and $\Delta E_{ST}$

The Compounds and Comparative Compounds obtained above were each prepared as sample solids. Then, a S1 value, a T1 value, and $\Delta E_{ST}$ were measured according to the following steps.

1. Preparation of Measurement Sample (1) A sample solution was prepared such that a sample solid was 4 parts by weight based on 100 parts by weight of methyl benzoate as a solvent.

(2) The sample solution prepared in Section (1) was spin-coated on each of an ITO substrate and a quartz substrate by using a spin coater MS-B100 (manufactured by Mikasa Co., Ltd.) to form a spin-coating film having a dry film thickness of 50 nm. Subsequently, by 1 hour of heating at a temperature of 120° C., a thin film sample was prepared.

2. Measurement of S1 Value, T1 Value, and $\Delta E_{ST}$ Value

By using the thin film sample on the quartz substrate prepared in Section 1.(2), a fluorescence spectrum and a phosphorescence spectrum were measured at 77K with a spectrofluorophotometer F-7000 (manufactured by Hitachi High-Tech Science Co., Ltd.). The singlet energy S1 was calculated from the obtained fluorescence spectrum, and the triplet energy T1 was calculated from the phosphorescence spectrum. In addition, $\Delta E_{ST}$ was estimated according to Formula x. The results are shown in Table 1.

$$\Delta E_{st} = S1 - T1 \qquad \text{Equation x}$$

TABLE 1

| | Compound No. | HOMO (eV) | LUMO (eV) | Peak Wavelength (nm) | FWHM (nm) | S1 (eV) | T1 (eV) | Δ $E_{ST}$ (eV) |
|---|---|---|---|---|---|---|---|---|
| Example 1 | Compound 1 | −6.1 | −3.5 | 447 | 13 | 2.78 | 2.53 | 0.26 |
| Example 2 | Compound 2 | −5.9 | −3.3 | 452 | 13 | 2.74 | 2.53 | 0.25 |
| Example 3 | Compound 25 | −6.1 | −3.4 | 451 | 11 | 2.74 | 2.55 | 0.28 |
| Comparative Example 1 | Comparative Compound 1 | −6.0 | −2.6 | 393 | 20 | 3.17 | 2.71 | 0.46 |
| Comparative Example 2 | Comparative Compound 2 | −6.4 | −3.6 | 446 | 12 | 2.84 | 2.34 | 0.50 |
| Comparative Example 3 | Comparative Compound 3 | −6.0 | −3.2 | 467 | 72 | 2.91 | 2.81 | 0.10 |

From the results of Table 1, it was confirmed that Compounds 1, 2, and 25 had a rigid structure, and thus had a narrow width of an emission spectrum. In addition, Compounds 1 and 2 were found to have a deeper LUMO and a longer wavelength compared to Comparative Compound 1, thereby having a peak wavelength of 440 nm to 480 nm in a blue wavelength region.

In addition, it was confirmed that Compounds 1, 2, and 25 had a peak wavelength in the blue wavelength region, and each had a smaller $\Delta E_{ST}$ compared to Comparative Compound 2 having a narrow spectrum width, thereby realizing light emission with high efficiency.

In addition, it was confirmed that Compounds 1, 2, and 25 had a narrow emission spectrum compared to Comparative Compound 3 as a general TADF material, thereby realizing high color purity.

Comparative Example 2: Calculation of E(S1), E(T1), and $\Delta E_{ST}$ in Ground State Evaluation was performed on the TADF properties of the compounds of the present disclosure. In detail, for each of Compounds 1 to 45 of the present disclosure, the singlet energy (E(S1)), the triplet energy (E(T1)), and the difference therebetween ($\Delta E_{ST}$) were calculated by the DFT. The results are shown in Table 3.

Calculation Method

E(S1), E(T1): calculation was performed by the functional B3LYP in the ground-state optimization structure that is obtained by DFT using the functional B3LYP and the basis function 6-31 G(d,p), and the TDDFT according to the basis function 6-31 G(d,p).

$$\Delta E_{ST}=E(S1)-E(T1)$$

Calculation software used: Gaussian 16 (Gaussian Inc.).

In addition, since it is known that $\Delta E_{ST}$ is calculated to be large in the above calculation method, corrections were made based on the calculated values and found values (Small (2020), 16(14), 1907569) of Comparative Compound 1 shown in Table 2, and for the calculated values, $\Delta E_{ST}\leq 0.45$ eV was determined to be acceptable. In addition, the emission wavelength (fluorescence wavelength) was similarly corrected, and for the calculated values, the range of 416 nm to 480 nm was determined to be acceptable.

TABLE 2

| | Calculated Value | | Found Value | |
|---|---|---|---|---|
| | S1 nm | Δ $E_{ST}$ eV | S1 nm | Δ $E_{ST}$ eV |
| Comparative Compound 1 | 369 | 0.583 | 393 | 0.46 |

TABLE 3

| Compound No. | S1 nm | S1 eV | T1 nm | T1 eV | Δ $E_{ST}$ eV |
|---|---|---|---|---|---|
| 1 | 431 | 2.88 | 502 | 2.47 | 0.41 |
| 2 | 438 | 2.83 | 509 | 2.44 | 0.39 |
| 3 | 437 | 2.84 | 508 | 2.44 | 0.40 |
| 4 | 425 | 2.92 | 492 | 2.52 | 0.40 |
| 5 | 425 | 2.92 | 497 | 2.49 | 0.42 |
| 6 | 416 | 2.98 | 471 | 2.63 | 0.35 |
| 7 | 416 | 2.98 | 471 | 2.63 | 0.35 |
| 8 | 420 | 2.95 | 486 | 2.55 | 0.40 |
| 9 | 433 | 2.86 | 490 | 2.53 | 0.33 |
| 10 | 422 | 2.94 | 494 | 2.51 | 0.43 |
| 11 | 419 | 2.96 | 494 | 2.51 | 0.45 |
| 12 | 426 | 2.91 | 504 | 2.46 | 0.45 |
| 13 | 431 | 2.88 | 510 | 2.43 | 0.45 |
| 14 | 416 | 2.98 | 490 | 2.53 | 0.45 |
| 15 | 418 | 2.97 | 492 | 2.52 | 0.45 |
| 16 | 429 | 2.89 | 497 | 2.49 | 0.40 |
| 17 | 446 | 2.78 | 505 | 2.46 | 0.32 |
| 18 | 463 | 2.68 | 512 | 2.42 | 0.26 |
| 19 | 432 | 2.87 | 503 | 2.47 | 0.41 |
| 20 | 432 | 2.87 | 503 | 2.47 | 0.41 |
| 21 | 432 | 2.87 | 503 | 2.47 | 0.41 |
| 22 | 469 | 2.64 | 513 | 2.42 | 0.23 |
| 23 | 450 | 2.76 | 506 | 2.45 | 0.30 |
| 24 | 465 | 2.67 | 507 | 2.45 | 0.22 |
| 25 | 467 | 2.66 | 505 | 2.46 | 0.20 |

TABLE 3-continued

| Compound No. | S1 nm | T1 nm | Δ $E_{ST}$ ev |
|---|---|---|---|
| 26 | 420 | 494 | 0.45 |
| 27 | 424 | 495 | 0.42 |
| 28 | 425 | 500 | 0.43 |
| 29 | 434 | 507 | 0.41 |
| 30 | 472 | 474 | 0.01 |
| 31 | 480 | 482 | 0.01 |
| 32 | 465 | 466 | 0.01 |
| 33 | 458 | 460 | 0.01 |
| 34 | 466 | 469 | 0.01 |
| 35 | 474 | 476 | 0.01 |
| 36 | 446 | 455 | 0.06 |
| 37 | 471 | 473 | 0.01 |
| 38 | 458 | 461 | 0.02 |
| 39 | 461 | 463 | 0.01 |
| 40 | 426 | 496 | 0.41 |
| 41 | 422 | 495 | 0.44 |
| 42 | 426 | 496 | 0.41 |
| 43 | 422 | 495 | 0.44 |
| 44 | 426 | 495 | 0.41 |
| 45 | 421 | 494 | 0.44 |

As shown in Table 3, Compounds 1 to 45 of the present disclosure were found to have small $\Delta E_{ST}$ values. Accordingly, Compounds 1 to 45 of the present disclosure are expected to have excellent TADF properties, and are expected to have high luminescence efficiency.

Example 4: Manufacture of Organic Light-Emitting Device

Device Examples 1 to 4

An ITO glass substrate was cut to a size of 50 mm×50 mm×0.5 mm and then, sonicated in acetone, isopropyl alcohol, and pure water, in this stated order, each for 15 minutes, and then, washed by exposure to UV ozone for 30 minutes. The following layers were deposited on the ITO electrode (anode) of the glass substrate.

First, HAT-CN (manufactured by e-Ray) was deposited on the ITO electrode to form a hole injection layer having a thickness of 10 nm. Next, Compound HT01 was deposited on the hole injection layer to form a hole transport layer having a thickness of 140 nm. Next, Compound H-H1 was deposited on the hole transport layer to form an electron blocking layer having a thickness of 5 nm to thereby form a hole transport region.

Compound H-H1 as a host material having hole transport properties (HT-Host compound), H-E1 as a host material having electron transport properties (ET-Host compound), phosphorescent complex Pt-1, and Compound 1 obtained above were co-deposited on the hole transport region to form an emission layer having a thickness of 40 nm. Here, the emission layer was formed such that a weight ratio of Compound H-H1 to Compound H-E1 in the emission layer is as shown in Table 4. Also, a concentration of Pt-1 in the emission layer is 7 wt % based on the total weight of Compounds H-H1 and H-E1, phosphorescent complex Pt-1, and Compound 1 (that is, the total weight of the emission layer). In addition, the emission layer was formed such that a concentration of Compound 1 in the emission layer is 0.2 wt % based on the total weight of Compounds H-H1 and H-E1, phosphorescent complex Pt-1, and Compound 1 (that is, the total weight of the emission layer). Further, Compounds H-H1 and H-E1 are host materials.

H-E1 was vacuum-deposited on the emission layer to form a hole blocking layer having a thickness of 5 nm. Then, TRE314 (manufactured by Toray Co., Ltd., an electron transport material) and LiQ were co-deposited on the hole blocking layer at a weight ratio of TRE314:LiQ=5:5 (unit: parts by weight) to form an electron transport layer having a thickness of 30 nm. Next, LiQ was deposited on the electron transport layer to form an electron injection layer having a thickness of 1 nm to thereby form an electron transport region.

Al (cathode) having a thickness of 100 nm was deposited on the electron injection layer to thereby manufacture an organic light-emitting device.

Then, in a glove box of a nitrogen atmosphere with water concentration of 1 ppm or less and oxygen concentration of 1 ppm or less, a glass sealing tube with a desiccating agent and an ultraviolet curing resin (manufactured by MORESCO, product name WB90US) were used to seal the organic light-emitting device manufactured by the above process. By sealing the organic light-emitting device, the manufacture of the organic light-emitting device was completed.

HT01

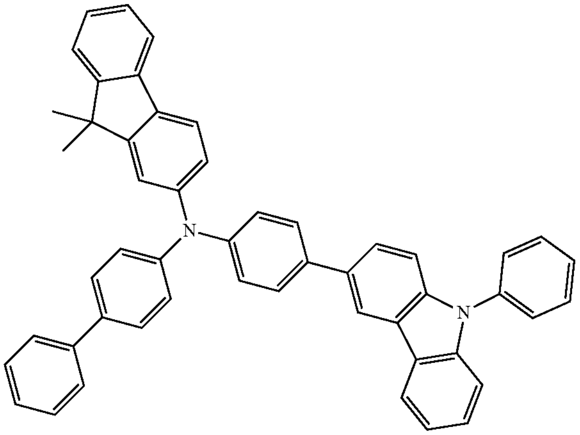

H-H1

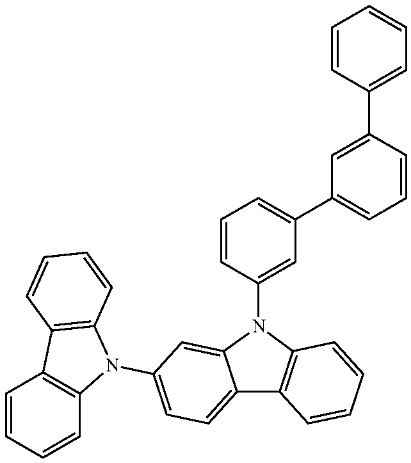

-continued

H-E1

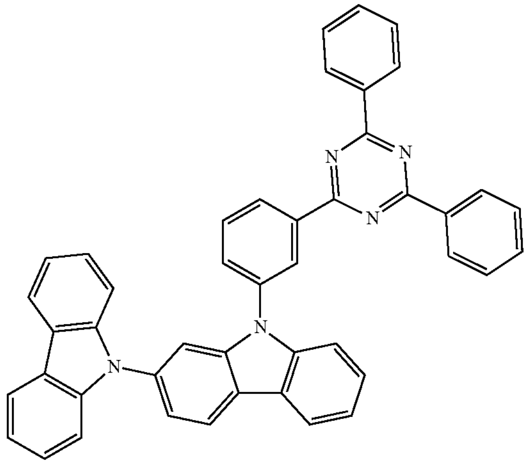

Pt-1

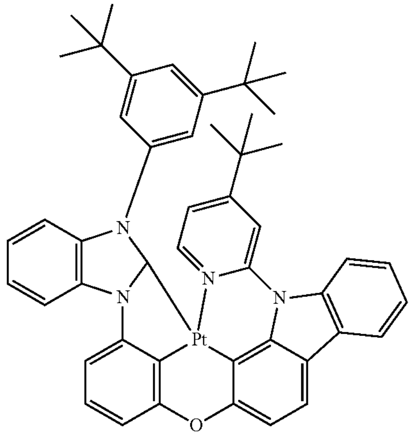

Evaluation of Organic Light-Emitting Device

The luminance, external quantum efficiency, and device lifespan of an organic light-emitting device were evaluated according to the following method, and the results are shown in Table 4.

The organic light-emitting device was allowed to emit light by continuously changing the voltage applied to the organic light-emitting device by using a DC constant voltage power supply (2400 source meter from KEITHLEY), and the brightness and emission spectrum at this time were measured with a luminance measuring device (manufactured by Topcon, SR-3).

Here, the external quantum efficiency was calculated from the emission spectrum, the luminescence amount, and the current value at the time of measuring. In addition, the lifespan (durability) of the device was shown as LT95 by measuring the amount of time taken when the emission luminance, which decays as time lapses, becomes 95% of the initial luminance when the device is continuously driven on a current value having an initial luminance of 1000 cd/$m^2$. LT95 in Table 4 is an absolute value (unit:time (hrs)). The emission peak wavelength and the FWHM of the peak of the emission spectrum was read from the result of measuring the emission spectrum.

TABLE 4

| Organic EL Device | Emission layer ratio Host ratio Compound H-H1:H-E1 (weight ratio) | Evaluation result of Organic EL Device Luminance [cd/m$^2$] | external quantum efficiency [%] | Peak Wavelength [nm] | Full width at half maximum (FWHM) of a peak of a fluorescence spectrum [nm] | LT95 [hrs] |
|---|---|---|---|---|---|---|
| Device Example 1 | 7.5:2.5 | 1000 | 10.2 | 459 | 40.7 | 7.8 |
| Device Example 2 | 7:3 | 1000 | 10.3 | 461 | 44.4 | 8.4 |
| Device Example 3 | 6.5:3.5 | 1000 | 10.1 | 462 | 47.4 | 7.5 |
| Device Example 4 | 6:4 | 1000 | 10.1 | 463 | 48.9 | 6.8 |

As shown in Table 4, it was confirmed that, in the organic light-emitting devices of Device Examples 1 to 4, finely adjusted blue light emission was realized, and the external quantum efficiency and device lifespan were also improved.

Example 5: Manufacture of Organic Light-Emitting Device

Device Example 5

An ITO glass substrate was cut to a size of 50 mm×50 mm×0.5 mm and then, sonicated in acetone, isopropyl, alcohol, and pure water, in this stated order, each for 15 minutes, and then, washed by exposure to UV ozone for 30 minutes. The following layers were deposited on the ITO electrode (anode) of the glass substrate.

First, HAT-CN (manufactured by e-Ray) was deposited on the ITO electrode to form a hole injection layer having a thickness of 10 nm. Next, Compound HT01 was deposited on the hole injection layer to form a hole transport layer having a thickness of 140 nm. Next, Compound H-H2 was deposited on the hole transport layer to form an electron blocking layer having a thickness of 5 nm to thereby form a hole transport region.

Compound H-H2 as a host material having hole transport properties (HT-Host compound), Compound H-E2 as a host material having electron transport properties (ET-Host compound), and Compound 1 obtained above were co-deposited on the hole transport region to form an emission layer having a thickness of 40 nm. Here, the emission layer was formed such that the concentration of Compound 1 in the emission layer was 1.5 wt % based on the total weight of Compounds H-H2, H-E2, and 1 (that is, the total weight of the emission layer). Compounds H-H2 and H-E2 are host materials.

Compound H-E2 was vacuum-deposited on the emission layer to form a hole blocking layer having a thickness of 5 nm. Then, TRE314 (manufactured by Toray Co., Ltd., an electron transport material) and LiQ were co-deposited on the hole blocking layer at a weight ratio of TRE314:LiQ=5:5 (unit:parts by weight) to form an electron transport layer having a thickness of 30 nm. Next, LiQ was deposited on the electron transport layer to form an electron injection layer having a thickness of 1 nm to thereby form an electron transport region.

Al (cathode) having a thickness of 100 nm was deposited on the electron injection layer to thereby manufacture an organic light-emitting device.

Then, in a glove box of a nitrogen atmosphere with water concentration of 1 ppm or less and oxygen concentration of 1 ppm or less, a glass sealing tube with a desiccating agent and an ultraviolet curing resin (manufactured by MORESCO, product name WB90US) were used to seal the organic light-emitting device manufactured by the above process. By sealing the organic light-emitting device, the manufacture of the organic light-emitting device was completed.

H-H2

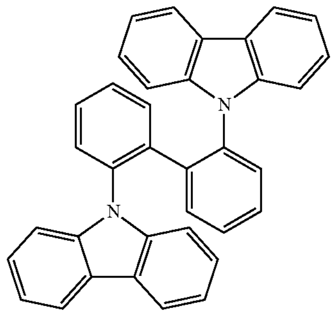

H-E2

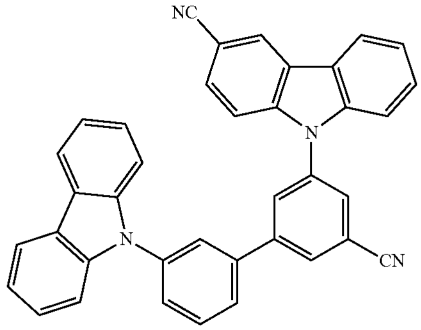

Device Comparative Example 1

An organic light-emitting device was manufactured in the same manner as in Device Example 5, except that Comparative Compound 2 was used instead of Compound 1 in the formation of the emission layer.

Evaluation of Organic Light-Emitting Device

The CIEx, CIEy, emission peak wavelength, FWHM, and external quantum efficiency of an organic light-emitting device were evaluated according to the following method.

The organic light-emitting device was allowed to emit light by continuously changing the voltage applied to the organic light-emitting device by using a DC constant voltage power supply (2400 source meter from KEITHLEY), and the luminance, emission spectrum, luminescence amount, CIEx, and CIEy at this time were measured with a luminance measuring device (manufactured by Topcon, SR-3).

The CIEx and CIEy represent x and y values of CIE chromaticity coordinates, respectively.

In addition, the emission peak wavelength and the FWHM of the peak of the emission spectrum was read from the result of measuring the emission spectrum.

The external quantum efficiency was calculated from the emission spectrum, the luminescence amount, and the current value at the time of measuring. In addition, the external quantum efficiency represents a value of external quantum efficiency when the current density calculated from the area of the organic light-emitting device during current driving is 0.2 (mA/$cm^2$).

The results are shown in Table 5.

TABLE 5

| Organic EL Device | Emission layer ratio: Host ratio (weight ratio) | Emission layer ratio: Dopant | CIEx | CIEy | Peak Wavelength (nm) | Full width at half maximum (FWHM) (nm) | external quantum efficiency (%) |
|---|---|---|---|---|---|---|---|
| Device Example 5 | H-H2:H-E2 = 4:6 | Compound 1 | 0.145 | 0.088 | 458 | 17 | 9.8 |
| Device Comparative Example 1 | H-H2:H-E2 = 4:6 | Comparative Compound 2 | 0.148 | 0.146 | 457 | 26 | 4.0 |

As shown in Table 5, it was confirmed that the organic light-emitting device of Device Example 5 had an emission peak wavelength equivalent to that of the organic light-emitting device of Device Comparative Example 1 and a narrow FWHM of about two-thirds of that of the organic light-emitting device of Device Comparative Example 1. In addition, since the organic light-emitting device of Device Comparative Example 1 was a fluorescent device, the external quantum efficiency thereof at 0.2 mA/$cm^2$ was 4.0%. However, in Device Example 5, since the $\Delta E_{ST}$ was small, the organic light-emitting device may be a TADF device, and accordingly, the upper limit of the external quantum efficiency of a fluorescent device was 9.8%, which exceeded 5%. From the above, it was confirmed that an organic light-emitting device using the heterocyclic compound according to an embodiment had a relatively narrow FWHM, realized finely adjusted blue light emission, and had improved external quantum efficiency.

As apparent from the foregoing description, an organic light-emitting device including the heterocyclic compound may have improved efficiency and/or color purity.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A heterocyclic compound represented by Formula 1:

Formula 1

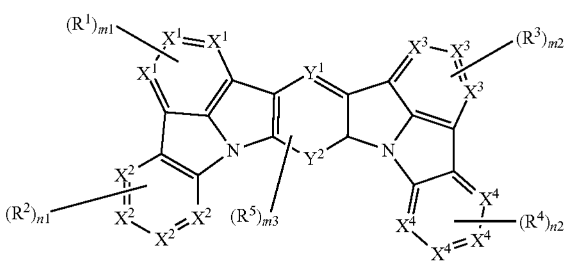

wherein, in Formula 1, $X^1$, $X^2$, $X^3$, and $X^4$ are each independently C or N, and at least one of three $X^1$(s), four $X^2$(s), three $X^3$(s), four $X^4$(s), or any combination thereof is N, $Y_1$ and $Y_2$ are each independently C or N, and at least one of $Y_1$ and $Y_2$ is N, $R^1$, $R^2$, $R^3$, and $R^4$ are each independently a hydrogen atom, a deuterium atom, a halogen atom, a substituted or unsubstituted aryl group having 6 to 14 ring-forming atoms, a substituted or unsubstituted heteroaryl group having 5 to 14 ring-forming atoms, a substituted or unsubstituted amino group, a substituted or unsubstituted arylamino group having 6 to 14 ring-forming atoms, a substituted or unsubstituted heteroarylamino group having 5 to 14 ring-forming atoms, or a substituted or unsubstituted arylboranyl group having 6 to 14 ring-forming atoms, $R^5$ is a hydrogen atom, a deuterium atom, a halogen atom, a substituted or unsubstituted aryl group having 6 to 14 ring-forming atoms, a substituted or unsubstituted heteroaryl group having 5 to 14 ring-forming atoms, a substituted or unsubstituted amino group, a substituted or unsubstituted arylamino group having 6 to 14 ring-forming atoms, a substituted or unsubstituted heteroarylamino group having 5 to 14 ring-forming atoms, a substituted or unsubstituted indolo[3,2,1-jk]carbazolyl group, or $—R^{51}—R^{52}$, $R^{51}$ is a substituted or unsubstituted arylene group having 6 to 14 ring-forming atoms or a substituted or unsubstituted heteroarylene group having 5 to 14 ring-forming atoms, $R^{52}$ is a substituted or unsubstituted amino group, a substituted or unsubstituted arylamino group having 6 to 14 ring-forming atoms, a substituted or unsubstituted hetero arylamino group having 5 to 14 ring-forming atoms, or a substituted or unsubstituted heteroaryl group having 5 to 14 ring-forming atoms, n1 and n2 are each independently 1, 2, 3, or 4, m1 and m2 are each independently 1, 2, or 3, and m3 is 0, 1, or 2.

2. The heterocyclic compound of claim 1, wherein $R^1$, $R^2$, $R^3$, and $R^4$ are each independently a hydrogen atom, a substituted or unsubstituted phenyl group, a substituted or unsubstituted pyridyl group, a substituted or unsubstituted biphenylboranyl group, or a monovalent group represented by Formula B1:

B1

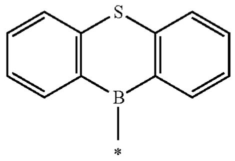

wherein, in Formula B1, * indicates a binding site to a neighboring atom.

3. The heterocyclic compound of claim 1, wherein at least one of $X^1$(s) is N, at least one of $X^2$(s) is N, at least one of $X^3$(s) is N, and at least one of $X^4$(s) is N.

4. The heterocyclic compound of claim 1, wherein n1 and n2 are each 3, and m1 and m2 are each 2.

5. The heterocyclic compound of claim 1, wherein, when two of $X^1$(s) and two of $X^3$(s) are each C, and m1 and m2 are each 2, one of $R^1$(s) and one of $R^3$(s) are each a hydrogen atom, and another one of $R^1$(s) and another one of $R^3$(s) are each a substituted or unsubstituted phenyl group, a substituted or unsubstituted pyridyl group, a substituted or unsubstituted biphenylboranyl group, or a monovalent group represented by Formula B1:

B1

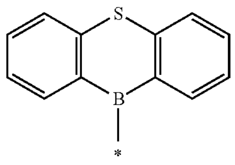

wherein, in Formula B1, * indicates a binding site to a neighboring atom.

6. The heterocyclic compound of claim 1, wherein, when three of $X^2$(s) and three of $X^4$(s) are each C, and n1 and n2 are each 3, two of $R^2$(s) and two of $R^4$(s) are each a hydrogen atom, and another one of $R^2$(s) and another one of $R^4$(s) are each a substituted or unsubstituted phenyl group, a substituted or unsubstituted pyridyl group, a substituted or unsubstituted biphenylboranyl group, or a monovalent group represented by Formula B1:

B1

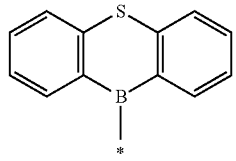

wherein, in Formula B1, * indicates a binding site to a neighboring atom.

7. The heterocyclic compound of claim 1, wherein m3 is 1 or 2.

8. The heterocyclic compound of claim 1, wherein $R^5$ is a hydrogen atom, a substituted or unsubstituted phenyl group, a substituted or unsubstituted carbazolyl group, a substituted or unsubstituted indolo[3,2,1-jk]carbazolyl group, a substituted or unsubstituted N,N-diphenylamino group, a substituted or unsubstituted phenoxazinyl group, or —$R^{51}$-$R^{52}$, and $R^{51}$ is a phenylene group, and $R^{52}$ is a substituted or unsubstituted N,N-diphenylamino group or a substituted or unsubstituted phenoxazinyl group.

9. The heterocyclic compound of claim 1, wherein the heterocyclic compound is represented by one of Group X:

Group X (1-2)

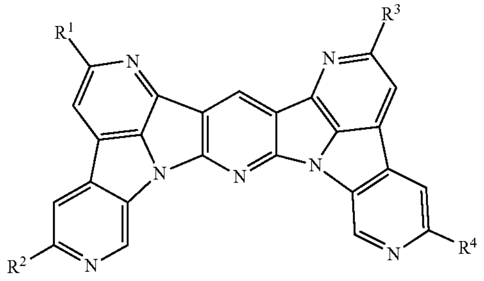

(1-3)

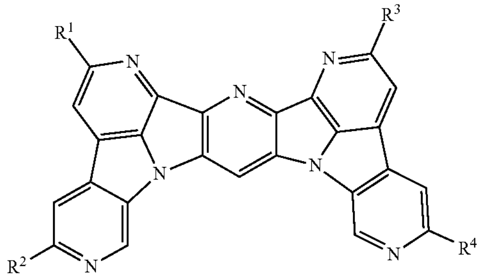

(1-4)

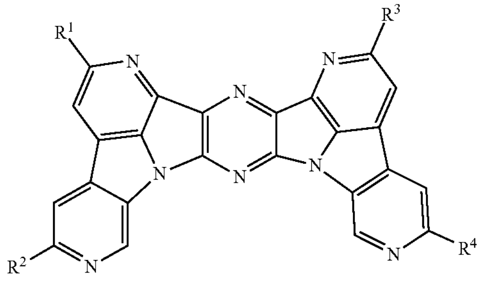

-continued
(1-8)
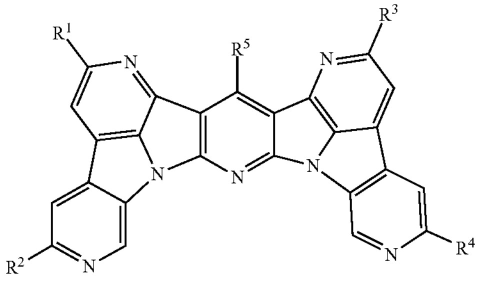
(1-9)
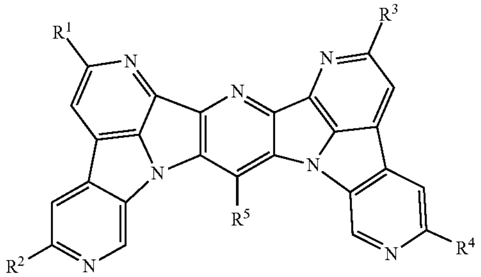
(1-11)
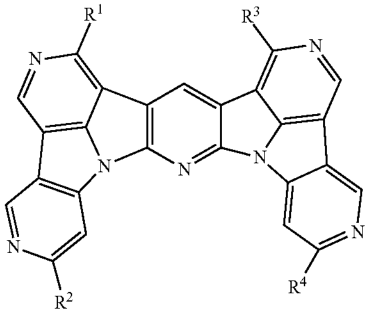
(1-12)
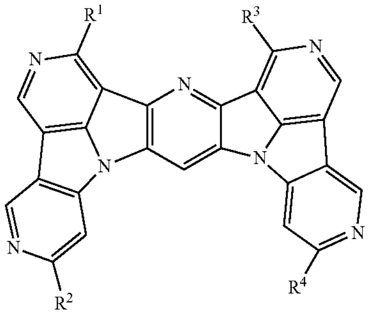
(1-13)
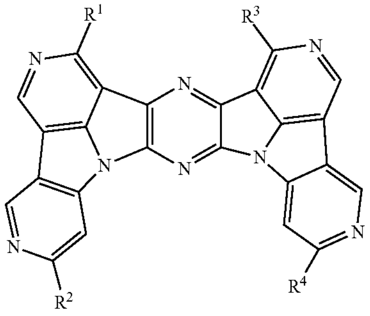
-continued
(1-17)
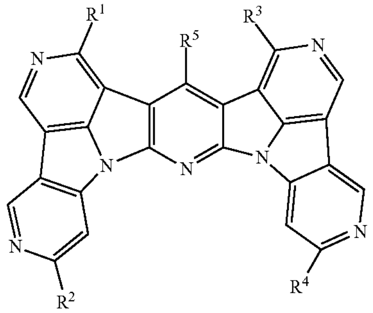
(1-18)
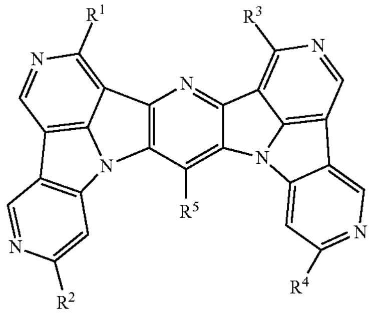
(1-20)
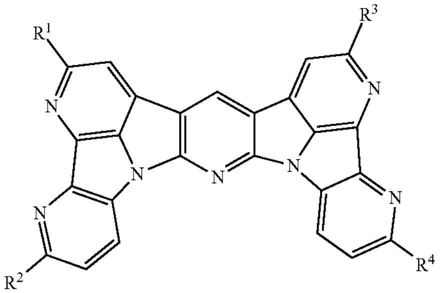
(1-21)
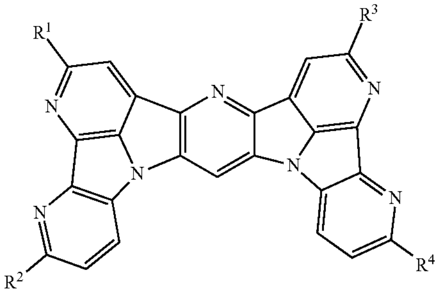
(1-22)
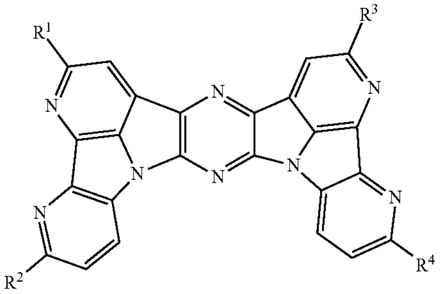

-continued
(1-26)
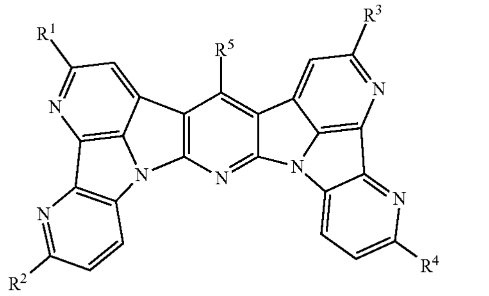
(1-27)
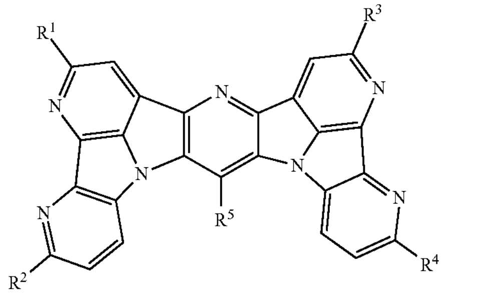
(1-29)
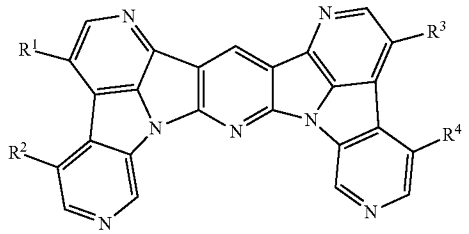
(1-30)
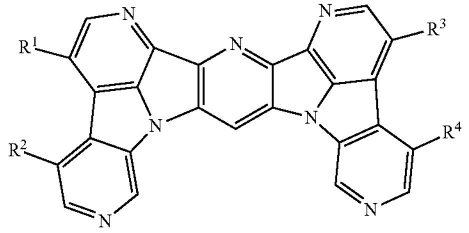
(1-31)
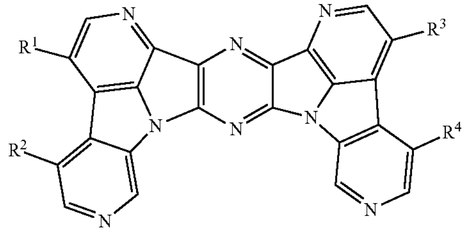
(1-35)
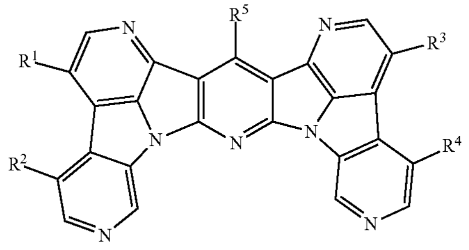
-continued
(1-36)
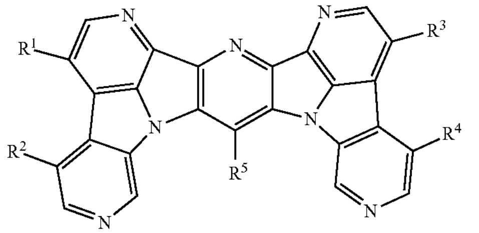
(1-45)
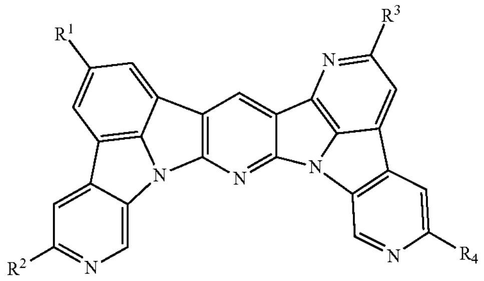
(1-46)
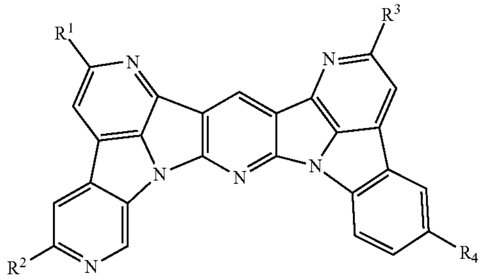
(1-47)
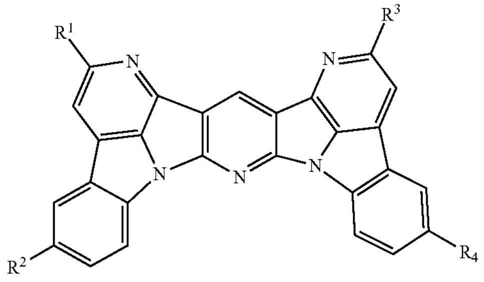
(1-48)
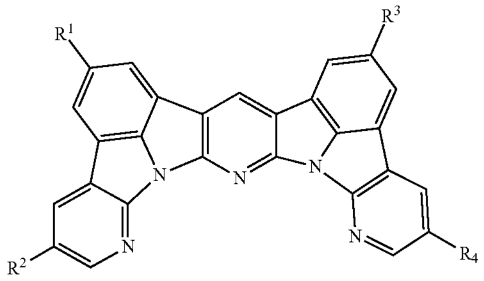

-continued
(1-49)
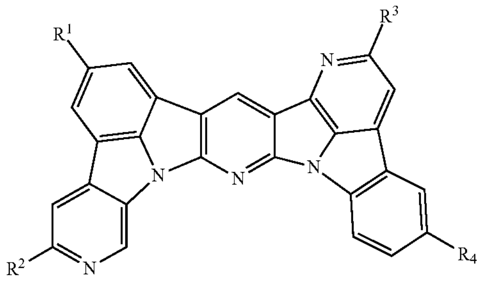
(1-50)
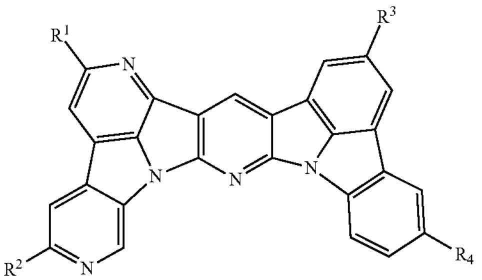
(1-51)
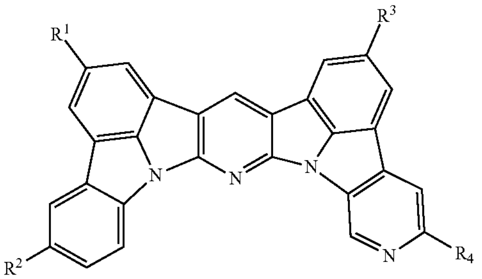
(1-52)
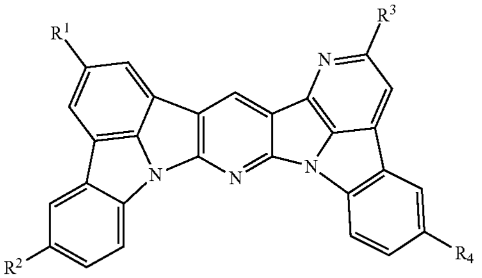
(1-53)
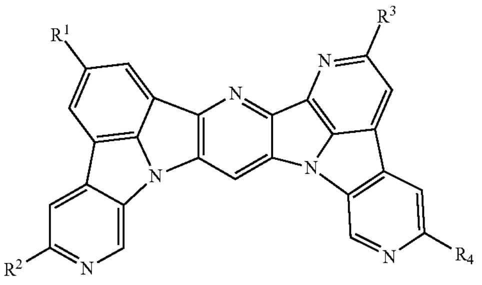
-continued
(1-54)
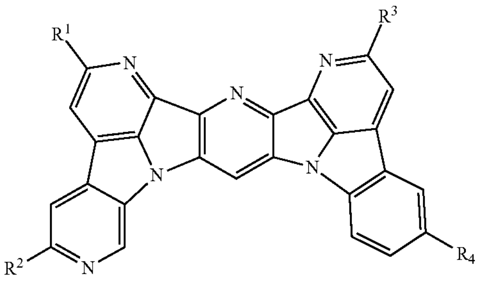
(1-55)
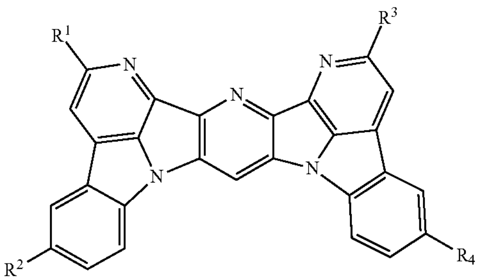
(1-56)
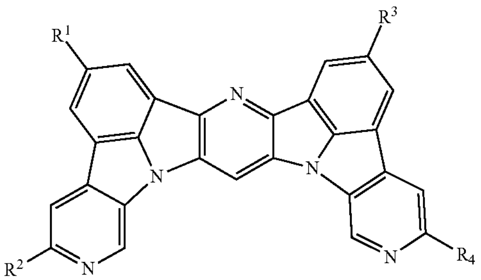
(1-57)
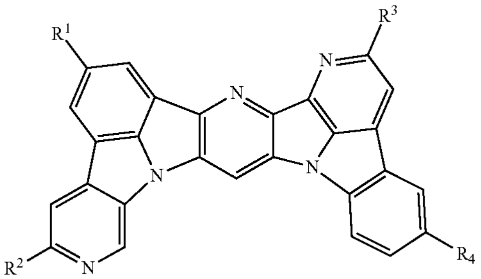
(1-58)
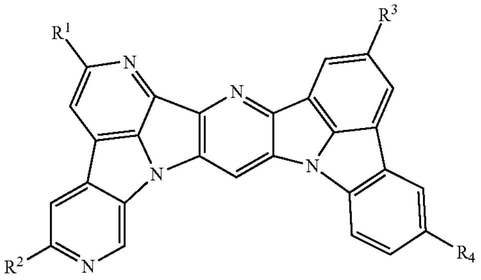

-continued
(1-59)
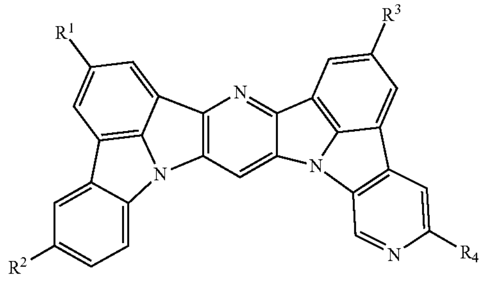
(1-60)
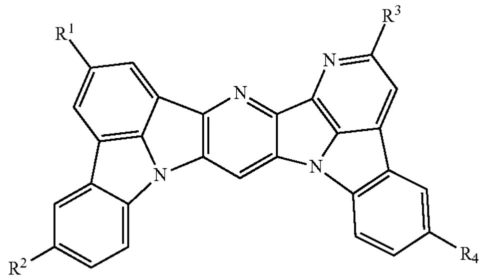
(1-61)
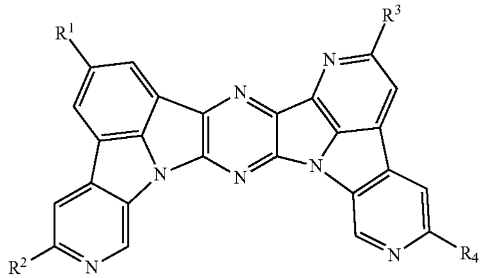
(1-62)
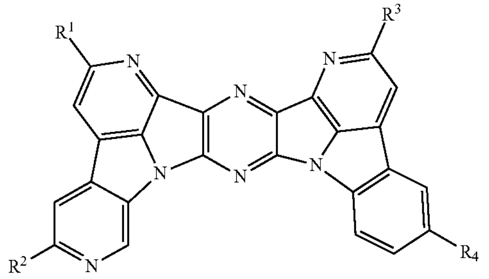
(1-63)
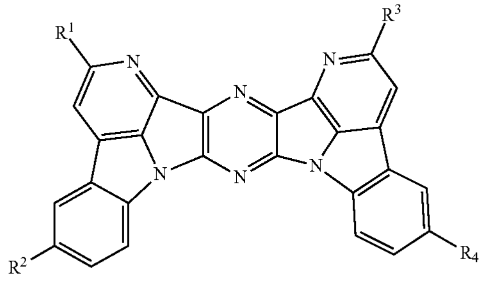
-continued
(1-64)
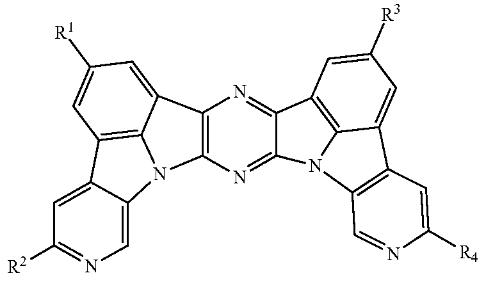
(1-65)
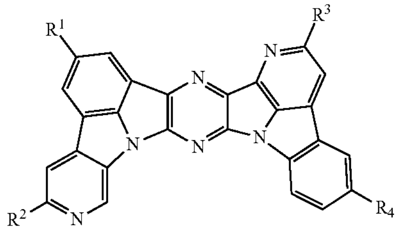
(1-66)
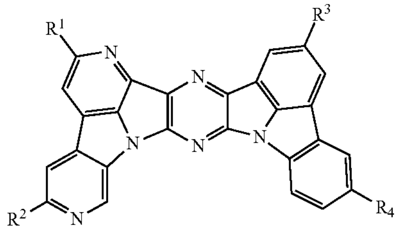
(1-67)
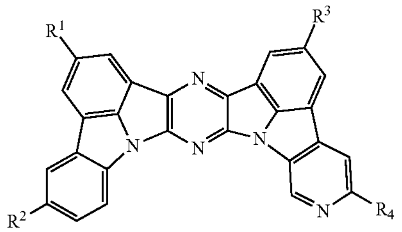
(1-68)
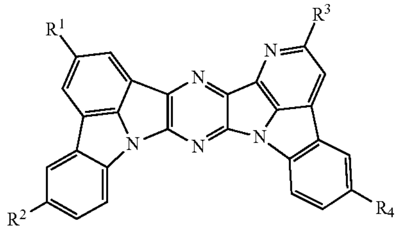
(1-93)
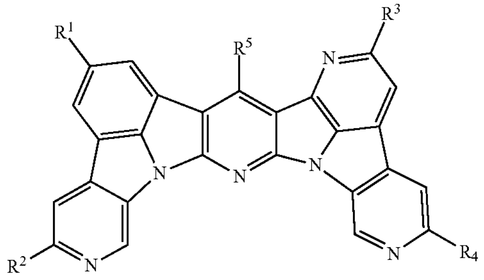

-continued
(1-94)
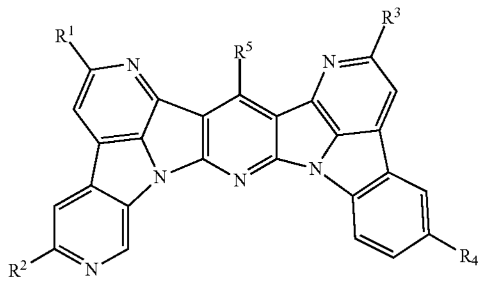
(1-95)
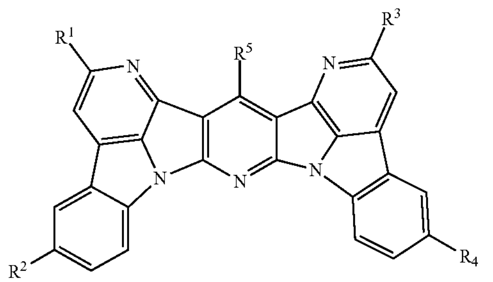
(1-96)
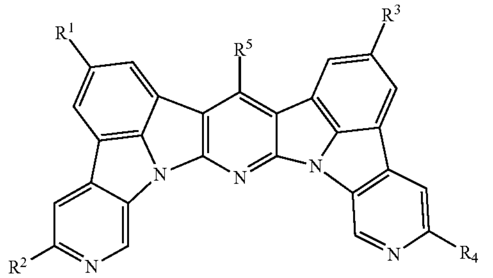
(1-97)
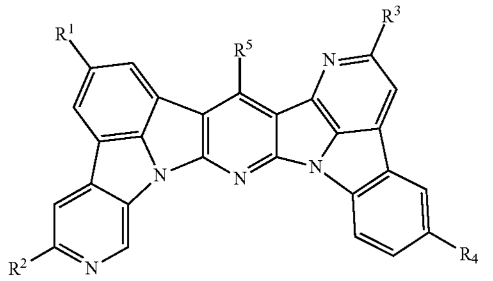
(1-98)
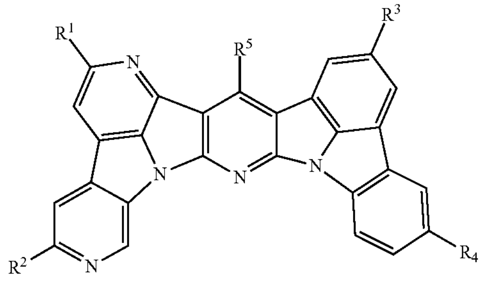
-continued
(1-99)
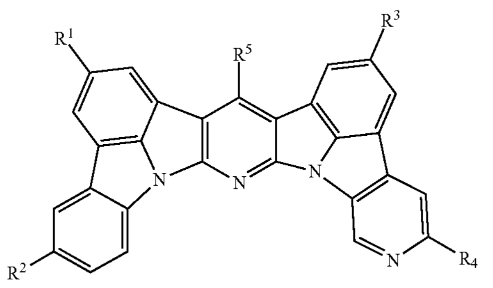
(1-100)
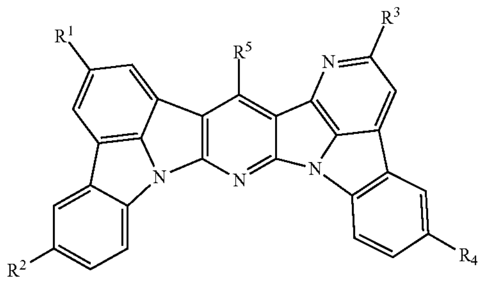
(1-101)
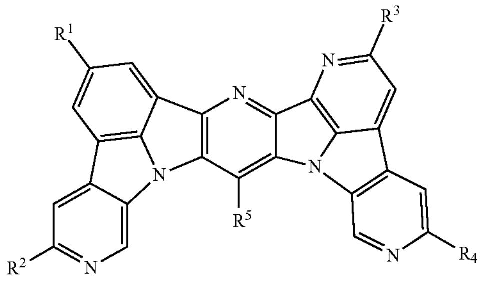
(1-102)
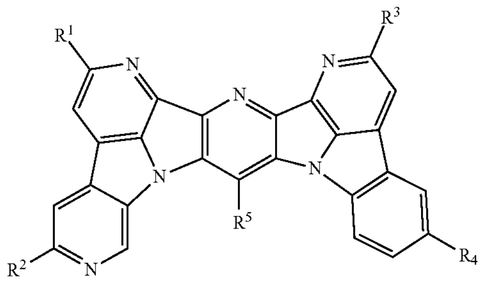
(1-103)
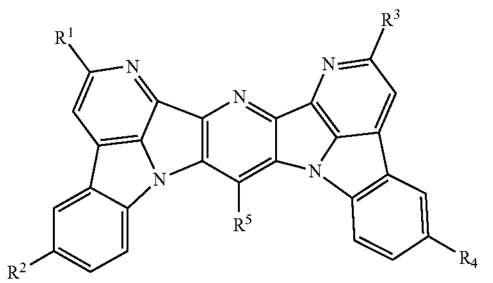

-continued
(1-104)
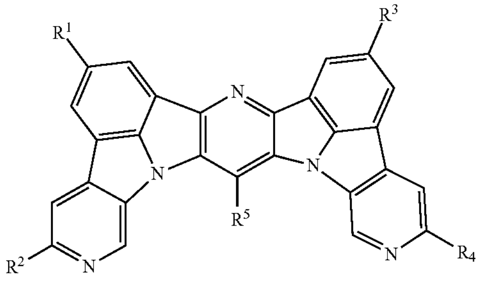
(1-105)
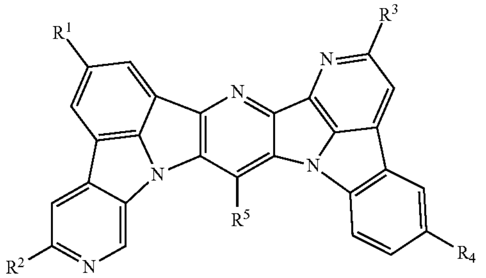
(1-106)
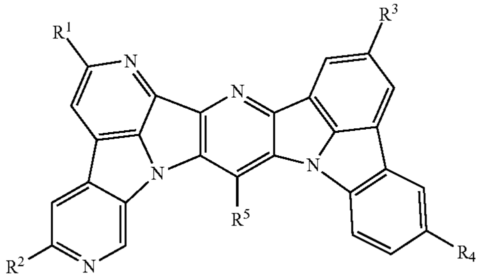
(1-107)
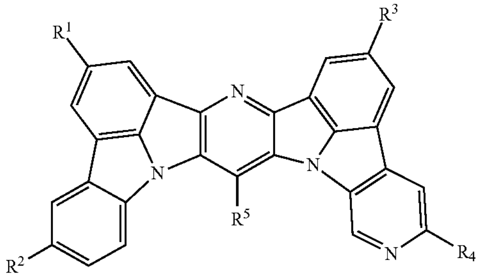
(1-108)
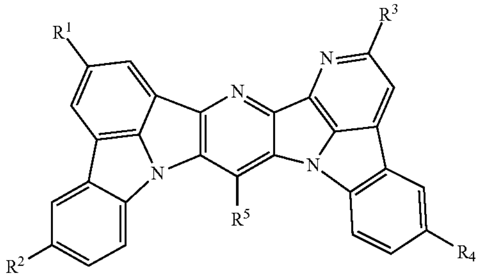
(1-117)
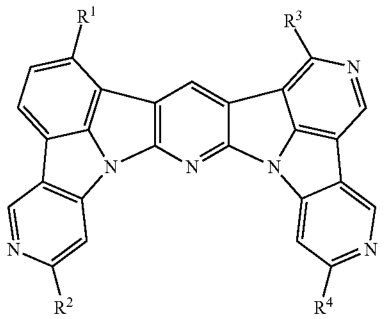
(1-118)
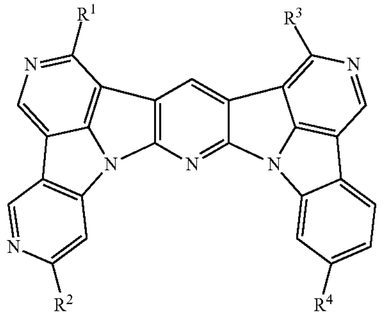
(1-119)
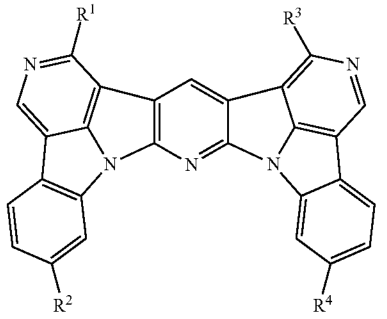
(1-120)
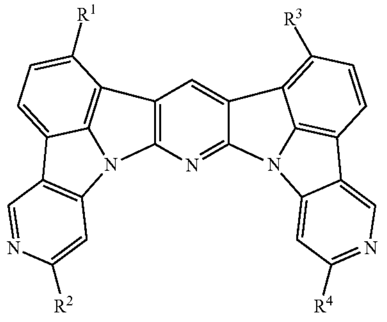
(1-121)
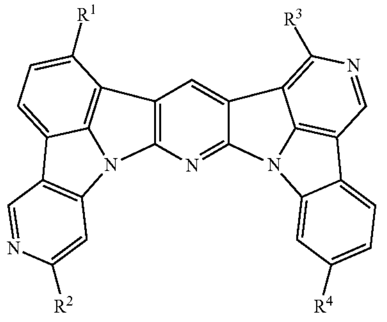

-continued
(1-122)
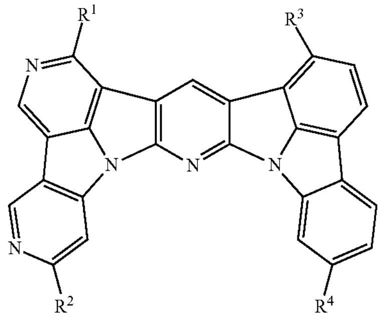
(1-123)
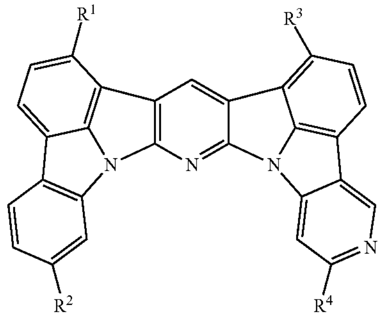
(1-124)
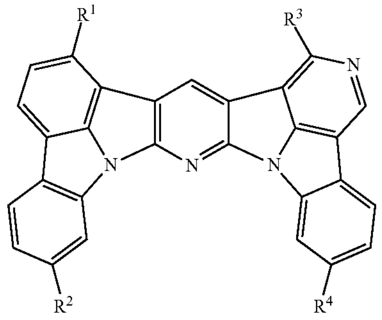
(1-125)
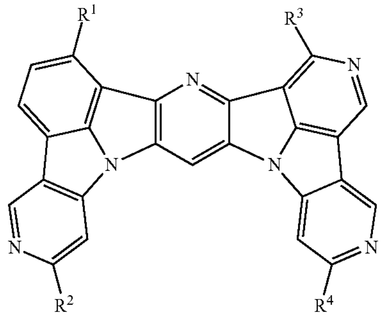
(1-126)
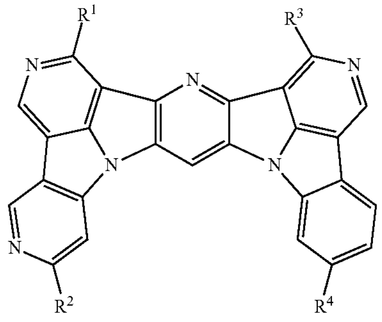
-continued
(1-127)
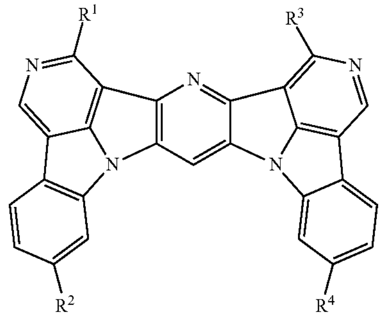
(1-128)
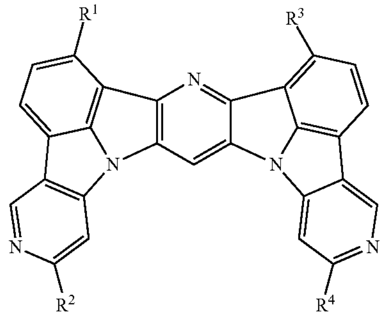
(1-129)
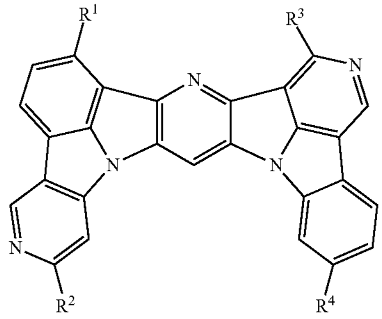
(1-130)
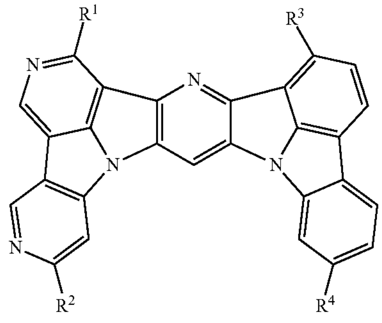
(1-131)
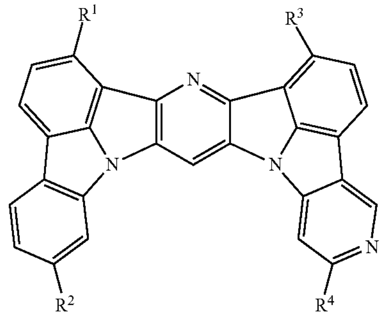

-continued
(1-132)
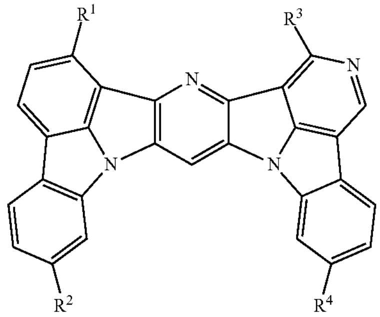
(1-133)
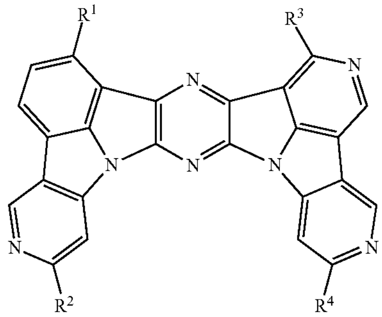
(1-134)
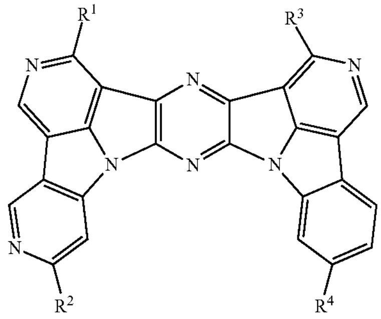
(1-135)
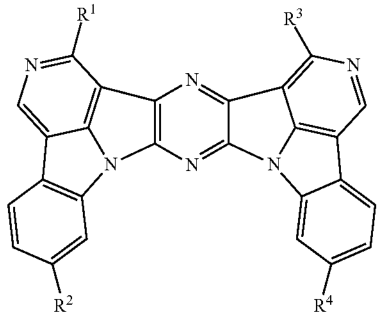
(1-136)
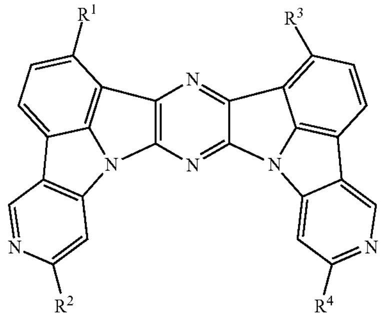
-continued
(1-137)
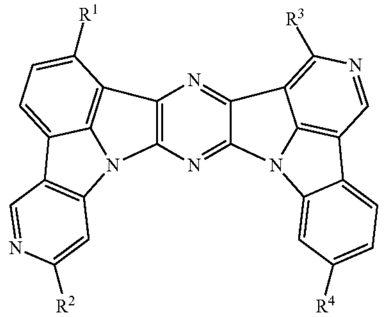
(1-138)
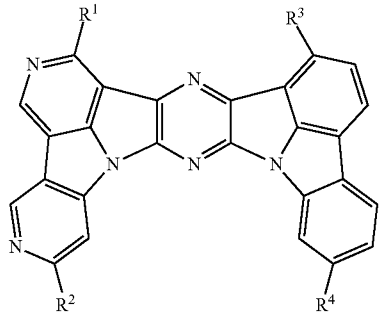
(1-139)
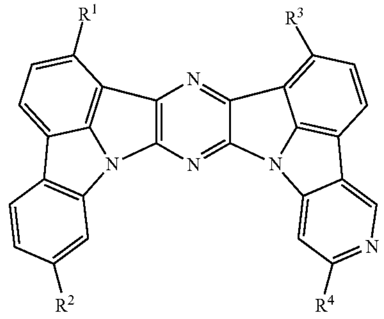
(1-140)
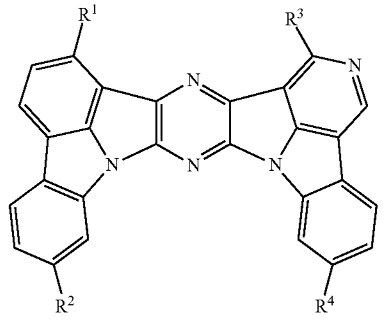
(1-165)
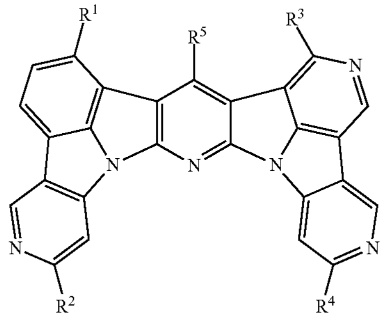

-continued
(1-166)
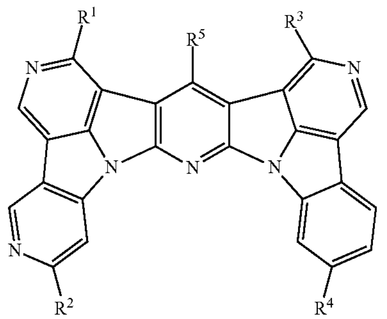
(1-167)
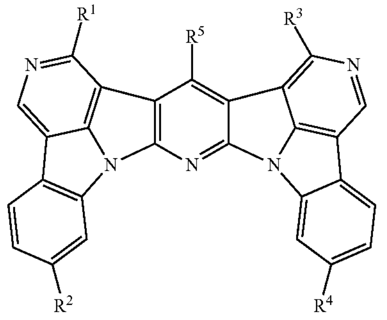
(1-168)
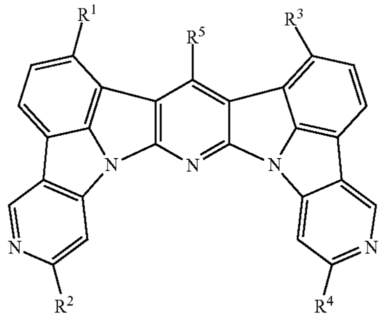
(1-169)
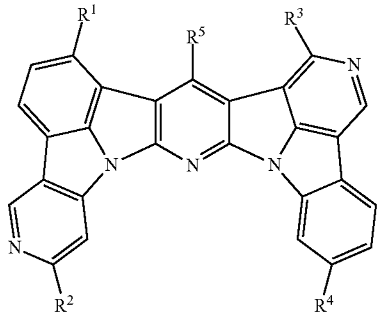
(1-170)
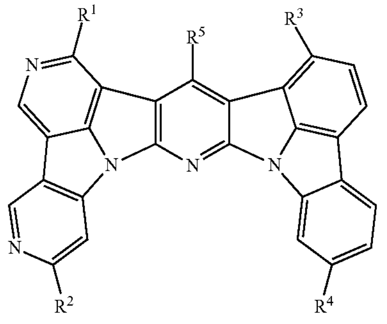
-continued
(1-171)
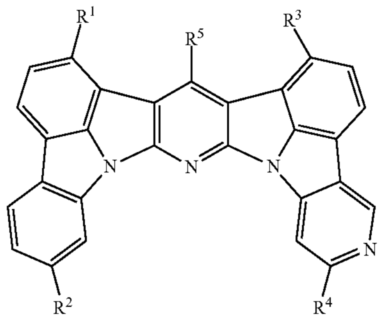
(1-172)
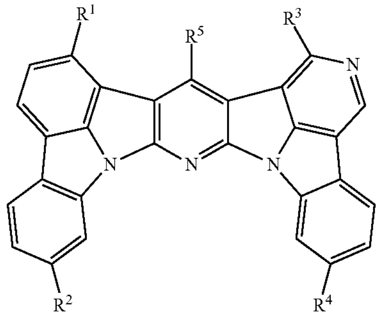
(1-173)
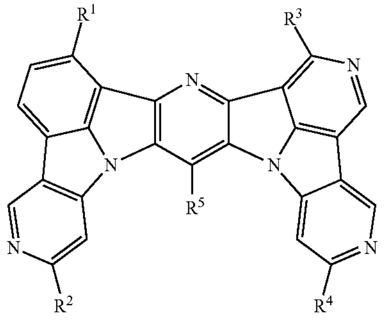
(1-174)
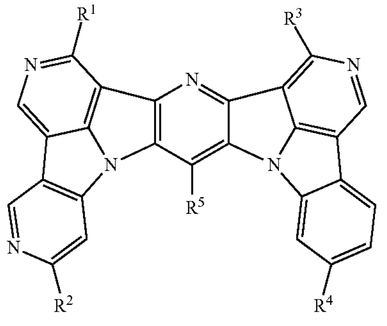
(1-175)
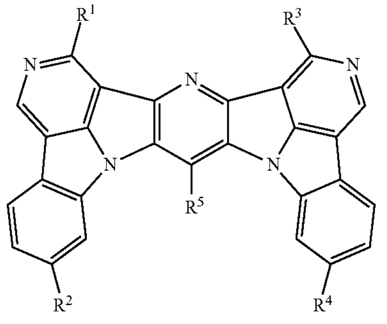

-continued
(1-176)
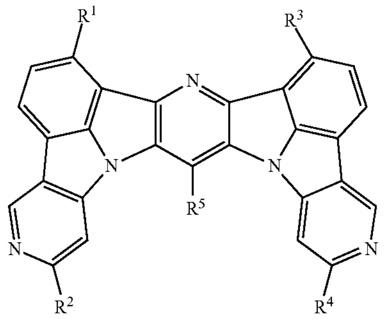
(1-177)
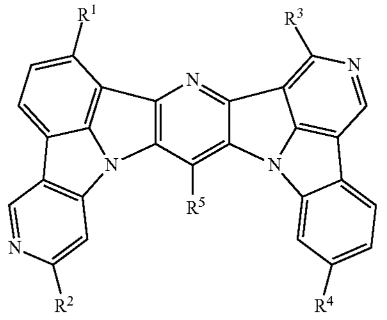
(1-178)
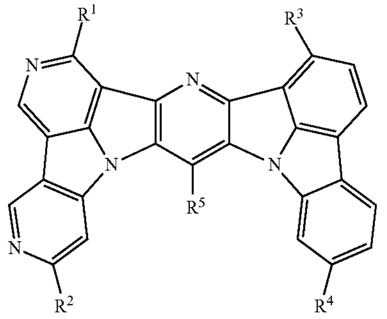
(1-179)
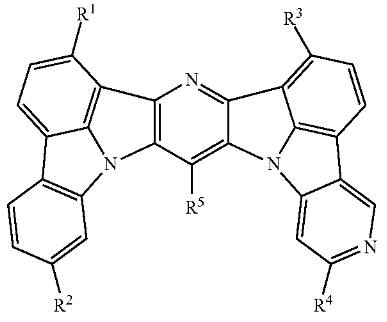
(1-180)
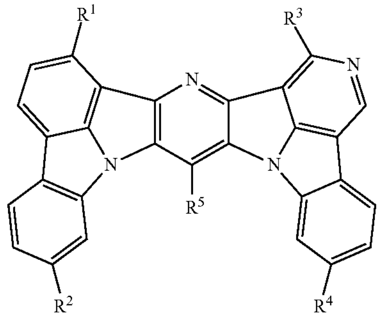
-continued
(1-189)
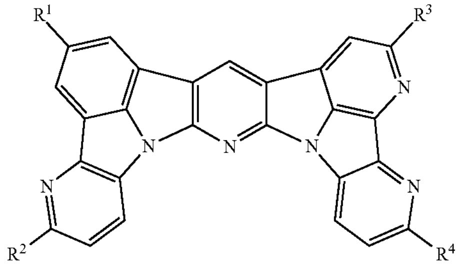
(1-190)
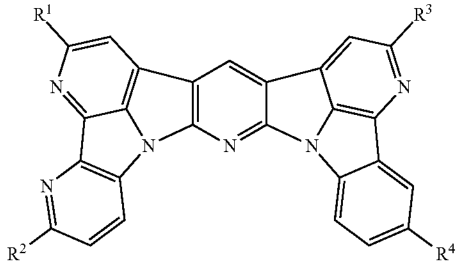
(1-191)
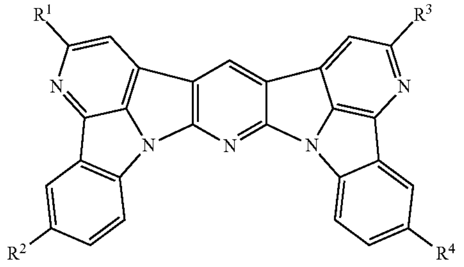
(1-192)
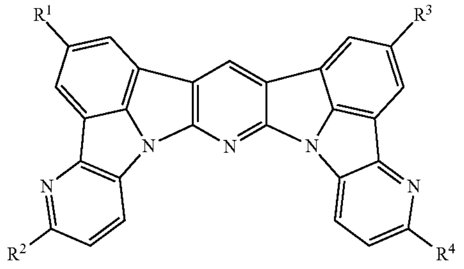
(1-193)
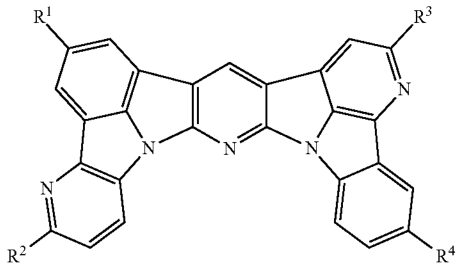
(1-194)
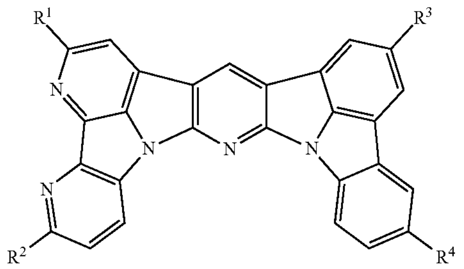

-continued
(1-195)
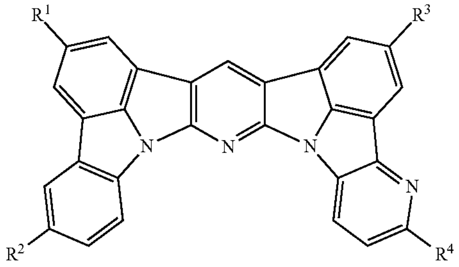
(1-196)
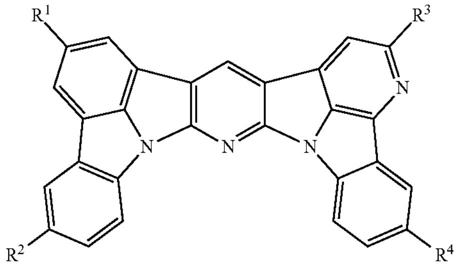
(1-197)
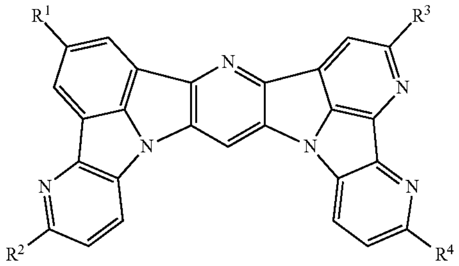
(1-198)
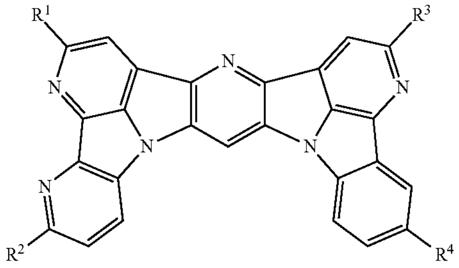
(1-199)
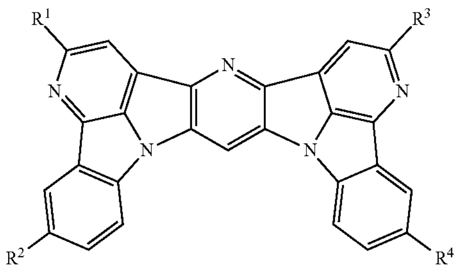
(1-200)
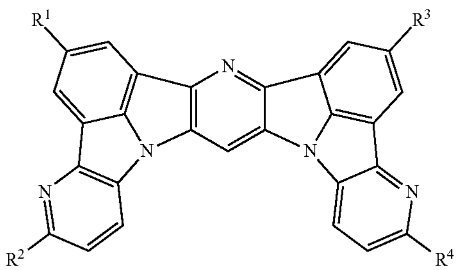
-continued
(1-201)
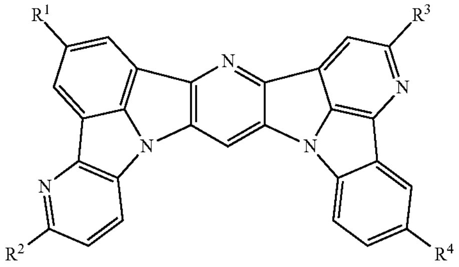
(1-202)
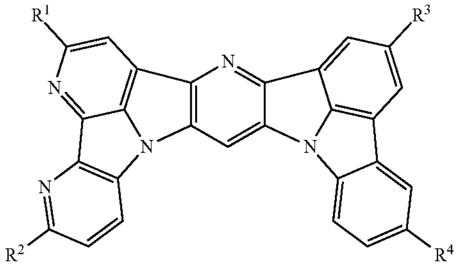
(1-203)
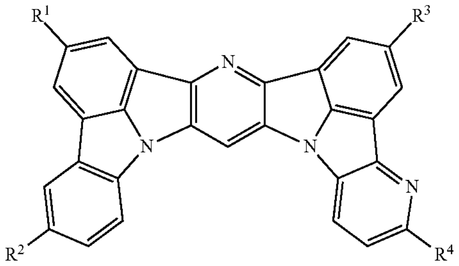
(1-204)
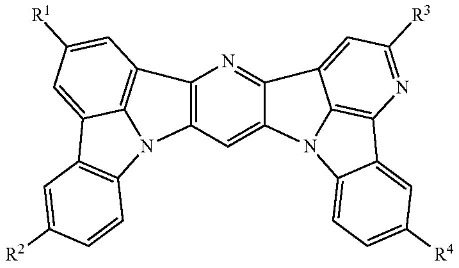
(1-205)
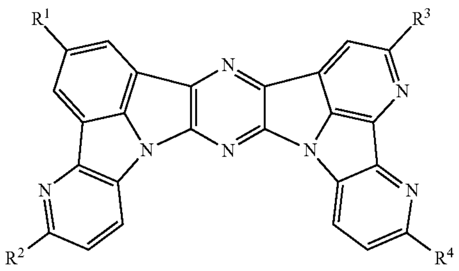
(1-206)
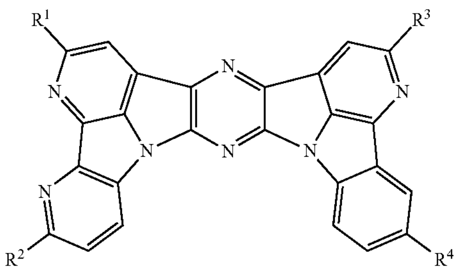

-continued
(1-207)
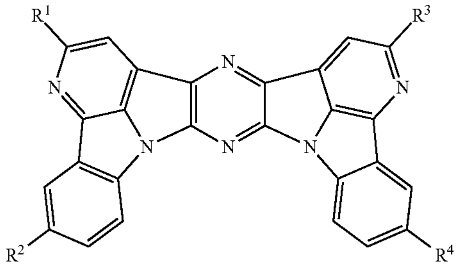
(1-208)
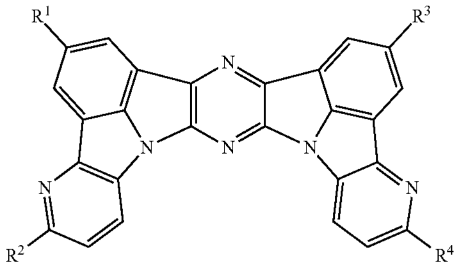
(1-209)
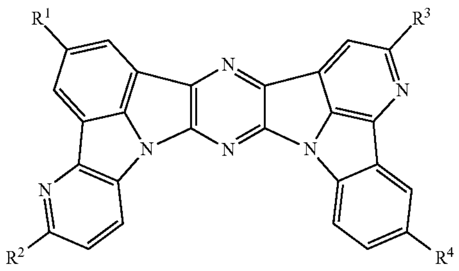
(1-210)
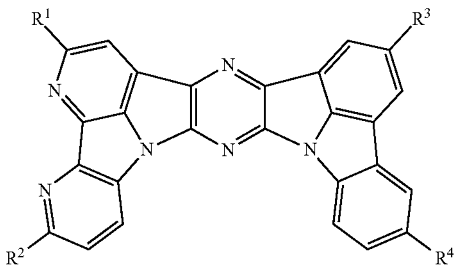
(1-211)
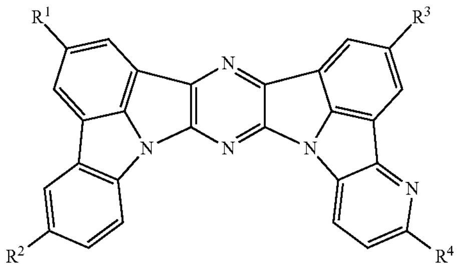
-continued
(1-212)
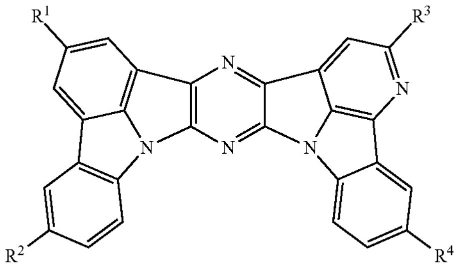
(1-237)
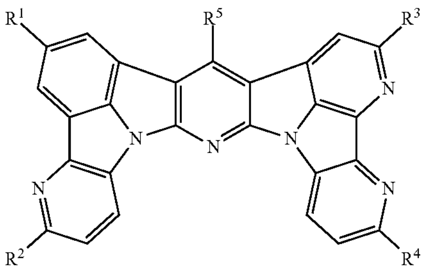
(1-238)
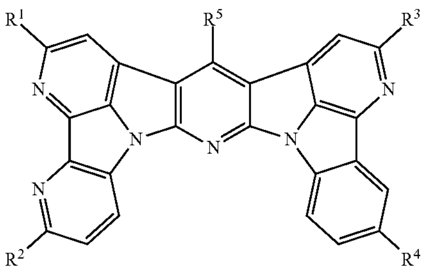
(1-239)
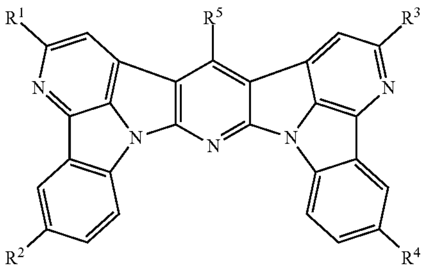
(1-240)
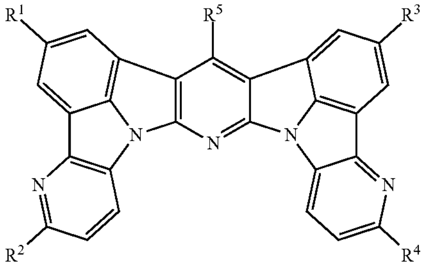

-continued
(1-241)
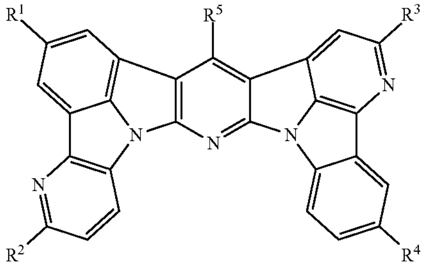
(1-242)
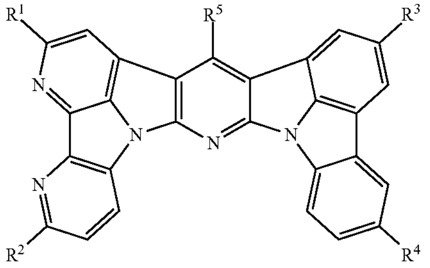
(1-243)
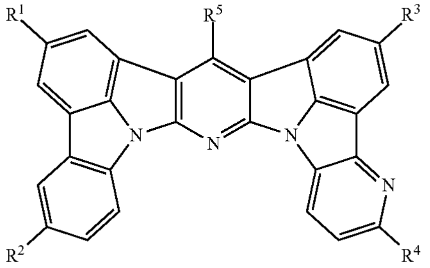
(1-244)
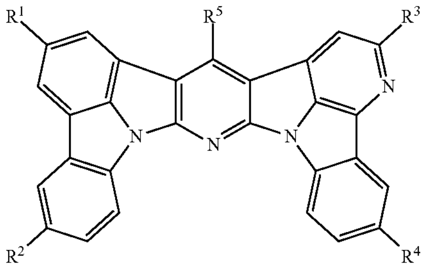
(1-245)
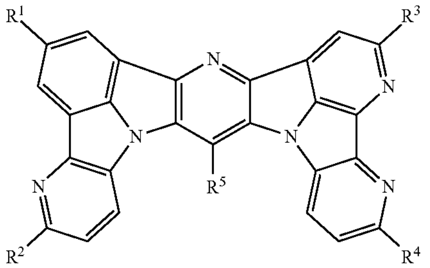
(1-246)
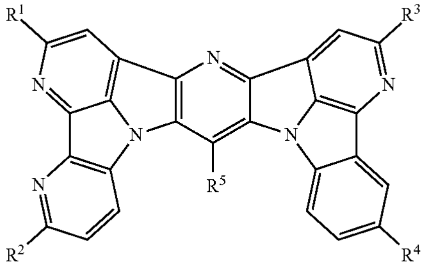
-continued
(1-247)
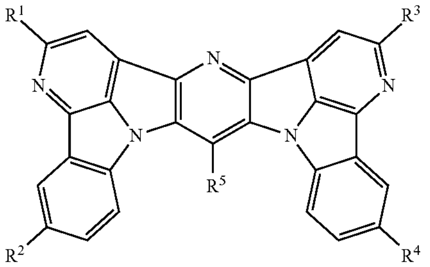
(1-248)
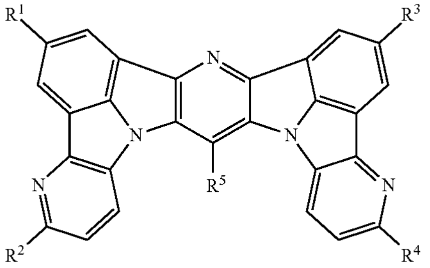
(1-249)
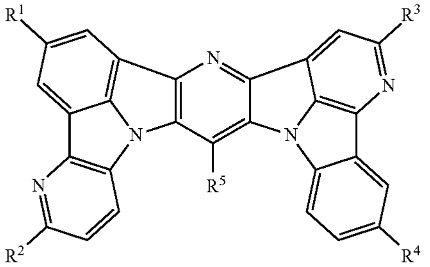
(1-250)
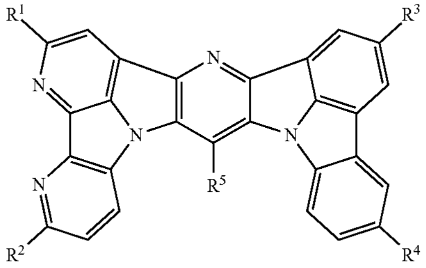
(1-251)
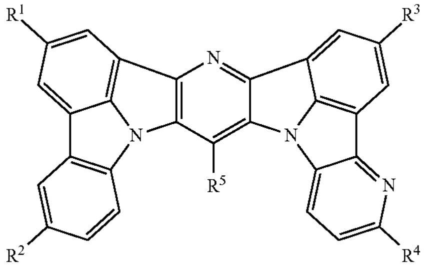
(1-252)
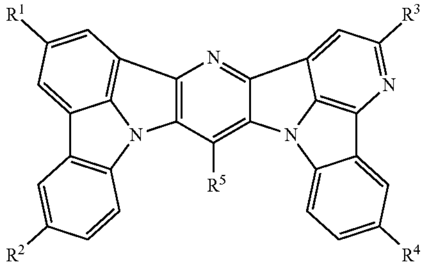

-continued
(1-261)
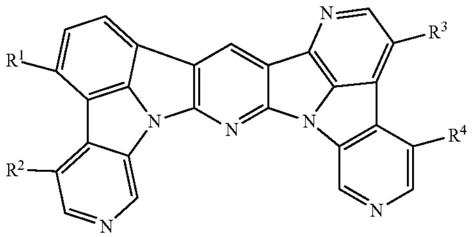
(1-262)
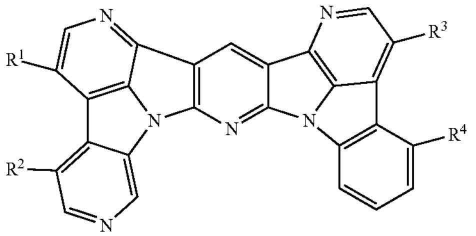
(1-263)
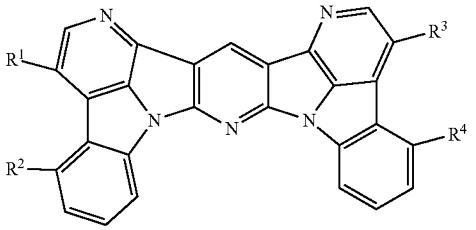
(1-264)
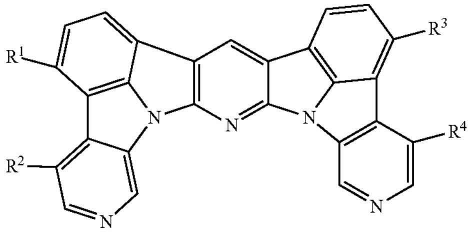
(1-265)
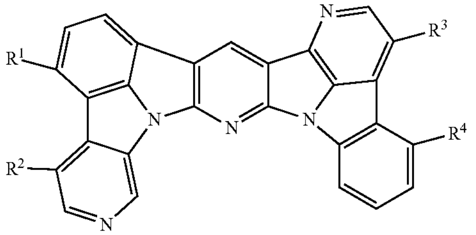
(1-266)
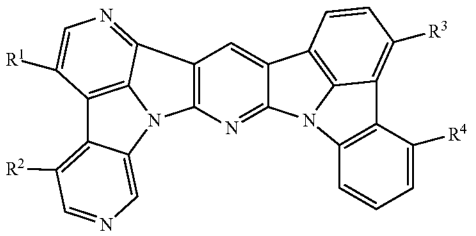
-continued
(1-267)
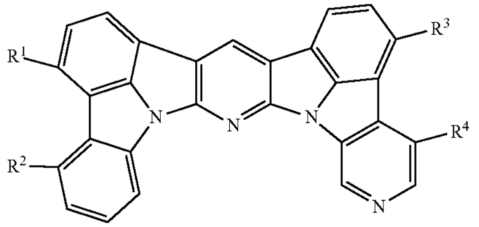
(1-268)
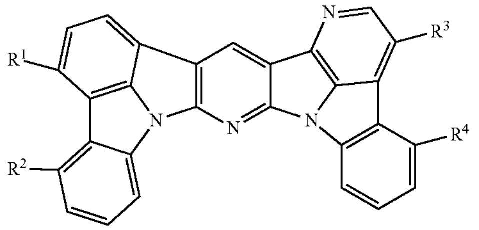
(1-269)
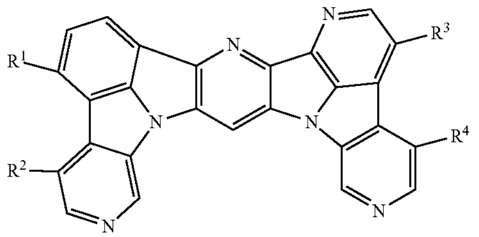
(1-270)
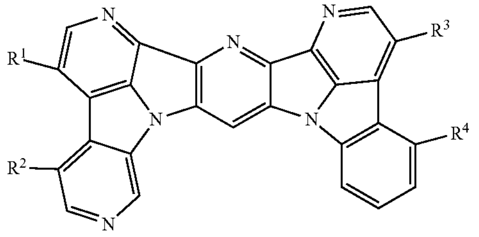
(1-271)
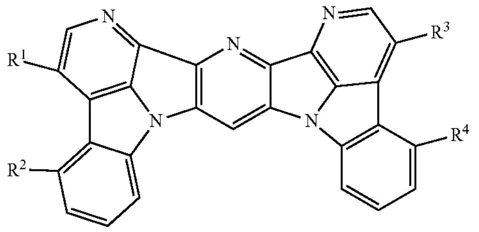
(1-272)
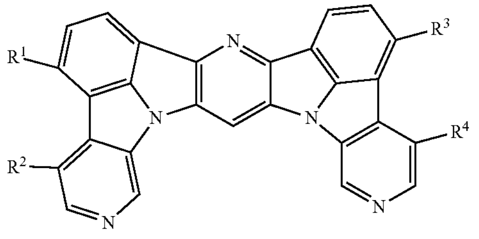

-continued
(1-273)
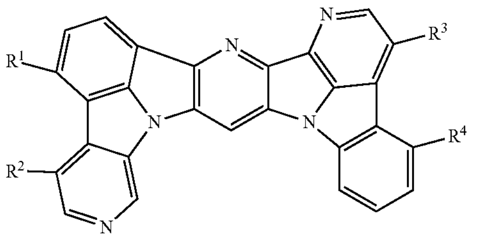
(1-274)
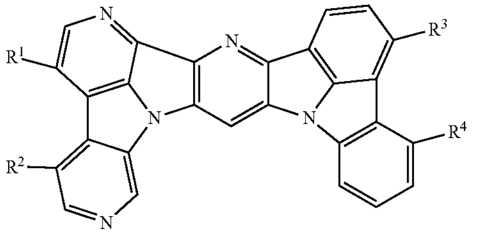
(1-275)
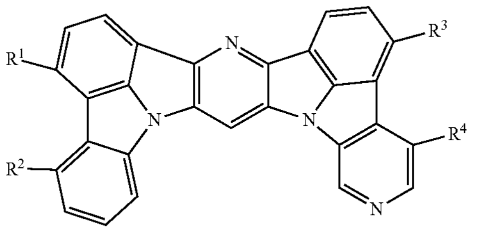
(1-276)
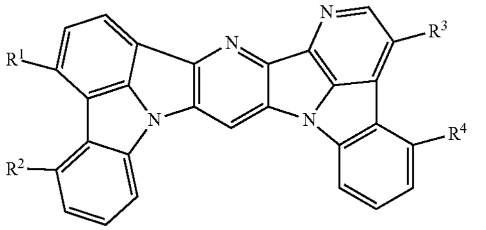
(1-277)
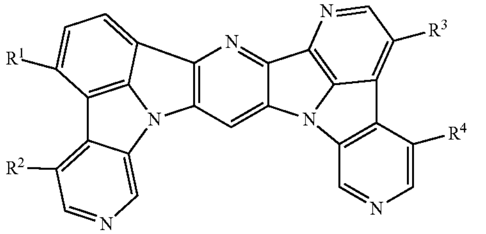
(1-278)
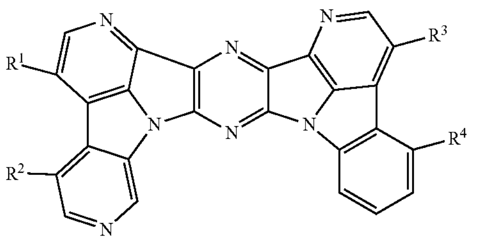
-continued
(1-279)
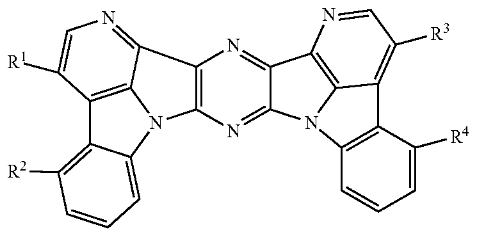
(1-280)
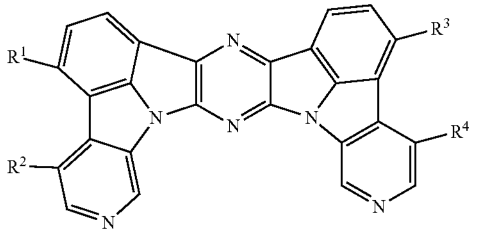
(1-281)
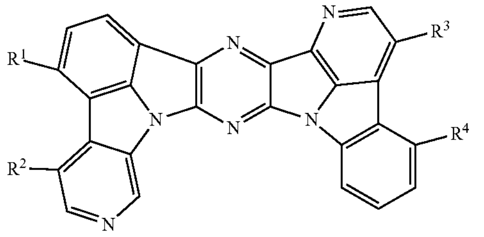
(1-282)
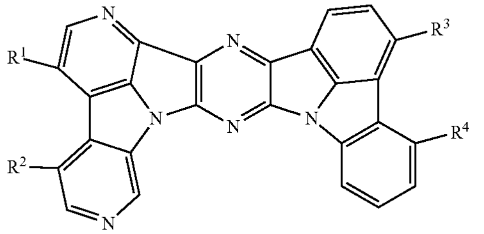
(1-283)
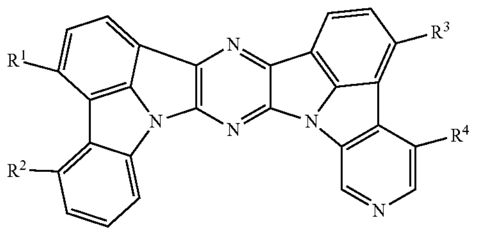
(1-284)
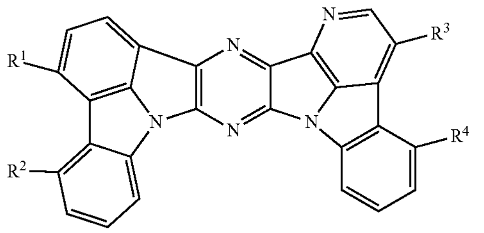

-continued
(1-309)
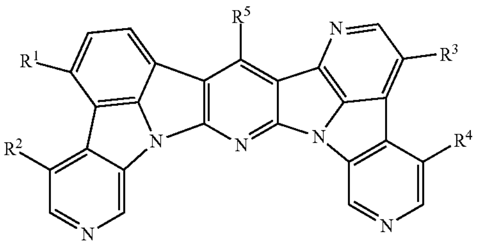
(1-310)
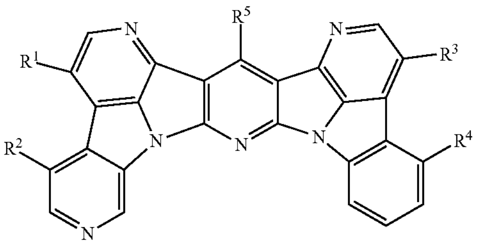
(1-311)
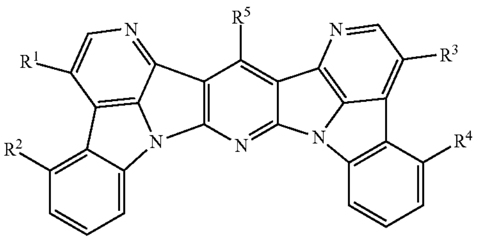
(1-312)
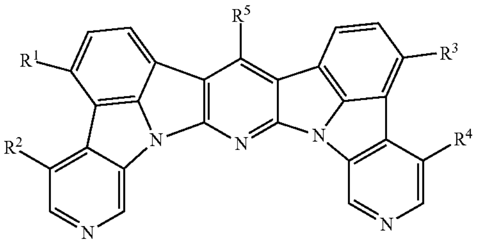
(1-313)
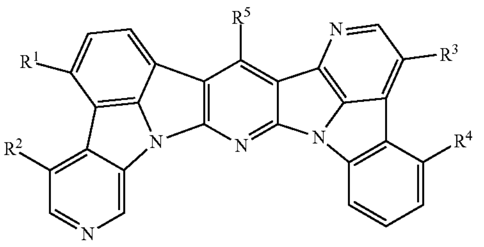
(1-314)
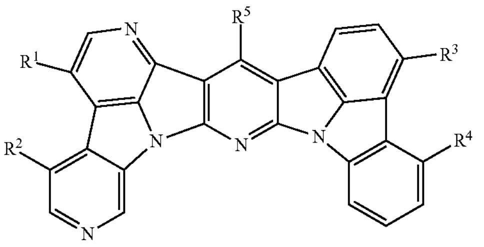
-continued
(1-315)
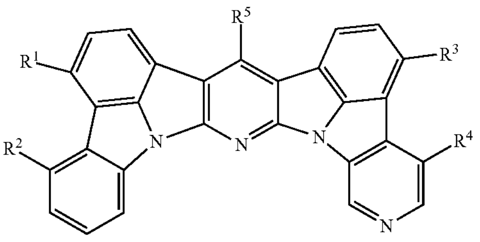
(1-316)
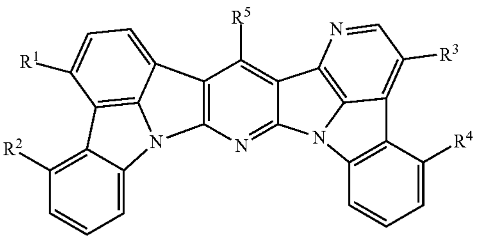
(1-317)
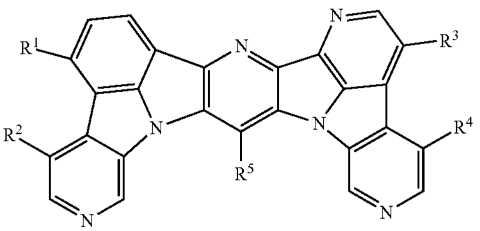
(1-318)
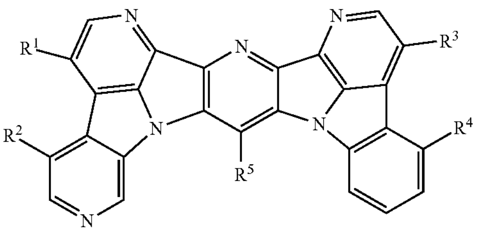
(1-319)
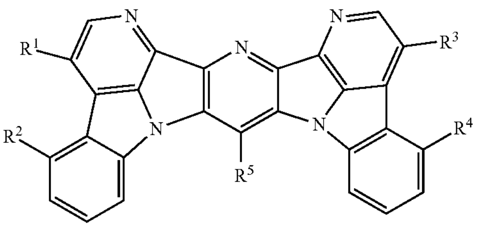
(1-320)
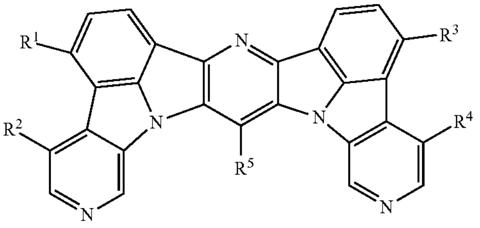

-continued (1-321)

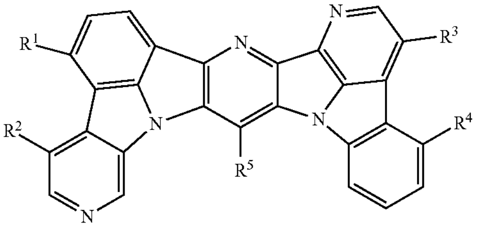

(1-322)

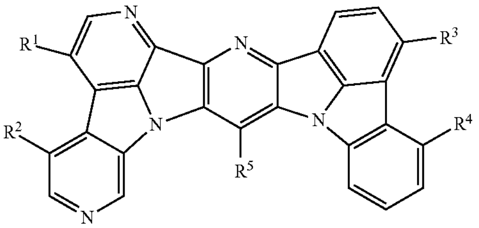

(1-323)

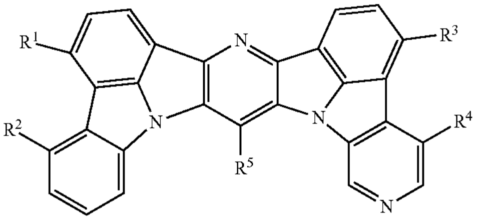

(1-324)

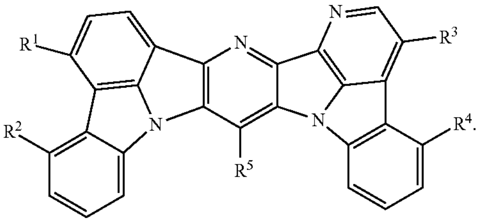

10. The heterocyclic compound of claim 1, wherein the heterocyclic compound is a compound of Group I:

Group I

4

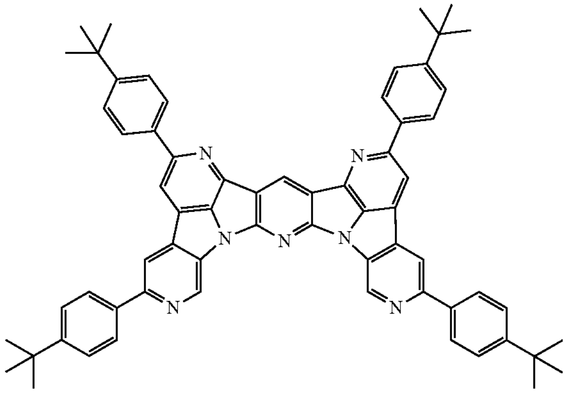

-continued

5

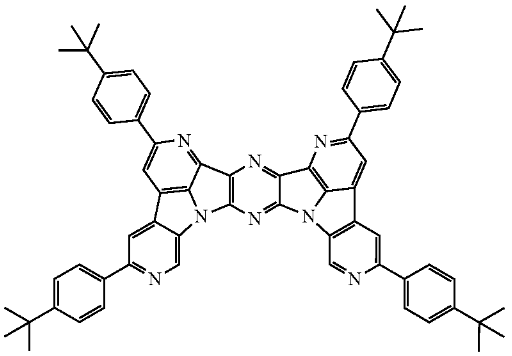

11. The heterocyclic compound of claim 1, wherein a highest occupied molecular orbital (HOMO) energy level of the heterocyclic compound is about −6.50 eV to about −4.6 eV, and a lowest unoccupied molecular orbital (LUMO) energy level of the heterocyclic compound is about −4.00 eV to about −2.60 eV.

12. The heterocyclic compound of claim 1, wherein a peak of a fluorescence wavelength of the heterocyclic compound is about 440 nm to about 480 nm, and a full width at half maximum (FWHM) of a peak of a fluorescence spectrum of the heterocyclic compound is about 20 nm or less.

13. The heterocyclic compound of claim 1, wherein AEST of the heterocyclic compound is about 0.3 eV or less.

14. An organic light-emitting device comprising:

a first electrode; a second electrode; an organic layer comprising an emission layer between the first electrode and the second electrode; and the heterocyclic compound of claim 1.

15. The organic light-emitting device of claim 14, wherein the emission layer comprises the heterocyclic compound.

16. The organic light-emitting device of claim 15, wherein the emission layer further comprises a host, the host is different from the heterocyclic compound, and the emission layer consists of the host and the heterocyclic compound.

17. The organic light-emitting device of claim 16, wherein the host does not emit light, and the heterocyclic compound emits light.

18. The organic light-emitting device of claim 15, wherein the emission layer further comprises a host and a dopant, the host, the dopant, and the heterocyclic compound are different from each other, and the emission layer consists of the host, the dopant, and the heterocyclic compound.

19. The organic light-emitting device of claim 18, wherein the host and the heterocyclic compound each do not emit light, and the dopant emits light.

20. An electronic apparatus comprising the organic light-emitting device of claim 14.

* * * * *